US009078982B2

(12) United States Patent
Lane et al.

(10) Patent No.: US 9,078,982 B2
(45) Date of Patent: Jul. 14, 2015

(54) SYSTEMS, METHODS AND DEVICES FOR CIRCULATORY ACCESS

(76) Inventors: Rodney J. Lane, Castlecrag (AU); Gregory J. Roger, Avalon (AU); Mark N. Phillips, Rozelle (AU); Jari Hyvarinen, Forestville (AU); Matthew J. Huckson, Mount Colah (AU); Samuel W. U. Liang, Penant Hills (AU)

( * ) Notice: Subject to any disclaimer, the term of this patent is extended or adjusted under 35 U.S.C. 154(b) by 719 days.

(21) Appl. No.: 12/734,546

(22) PCT Filed: Nov. 7, 2008

(86) PCT No.: PCT/AU2008/001653
§ 371 (c)(1),
(2), (4) Date: Jun. 14, 2011

(87) PCT Pub. No.: WO2009/059371
PCT Pub. Date: May 14, 2009

(65) Prior Publication Data
US 2011/0257577 A1  Oct. 20, 2011

Related U.S. Application Data

(60) Provisional application No. 60/996,246, filed on Nov. 7, 2007.

(51) Int. Cl.
*A61M 37/00* (2006.01)
*A61M 1/36* (2006.01)
(Continued)

(52) U.S. Cl.
CPC .......... *A61M 1/3653* (2013.01); *A61M 1/3613* (2014.02); *A61M 39/0247* (2013.01);
(Continued)

(58) Field of Classification Search
CPC . A61M 39/0247; A61M 1/3655; A61M 1/36; A61M 1/3621; A61M 2025/1052; A61B 2017/1107; A61F 2/06

USPC ................ 604/4.01, 6.11, 6.1, 6.09
See application file for complete search history.

(56) References Cited

U.S. PATENT DOCUMENTS 4,164,221 A   8/1979  Bentley et al.
4,421,507 A  12/1983  Bokros
(Continued)

FOREIGN PATENT DOCUMENTS

WO   WO 00/38763 A1   7/2000
WO   WO 00/41640 A1   7/2000
(Continued)

OTHER PUBLICATIONS

International Search Report dated May 6, 2009 for PCT/AU2008/001653.
(Continued)

*Primary Examiner* — Leslie Deak
*Assistant Examiner* — Andrew J Mensh
(74) *Attorney, Agent, or Firm* — Baker & Hostetler LLP

(57) ABSTRACT

Systems, methods, and devices are disclosed that permit the use of hyperperfusion, or regional hyperperfusion to targeted areas by the use of an arterial and/or venous access system which allows repeatable, transcutaneous insertion without any need for repeat anesthesia. The systems, methods and devices use various combinations of catheters and/or balloons. Furthermore, systems, methods, and devices are disclosed that permit drugs or other treatment products to be delivered using hyperperfusion, or regional hyperperfusion, to targeted areas by the use of arterial and venous access system and associated catheters and balloons which allow repeatable, transcutaneous insertion without any need for repeat anesthesia.

5 Claims, 67 Drawing Sheets

(51) Int. Cl.
*A61M 39/02* (2006.01)
*A61M 25/10* (2013.01)
*A61F 2/06* (2013.01)
*A61B 17/11* (2006.01)

(52) U.S. Cl.
CPC ........... *A61B2017/1107* (2013.01); *A61F 2/06* (2013.01); *A61M 1/36* (2013.01); *A61M 1/3621* (2013.01); *A61M 1/3655* (2013.01); *A61M 2025/1052* (2013.01); *A61M 2039/0258* (2013.01); *A61M 2039/0276* (2013.01); *A61M 2039/0279* (2013.01); *A61M 2206/14* (2013.01); *A61M 2206/20* (2013.01)

(56) References Cited

U.S. PATENT DOCUMENTS

| | | | |
|---|---|---|---|
| 4,804,369 A * | 2/1989 | Lapeyre et al. | 604/175 |
| 4,851,054 A | 7/1989 | Fukuzuka et al. | |
| 4,857,054 A | 8/1989 | Helfer | |
| 5,069,662 A | 12/1991 | Bodden | |
| 5,104,373 A | 4/1992 | Davidner et al. | |
| 5,186,713 A | 2/1993 | Raible | |
| 5,391,142 A | 2/1995 | Sites et al. | |
| 5,810,810 A * | 9/1998 | Tay et al. | 606/50 |
| 5,817,046 A | 10/1998 | Glickman | |
| 5,910,252 A | 6/1999 | Truitt et al. | |
| 6,083,215 A | 7/2000 | Milavetz | |
| 6,270,489 B1 | 8/2001 | Wise et al. | |
| 6,315,768 B1 | 11/2001 | Wallace | |
| 6,595,941 B1 | 7/2003 | Blatter | |
| 6,659,289 B1 | 12/2003 | Masuko et al. | |
| 7,025,741 B2 | 4/2006 | Cull | |
| 7,144,381 B2 * | 12/2006 | Gertner | 604/5.01 |
| 7,766,853 B2 | 8/2010 | Lane | |
| 8,419,672 B2 | 4/2013 | Lane | |
| 2004/0019310 A1 | 1/2004 | Hogendijk | |
| 2006/0142633 A1 | 6/2006 | Lane et al. | |

FOREIGN PATENT DOCUMENTS

| | | |
|---|---|---|
| WO | WO 2006/026805 | 3/2006 |
| WO | WO 2009/059371 A2 | 5/2009 |

OTHER PUBLICATIONS

Globalspec, Product & Service Category Results, 1999, p. 1 of 1, http://search.globalspec.com/ProductFinder/FindProducts?query=ball%20valve&se=ggka.

International Patent Application No. PCT/AU05/01300: International Search Report dated Nov. 1, 2005.

Meyns, "Ascending Versus Descending Aortic Balloon Pumping: Organ and Myocardial Perfusion During Ischemia", Annals Thoracic Surgery, Oct. 2000, 70(4),1264-1269.

* cited by examiner

SYSTEMS, METHODS AND DEVICES FOR CIRCULATORY ACCESS

CROSS-REFERENCE TO RELATED APPLICATIONS

This application is the National Phase application of International Application No. PCT/AU2008/001653, filed 7 Nov. 2008, which designates the United States and was published in English, and which claims priority to U.S. Provisional Application No. 60/996,246 filed 7 Nov. 2007. This application is also related to International Application No. PCT/AU2005/001300, filed Aug. 25, 2005. Each of these applications, in their entirety, are incorporated herein by reference.

FIELD

The present disclosure relates generally to systems, methods and devices that permit access to a warm blood animal's including their circulatory system. In some aspects, the systems, methods and devices disclosed use implanted device(s) and/or balloon catheter(s) to permit access to warm blood animals, including, but not limited to, regional hyperperfusion, regional targeting of therapeutics agents and/or providing for intermittent and recurrent access to the arterial and/or venous circulation of warm blooded animals. In some aspects, the systems, methods and devices disclosed can be used to treat targeted regions or target organs of warm blooded animals.

BACKGROUND

There are a number of catheters for infusion available; most of which have not been tested for prolonged intermittent suprasystolic pressures and some of the commonly used catheter balloons have difficulty with maintaining their integrity. See, for example, U.S. Pat. No. 5,817,046 or *Thoracic Surgery* 2000; 70: 1264-9.

There are implantable systems used for haemodialysis using external fistulae. The function of such systems is to filter blood at low pressures. Most systems remove and filter and return blood to the venous circulation. These systems are not used for intermittent hyperperfusion for ischemia as fistulae under these circumstances render the limb even more ischemic. Furthermore, such a fistula creates a "steal" phenomenon and chronically reduces total inflow pressure to the distal ischemic part. This is the mediator of the vessel proliferation via secretion of proliferative hormones. Furthermore, the anastomotic techniques required at normal pressures would not withstand the hyperperfusion pressures. A cannulation system for perfusing a patient's circulatory system has been disclosed in PCT/AU2005/0001300. The use of regional perfusion in tumours has been disclosed and available since the 1950's. Demonstration of high concentration of cytotoxic drugs has been delivered intra-arterially with occlusion of the venous system, via ligature tourniquet. See, for example, U.S. Pat. No. 5,069,662.

However, there is a need for improved systems, methods and devices that permits drugs or other treatment products to be delivered using regional, isolated, or partially isolated, hyperperfusion to targeted areas by the use of arterial and venous access system and associated catheters and balloons which allow repeatable, transcutaneous insertion without any need for repeat anaesthesia. There is also a need for improved systems, methods, and devices that permits drugs or other treatment products to be delivered using regional, isolated, or partially isolated means and which allow repeatable intermittent access without any need for repeat anaesthesia. There is also a need for systems, methods, and devices that permit drugs or other treatment products to be delivered using regional hyperperfusion to targeted areas with no, or limited, contact with the circulatory system of the warm blooded animal which allow repeatable and intermediate access to the treatment area without any need for repeat anaesthesia. In addition, there is also a need for such systems, methods, and devices that may be combined with such systems, methods and devices that have contact with the circulatory system of the warm blooded animal. There is also a need for systems, methods and devices that use implanted device(s) and/or balloon catheter(s) to permit regional hyperperfusion, regional targeting of therapeutics agents and/or provide for intermittent and recurrent access to the arterial and/or venous circulation of warm blooded animals. In addition, a need exists for systems, methods and devices that can be used to treat targeted regions or target organs of warm blooded animals, such as for systems, methods and devices for the intermittent and recurrent cannulation that allows for isolation (both arterial and venous) of a body part or parts, region or regions, organ or organs, or limb or limbs from the remainder of the systemic circulation. There is also a need for systems, methods, and devices wherein a therapeutic agent and circulating blood or fluid can, if desired, be discarded or partially removed from the body, such as to reduce or minimize the negative impact of higher concentrations of therapeutics agents and/or side effects of a treatment on the body. There is also a need for systems, methods, and devices that use specific types of balloon catheters for use in certain treatments and that have an improved access system design and features, such as; a design for simultaneous access to the arterial and venous circulation, and/or a design for the use of a hyperperfusion system without the use of balloon catheters. These and other advantages are disclosed herein. For the foregoing reasons, it is desirable to have improved systems, methods and devices that permit access to a warm blood animal's circulatory system.

SUMMARY

Certain embodiments disclosed herein provide systems, methods, and devices that permit drugs or other treatment products to be delivered using regional hyperperfusion to targeted areas by the use of arterial and venous access system and associated catheters and balloons which allow repeatable, transcutaneous insertion without any need for repeat anaesthesia.

Certain embodiments disclosed herein provide systems, methods and devices that use implanted device(s) and/or balloon catheter(s) to permit regional hyperperfusion, regional targeting of therapeutics agents and/or provided for intermittent and recurrent access to the arterial and/or venous circulation of warm blooded animals.

Certain embodiments disclosed herein provide systems, methods and devices that can be used to treat targeted regions or target organs of warm blooded animals.

Certain embodiments disclosed herein provide systems, methods and devices for the intermittent and recurrent cannulation and isolation (both arterial and/or venous) of a body part, region, or limb from the remainder of the systemic circulation.

Certain embodiments disclosed herein provide systems, methods, and devices wherein the therapeutic agent and circulating blood or fluid can, if desired, be discarded or partially removed from the body.

Certain embodiments disclosed herein provide systems, methods, and devices, wherein the negative impact of higher concentrations of therapeutics agents can be reduced or minimized so as to reduce the negative impact and/or side effects of the treatment on the body will be reduced.

Certain embodiments disclosed herein provide systems, methods, and devices that use specific types of balloon catheters for use in certain treatments.

Certain embodiments disclosed herein provide systems, methods and devices that improve access system design and features, such as; a design for simultaneous access to the arterial and venous circulation and a design for the use of the hyperperfusion system without the use of balloon catheters.

Certain embodiments combine an implantable system for intermittent and recurrent access to the arterial and/or venous circulation of a warm blooded animal simultaneously or separately with balloon catheters for occlusion or perfusion.

Certain embodiments combine an implantable system for intermittent and recurrent access to the arterial and/or venous circulation of a warm blooded animal simultaneously or separately with multiple access ports with balloon catheters for occlusion or perfusion.

Certain embodiments disclosed herein provide systems, methods, and devices that permit drugs or other treatment products to be delivered using regional hyperperfusion to targeted areas with no, or limited, contact with the circulatory system of the warm blooded animal which allow repeatable and intermediate access to the treatment area without any need for repeat anaesthesia. These embodiments may be combined with embodiments that have contact with the circulatory system of the warm blooded animal.

Certain embodiments disclosed herein provide systems, methods, and devices that permit the use of regional hyperperfusion to targeted areas by the use of arterial and/or venous access system which allow repeatable, transcutaneous insertion without any need for repeat anaesthesia and use at least one external compressive system capable of varying the diameter and therefore blood flow through vessels from the exterior of the vessel.

Certain embodiments disclosed herein provide systems, methods, and devices that use at least one circumferential sealing device impacted to the skin and subcutaneous junction to minimise, or substantially minimise bleeding.

Certain embodiments disclosed herein provide systems, methods, and devices that permit blood and/or fluid flow control to the cerebrum using regional hyperperfusion for the treatment of ischaemic stroke.

BRIEF DESCRIPTION OF THE DRAWINGS

Illustrative embodiments will be discussed with reference to the accompanying drawings wherein.

Figure 1:
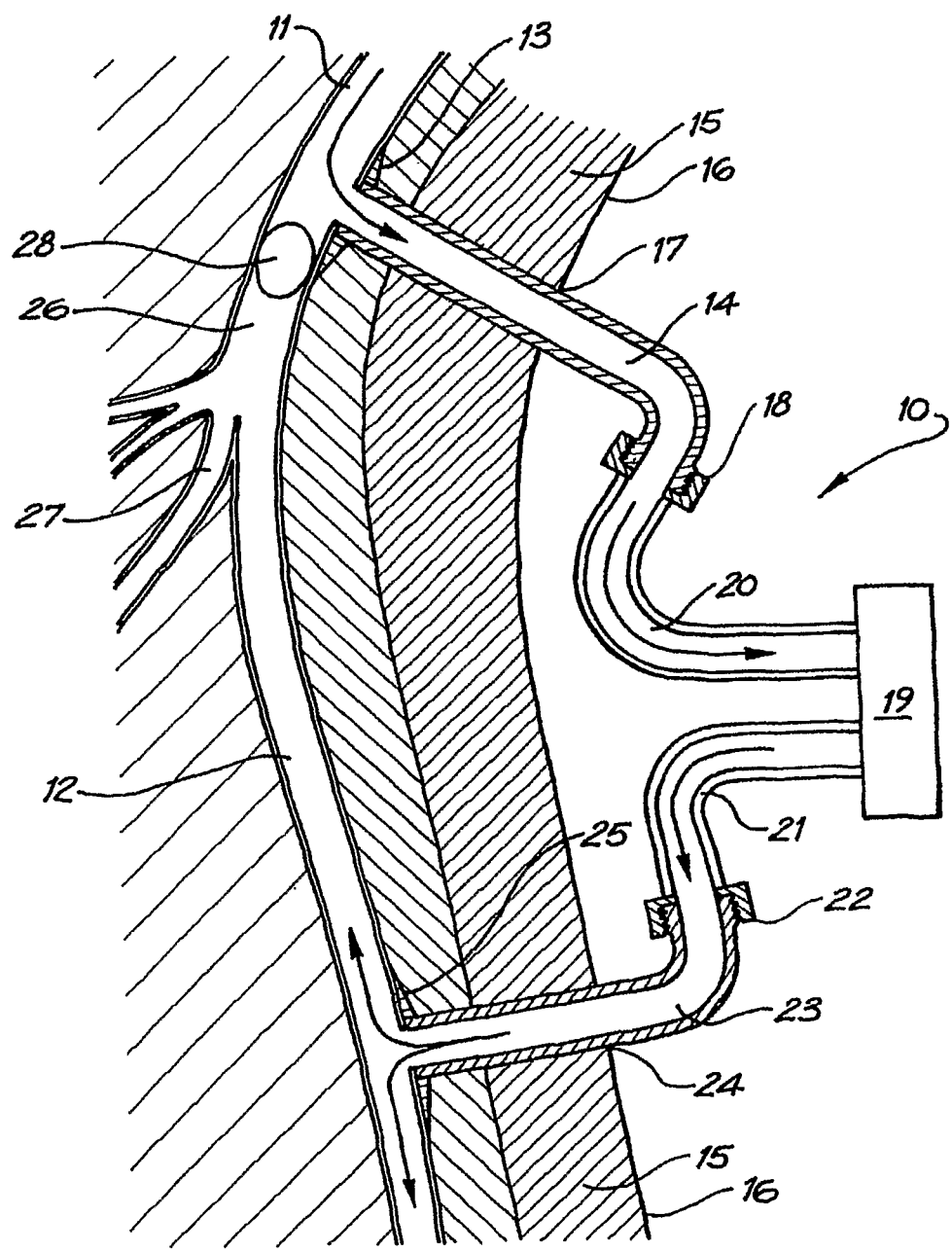
FIG. 1 is a schematic representation of a short term hyperperfusion system according to certain embodiments.

In the following description, like reference characters designate like or corresponding parts throughout the several views of the drawings. It is to be understood that the disclosed embodiments and the illustrations may be used and combined in different ways as well as being altered and modified to achieve the desire results of the systems, methods and devices disclosed in this application.

DETAILED DESCRIPTION

The devices, methods and systems disclosed herein can be used in a number of ways to access the circulatory systems, organs, and regions of the body and may be used to treat a large number of issues in warm blooded animals with occlusion or perfusion. The devices, methods and systems disclosed herein can be also used to permit drugs or other treatment products to be delivered using regional hyperperfusion to targeted areas with no, or limited, contact with the circulatory system of the warm blooded animal which allow repeatable and intermediate access to the treatment area without any need for repeat anaesthesia. The devices, methods and systems disclosed herein can be also used to permit drugs or other treatment products to be delivered to targeted areas with no, or limited, contact with the circulatory system of the warm blooded animal which allow repeatable and intermediate access to the treatment area without any need for repeat anaesthesia. These embodiments may be combined with embodiments that have contact with the circulatory system of the warm blooded animal.

In some aspects, regional hyperperfusion may be used to provide increased blood flow and blood pressure and to increase the concentration of a therapeutic modality supplied to a target organ or organs, limb or limbs, region or regions, or body part or parts of a warm blooded animal. Regional hyperperfusion generally involves the delivery of increased flow, increased blood pressure, and/or an increased amount of a therapeutic substance or modality to a target organ or organs, limb or limbs, region or regions, or body part or parts of a warm blooded animal when compared to normal cardiovascular circulation to the target organ or organs, region or regions, limb or limbs, or body part or parts.

However, not all aspects disclosed herein require use of hyperperfusion as part of the treatment. Certain aspects may be used in conjunction with or in the absence of hyperperfusion. Some aspects provide implantable devices, methods, and systems for intermittent and recurrent access to the arterial and/or venous circulation of a warm blooded animal either simultaneously or separately with multiple access ports. Providing such access opens once-difficult treatments to now achieve more optimal results and further make up a vast range of treatments that would otherwise not be possible or more difficult to perform with less optimal results. For example, certain systems, methods, and devices can be used where it is desirable for the therapeutic agent or agents, blood or fluid being used in treatment to be modified outside the body and/or discarded or partially removed from the body.

Another example is where the systems, methods, and devices, are used to introduce higher concentrations of therapeutics agents to a target organ or organs, limb or limbs, region or regions, or body part or parts of a warm blooded animal and then remove, or substantially remove, the therapeutic agents from the body to reduce or minimize the negative impact and/or side effects of the treatment on the body.

Another example is using the devices, methods and systems herein in combinations with other therapeutic modalities, such as for example, but not limited to, drug therapy, chemotherapy, hyperbaric therapy, cryogenic therapy, hyperthermic, hypothermic, and/or cytotoxic perfusion (with greater volume and/or concentration of cytotoxic drugs than normally used). It is also possible to combine the disclosed implantable systems for intermittent and recurrent access to the arterial and/or venous circulation of warm blooded animal either simultaneously or separately with multiple access ports with balloon catheters systems to achieve a number of results. Typically, the balloons are used to isolate a particular region of the body for treatment. It is of course also possible to combine the disclosed treatments in a number of ways.

One aspect of the methods, systems and devices disclosed herein is the access device. In certain embodiments, this device may be used to provide access to the circulatory system of a warm blooded animal to circulate blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or some other therapeutic modality, or combinations of the above at various pressures.

Typical examples of the access device are illustrated in the figures discussed below. In many embodiments, the access device will have housing. In certain embodiments, the housing will be biocompatible, or a portion of it will be biocompatible and will extend through the skin line and the subcutaneous tissue and be capable of being in fluid communication with vessel(s) of the circulatory system. The housing may be made of many materials, for example, silicone, inert elastic plastics, thermoplastics and/or elastomer materials, and may be coated with various materials if desired. For example, it may be coated with materials or substances that provide some therapeutic benefit or some functional benefit to the device. For example, anticoagulants antibiotic, and/or friction reduction coatings (PTFE or low friction materials, and/or expanded PTFE). In certain embodiments, it may be desirable that the housing, or a portion of the housing be made of materials sufficiently flexible, resistant to cracking, resistant to tearing, or combinations thereof of these properties such that the housing may be clamped off multiple times if desired. In certain aspects, the housing may be made of a single material or combinations of materials, including but not limited to, materials that have been surface modified. In certain aspects, the housing made be made of outer tubing and an inner sleeve or different portions of the housing may be constructed of different combinations of materials. In certain aspects, the housing, or that portion that extends into the body may be manufactured from biocompatible and/or non-biocompatible materials such as polyester, Gore-Tex, polytetrafluoroethylene (PTFE), expanded polytetrafluroethyline (ePTFE), polyethylene, polypropylene, polyurethane, silicone, steel, stainless steel, titanium, Nitinol, or other shape memory alloys, copper, silver, gold, platinum, Kevlar fibre, carbon fibre, or combinations thereof. Where non-biocompatible materials may come in contact with the anatomic structure, the components made from non-biocompatible materials may be covered or coated with biocompatible material. In some aspects, the coefficient of friction between plunger tip and housing is to be minimised or sufficient to prevent the generation of too much frictional force. Means for providing an appropriate coefficient of friction between the plunger tip and the housing are disclosed herein. Such forces may stretch the housing and generate undesired force on the anastomosis site during plunger insertion/removal. In some aspects, the internal surface roughness of housing, or portions of the housing, should be smooth, or sufficiently smooth, so as to reduce or minimize thrombogenicity. In some aspects, it is desirable that the housing, or portions of the housing be sufficiently stiff in longitudinal direction to keep plunger tip stopping at a correct distance. In some aspects, reinforcing structure may be used to provide sufficient stiffness such as an exterior metal structure of struts. Means for providing sufficiently stiff housing are disclosed herein. In some aspects, the housing, or portions of the housing need to be sufficiently flexible so as to permitting the housing, or portions of the housing to be clamped off using a standard clamp 1, 2, 3, 4, or 5 times per day over 3, 5, 10, 20, 28 day, 2, or 3 months. In other words, the housing, or portions of the housing, have sufficient fatigue resistance to be clamped on and off over periods of time during use. In some aspects, that housing, or portions of the housing, need to withstand pumping pressures of from 80 to 500 mmHg, 120 to 400 mmHg, 100 to 350 mmHg, up to 300 mmHg, up to 200 mmHg, or up to 500 mmHg without failure. In some aspects, the housing, or portions of the housing will have sufficient wall thickness to prevent collapse under pressure created by tissue in subcutaneous tunnel. In some aspects, the housing length typically allows sufficient room for the housing to be clamped once the plunger tip is retracted. In some aspects, the access device housing requires a sufficient internal diameter such that fluid flow or blood flow may be calculated. For example, but not limited to, an internal diameter of between 4 to 12 mm, 5 to 9 mm, or 6 to 8 mm.

In certain embodiments, it is desirable that the housing, when inserted, be at an angle sufficiently, or substantially, close to the body such that the housing and the access device is less likely to be bumped or partially dislodged during use. In certain aspects, the angle of the insertion of the housing and access device relative to the surface of the body at the insertion location in the warm blood animal may provide additional advantages. The housing may be placed at an angle that makes the insertion, and/or the removal, of catheter or balloon systems easier to accomplish. The angles may depend on where the catheter or balloon systems are being placed inside the body or vessel. In certain embodiments, it is often useful to have the housing at an angle that makes the insertion, and/or the removal, of the catheter or balloon systems easier to accomplish. In certain embodiments, the housing will be placed at angle of from about 5° to about 175°, about 5° to about 40°, about 5° to about 45°, about 10° to about 40°, about 65° to about 90°, about 60° to about 90°, about 70° to about 85°, about 65° to about 80°, about 15° to about 175°, about 25° to about 150°, about 35° to about 150°, about 35° to about 120°, about 40° to about 60°, or about 75° to about 110°, each relative to the surface of the body at the insertion point. In some aspects, that housing will be about 35°, about 40°, about 45°, about 55°, about 65°, about 75°, or about 90° relative to the surface of the body at the insertion point. The angle relative to the surface of the body may be measured from a point on the surface of the body above the insertion point of the access device to the access device.

Using the embodiments disclosed herein enables recurrent and greater flexibility in treating the patients via intermittent and recurrent access and control of fluid or blood flow to a warm blooded animal's circulatory system. Accordingly, the blood or fluid supply and/or drainage from a specific organ, region, or body part may be totally, substantially, or partially controlled. Once the blood supply and drainage is controlled at the desired level, it is possible to deliver therapeutic agents to the isolated organ, region or body part without these agents circulating, substantially circulating, or partially circulating in the systemic circulation. One advantage of the embodiments disclosed herein is that therapeutic agents or treatments can be delivered more effectively to the targeted treatment region while at the same time minimizing, partially minimizing, reducing, or substantially reducing the delivery of the therapeutic agents to areas of the body that are not to be treated, thereby reducing, substantially reducing, or partially reducing unwanted side effects.

Using the embodiments disclosed herein, the time that therapeutic agents or treatments are in contact, substantial contact, or partial contact with the treatment area may be reduced by between about 90% and about 5%, about 90% and about 10%, about 80% and about 20%, about 70% and about 30%, about 70% and about 20%, about 60% and about 40%, about 60% and about 10%, about 60% and about 20%, or between about 50% and about 30%. Using the embodiments disclosed herein, the time that therapeutic agents or treatments are in contact, substantial contact, or partial contact with the body may be reduced by between about 90% and about 5%, about 90% and about 10%, about 80% and about 20%, about 70% and about 30%, about 70% and about 20%, about 60% and about 40%, about 60% and about 10%, about 60% and about 20%, or between about 50% and about 30%. Using the embodiments disclosed herein the time that therapeutic agents or treatments are in contact, substantial contact, or partial contact with the non treatment areas of the body may be reduced by between about 90% and about 5%, about 90% and about 10%, about 80% and about 20%, about 70% and about 30%, about 70% and about 20%, about 60% and about 40%, about 60% and about 10%, about 60% and about 20%, or between about 50% and about 30%.

Another advantage to the embodiments disclosed herein is that therapeutic agents or treatments that in the past caused too many unwanted side effects will now potentially be available for use. Using the embodiments disclosed herein it is possible to use the above variations in different combinations to deliver more effective therapeutic treatments or agents while at the same time minimizing, partially minimizing, reducing, or substantially reducing or partially reducing unwanted side effects.

Another advantage of using certain embodiments disclosed herein is that the systems, methods and/or devices permit intermittent access and/or modulation of the pressures being applied during hyperperfusion of a treatment region resulting in better control over the collateral development of vessels. For example, in some embodiments, such treatment may result in a modulating effect of wall tension and shear stress on vessel development; and/or the ability to continually adapt flow and pressure characteristics. These advantages provide for a more effective hyperperfusion treatment. One desired result of certain hyperperfusion embodiments disclosed herein is to stimulate the up regulation of angiogenic factors. Another desired result of certain hyperperfusion embodiments disclosed herein is to inhibit, or reduce growth inhibitors, in order to promote angiogenesis. In certain embodiments, hyperperfusion as disclosed herein can be used to stimulated angiogenic factors, reduce angiogenic inhibitors, or combinations thereof. For example, certain embodiments disclosed may be used to inhibit or reduce growth factors such as endostatin or angiostatin in the body. For example, one collateral growth factor is Monocyte Chemo attractant Protein (MCP1). This substance stimulates chemotaxis of monocytes with subsequent diapedesis. Other example of promoters of angiogenesis that may be used are angiopoietin-1, basic fibroblast growth factor (bFGF), vascular endothelial growth factor (VEGF) or combinations thereof. Examples of inhibitors of angiogenesis that may be used are endostatin, angiostatin, $AZD_{2171}$ (Recentin™-AstraZeneca), resveratrol, genistein, catechins, or combinations thereof. The end result is collateral growth. Continued infusions of MCP1 over a period of time can result in significant arteriogenesis in warm blooded animals. Continued infusions of MCP1 over about 5 hours to about 100 hours, about 10 hours to about 80 hours, or about 20 hours to about 60 hours can result in angiogenesis in warm blooded animals. For example, continued infusions of MCP1 for about 20 hours, about 30 hours, about 40 hours, about 50 hours, about 60 hours, or about 70 hours can result in significant arteriogenesis in animals. Increased use stress increases MCP1 production. For example, using certain embodiments disclosed herein, you can treat human patients with hyperperfusion over 5 to 30 hours, 10 to 25 hours, 5 to 25 hours, or 10 to 20 hours and then provide a break in treatment of 5 to 15 hours, or 5 to 10 hours and then repeat treatment an additional number of times as needed (for example, repeat treatment 1, 2, 3, or 4 additional times). In certain treatments the human patient will be treated 1 to 3 times for between 20 to 30 hours with appropriate breaks between treatments of from 6 to 10 hours. The treatment period can extend from 1 day to 28 days, 3 days to 6 days, 3 days to 10 days, 4 days to 7 days, or as required by the particular treatment. Treatment can be halted for a longer period than this. In certain embodiments, the treatment could be started for 4 to 12 hours or the desired treatment time and then halted for 2 hours to 40 days, 12 hours to 20 days, 1 day to 22 days, 2 days to 10 days, 3 days to 15 days, 5 days to 26 days, 8 days to 15 days, or other desired time periods. The device will be approved for 28 day use, which means that potentially treatment could be stopped for a period of up to 26 days. In certain embodiments, at least one treatment time will be combined with at least one non-treatment time. In certain embodiments, at least two treatment times will be combined with at least one non-treatment time. In certain embodiments, at least three treatment times will be combined with at least two the non-treatment times. Other variations are contemplated.

Another advantage of using certain embodiments disclosed herein is that the systems, methods and/or devices permit increased flow through arteries and/or veins without increasing or substantially increasing pressure on the walls of those arteries and/or veins. This results in an increased shear stress on the endothelium of the vessel. In some aspects, this results in a constant, or substantially constant, or pulsed increase in shear stress or wall tension on the smooth muscle cells of the vessel. This results in an increased shear stress on the endothelium of the vessel that is constant, or substantially constant, as compared with normal pretreatment flow and over time as the vessel dilates fluid velocity will decrease and shear stress will decrease.

Another advantage of using certain embodiments disclosed herein is that the systems, methods and/or devices provide for continuous dilation of the smooth muscle cells in the arteries or veins, thus, promoting of angiogenesis by preventing, substantially preventing or reducing contraction of the smooth muscle cells. This results in an increase in wall tension on the smooth muscle cells of the vessel.

Another advantage of using certain embodiments disclosed herein is that the systems, methods and/or devices provide control of pulse pressure. By pulse pressure we mean the difference between systolic and diastolic pressure within the area being treated. This results in constant or substantially constant dilation and stressing of the vascular walls to increase the drive to angiogenesis during hyperperfusion. This also results in greater perfusion of the vessels during hyperperfusion. Increasing pulse pressure which tends to occur in other known methods increases or substantial increases the chance of converting a patient from an ischemic infarct to a hemorrhagic infarct.

Another advantage of using certain embodiments disclosed herein is that the systems, methods and/or devices are more capable of controlling the beat-to-beat direct infusion of the arteries, vessels, organs or regions of the body being treated.

Another advantage of using certain embodiments disclosed herein is that the systems, methods and/or devices do not induce, reduce, or substantially reduce certain physiological responses. For example, but not limited to, a general sympathetic response due to complete, or partial, occlusion of major arteries; general hypertension caused by an angiotensin response; adrenaline responses, which cause cerebrovaso constriction; mediation of aortic and carotid receptors via a vagal response thereby causing a decreases in the heart rate (bradycardia); and/or combinations thereof.

In certain embodiments, the access device will have a head assembly located in the upper portion of the access device. As disclosed herein, there are numerous variations to the construction of the head assembly depending on the application. In certain aspects, the head assembly is capable of permitting fluids to communicate through the access device and into and/or out of the circulatory system. In certain aspects, the head assembly is capable of providing intermittent access over a period of time ranging from 1 hour to 1 year, 10 hours to 6 months, 1 day to 6 months, 2 days to four months, 2 days to 3 months, 1 day to 2 months, or 1 day to 45 days. In certain aspects, the head assembly is capable of permitting intermittent access to at least one vessel. In certain aspects, the head assembly is capable of permitting intermittent access of other devices and/or fluids to at least one vessel. In certain aspects, the head assembly is capable of permitting at least one catheter to be inserted and/or removed through the access device and into at least one vessel. In certain aspects, the head assembly is capable of permitting at least one balloon catheter to be inserted and/or removed through the access device and into and/or out of at least one vessel being accessed. In certain aspects, the head assembly is capable of permitting a plurality of catheters and/or balloon assemblies to be inserted and/or removed through the access device and into at least one vessel being accessed.

In certain aspects, once the access device has been inserted into the warm blooded animal and configured for the desired use, the device may be left in place over the treatment period, or as desired, without the need to remove that portion of the access device that has been inserted into the warm blooded animal. This permits intermittent and recurrent access to the desired treatment region without the need to anaesthesia the warm blooded animal and reinsert a catheter each time access is desired. This permits frequent access to the targeted region of the body or targeted portion of the circulatory system.

In certain embodiments, the head assembly will be associated with at least one housing, with at least one plunger stem, with at least one plunger head, with at least one handle, with at least one locking pin, with at least one detachable cap through which the at least one plunger stem projects, with at least one inflow/outflow port, and/or combinations thereof. The plunger head may be constructed from a variety of materials. In certain aspects, the plunger head may be constructed of a biocompatible material such as PTFE. In certain aspects, the plunger head can be made of materials, that are sufficiently inelastic, for example, but not limited to, certain compositions of PTFE, high density poly ethylene (HDPE) or other inelastic plastics. In certain aspects, it may be desirable that the plunger head be blood compatible, or substantially blood compatible, that is does not cause, or substantially cause, damage to blood cells, thrombosis, cell adhesion, and platelet activation. In certain aspects, the plunger shaft and/or plunger head may be constructed from suitable materials, such as biocompatible materials or non-biocompatible materials that are coated with biocompatible materials or combinations of these materials as long as the appropriate properties are achieved. In certain aspects, the plunger head will be connected or operate in cooperation with a plunger shaft. In certain aspects, the plunger head and shaft may be constructed as one unified piece or may be constructed of two or more pieces. In some aspects, the shape of the plunger head may be modified; for example, the plunger head may have ribs, indentation, or sections removed from the outer surface, such as a concentric ring or rings, or combinations thereof. In some embodiments, the first rib, ring or indentation is positioned sufficiently proximal to the distal end of the plunger head so that the chance of the first rib, ring or indentation being inadvertently pushed out the front of the housing tube is minimised. In certain aspects, it may be desirable to modify the contact surface area between the plunger head's outer surface and the lumen's inner surface to either reduce or increase the force needed to insert and remove the plunger head from the lumen. In certain aspects, it may be desirable to modify the surface contact area of either the lumen or the plunger head (or both) to reduce or increase the ease of removal from the lumen. The shape of the plunger tip may vary. Typically, the plunger head tip will be flat, substantially flat, or concave, substantially concave, convex, or substantially convex or combinations thereof. In some aspects the plunger tip will nominally protrude from the housing or lumen by 0.1 to 2 mm, 0.2 to 1 mm, 0.25 to 0.75 mm, or 0.4 to 0.6 mm. One function of certain embodiments of the plunger head tip is to seal the proximal end of the lumen and to prevent or reduce the formation of thrombi in use. Plunger head means for preventing or reducing the formation of thrombi are disclosed herein. Another function of the plunger head in cooperation with the housing is to prevent fluids or blood from entering the vessel under vessel pressures of from 70 to 500 mmHg, 80 to 300 mmHg, 100 to 160 mmHg, up to 150 mmHg, up to 120 mmHg, up to 200 mmHg, up to 300 mmHg, or up to 500 mmHg. Plunger head means in cooperation with the housing for preventing fluids or blood from entering the vessel under vessel pressures of from 70 to 500 mmHg, 80 to 300 mmHg, 100 to 160 mmHg, up to 150 mmHg, up to 120 mmHg, up to 200 mmHg, up to 300 mmHg, or up to 500 mmHg are disclosed herein. In some aspects, the plunger head mechanism should cause minimal friction with the housing, and in particular in the bonded area. Another function of certain embodiments of the plunger head is to minimize, or reduce irregular flow of fluids or blood. Plunger head means for minimizing or reducing irregular flow of the fluids are disclosed herein. Another function of the plunger head is not creating a cavity or minimizing cavities at the anastomosis. In some aspects, the plunger head tip will have to be narrowed in diameter to prevent interference with the bonded area and still fill the tube to prevent dead spaces. In some aspects, the plunger head is compatible with and allow insertion of a stylet and the fit or cooperation between the plunger head and the stylet is sufficient to create an appropriate seal.

Alternatively, the plunger head may be constructed from any suitable materials, such as biocompatible materials or non-biocompatible materials that are coated with biocompatible materials or combinations of these materials as described elsewhere herein, that have appropriate properties to serve their intended function as disclosed herein. In certain aspects, the plunger may be designed to reduce the tension placed on the anastomosis during insertion and removal. In certain aspects, when the access device housing is attached to the vessel at certain angles, the distal end angles may have to be "keyed" such that the angled plunger lined up with the angled cut on the end of the housing tube. This may not be needed depending on the design of the other components of the access device. In certain embodiments, the plunger shaft and plunger head may be cannulated to provide for access through some portion of the plunger shaft and the plunger head for angiographic purposes and for addition of therapeutics, such as any therapeutics as described herein, for example drip solutions such as saline, dextrose or heparin solutions. Typically, when the plunger shaft and head are cannulated other means will be provided to open or shut off access to the access hole. One example would be the use of a stylet as disclosed herein. It is also contemplated that angiographic or drip access may be provided by an indentation of the surface of the plunger. Means will still need to provided to open or shut off such access during use of the access device. In certain aspects, the plunger shaft cannula may be positioned in the center of the plunger shaft while in other embodiments, the plunger shaft may include none, 1, 2, 3, or 4 cannulae each having a means to open or shut access during use. For example, cooperating stylet, or stylets may be used.

In certain embodiments, the stiffness of the plunger may vary. In some aspects the plunger may be made of an appropriate material so that the plunger is stiff, substantially, stiff, flexible, or substantially flexible. The desired flexibility or lack of flexibility of the plunger will depend on the particular application and the particular device being used. In certain situations use of a flexible plunger, or substantially flexible, plunger may be desirable because if combined with the appropriate housing tube, the device may be taped, or secured in some manner, closer to the patients body. This may prevent accidental bumping of the device when attached to the patient.

In certain embodiments, the access device will be equipped with a safety cap to prevent leakage of blood or fluids from the access device. In addition, the safety cap may be used to prevent accidental removal of plunger shaft and stylet. In some aspects, the safety will have an external profile intended to assist in hand tightening.

The access devices disclosed herein in certain aspects need not be of the plunger type, and other kinds of access devices which permit intermittent connection between the circulatory and perfusion systems may be used. For example, the access device may be a percutaneously controllable valve which, when open, permits access between the circulatory system and the perfusion system. Such a valve may be constructed from metal, tissue or polymeric material and may incorporate any suitable flow control mechanism, such as for example, a tilting disc, flap, ball or membrane and the like as its flow control means.

In certain embodiments, it may be desirable that the plunger stem be capable of being locked in desired positions and to prevent movement of the plunger stem if it is locked into a position. For example, it may be desirable that the plunger stem or plunger head can be locked in a position that prevents, or substantially prevents, back pressure of the patient's arterial system from altering the position of the plunger stem or plunger head. In certain embodiments, it may be desirable to place sterile antibiotic containing and/or anti-coagulated fluids in the housing or lumen when not in active use but attached to the patient. In some aspects, it may be desirable to have a head assembly wherein the interior of the housing may also be repeatedly accessed to remove any residual fluid or blood. In some aspects, a locking ring may be used to aid the clamping of the shaft seals onto the access device housing.

In certain embodiments, the device will use a suture foot to assist in the anastamosis. The suture foot can be configured in various shapes and the shape may vary depending on the angle of connection of the access device to the vessel. In some aspects, it is desired that the foot be shaped such that the cavity formed with the vessel wall will be smooth or substantially smooth. In some aspects, it will be desirable to shape the foot such that minimal dead space is created or generated in the anastomosis region. The foot may be made of a number of materials. In some aspects, it is desirable that the foot is to be made from a tear proof or tear resistant suturing material, for example, but not limited to ePTFE (woven or knitted) Dacron (woven or knitted), or combinations thereof. In some aspects, the material may be selected so as to not irritate the vessel wall. The foot may be attached to the housing in a number of ways using mechanical or chemical bonding means or combinations thereof. For example, silicone housing and the foot may be bonded using a cyanoacrylate adhesive and primer combination. Other adhesives may also be used. In some aspects, the mechanical or chemical bond created should be able to with stand the physical forces it will be subjected to during use. In some aspects, it will need to be able to withstand a tensile loading of 0.5 to 6 kg, 1 to 5 kg, 2 to 4 kg, at least 2 kg, at least 3 kg, or at least 5 kg during testing. In some aspects, a cyanoacrylate adhesive may be used to bond the ePTFE suture foot to a silicone housing and it is desirable the bond be substantially leak proof and not substantially degrade due to sterilisation (EtO) or time. One example of an acceptable adhesive is Loctite adhesive 4061 cyanoacrylate adhesive and 7701 polyolefin primer.

In some embodiments, it may be desirable to optionally add reinforcement means or reinforcement structure to the access device to further stabilize the attached access device. This can be accomplished in a number of ways. For example, a structure (such as an arterial vessel attachment cap) may be affixed to the vessel in proximity to where the access device is in communication with the vessel. Another example is a reinforcing sleeve to support the anastomosis site in the presence of high infusion pressures. These reinforcement structures may be manufactured from biocompatible and/or non-biocompatible materials or combinations thereof. For example, but not limited to, polyester, Gore-Tex, polytetrafluoroethylene (PTFE), expanded polytetrafluoroethylene (ePTFE), polyethylene, polypropylene, polyurethane, silicone, steel, stainless steel, titanium, Nitinol, or other shape memory alloys, copper, silver, gold platinum, Kevlar fibre, carbon fibre, or combinations thereof. In certain aspects, where non-biocompatible materials may come in contact with the anatomic structure, the components made from non-biocompatible materials may be covered or coated with biocompatible material and may reinforce or support the connection of the housing to the vessel. The devices disclosed herein may optionally provide support or reinforcement structures or skirts at, or near, the skin line to assist in securing the skin or tissue against the housing. This may help minimize movement of the device at the attachment point and/or to reduce the possibility of infection. In addition, in certain embodiments at least one second skirt or outer protective layer may be used. These reinforcement structures or skirts may be manufactured from biocompatible and/or non-biocompatible materials or combinations thereof. For example, but not limited to, polyester, Gore-Tex, polytetrafluoroethylene (PTFE), expanded polytetrafluoroethyleine (ePTFE), polyethylene, polypropylene, polyurethane, silicone, steel, stainless steel, titanium, Nitinol, or other shape memory alloys, copper, silver, gold, platinum, Kevlar fibre, carbon fibre, or combinations thereof. In certain aspects, where non-biocompatible materials may come in contact with the anatomic structure, the components made from non-biocompatible materials may be covered or coated with biocompatible material and may reinforce or support the connection of the housing to the vessel. For example, see FIGS. 32, 33, and 34. These figures show a reinforcing skirt that may be added to certain embodiments to prevent or reduce fluid or blood leaking from the sewing cuff. These figures show reinforcing skirts attached at or near the skin line or attached to the vessel.

In those embodiments that use access ports, the number of access ports and the structure of the access port can vary with the structure allowing multiple and different catheter and balloon systems to be used simultaneously. The access ports may function in a variety of ways to provide intermittent or continuous access to the circulatory systems. In certain aspects, the number of access ports can vary between none and six, between one and six, between two and four, between three and five, between one and three, and between two and three. In certain aspects, the number of access ports may be limited by the internal diameter of the access device and the outer diameter of the catheters.

In certain embodiments, the catheter used will have a superficial portion, a middle portion, and a vascular portion. Depending on the application, the catheters used can vary in diameter and length. For example, the length can vary from 3 cm to 2 meters, 5 cm to 1 meter, 5 cm to 750 cm, 5 cm to 500 cm, 5 cm to 250 cm, 5 cm to 100 cm, 5 cm to 50 cm, 10 cm to 40 cm, 15 cm to 60 cm, 20 cm to 55 cm, 25 cm to 50 cm, 30 cm to 45 cm or 35 cm to 40 cm. For example, the diameter can vary from 0.1 mm to 5 cm, 0.1 mm to 4 cm, 0.1 mm to 3.5 cm, 0.1 mm to 3.0 cm, 0.1 mm to 2.5 cm, 0.1 mm to 2.0 cm, 0.1 mm to 1.5 cm, 0.1 mm to 1.0 cm, 0.1 mm to 9 mm, 0.1 mm to 8.0 mm, 0.1 mm to 7.0 mm, 0.1 mm to 6.0 mm, 0.1 mm to 5 mm, 0.1 cm to 4 mm, 0.15 mm to 3.5 mm, 0.25 mm to 3.0 mm, 0.5 mm to 2.5 mm, 0.75 mm to 2.0 mm, 1.0 mm to 5.0 mm, or 1.0 mm to 4.0 mm.

In certain aspects, the catheter lumen may have at least one interior portion, at least two interior portions, at least three interior portions, at least four interiors portions, at least five interior portions, or at least six interior portions which may define various separate lumens for various uses such as for example, fluid flow in and or out of a vessel, insertion of monitoring or diagnostic equipment or devices, or inflation or deflation of a gas supply. Typically, the interior portions are capable of permitting the movement of fluids including gases through the lumen. The interior portions may also be used to pass wires, or other measurement or monitoring devices, probes or controllers, through a portion of the lumen. In certain embodiments, it is desirable to use occlusion members.

In certain aspects, the catheter has a catheter lumen communicating with a superficial portion and a vascular portion of the catheter systems. The superficial portion of the catheter lumen may be in communication with the upper portion of the access device and the vascular portion may be is in communication with the vessel. The catheter also may have a middle portion that is in communication with the superficial portion and the vascular portion and an access device's housing or cannula. In certain aspects, the superficial portion of the catheter lumen is in communication with a port on the access device and the occlusion member is in communication with the vascular portion of the catheter lumen. In certain embodiments, the occlusion member may be an elastomeric balloon.

Each of the balloons may communicate with at least one inflation/deflation lumen and at least one inflation/deflation port.

In certain aspects, the catheter lumen will also permit the flow of fluids or blood through the lumen. In certain aspects, the lumen will also permit the insertion of other devices such as filters, pressure sensors, temperature sensors, pH sensors, $S_{O2}$ sensors, salinity sensors, and other measurement or monitoring devices. In certain aspects, the inflation port may be located in the upper portion of the access device. The balloon may be a toroidal balloon or a device of any other appropriate shape, which may surround a portion of the fluid flow lumen and allow passage of blood and other fluids through the fluid flow lumen. The occlusion member may be moveable longitudinally and inserted through the access device and into the vessel. In other embodiments, the occlusion member may consist of a balloon having more than one opening at its center or may surround a portion of a fluid flow lumen for the passage of blood, or may consist of more than one expandable balloons allowing passage of blood through the gap between the arterial wall and the expanded balloons. Certain embodiments use balloon catheter systems in combination with the access device. The structure and function of the balloons can vary depending on their use with a particular treatment.

In certain embodiments, it is desirable that the balloon catheter systems be capable of withstanding, or substantially withstanding, suprasystolic pan-cycle pressures and be suitable for insertion and removal to and from the access system. The balloon catheter systems used in these applications are capable of withstanding, or substantially withstanding, suprasystolic pan-cycle pressures of from 200 mmHg to 400 mmHg. In other aspects, the balloon catheter systems used are capable of withstanding, or substantially withstanding suprasystolic pan-cycle pressures of from 120 mmHg to 160 mmHg, 160 mmHg to 200 mmHg, 200 mmHg to 240 mmHg, 240 mmHg to 350 mmHg, or 350 mmHg to 400 mmHg. Other aspects include combining an implantable system for intermittent and recurrent access to the arterial and/or venous circulation of a warm blooded animal either simultaneously or separately with multiple access ports with at least one balloon catheter system to hyperperfuse the coronary arteries, i.e., the system may have a large central lumen, may be capable, or substantially capable, of occluding the ascending aorta in diastole and be capable of counterpulsation and may be compatible with the access system as described. To be able to occlude the ascending aorta in diastole, it is preferred that the balloon catheter system be capable of withstanding pressures, or substantially withstanding, of from 70 mmHg to 200 mmHg. In other aspects, it is desirable that the pressures tolerated, or substantially tolerated, range from 70 mmHg to 300 mmHg, 90 mmHg to 250 mmHg, 90 mmHg to 180 mmHg, 70 mmHg to 180 mmHg, or 70 mmHg.

In certain aspects, the balloon catheter system may be capable of counterpulsation. In many of these aspects, it is possible to have counterpulsation balloon catheters passed through the access device simply and effectively, without any significant loss of blood. It is preferred that the balloon catheter system be compatible with the access system. The variables that may be measured to demonstrate the effectiveness of such a treatment include: blood flow in the left and/or right coronary arteries, cardiac ejection fraction, cardiac work, cardiac outflow, peak systolic pressure, minimal diastolic pressure, mean root aortic pressure, intraventricular diastolic pressure, left atrial pressure, central venous pressure, and pulmonary wedge pressure. See, for example, the system disclosed in FIGS. 9 and 11 both of these systems may be used for counter-pulsation.

In certain embodiments, it may be desirable to use no balloons, 1, 2, 3, 4, 5, or 6 occlusion balloons as well as other means for altering the flow of the fluid through the vessel or combinations thereof. For example, in an embodiment of a treatment method for the liver it may be desirable to use three balloons in various arteries and one balloon in a vein. As another example, in the kidney it may be desirable to use one balloon for an artery and one balloon for a vein per kidney. While for treating the brain, it may be desirable to use one balloon for an artery and one balloon for a vein per side of the brain being treated. For limbs such as legs or arms it may make sense to use one or two balloons depending on the treatment. For the pelvis, some embodiments may use two balloons for the arteries and one for the vein. For the heart, some embodiments will use two balloons, one for the right coronary artery and one for the left coronary artery. The above examples are only disclosed as examples and other combinations of balloon configurations and numbers are contemplated. The size and shape of the balloons used can vary depending on the particular application and the desired effect of using the balloons. For example, balloons used in treating the heart will typically be longer and more flexible than some of the other applications. In certain aspects, longer more flexible balloons may be desirable because the longer the balloon the less pressure per square cm is needed to effectuate a seal with the vessel during hyperperfusion.

Other aspects disclose combining an implantable system for intermittent and recurrent access to the arterial and/or venous circulation of a warm blooded animal simultaneously or separately with multiple access ports with a balloon catheter system that includes a bio-compatible balloon capable, or substantially capable, of hyperperfusion of the hepatic artery while occluding other branches of the coeliac trunk and the gastroduodenal artery and which is compatible with certain an access systems. In certain embodiments, it is preferred that the balloon catheter system be compatible with the access systems disclosed herein. In certain aspects, to be capable, or substantially capable, of hyperperfusion of the hepatic artery with occlusion of other branches of the coeliac trunk and the gastroduodenal artery it is desirable that the system be capable of withstanding treatment pressures of from 85 mmHg to 350 mmHg. In other aspects, it is desirable that the treatment pressures tolerated will range from 70 mmHg to 500 mmHg, 70 mmHg to 120 mmHg, 85 mmHg to 130 mmHg, 200 mmHg to 500 mmHg, 200 mmHg to 400 mmHg, 200 mmHg to 300 mmHg, 120 mmHg to 200 mmHg, or 120 mmHg to 160 mmHg.

Figure 62:
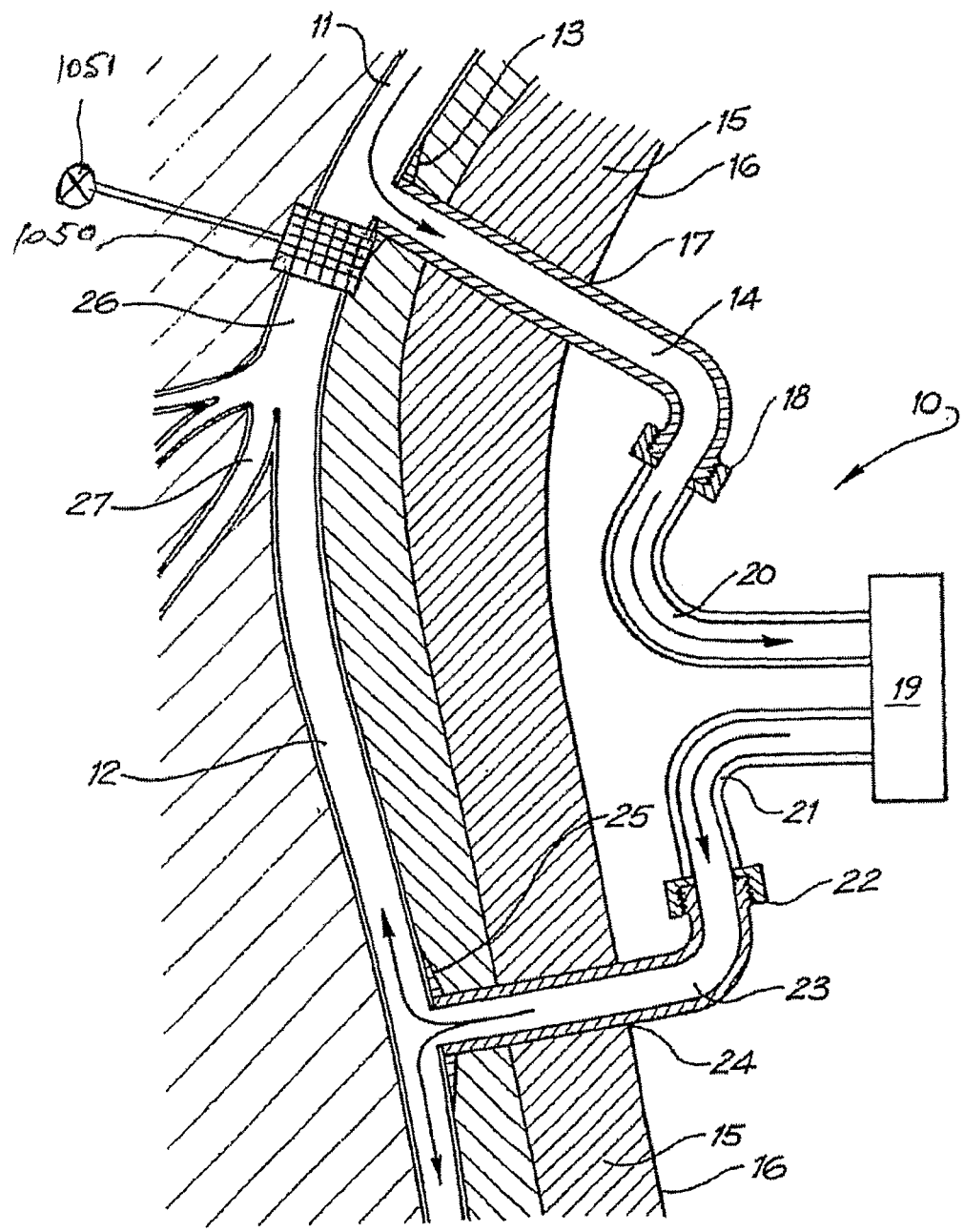
FIG. 62 is a schematic representation of a system according to certain embodiments.

In certain embodiments it may desirable to use externally applied occlusive balloons to control the direction and/or the amount of blood or fluids flowing through the system. One example of such a system, device and method is illustrated in FIG. 62. Such external balloons may be used to replace one or more of the endoluminal balloons with at least one externally applied vascular occlusive balloon (exoluminal balloon system). The external balloons used may be made of various suitable materials, for example silicone, polypropylene, polyethylene, polyurethane, an elastomer or other suitable material. The blood or fluid flow is directed into the pump by inflating the balloon and isolating the limb or organ from the remainder of the body. Various ways, such as a one way valve, may be used to inflate and deflate the external balloons as desired.

In certain embodiments it may be desirable to use a combination of external and internal balloons together in the same application.

Figure 63:
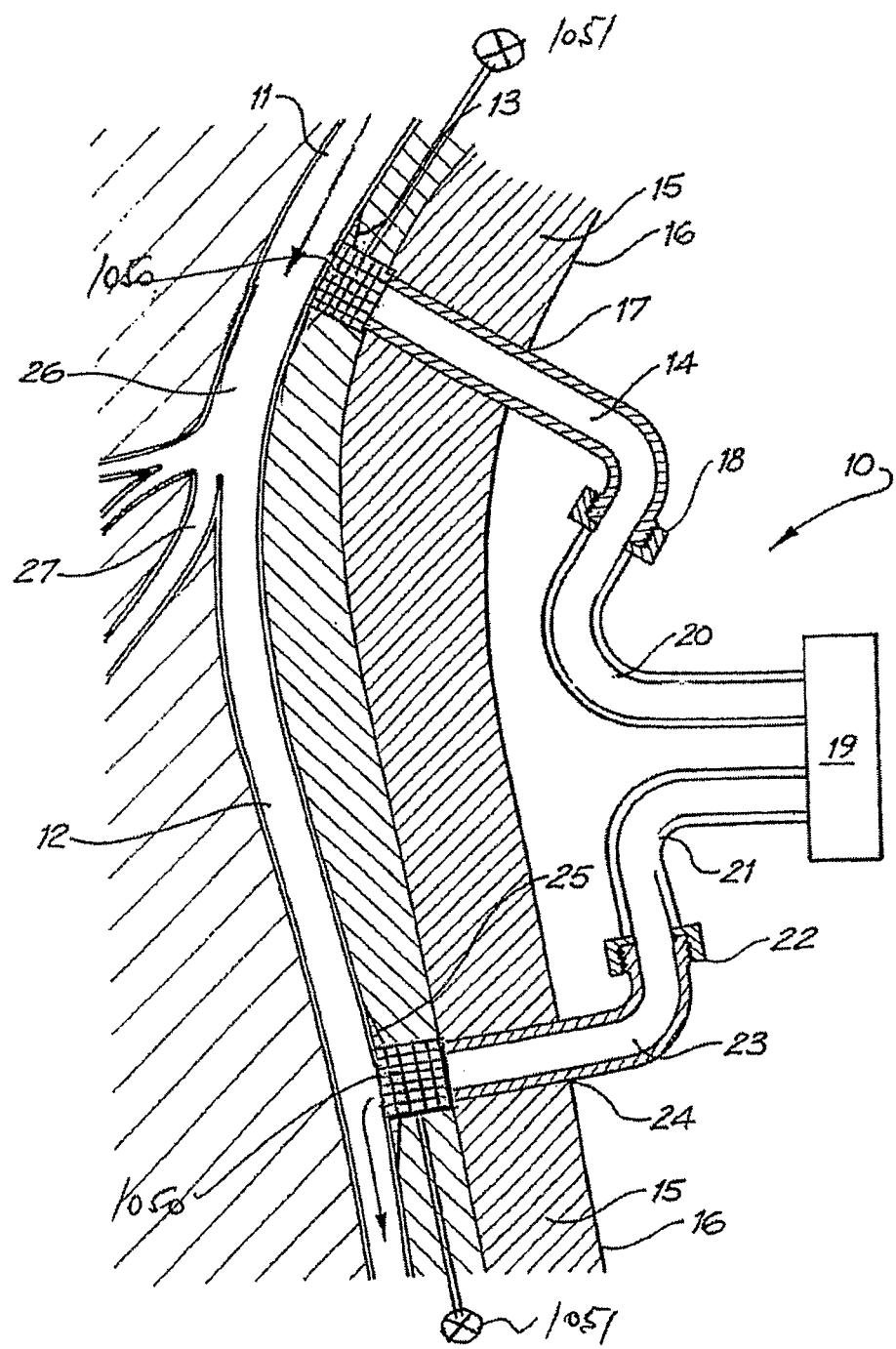
FIG. 63 is a schematic representation of a system according to certain embodiments.

In certain embodiments the plungers disclosed in certain systems, methods, and devices may be replaced by externally occlusive balloons. One example of such a system, device and method is illustrated in FIG. 63. In certain aspects, at least one occlusive balloon may be used in combination with at least one plunger. One advantage to using at least one external balloon is that the external balloons may minimize or substantially minimize the dead space between the native vessel and the access devices.

In certain embodiments of the methods, systems, and devices disclosed it may be desirable to minimize, or substantially minimize bleeding that may be associated with hyperperfusion or other applications disclosed. To minimise, or attempt to minimize, the problem various steps may be taken, including but not limited to one or more of the following: double anastomoses being performed at the junction of the vessels and the access system, fluid sealing devices placed around the access systems to increase the lateral pressure on the skin subcutaneous tissue, and sealing circumferential devices, which increase the pressure on transcutaneous exits of the balloon control device.

Certain embodiments of the access device disclosed will have a suture foot at access end which, when the device is in use, provides fluid communication between vessel and lumen. The access device will have a sleeve which provides for support of the device and lumen and sealing and/or leak minimization/elimination at the point of penetration to the skin or penetration of the vessel. The access device will have a one or more flow ports that has been capped with one or more connectors and/or one or more end caps. The one or more flow ports may be inserted into lumen and bonded, sealed or otherwise connected to the lumen to provide for connection to various devices using various flow and/or end caps. The connector facilitates connection of the end cap to the access device at the external end in order to place the access device into the hold configuration such that no flow, or substantially no flow, is occurring through the lumen and the access device when not in use. The access device, the suture foot, the lumen, the sleeve, the one or more flow ports, the one or more connectors and the one or more end caps of the device may be constructed from any suitable materials that have appropriate properties to serve their intended function. The access device may be equipped with a cannulated plunger shaft and stylet. Frictional problems may be reduced by the device having a flexible silicone section which would cross the cutaneous boundary (used for clamping off). This then is bonded to a PTFE section of tube which has a tight running fit with the plunger. The head of the access device had a seal system which surrounds the plunger shaft. This means that when the plunger is withdrawn up through the PTFE and in to the clearance fit of the silicone, the blood or fluid pressure would be prevented from exiting the device allowing time to clamp off below the plunger tip. The sealing system is held in place by a lock ring mechanism. The seal, or seals, may have a keyway system of two pins and a pin on the plunger shaft which means that the device is typically inserted at a particular orientation. The design has a bespoke attachable pumping head with central access for the balloon (using a Cook iris seal). The return pumped flow is attached using a Luer fitting.

In certain embodiments, an angled anastomosis is used using a shaped suture foot rather than the angled plunger. This means that keying and orientation of the other components was not needed. Furthermore, the seals and internal components were reduced in size so that the main body was a smaller diameter allowing the device to sit more comfortably close to the skin. In addition, a fast curing adhesive with material specific primer was used between the silicone and the PTFE producing a fast sealing, extremely tough bond.

Certain embodiments of the access device disclosed will have at least one suture foot at access end, which, when the device is in use, provides fluid communication between vessel and lumen.

In certain embodiments of the access device, the friction between the plunger tip and the PTFE section of tube is further improved by using a plunger tip design that has ribs where sealing is retained whilst minimising contact area and friction with the main access lumen. In these embodiments the modification to the plunger tip overcame friction issues that resulted in the need for the PTFE front tube. Furthermore, the suture foot has been altered from ePTFE to woven Dacron which make it easier to be joined to the silicone clamping hose using silicone adhesive. This removed one critical subcutaneous joint, reducing the risks associated with the use of the device.

In certain embodiments, a ribbed plunger tip with about a 4 mm pitch and about 0.3 mm interference with the silicone tube is used. The plunger tip has a flat face. The plunger is designed such that the tip will nominally protrude from the silicone hose by about 0.5 mm. The first rib is positioned about 3 mm proximal so that the chance of the rib being inadvertently pushed out the front of the tube is minimised. The polyester suture foot is made from ePTFE or woven Dacron. The foot uses a standard vascular graft which has woven polyester, crimped in to a corrugated tube to improve patency and increase the stretch properties of the tube. Metal reinforcing struts along the outside of the silicone tubing do not have to be used, if desired. In these embodiments, issues where stretching of the tube caused by high friction with the plunger tip is alleviated by the ribbed plunger tip design. The infection cuff is moved towards the foot end of the device. An extra connector is included which has two sealable ports, along with a fluid flow Luer fitting. This allows a balloon system with fluid return plus extra access for a second balloon such as a pressure transducer or angiographic balloon.

The plunger shaft used in the disclosed embodiments may be made of a number of materials. For example, but not limited to PTFE, other plastics, metals or combinations thereof. In some aspects, the plunger shaft will need to be sufficiently stiff so that it can be inserted and withdraw as needed during the treatment and withstand the transmitted longitudinal force during insertion In some aspects, the plunger shaft will be cannulated. In some aspects, the plunger shaft's distal end is to have a locking mechanism for securing connection to other fittings in the access device head. Many locking mechanisms may be used, for example a Luer locking mechanisms. In some aspects, the plunger shaft's outer diameter may be less then the outer diameter of the plunger tip. This may be useful to allow full flow of any saline/heparin solution to be backfilled behind plunger tip. In some aspects, the plunger shaft may have cut-outs at distal end to allow back-flushing of device with sterile solution and venting of solution so as not to pressurise the assembly. In some aspects, the plunger shaft may have a sufficiently smooth surface so as to create a good interface with the shaft seals. In some aspects, the plunger shaft to have a shoulder preventing it from being inserted too far. In some aspects, the plunger shaft may have a shoulder which allows connection of removal tools. In some aspects, the plunger shaft may have a threaded end which allows simple connection of replaceable plunger tips. Other connections means may also be used.

In certain embodiments, of the access devices disclosed, a barrier material or cuff will be included at the distal region of the access device. This barrier or cuff may be made from a number of materials and may be attached to the housing using either mechanical or chemical means. For example, woven or felt ePTFE or Dacron may be used in certain aspects. In some aspects, the barrier will be in the form of a band around the housing and will be made of Dacron attached to the housing using a biocompatible adhesive. In some aspects, it is desirable if the adhesive provides a continuous, or substantially continuous bond so that there is no infection route, or substantial infection route, between the Dacron and the housing. In some aspects, it is desirable for the adhesive to have sufficient strength to resist forces arising from potential pull-out of the device, so that the Dacron felt cuff and the surrounding tissue protect the anastomosis when implanted. For example, NuSil Med1134 or NuSil MED6-6606 dispersion may be used. In some aspects, the barrier or cuff will be positioned on the housing such that upon implanting the device, barrier or cuff will be subcutaneous. The cuff or barrier may provide a barrier to infection and allow tissue in growth. In some aspects, the barrier or cuff may be sufficiently wide so as to provide an adequate barrier against infection. For example, 3 to 14 mm, 4 to 12 mm, 5 to 10 mm, or 7 to 9 mm. In some aspects, 1, 2, or 3 barriers or cuffs may be used. In some aspects, and the barriers or cuffs do not overlap each other and there is a spacing between the barriers or cuff.

In certain embodiments, of the access devices disclosed, the device may have additional sealing systems incorporated or secondary sealing systems. Such secondary seals may permit the withdrawal of the first seal (the plunger) into the device housing to permit clamping of the housing without, or substantially reduced, leakage. In certain aspects, the secondary seals may have a sufficiently low friction of interaction with the plunger shaft. The secondary seals may be made of any acceptable material such as various plastics, silicone, or combinations thereof. In some aspects, the materials used may have a sufficiently low hardness rating so as to allow the seals to conform to the seats and shaft to provide a sufficient seal. In some aspect, the seals used should be able to with stand a compression of between 3 to 15%, 4 to 12%, or 6 to 10%.

In certain embodiments, the connections from the access device to the pump or other devices that move fluids may use the same connections method as used on the device, for example lock ring to fittings. In some aspects, the pumping housing or connectors may allow leak free insertion of catheters. In some aspects, the pump housing or connectors may allow blood or fluid inflow from an extracorporeal pump to the anastomosis site. In some aspects, it is desirable for the blood or fluid pathways to minimise, or substantially minimise, stagnant areas and prevent, or substantially prevent thrombus formation. In some aspects, it is desirable for the blood or fluid pathways to minimise, or substantially minimise impact of the blood or fluids and to prevent or reduce hemolysis. In some aspects, the pump connector return system should have similar functions and characteristics. In some aspects, the blood or fluid return will be configured so that the return is tangential, or substantially tangential to the access device to eliminate areas of stagnant flow that can result in thrombus formation.

Figure 47:
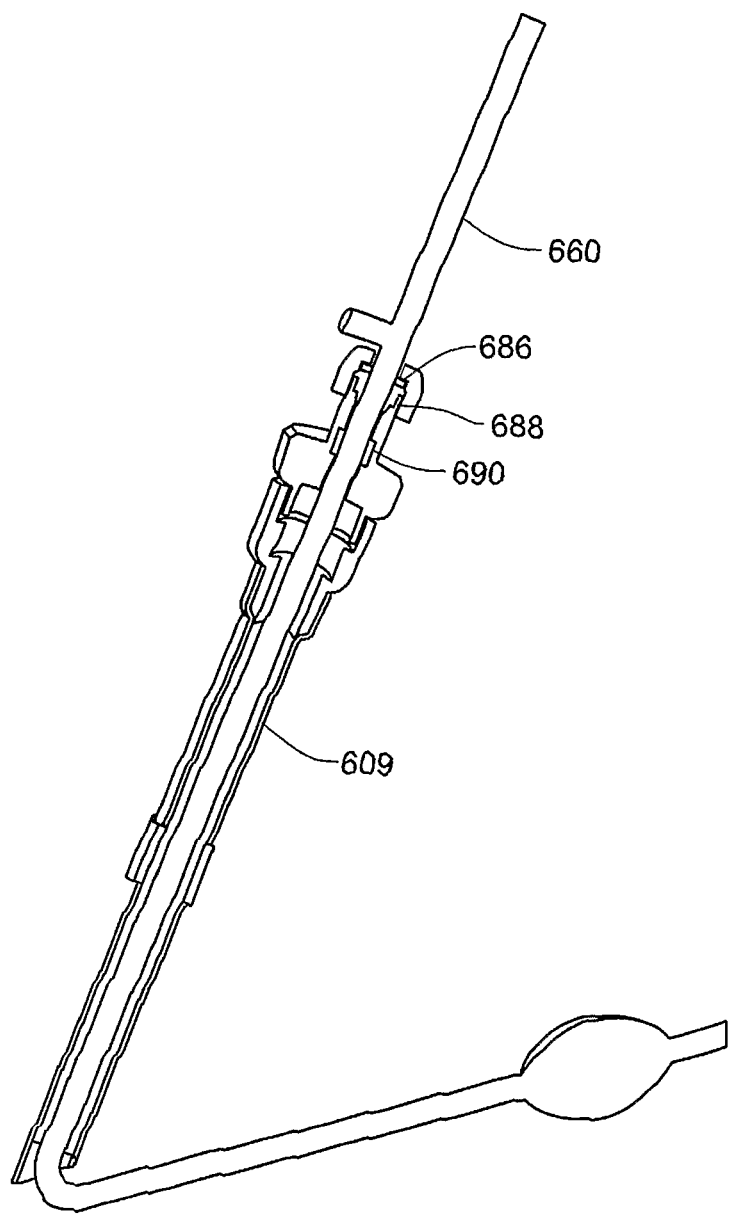
FIG. 47 is a cross sectional view of the embodiment of FIG. 46.

In some embodiments, sealing members, as for example shown in FIG. 47 may be used (such as a duckbill valve). Other sealing members may be used in certain embodiments such as check valves and/or flow control valves. In some aspects, it is desirable that the selected valve allows, or substantially allows, fluid to flow in one direction only. In some aspects, sealing member may be selected from desirable means that allow, or substantially allow, fluid to flow in only one direction and prevent fluid from moving backwards by using the fluid itself (for example with a duckbill valve) or other valve configurations such as a spring valve and/or a check valve. In some aspects, the sealing member may be selected from any desirable means for allowing, or substantially allowing, fluid to flow in one direction and prevent fluid from moving backwards. These sealing members may be may be constructed from any suitable biocompatible or non-biocompatible material as described herein, such as for example silicone. Many suitable valve configurations may be used. In some embodiments, the duckbill valve may prevent or limit backflow through the port in which it is inserted, while providing access to lumen for balloon catheters that may be threaded through the lobes of the duckbill valve. The leaflets of the duckbill valve may be of suitable materials that may form around completely, or in part, such a balloon catheter in order to limit leakage or backflow through the relevant access port. In some aspects, the seal should be capable of withstanding full arterial pressure while closed, for example, 80 to 500 mmHg, 100 to 300 mmHg, 100 to 200 mmHg, up to 200 mHg, up to 300 mmHg, or up to 400 mmHg. In some aspects, the seals provides a back up seal against full pumping pressure when opened by the catheter being inserted and further limit the leakage flow.

The systems, methods and devices herein can be used with a number of other components. One aspect is to use the disclosed embodiments to circulate blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of one or more of the above. Various pressure arrangements are possible using various pumping components or other fluid moving devices. In certain aspects, it may also be desirable to switch from one pressure range to another pressure range and back and forth, or from a series of pressure ranges, For example, it may be desire in certain treatments to move from a high pressure to low pressure range and sometimes back and forth between pressure ranges. By low pressure we mean ranges of from 70 mmHg to 120 mmHg, 85 mmHg to 130 mmHg, 85 mmHg to 110 mmHg, or 90 mmHg to 120 mmHg as measured at by what is delivered to the body. By high pressures we mean pressure from 200 mmHg to 500 mmHg, 200 mmHg to 400 mmHg, 200 mmHg to 300 mmHg, 220 mmHg to 350 mmHg, or 250 mmHg to 340 mmHg as delivered to the body. It is also possible to delivery other pressure ranges of 70 mmHg to 500 mmHg, 110 mmHg to 250 mmHg, 120 mmHg to 200 mmHg, or 120 mmHg to 160 mmHg. In order to achieve the desired treatment pressures, the pressures settings at the pumps or fluid moving device may vary in order to deliver the desire treatment pressures to the body. Fluid or blood pumps or other devices that are capable of moving fluids or blood may be used. Examples of pumps that may be used include rotary pumps, roller pumps, pulsating pumps, non pulsating pumps or combinations thereof. In addition, the above treatment pressure can be combined with the flow volumes of from 10 ml to 1400 ml per minute, 5 ml to 40 ml, per minute, 10 ml to 25 ml per minute, 25 ml to 1000 ml per minute, 50 ml to 1200 ml per minute, 10 ml to 180 ml per minute, 100 ml to 250 ml per minute, 140 ml to 500 ml per minute, 100 ml to 800 ml per minute, 500 ml to 1400 ml per minute. The desired treatment pressures and flow volumes will depend on the treatment being performed.

In certain embodiments, a base line blood or fluid pressure is sometimes measured with the access system in place. Thereafter, the system is used to increase the blood or fluid pressure to treat or hyperperfuse the area being treated. The treatment may involve hyperperfusion alone or in combination with other treatments. For example, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of one or more of the above. The treatment protocol can vary as needed for the desired treatment. The exact combination will be somewhat dictated by the treatment trying to be achieved. For example, but not limited to, it may involve on and off hyperperfusion by itself, hyperperfusion in one session, the addition of drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of one or more of the above without hyperperfusion, in combination with hyperperfusion, or between periods of hyperperfusion. The exact combination will vary but will often take advantage of the ability of the access device to provide intermittent and recurrent access to the arterial and/or venous circulation of a warm blooded animal.

This treatment or hyperperfusion can be done over a selected time period and can be repeated as treatment dictates using the ability of the access device to provide intermittent and recurrent access to the arterial and/or venous circulation of a warm blooded animal. In certain aspects, the hyperperfusion will often be carried out for a period of time and then stopped for a period of time. The desired treatment will often dictate the number and lengths of the periods of treatment or hyperperfusion as well as the periods of rest between treatment and hyperperfusion treatment. For example, the treatment or hyperperfusion may be carried out on a patient for 4 to 12 hours and then stopped for 4 to 12 hours and then repeated as needed, for 4 to 30 hours and then stopped for a period of time such as 4 to 12 hours and repeated as needed, for 10 to 30 hours and then stopped for 4 to 48 hours and then repeated as needed, for 10 to 36 hours and then stopped for 4 to 24 hours and then repeated as needed. In certain embodiments, disclosed herein you can treat human patients with hyperperfusion over 5 to 30 hours, 10 to 25 hours, 5 to 25 hours, or 10 to 20 hours and then provide a break in treatment of 5 to 15 hours, or 5 to 10 hours and then repeat treatment an additional number of times as needed (for example, repeat treat 1, 2, 3, or 4 additional times. In certain treatments the human patient will be treated 1 to 3 times for between 20 to 30 hours with appropriate breaks in between treatments of from 6 to 10 hours. The treatment period can extend from 1 day to 28 days, 3 days to 6 days, 3 days to 10 days, 4 days to 7 days, or as required by the particular treatment. Treatment can be halted for a longer period than this. In certain embodiments, the treatment could be started for 4 to 12 hours or the desired treatment time and then halted for 2 hours to 40 days, 12 hours to 20 days, 1 day to 22 days, 2 days to 10 days, 3 days to 15 days, 5 days to 26 days, 8 days to 15 days, or other desired time periods. The device will be approved for 28 day use, which means that potentially treatment could be stopped for a period of up to 26 days. In certain embodiments, at least one treatment time will be combined with at least one non-treatment time. In certain embodiments, at least two treatment times will be combined with at least one non-treatment time. In certain embodiments, at least three treatment times will be combined with at least two the non-treatment times. Other variations are contemplated. During the period that the treatment or hyperperfusion is stopped, it is still possible, if desired to provide drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of one or more of the above. For example an antibiotic or saline drip. It is also possible to combine the treatments using the access device, methods and/or systems with other treatments such as, but not limited to, injections, oral drug delivery, radiations, and so forth. One concern with treating or hyperperfusing for too long of a period of time is the potential development of blood clots. Therefore, in some aspects, it may be desirable to use drugs or agents that reduce the chances that blood clots may develop. One of the many advantages of the disclosed embodiments is the housing and other portions of the access device stay in place as the treatment is activated and stopped over a range of time periods and protocols as desired. Furthermore, the blood or fluid pressure can also be adjusted and monitored as desired. The blood or fluid pressure may be increased to approximately 10% or more, 20% or more, 25% or more, 30% or more, 40% or more, 50% or more, 60% or more, 70% or more, 80% or more, 90% or more, or 100% or more over the measured baseline blood or fluid pressure in the vessel.

This treatment (such as drug treatment, hyperperfusion treatment, or combinations thereof) can be done over a selected time period and can be repeated as treatment dictates using the ability of the access device to provide intermittent and recurrent to a warm blooded animal. In certain aspects, the treatment will often be carried out for a period of time and then stopped for a period of time. The desired treatment will often dictate the number and lengths of the periods of treatment as well as the periods of rest between treatment. For example, the treatment may be carried out on a patient for 4 to 12 hours and then stopped for 4 to 12 hours and then repeated as needed, for 4 to 30 hours and then stopped for a period of time such as 4 to 12 hours and repeated as needed, for 10 to 30 hours and then stopped for 4 to 48 hours and then repeated as needed, for 10 to 36 hours and then stopped for 4 to 24 hours and then repeated as needed. In certain embodiments, disclosed herein you can treat warm blood animals over 5 to 30 hours, 10 to 25 hours, 5 to 25 hours, or 10 to 20 hours and then provide a break in treatment of 5 to 15 hours, or 5 to 10 hours and then repeat treatment an additional number of times as needed (for example, repeat treat 1, 2, 3, or 4 additional times. In certain treatments the warm blood animal will be treated 1 to 3 times for between 20 to 30 hours with appropriate breaks in between treatments of from 6 to 10 hours. The treatment period can extend from 1 day to 28 days, 3 days to 6 days, 3 days to 10 days, 4 days to 7 days, or as required by the particular treatment. Treatment can be halted for a longer period than this. In certain embodiments, the treatment could be started for 4 to 12 hours or the desired treatment time and then halted for 2 hours to 40 days, 12 hours to 20 days, 1 day to 22 days, 2 days to 10 days, 3 days to 15 days, 5 days to 26 days, 8 days to 15 days, or other desired time periods. The device will be approved for 28 day use, which means that potentially treatment could be stopped for a period of up to 26 days. In certain embodiments, at least one treatment time will be combined with at least one non-treatment time. In certain embodiments, at least two treatment times will be combined with at least one non-treatment time. In certain embodiments, at least three treatment times will be combined with at least two the non-treatment times. Other variations are contemplated, for example during non-treatment periods drugs, therapeutic agents, other agents, or combinations thereof may be provided via the access device to the warm blood animal. During the period that the treatment is stopped it is still possible, if desired to provide drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of one or more of the above. For example an antibiotic or saline drip. It is also possible to combine the treatments using the access device, methods and/or systems with other treatments such as, but not limited to, injections, oral drug delivery, radiations, and so forth. One concern with treating or hyperperfusing for too long of a period of time is the potentially development of blood clots. Therefore, in some aspects, it may be desirable to use drugs or agents that reduce the chances that blot clots may develop. One of the many advantages of the disclosed embodiments is because the housing and other portions of the access device stay in place the treatment can be activated and stopped over a range of time periods and protocols as desired. Furthermore, the blood or fluid pressure can also be adjusted and monitored as desired. The blood or fluid pressure may be increased to approximately 10% or more, 20% or more, 25% or more, 30% or more, 40% or more, 50% or more, 60% or more, 70% or more, 80% or more, 90% or more, or 100% or more over the measured baseline blood or fluid pressure in the vessel.

In certain aspects, it may be desirable to use or add equipment to filter the blood or fluids being circulated in the treatment system. In certain aspects, it may be desirable to use or add blood oxygenators, such as membrane or bubble oxygenators, hyperthermic treatment equipment, hypothermic equipment, dialysis equipment, devices that permit the taking of artery or vein blood samples, monitoring equipment, filtering equipment, balloon catheter monitoring and control devices such as counterpulsation devices for cardiac applications or balloon pressurization controllers, (for example, for cardiac application every time heart beats the balloon may be deflated and every time the heart rests the balloon may be inflated), computer systems for controlling or monitoring the various equipment, external tubing, pumps, flow controllers, drug delivery devices, blood monitoring devices, such as blood pH, $S_{O2}$, pulse or other blood monitoring devices, sampling devices, nutrient suppliers (such as saline or dextrose drips), blood or fluid cleaning or scrubbing devices (including, for example, chemical and physical filters), blood temperature control devices or other suitable devices or combinations thereof. In certain aspects, it may be desirable to add or use devices or equipment where the fluid may be monitored and/or sampled, may have its chemical, physical or kinetic properties modified and may have various substances added to and/or removed from it in accordance with a specific treatment regimen and according to the individual device or devices used.

Other aspects include combining an implantable system for intermittent and recurrent access to the arterial and/or venous circulation of a warm blooded animal simultaneously or separately with multiple access ports with a balloon catheter system that includes at least one bio-compatible balloon and is capable, or substantially capable, of collecting hepatic vein flow without substantially obstructing flow through the inferior vena cava and is compatible with embodiments of the access system as described. In this application the access system typically will be large enough to accept a catheter, to create negative pressure between at least two isolation balloons, be stiff enough not to collapse under the negative pressure, and have a flow through tube with a large enough cross sectional diameter not to impede, or substantially impede inferior vena cava flow. See, for example, the system disclosed in FIGS. 23, 24, and 25. This is made possible by the features that allow the device to collect the blood outflow from the liver, while the balloon catheter does not obstruct the flow within the inferior vena cava.

A disadvantage of known inflatable balloons is that they can malfunction in several ways. For example, spontaneous deflation, bursting, impingement against the vessel wall and long term over inflation may cause internal damage with thrombosis and/or internal hyperplasia. In certain embodiments, to avoid balloons as a means of redirecting flow a biocompatible spatula shaped device may be used. In some embodiments, such a spatula may be between the inflow and outflow of a double D inflow/outflow tube and can occlude or substantially occlude a vessel with isolation of the low and high pressure sides. An alternative embodiment is an external exclusion device which is an L-shaped rod. When approximated to the access system high and low pressure parts of the vessel are separated. In other embodiments, the systems can be used with an interposition prosthetic graft to avoid the recurrent movement of the vessel wall and possible damage with occlusion of the separating device.

Certain embodiments disclosed herein permit control of the volume of fluids, such as blood, flowing in and out of a target region of the body. The various arrangements and configurations of catheters and balloons disclosed herein provide systems and devices that may supply and isolate the circulatory system of an organ or organs, limb or limbs or body part or parts. In place of blood it may be possible to use saline, plasma, synthetic and/or natural blood products, some other therapeutic modality, or combinations of the above. These systems may permit the removal of circulatory inflow and/or permit the removal of circulatory outflow from an organ or organs, limb or limbs or body part or parts, thereby isolating the portion of the circulatory system from the remainder of the circulatory system of a warm blood animal. In certain aspects, the systems disclosed permit the isolation of inflow only to a target region. Such systems may be used in many portions of the circulatory system of the body. Usually these systems are desirable configurations for use with arteries. In particular, they are desirable configurations for use with arteries that are blocked to some degree. There are many diseases where the arterial inflow to a part of the body is insufficient, usually associated with blocked arteries. Common examples are ischemic cardiac disease or thrombotic stroke, ischemic peripheral vascular disease (often associated with gangrene) vascular insufficiency and vasculogenic impotence. One advantage is that some embodiments of the access system allow an increase in distal flow greater than the cardiac output that result in eventual growth of new vessels by increasing the endothelial shear stress. These diseases, and others, may be treated using various embodiments of the systems and devices disclosed. Additional procedures such as hyperthermia, hyperoxygenation and the discard of cytotoxic agent-containing serum is also available with the use of a cell saving system such as in certain embodiments herein.

Certain embodiments disclosed permit control of the volume of the blood, or other liquids, in and/or out of a totally isolated region of the body where both the arterial and venous circulation is isolated from the remainder of the circulatory, system. There are many diseases or other treatment situations where it is desirable to isolate a region of the body and control the in flow and/or out flow of blood, or other liquids, from that isolated region. Common examples of such treatment situations or diseases are neoplasias, infectious and degenerative disorders. These situations may be treated using various embodiments of the systems and devices disclosed. Furthermore, the degree of isolation of a particular region can be controlled using embodiments disclosed, from total isolation to a range of situation where the isolation is not total. Using embodiments disclosed it is also possible with these systems and devices to substantially isolate or partially isolate a particular region to a desired degree. It is also possible to alter the degree of isolation at various times of a treatment if desired. Total isolation is defined for our purposes as the direct or indirect control of the majority of the significant fluid or blood flow to an organ or organs, region or regions, limb or limbs, or body part or parts. Any organ or body part may have a decreased inflow associated with resulting pathology. Certain embodiments of the peripheral access system disclosed allow intermittent arterial and venous access over many days, weeks and months providing for increased arterial supply over that normally provided by the circulation and removing venous efferent as required. Access of the circulatory system multiple times over an extended period of time without having to surgically reinsert a device into the body allows the treatment to be continued and discontinued as desired. This access results in flexibility in treatment procedures and protocols. Certain methods, systems and devices disclosed herein provide for intermittent and recurrent access to the arterial and/or venous circulation of a warm blooded animal simultaneously or separately. In certain embodiments, the measurement of flow volume may be useful. Depending on the embodiment and the application, the flow volume will vary for example, but not limited to, from 10 ml to 1400 ml per minute, 5 ml to 40 ml, per minute, 10 ml to 25 ml per minute, 25 ml to 1000 ml per minute, 50 ml to 1200 ml per minute, 10 ml to 180 ml per minute, 100 ml to 250 ml per minute, 140 ml to 500 ml per minute, 100 ml to 800 ml per minute, 500 ml to 1400 ml per minute. The desired flow volumes will depend on the treatment being performed. In some aspects, drug treatments may be at lower flow volumes but not always. In some aspects, hyperperfusion will be at greater flow volumes but not always. In some aspects, it may be desirable to vary the flow volume during the treatment.

Hyperperfusion and isolated hyperperfusion increase the blood flow and blood pressure to a targeted region or regions, limb or limbs, organ or organs, or body part or parts above the inflow pressure that is supplied by the body. Using certain embodiments disclosed herein, intermittent and recurrent access to the desired treatment area is possible. In certain embodiments, the systems disclosed may be used for intermittent and recurrent access so that hyperperfusion can be used to treat a number of diseases, for example peripheral vascular disease and other diseases disclosed herein. Furthermore, use of the systems, methods and/or devices disclosed provide better control over the collateral development of vessels and results in a modulating effect of wall tension and shear stress on vessel development. As peripheral resistance decreases, the pressure required to maintain a desired volumetric flow rate decreases. The ability to continually adapt flow and pressure characteristics over extended time periods results in more effective treatment or hyperperfusion treatment. The hyperperfusion systems, methods and devices disclosed results in increases in flow through vessels with less increase in pressure on the vessel walls. The hyperperfusion embodiments disclosed also result in continuous dilation of the smooth muscle cells in the vessels which further aids recovery and promotes angiogenesis. Better control over pulse pressure may also be achieved and pulse pressure will tend to be lower as treatment proceeds. In some aspects, pulse pressure tend towards or will approach zero during treatment.

Certain embodiments disclose combining implantable systems for intermittent and recurrent access to the arterial and/or venous circulation of warm blooded animal simultaneously or separately with multiple access ports with a balloon catheter system that is capable, or substantially capable, of hyperperfusion of specific branches of a vessel while having a throughput catheter able to provide normal, or substantially normal, supply to the distal region, organ or limb. In certain aspects, disclosed systems are capable, or substantially capable, of hyperperfusion of the specific branches of a vessel while having a throughput catheter able to provide normal, or substantially normal, supply to the distal organ or limb it is desirable that the system be capable of withstanding treatment pressures of 70 mmHg to 500 mmHg, 70 mmHg to 120 mmHg, 70 mmHg to 90 mmHg, 90 mmHg to 500 mmHg, 200 mmHg to 400 mmHg, or, 80 mmHg to 200 mmHg.

In certain aspects, it is desirable that the balloon catheter system be compatible with the access systems disclosed herein. A specific example of the perfusion or hyperperfusion of a specific side branch is the perfusion or hyperperfusion of the left or right internal mammary arteries or grafts (also known as left and right internal thoracic arteries or grafts). These arteries can become narrowed due to arterial wall spasm (vasospasm). This can be seen radiologically as the 'string sign' in a local narrowing of the vessel. Pan-cycle, suprasystolic, hyperperfusion specifically of the mammary arteries, combined with vasodilator drugs, via the access device may be an effective method of treating this problem. Even if the internal mammary artery is patent and functioning normally, an infusion of high concentration into the coronary arteries is known to have therapeutic value. However, if given systemically, pan-cycle, suprasystolic, hyperperfusion increases vasoconstriction which may lead to peripheral ischemia, ulceration, gangrene, and amputation. In limb tumours (for example, osteogenic sarcoma) direct hyperperfusion of therapeutic agent into an isolated segment of the main artery supplying the tumour will result in an increased concentration of the agent in that region. Often, the arterial inflow into these tumours is from multiple sources, therefore conventional direct cannulation is not possible, and the regional perfusion or hyperperfusion through the specific cannulae and access device is a major benefit. See, for example, the system disclosed in FIG. 26.

Isolated hyperperfusion may be used to increase the blood flow and blood pressure to a limb or limbs, organ or organs, region or regions or body part or parts above the inflow pressure that is supplied by the body. Generalized systemic hypertension is known to cause organ damage both acutely and chronically, particularly in susceptible organs such as the brain, kidneys and heart. To avoid damage to other regions, an organ blood supply may be isolated from the remainder of the vascular system. A balloon catheter system combined with an access system can be used with acute or chronic application and has the ability to be repeatable as often and as long as necessary. By combining implantable systems, as disclosed, for intermittent and recurrent access to the arterial and/or venous circulation of a warm blooded animal simultaneously or separately with multiple access ports with at least one balloon catheter system that is capable, or substantially capable, of hyperperfusion of specific organs such as the brain or pancreas which has specific lengths extending on the side of the entry and exit of the blood supply to the access system. In some tumours, a multi-access head, which can be attached to the access device, allows multiple vessel segments to be completely or substantially completely occluded or controlled. For example, carcinoma of the head of the pancreas, which receives its blood supply from the superior pancreaticoduodenal artery, may be treated by placing a balloon catheter distal in the superior pancreaticoduodenal artery to prevent dilution of the therapeutic agent to the spleen and body of the pancreas, while simultaneously obstructing and controlling arteries proximal to the orifice of the superior pancreaticoduodenal artery via another balloon catheter or other occlusion member. Therapeutic agents can then be selectively administered to the head of the pancreas by perfusing or hyperperfusing them into the segment between the balloon catheters and occlusion members. Certain embodiments are capable, or substantially capable, of hyperperfusion of the specific organs such as the brain or pancreas which has specific lengths extending on the side of the entry and exit of the blood supply to the access system. It is desirable that in certain aspects, some systems adapted to treat the brain be capable of withstanding treatment pressures of from 70 mmHg to 200 mmHg, 100 mmHg to 180 mmHg, 120 mmHg to 170 mmHg, 90 mmHg to 170 mmHg, or, 80 mmHg to 200 mmHg. It is desirable that in certain aspects, adapted to treat the limbs or organs that some of disclosed systems be able to withstand treatment pressure from 70 mmHg to 500 mmHg, 70 mmHg to 350 mmHg, 70 mmHg to 150 mmHg, 200 mmHg to 500 mmHg, 200 mmHg to 400 mmHg, 100 mmHg to 300 mmHg, 120 mmHg to 200 mmHg, or 120 mmHg to 160 mmHg.

Certain embodiments disclosed herein provide simultaneous arterial and/or venous access and normalisation of the blood supply in between treatments where the access system is closed. Under these circumstances both arterial and or venous systems can be controlled and isolated from the systemic circulation from time to time as required.

In certain aspects, intermittent and recurrent regional hyperperfusion can be achieved by a peripheral access system where fluids or blood can be infused at pressures greater than 100 mmHg, 150 mmHg, 200 mmHg, or 250 mmHg throughout the cardiac cycle. In other embodiments, the pressures will be between 70 mmHg to 500 mmHg, 70 mmHg to 350 mmHg, 70 mmHg to 150 mmHg, 200 mmHg to 500 mmHg, 200 mmHg to 400 mmHg, 100 mmHg to 300 mmHg, 120 mmHg to 200 mmHg, or 120 mmHg to 160 mmHg. In certain embodiments, the perfusion process can be repeated for over the desired time period and repeated as desired. For example, the treatment or hyperperfusion may be carried out on a patient for 4 to 12 hours and then stopped for 4 to 12 hours and then repeated as needed, for 4 to 30 hours and then stopped for a period of time such as 4 to 12 hours and repeated as needed, for 10 to 30 hours and then stopped for 4 to 48 hours and then repeated as needed, for 10 to 36 hours and then stopped for 4 to 24 hours and then repeated as needed. During the period that the treatment or hyperperfusion is stopped it is still possible, if desired to provide therapeutic agents. In certain embodiments, the disclosed systems are suitable for treatment of an ischemic limb with small vessel disease where other treatments such as bypass, endarterectomy, sympathectomy or pharmacological manipulation are not considered to be appropriate. This problem is common in diabetics. An advantage of certain embodiments is to prevent the need or limit the need for amputation. In addition to the above advantages, it is possible using certain systems to simultaneously perfuse the limb or organ using the disclosed occlusion members.

For example, using a system disclosed, in FIGS. 37-43 and 56-59, the response in a human patient to isolated hyperperfusion for small vessel disease with gangrene is shown. In this treatment, the pan-cycle inflow pressures of approximately 300 mmHg were required to increase the limb flow from 80 ml/min (resting) to 350 ml/min. The resting mean pressure of 100 mmHg was produced by the heart. After 53 hours of intermittent isolated hyperperfusion, the pressure required from the extracorporeal pump to produce 350 ml/min was only 110 mmHg, i.e., very close to normal cardiac performance. The patient did not require a below knee amputation, as was initially recommended prior to isolated hyperperfusion, and as soon as the flow increased the symptoms of rest pain and paresthesia disappeared.

One advantage of certain embodiments of the disclosed systems, methods and devices is that the access devices can be left in the body for the desire period of time or extended periods of time up to 7 days, 15 days, 28 day, 2 months, 3 months, 4 months, 5 months, or 6 months. In other embodiments, the device can be left in the body for 1 day to 7 days, 2 days to 6 days, 3 days to 6 days, 1 week to 4 months, 1 week to 3 months, 1 week to 2 months, 2 weeks to 4 months, 2 weeks to 3 months, 2 weeks to 2 months, 3 weeks to 4 months, or 3 weeks to 2 months without having a substantial adverse impact on the patient.

In a typical treatment of the leg, the pump flow may be started at 500 ml/min with pressure 300 mmHg and then as the vessels remodel pressure will decrease towards normal cardiac pressure which is 110 mmHg and the flow will be maintained at 500 ml/min results in greater larger diameter vessels or more blood vessels Thus, the systems permit monitoring of the pressures and volumes needed to hyperperfuse and as the pressure needed reduces over treatment time, the hyperfusion pressures can be increased or decreased until the treatment is deemed to have been completed.

Another way to measure the success of the results achieved is to use something like the an ankle brachial index (ABI). The Ankle-Brachial Index (ABI—blood pressure at the ankle divided by the blood pressure in the arm) is a common method used to diagnose peripheral vascular disease. The ABI may be expressed as the ratio of arterial pressure in the ankle to that of the brachial artery in the arm. In a normal individual, the systolic pressure in the leg is the same or slightly higher than the systolic pressure found in the arm, and will give an ABI of 1 or greater than 1. A reading of about 0.4 to 0.9 typically will indicate an intermittent claudication present. A reading of 0.25 to 0.4 typically will indicate rest pain being present and a reading of less than 0.25 will typically indicate ulcers and/or gangrene. Typically in a diseased person with a limb that is ischemic the ABI will be approximately below 0.9 and often around 0.5. At 0.5 a person will typically feel pain in that limb. Typically, in a limb that is being considered for amputation the ABI will less than 0.2 on exercise. However, in diabetic limbs the ABI measurement may be inaccurate and give inappropriately high measurements due to the hardening and incompressibility of the arteries in the affected limb. Using certain embodiments it is possible to improve the ABI after treatment by greater than 10%, 30%, 50%, 80%, 120%, 200%, 250%, 300%, 400%, or 500%. The ABI is a measurement of distal blood pressure and therefore flow. However, in some patients, particularly patients with diabetes, the ABI is not measurable due to the hardening of their arteries. To supplement ABI, laser Doppler can be used to measure the blood flow in a sample area. Thermography has also been demonstrated to give an accurate measure of the skin blood flow and limb viability. Improvements from using certain embodiments can also be measured using contras agents. Improvements in superficial flow can also be measured by comparing pre and post treatment skin temperature using thermography.

In certain embodiments, it may be desirable to provide access to the circulatory system where higher pressure is not needed. For example, in treatments where the delivery of therapeutic modalities are desired. In certain embodiments, it may also be desirable to switch from one pressure range to another pressure range, e.g., high pressure to low pressure and back to high pressure, or low pressure to high pressure. In addition, using disclosed embodiments it is possible to provide super systolic pressures that enable large amounts of blood and oxygen to be delivered to the target portion of the body.

In addition, in certain embodiments, the system may include when desired a throughput channel to allow normal perfusion of the distal non targeted parts. For example, see FIGS. 7 and 19. In other aspects, some embodiments of the systems may include a membrane oxygenator to provide oxygenation or to maintain adequate oxygenation. In other aspects, a cell saving system may be used to allow preservation of red cells while discarding other components of the blood such as a high concentration of therapeutic agent in the serum, which can cause a toxic effect, and some embodiments may also include hyperthermic system. For example, a cell saving system to remove and discard the serum after repeated organ infusion using cis-platinum may be desired as part of the access to the hepatic artery and the superior and inferior mesenteric arteries.

In other aspects, an ability to remove the outflow from the target organ via a catheter may require a throughput system to allow normal venous egress to avoid venous hypertension, while still allowing isolation and/or collection of the desired blood.

In other aspects, it may be desirable to have intermittent obstruction of the superior and inferior mesenteric artery and other branches of the coeliac trunk in order to decrease the hepatic vein flow via the portal venous system. In certain infusion systems, it may be desirable to have an access system involved in the common femoral artery or, in the upper limb, the axillary artery. A venous access system would involve the common femoral vein. One advantage of such a system is the repeatable access. Another advantage is that the treatment permits use of high concentrations of a therapeutic agent to create the desired cytotoxic affect, while limiting or substantially minimizing leakage of the toxic chemotherapeutic agents into the general circulation, reducing hair loss, G.I. upset and bone marrow depression. Other advantages of such embodiments include reduced or minimized damage to the to the arterial and venous circulation due to the cannulation and avoidance of flow changes particularly related to obstruction of the inferior vena cava which may lead to life threatening cardiac consequences. Use of multiple access ports allows control of other contributing vessels such as the superior mesenteric artery inflow as well as the other branches of the coeliac artery when isolating the liver. Hyperperfusion can be used via the hepatic artery i.e. to increase the flow and pressure through the hepatic artery allowing for complete isolation of the liver without the toxic side effects and increased time of infusion In certain embodiments, the access devices disclosed herein will act as a junction between an extracorporeal pump and the vessel circulation, and permit easy and repeatable access to the vessels and circulatory system of the body over a period of implantation of about 28 days. Allow both inflow and outflow of blood or fluids through the access device. In some aspects, allow a patient to be connected to an extracorporeal pump repeatedly for duration of implantation up to about 28 days. In some aspects, allow patient mobility during the time that the device is implanted. In some aspects, withstand supra systolic pressures generated by the pump up to 300 mmHg and allow high flow rates up to 400 mL/min without generation of excessive shear stresses. In some aspects, prevent, or substantially reduce any blood fluid leakage from the access device when it is free from external connections. In some aspects, prevent, or substantially reduce, blood leakage when connections are made. In some aspects, maintain blood or fluid turbulence to acceptable levels at anastomosis site. In some aspects, allow high blood flow rates up to 400 mL/min without significant hemolysis or thrombosis. In some aspects, be non conducive to thrombosis or emboli. In some aspects, be resistant to exit-site infection and prevent septicaemia (systemic infection). In some aspects, allow simple, leak-free, accurate anastomosis with the host artery. In some aspects, the diameter of proximal tip may be compatible with size of vessel. In some aspects, the materials used may be biocompatible as per ISO 10993 for an externally communicating device in contact with circulating blood fluid for up to about 28 days and be suitable for intended treatment patients. In some aspects, prevent backflow caused by the high-pressure return flow from the pump. In some aspects, be fixed, attached, or configured in such a way as to minimise the risk of dislodgement during connection procedures and patient movement. In some aspects, allow infusion of drugs, therapeutic agents and other diagnostic materials (for example, angiographic contrast) and the materials need to be compatible with common drugs, therapeutic agents and other diagnostic materials used. In some aspects, permit easy removal when treatment is no longer necessary. In some aspects, the plunger assembly will need to be changed regularly including but not limited to the plunger tips and plunger shaft seal. In some aspects, the device is to be cleaned regularly. In some aspects, the pumping seal components and other components will need to be replaced after each use. In some aspects, the connector components are designed to be sterilised after use. In some aspects, the catheters and pump hoses are single-use only devices.

In addition, to the treatments disclosed above, a wide range of other treatments are possible using one or more of the embodiments disclosed. The present embodiments are not limited to a particular treatment disclosed and the following are provided as examples only.

Certain embodiments can be used to treat cardiac situations. In certain embodiments, it may be desirable to modify the hyperperfusion balloon systems and the techniques herein by including counterpulsation of the balloon catheter or catheters. It is often desirable for the hyperperfusion catheter to be of sufficient calibre to generate flow without causing haemolysis while increasing coronary artery flow in excess of 200 ml/min with diastolic pressures greater than normal. In certain embodiments, catheter will be of a calibre of between 0.5 mm to 5 mm, 1 mm to 5 mm, 1 mm to 3 mm, 1.5 mm to 3.5 mm, or 1 mm to 4 mm. Typically, a healthy person will have blood flow of from 250 ml/min to 800 ml/min and this blood flow rate will vary depending upon the person. In some aspects, it is preferred that a balloon be able to occlude, or semi-occlude, the ascending aorta to create a closed, or substantially closed, segment between the aortic valve and the balloon with the only, or primary, egress of blood from the hyperperfusing system being the coronary arteries or coronary artery bypass grafts.

In animal experiments, the mean root aortic pressure can be a good indicator of coronary flow and may be related to the coronary artery flow—as mean root aortic pressure increases, coronary flow increases, assuming there that the aortic valves are not damaged. Using counterpulsation treatment, coronary artery flow can be altered by varying the ratio of intraaortic counterpulsation balloon inflations to heart beats (i.e. one balloon inflation per heart beat, one balloon inflation per two heart beats, one balloon inflation per three heart beats, etc.) or by altering the volume of helium used to inflate the intraaortic balloon—an increase in the volume will increase the size of the balloon and increase the coronary flow. Using hyperperfusion and counterpulsation and pressure as an indicator of coronary flow, cardiac failure was induced by halothane inhalation in anesthetised sheep. The mean root aortic pressure in the normal control sheep was 90 mmHg. Upon induction of cardiac failure the mean aortic root pressure fell to 30 mmHg. With aortic root counterpulsation alone the pressure climbed to a mean of 45 mmHg. With hyperperfusion in conjunction with counterpulsation the mean root aortic pressures increased dramatically to a mean of 105 mmHg. Further experimentation showed that the pressure (i.e. mean root aortic pressure) could be adjusted by varying the hyperperfusion pump inflow as required.

In certain embodiments, the counterpulsation systems may decrease the cardiac afterload, i.e., by decreasing the pressure the heart sees on deflation of the balloon in the descending aorta on their own and may also increase coronary flow. In some aspects, the use of a counterpulsation system alone is therapeutically beneficial. The counterpulsation hyperperfusion system has multiple applications particularly in refractory angina, inoperable coronary artery disease, congestive cardiac failure and ischemic cardiomyopathy. In the acute situations following myocardial infarction, counterpulsation and hyperperfusion can be used with other cardio therapeutic agents. Additionally combined counterpulsation and hyperperfusion may help overcome complications commonly encountered in removing patients from the pump, the access system can be used from the groin or axilla, the system can be used as part of the normal extracorporeal bypass e.g. aortic valve surgery and then access for atrio-femoral bypass and in the longer term, intermittent counterpulsation hyperperfusion may be used as a bridge to cardiac transplant. The benefit of combing the systems is that the sheer stress created in the coronary arteries by hyperperfusion encourages collateral growth.

In certain embodiments, coronary artery flow can be increased by using the R Wave on the electrocardiogram ECG to trigger a pulse hyperperfusion flow to the coronary arteries or coronary artery bypass grafts. The increase flow to the aortic root occurs in diastole, this allows the heart to avoid pumping against an external pump in systole. These embodiments decrease the afterload and, therefore, decrease a risk of aortic incompetence related to the increased pressure on the aortic valve. In certain embodiments, the hyperperfusion and counterpulsation can be housed together to reduce the size of the device with increased affordability.

Certain embodiments disclosed herein provide systems, methods and devices for treatment of acute ischemic stroke and occlusive cerebrovascular disease by taking advantage of the collateral cerebral circulation. Such embodiments permit intermittent and recurrent access to the circulatory system which creates greater flexibility in the treatments provided to a warm blooded animal. Certain aspects disclosed can be used to promote re-vascularisation after ischemic strokes such as embolic or thrombotic stroke. Following vessel occlusion (by a thrombus or embolus) there are neurons that do not function normally. The region formed by these poorly functional or non-functional neurons is referred to as the umbra or shadow. When occlusion of a blood vessel interrupting the flow of blood to a region of the brain occurs, survival of the affected brain tissue depend on the number and size of its collateral arteries. Effective stroke therapies therefore rely on the ability to respond to treatment quickly, since the longer the brain is deprived of blood flow, the greater the damage that occurs. Certain embodiments disclosed herein may be used to enhance and provide intermittent and recurrent access, contralateral blood flow across the Circle of Willis to improve and maintain perfusion to an ischemic region distal to an occluded intra/extracranial cerebral artery, and thus can be utilized in stroke patients immediately after onset of symptoms to maintain viability of the cerebral tissue until the obstructing lesion is removed by an intervention or resolved with time.

If the patient's extracranial vessels are occluded then the hyperperfusion is performed (via the access device) in the contralateral extracranial vessels. Then, via the 'Circle' of Willis' in the brain, the ipsilateral intracranial vessels may be hyperperfused. This cross-circulation is the reason why many patients with a complete extra-cranial occlusion on one side are totally asymptomatic. Hyperperfusion provides pan-cycle, controllable increased cerebral perfusion pressure. 'Autoregulation' is the intrinsic control of vessel flow and pressure in the cerebral vasculature. Ischemic neuronal tissue loses this autoregulation which therefore increases the blood flow to the ischemic region.

Embolic cerebral occlusion or isolated intracerebral distal occlusions can be hyperperfused directly via the ipsilateral carotid artery. In certain aspects, it may be desirable to combine intermittent and recurrent access hyerperfusion with a fluid or blood filter which entraps any thromboembolic debris flowing through the circuit before blood is perfused to an artery. In certain aspects, the access device is implanted and the appropriate catheters are inserted with assistance of a guide wire and the distal end of the first catheter is inserted into the contralateral carotid artery. Blood may be aspirated from the artery through the lumen and port of a first catheter where it may be sent to various equipment and devices, such as pumps, flow controllers, drug delivery devices, blood monitoring devices, such as blood pH, $S_{O2}$, pulse or other blood monitoring devices, blood oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable devices and hyperperfused using a pump and reintroduced into the contralateral carotid artery through the lumen and port of a second catheter. An expandable occlusion member, e.g., a balloon, may be expanded on the second catheter to the distal port to control the flow rate more effectively.

In this manner, augmented contralateral hyperperfusion may provide enhanced reversal of blood flow across the Circle of Willis to compensate for the sudden decrease of flow in the occluded artery. The flow rate can be controlled using the access systems pumps and by deflating or inflating the balloon, e.g., the flow rate increases as the balloon is deflated. The augmented contralateral hemispheric blood flow, which helps to reverse flow across the Circle of Willis, may provide retrograde arterial collateral enhancement to the ischemic area distal to the occlusion and/or enhance the pressure differential across the occluding lesion, which may be sufficient to dislodge any thromboembolic material. Blood aspirated from the symptomatic artery is, in certain embodiments, passed through a blood filter optionally included in the proximal end of the first or second catheter or in the pump to entrap any embolic debris before the blood is returned to the contralateral carotid artery.

There are several advantages in using the embodiments disclosed herein, including but not limited to, intermittent and recurrent access to the circulatory system which enables greater flexibility in the treatments and agents used. The disclosed systems can be used: to treat stroke patients or patients suffering from a symptom of a stroke, to supply neuroprotective agents locally into an occluded area, thereby providing greater local benefit and fewer systemic side effects, to infuse hypothermic fluid or blood to the ischemic area, as an angioplasty device by inflating the balloon over the stenotic arterial lumen to enlarge the luminal diameter, in treating acute stroke patients with few systemic side effects, to treat symptomatic vertebral artery occlusion, to maintain cerebral perfusion in patients with asymptomatic flow limiting carotid stenosis undergoing major cardiothoracic surgeries or in patients with hemodynamic instability, e.g., cardiogenic or septic shock, and/or to maintain perfusion to the distal ischemic area, even without removal of the occlusion, to minimize neurologic damage while alternative intervention is being considered. In certain aspects, Heparin may be administered through the access device to provide anticoagulation, thereby preventing thrombi forming in the vessels.

In certain aspects, blood may be delivered or returned to the affected region via the access system with mild to moderate hypothermia, such as at a temperature of about 32 to 34 degree C., 30 to 36 degree C., or 31 to 35 degree C.

An advantage of certain embodiments disclosed is the use of regional hyperperfusion to increase collateral development thereby increasing total peripheral flow. Chronic arterial occlusion leads to ischemia of the affected part: with associated loss of function and ischemic symptoms and signs. The degree of ischemia relates to the degree of alternate bypass channels available (collaterals). The size and number of these vessels depends upon the pressure gradient across the occluded arterial segments. Typically, the greater the gradient used the more aggressive the collateral development. This process is mediated by the sheer stress at the internal wall. Hyperperfusion increases flow, (shear stress) and blood pressure which dilates the vessels thereby increasing collateral wall tension—both shear stress and wall tension increase collateral development.

Other aspects include combining an implantable system for intermittent and recurrent access to the arterial and/or venous circulation of a warm blooded animal simultaneously or separately with multiple access ports with a balloon catheter system that is capable, or substantially capable, of hyperperfusion and isolation of the pelvic vessels left, right or both. In certain aspects, it is desirable that the balloon catheter system be compatible with the access systems disclosed herein. Arterial hyperperfusion can increase the shear stress which is responsible for collateral vessel growth. Vasculogenic impotence has two main aetiologies—obstruction of the arteries and dilation of the veins. Pudendal vessels can be selectively hyperperfused via the access device to create new collateral arteries. Venogenic impotence can be treated by serial embolisation of the cavernosal outflow—creating pelvic hypertension and therefore minimising 'venous leakage' from the cavernosal tissue. Cancers of the uterus, prostate, bladder, and any other carcinomas deriving nutrients from the pelvic vessels can be selectively isolated from the systemic circulation and treated with high concentrations of therapeutic agents. See, for example, the system disclosed in FIG. 26.

Figure 2:
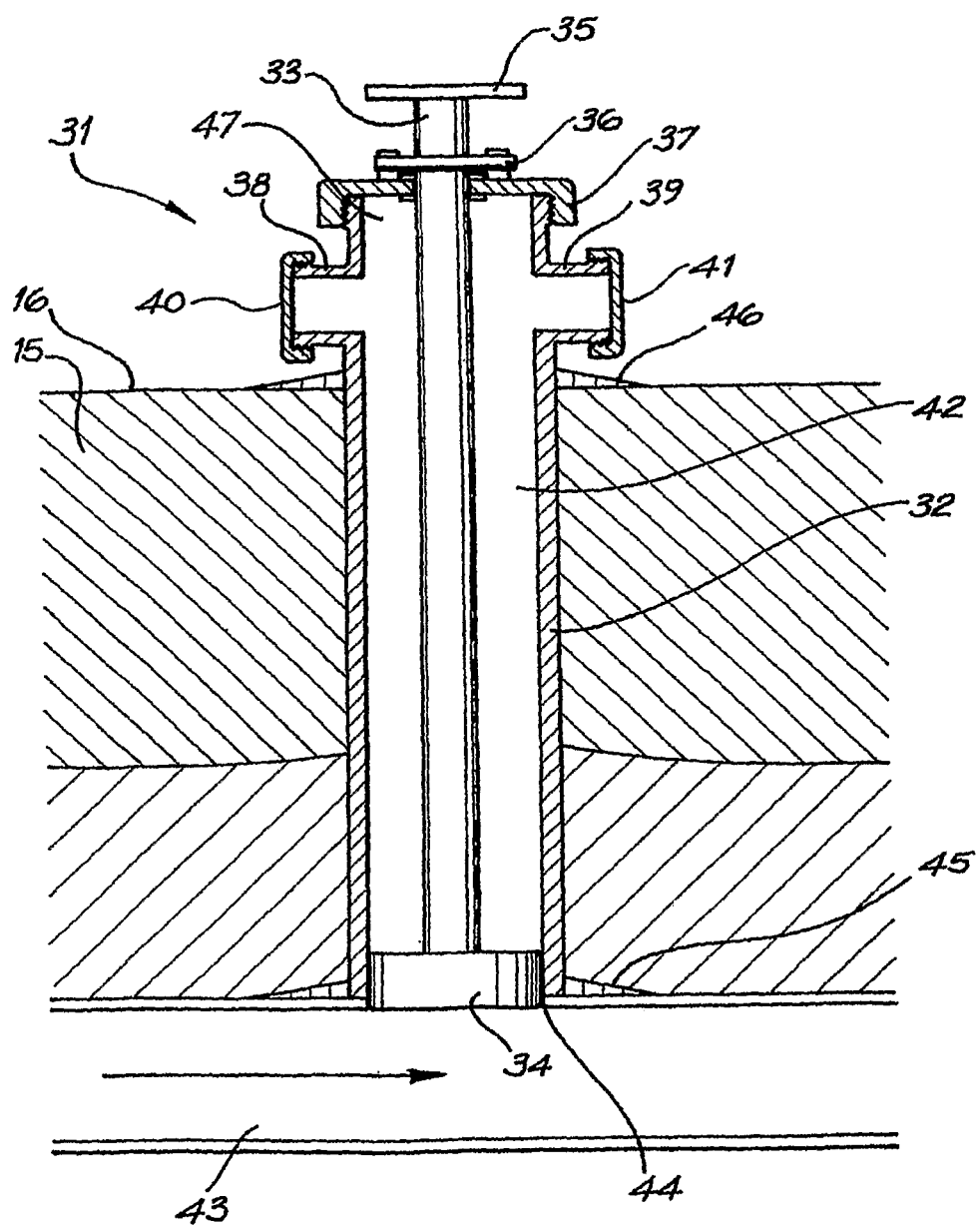
FIG. 2 is a cross sectional view of an inflow cannula access device with the plunger extended to prevent blood flow into the cannula.

Embolectomy can be used to treat acute embolic events to the lower limbs, however, the treatment is often incomplete with loss of limb or digits. Certain embodiments use regional isolated hyperperfusion to increase the regional inflow pressure and flow resulting in growth of new vessels and/or improvement in the circulation capability of existing vessels and damaged vessels. These embodiments improve the chances for not having to remove limbs or digits. In animal experiments in sheep it has been shown that using embodiments disclosed herein it is possible to increase regional flow through collaterals. FIG. 1 shows an example a design where the lower limb has been made ischaemic by ligature. The two graphs in FIG. 2 show the pressure distal to the ligature with and without an external pumping. These results show that more flow can be pumped through collaterals with the aid of an external pump than the heart can produce through the normal circulation without ligature.

Grafts often fail due in part to insufficient vessels for the blood to circulate into the tissues at the lower end of the graft. Therefore stasis occurs within the graft resulting in thrombosis. Certain embodiments provide hyperperfusion systems that promote new vessel growth and/or enhancement of damaged vessels through collateral growth. This results in improved circulation into the ischemic areas. This collateral growth represents an improvement over existing treatments. Furthermore, the access system and hyperperfusion may be performed in patients who are unwell and can be done using local anaesthetic as opposed to most bypass grafts. Use of local anaesthetic is important because the patients often have intercurrent disease, cardiac disease, respiratory disease, and/or renal impairment, each of which reduce the patient's suitability for general anaesthesia. The implantation of the access device is a relatively minor operation making it more suitable for a local anaesthetic, additionally the repeated access to the device for the specific perfusion or hyperperfusion does not require a general or local anaesthetic. In addition, certain aspects disclosed permit the bypass of graft failures which are often recurrent in the lower limbs associated with poor runoff. Hyperperfusion can be used to increase flow through a graft (whether natural or synthetic) to increase collateral growth and flow distal to the graft and improve the long-term patency. Certain aspects disclosed permit coronary artery bypass grafting where the internal mammary artery shows spasm (producing the "string sign") angiographically. Certain hyperperfusion systems disclosed can be used to overcome spasm combined with vasodilators.

Another application of certain embodiments to chronic arterial problems are those associated with vasculogenic impotence which affects 17% of males >55 years. In the vast majority vasculogenic impotence is cause by occlusions at the base of the erectile tissue. Using certain embodiments it is possible to increase the total flow to the erectile tissue and cause neovascularisation. See for example, FIG. 26. The perfusing catheter may be inserted in the internal iliac artery to directly cannulate and isolate the internal pudendal vessels with a balloon. Treatment with pan-cycle hyperperfusion of greater then 200 mmHg of is believed to produce neovascularisation in the distal vessels.

There are many known therapeutic agents for treating, for example cancer or other diseases that are not used because current methods deliver them to the body in a manner that induces toxic or undesirable reactions and/or side effects in the patient. By using certain embodiments, it is possible to deliver such therapeutic agents to a targeted region of the body such as a particular organ without inducing, or reducing, toxic side effects such as bone marrow depression, gastrointestinal upset and hair loss i.e. to regionalise the therapy. Examples of such drugs may be 5-Fluorouracil (5-FU) or cisplatin. In certain other embodiments, it is possible to deliver such therapeutic agents to a targeted region of the body and then flush such therapeutic agents out of the body, thus reducing the time that the therapeutic agent has to be absorbed into portions of the body that are not being treated. This ability to target introduction of the agent and quickly flush the agent from the body results in a reduction of toxic side effects or other undesirable reactions caused by the therapeutic agent while treating the disease at issue. The success of flushing of the agent can be measured by looking at the volume of blood, or fluid, that put into the body and, measuring the amount of blood, or fluid that is pulled out of the body. Measurement of treatment success may be looked at it terms of remission time, cure rate, 5-year survival, and major/minor complications.

In certain embodiments, it is possible to deliver higher concentrations or doses of therapeutic agents, than would otherwise be prescribed, to a targeted region of the body such as a particular organ without inducing, or reducing toxic, side effects.

In certain preferred embodiments, treatment with therapeutic agents can be achieved by occlusion of the blood inflow to an organ which is infused with a complete extracorporeal circulation using the venous return as the arterial inflow to the isolated organ, limb, or body part. Often the importance of regionalisation to the access system via the multiple access heads is its repeatability. Titration of dose and timing of the therapeutic cycle will sometimes determine where the access system is situated and how often it is used and how long it is left in situ.

In certain embodiments, the systems disclosed permit high concentrations of a therapeutic agent to be delivered to a specified region. Such a system may include: at least one catheter input to at least one arterial supply; an isolation of the remainder of the arterial circulation via occlusion members such as inflated balloons; at least one port for introduction of the therapeutic substance remote from the arterial supply; an ability to remove the outflow from the target organ via a catheter; and an externally controllable pump for control of circulation with entry towards the pump from the venous outflow and entry into the treated region via the arterial inflow.

Liver isolation for treatment of hepatic secondary tumour growths or other liver diseases illustrates this principle. Controlling the inflow and outflow and recirculating the therapeutic agent or agents allows minimisation of systemic side effects such as hair loss, haemopoietic disturbances such as pancytopenia, gastro-intestinal disturbances such as nausea and vomiting and vital organ malfunction such as nephrotoxicity. In this example, the procedure of using the system for isolation includes: removing blood, specifically from the hepatic veins while allowing IVC flow via a flow through catheter; adding a therapeutic agent; returning the blood flow to the hepatic artery using a pump; and controlling inflow to the liver via the hepatic arteries, and portal blood flowing into the outflow tubing. The blood flows into the profunda femoris artery and flows into other portions of the circulatory system as vein (by controlling flow in the superior and inferior mesenteric arteries as well as the coeliac trunk).

An illustrative embodiment of some embodiments is shown in FIG. 1. The hyperperfusion system 10 shown schematically in FIG. 1 is connected between a cardiac side artery 11 and, in this instance, the superficial femoral artery 12. The system 10 is connected to the artery 11 by arterial connector 13 at the inner end of an outflow cannula 14 which penetrates through the subcutaneous tissue 15 and the skin line 16 at exit 17. At the outer end of the cannula 14 there is a threaded connector 18 by means of which the outflow cannula 14 is connected to the low pressure side of an external medical device 19 such as a blood pump or haemodialysis machine by tubing 20.

The high pressure side of the medical device 19 is connected by tubing 21 to threaded connector 22 at the outer end of an inflow cannula 23 which enters the skin line 16 through entry 24 and penetrates through the subcutaneous tissue 15. The inner end of the inflow cannula 23 is connected to the superficial femoral artery 12 by arterial connector 25. In this embodiment, the hyperperfusion system 10 is coupled to the patient's lower limb and the blood is pumped at super-systolic pressures towards the common femoral artery 26 and then to the profunda femoris artery 27. The common femoral artery 26 is occluded by an implanted occlusion device or balloon 28 which selectively blocks flow between the artery 11 and the common femoral artery 26 and essentially allows the pumping system to work in series with the patient's normal circulatory system. This embodiment with some modification can also be used on other portions of the body such the arms, the feet or the hands. Using this embodiment it is possible to provide supra systolic pressures enabling large amounts of blood and oxygen to be delivered to the target portion of the body.

Figure 3:
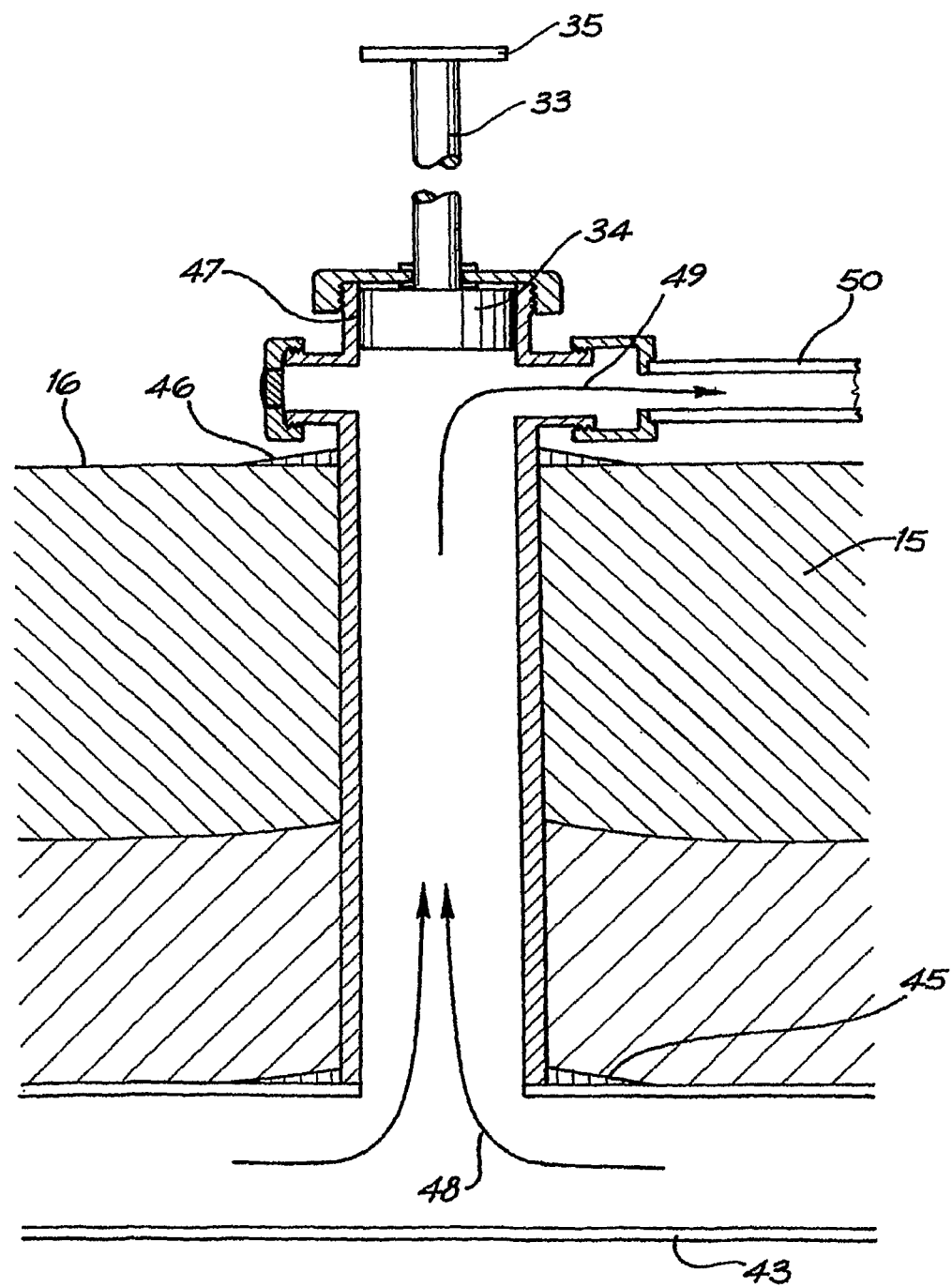
FIG. 3 is a view similar to that of FIG. 2 with the plunger of the cannula retracted to allow blood flow through the cannula.

The cannula shown in FIGS. 2 and 3 is illustrative of certain embodiments of an access device that may be used. The access device 31 which has a housing 32, a plunger stem 33 which has a head 34, a handle 35 and a locking pin 36. The upper end of the housing 32 is closed by detachable cap 37 through which the plunger stem 33 projects. The inflow/outflow port 38 and 39 which are closed by detachable caps 40 and 41 are in fluid communication with the lumen 42 of the access device 31. The access device shown in FIGS. 2 and 3 may also provide access to the circulatory system where high pressure is not needed. In certain embodiments, it may be desirable to provide access to the circulatory system where high pressure is not needed. For example, in treatments where the delivery of therapeutic modalities are desired.

As shown in FIGS. 2 and 3, the biocompatible housing 32 extends through the skin line 16 and penetrates the subcutaneous tissue 15 to join artery 43. An arteriotomy 44 allows fluid communication between the artery 43 and the lumen 42. The plunger head 34 may be constructed of a biocompatible material such as Polytetrafluoroethylene or HDPE. The locking pin 36 is adapted to lock the plunger stem 33 at any desired position to prevent undesired movement of the plunger stem 33 by back pressure of the patient's normal arterial system. An arterial attachment cap 45 is provided at the arteriotomy 44 to reinforce the connection of the housing 32 to the artery 43. Similarly, at the skin line 16 there is an attachment cap 46 which secures the skin against the housing 32 to minimise movement and to reduce the possibility of infection. The structure and design of the various components of the embodiment illustrated in FIGS. 2 and 3 can be varied as long as the function performed is maintained. For example, the structure and capping of the inflow and outflow ports or the number of ports can be altered and varied. Certain embodiments may not have caps on the ports. In certain embodiments, the plunger may be removed and another mechanism used to achieve a similar function.

An illustrative embodiment of the access device 31 is shown in FIG. 2 with the plunger head 34 in its closed position and in FIG. 3 the plunger head is in its open position where it is positioned in the upper cavity 47 of the housing 32 beyond the port 38 and 39 so as to allow fluid or blood flow through the lumen 42 of the cannula 31 as indicated by the arrows 48 and 49. In use, the cap 41 is removed and the port 39 connected to tubing 50 leading to an external blood pump device.

The cap 40 may be selectively removed to allow access to the interior of the device 31 and may allow for the insertion of an occlusion device and/or pharmaceuticals. Lumen 42 may also be filled with sterile antibiotic containing anti-coagulated saline when not in use. The interior of the housing 32 may also be accessed by the removal of cap 40 to remove any residual fluid or blood.

Figure 4:
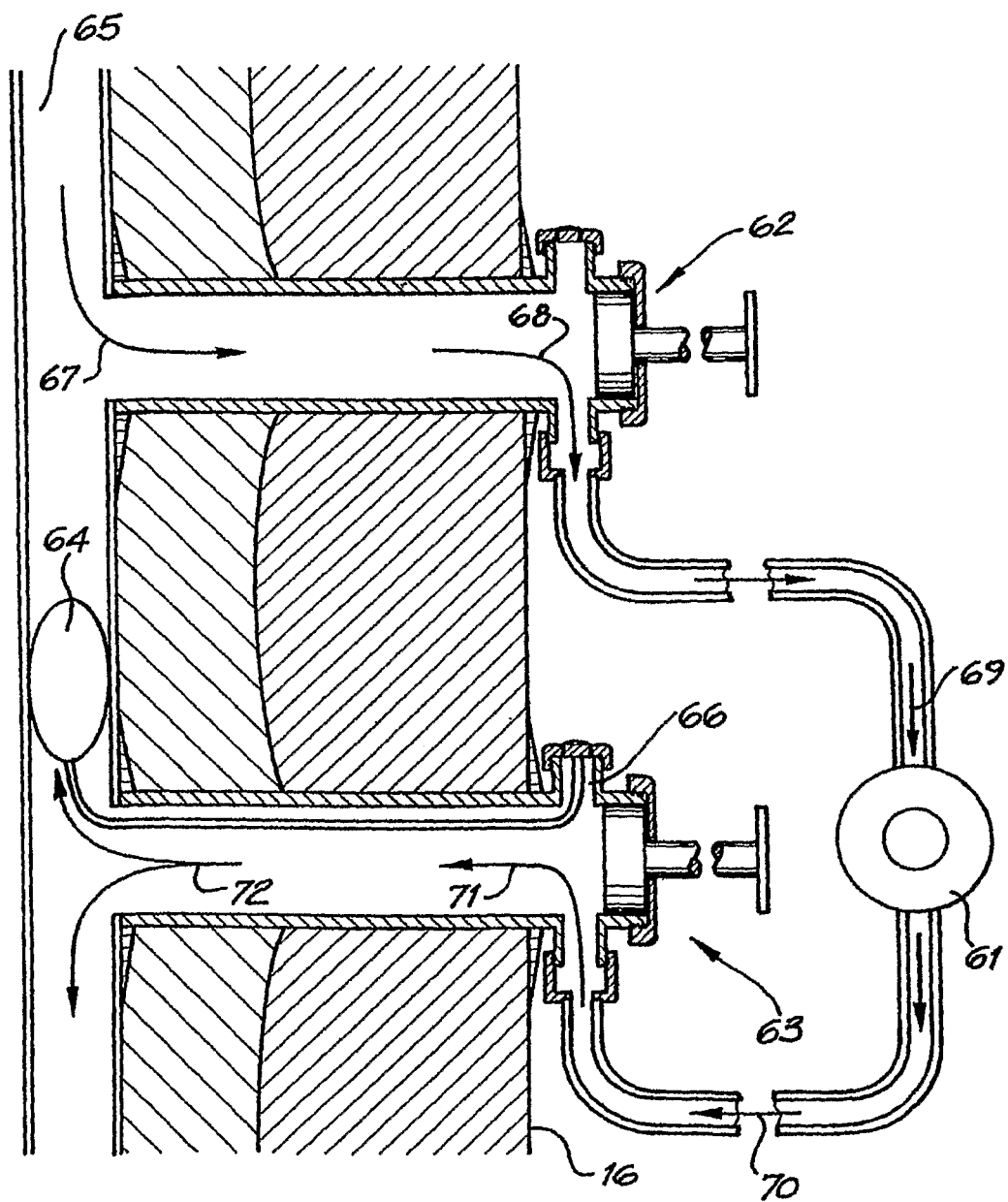
FIG. 4 is a schematic representation of a system according to certain embodiments.
Figure 5:
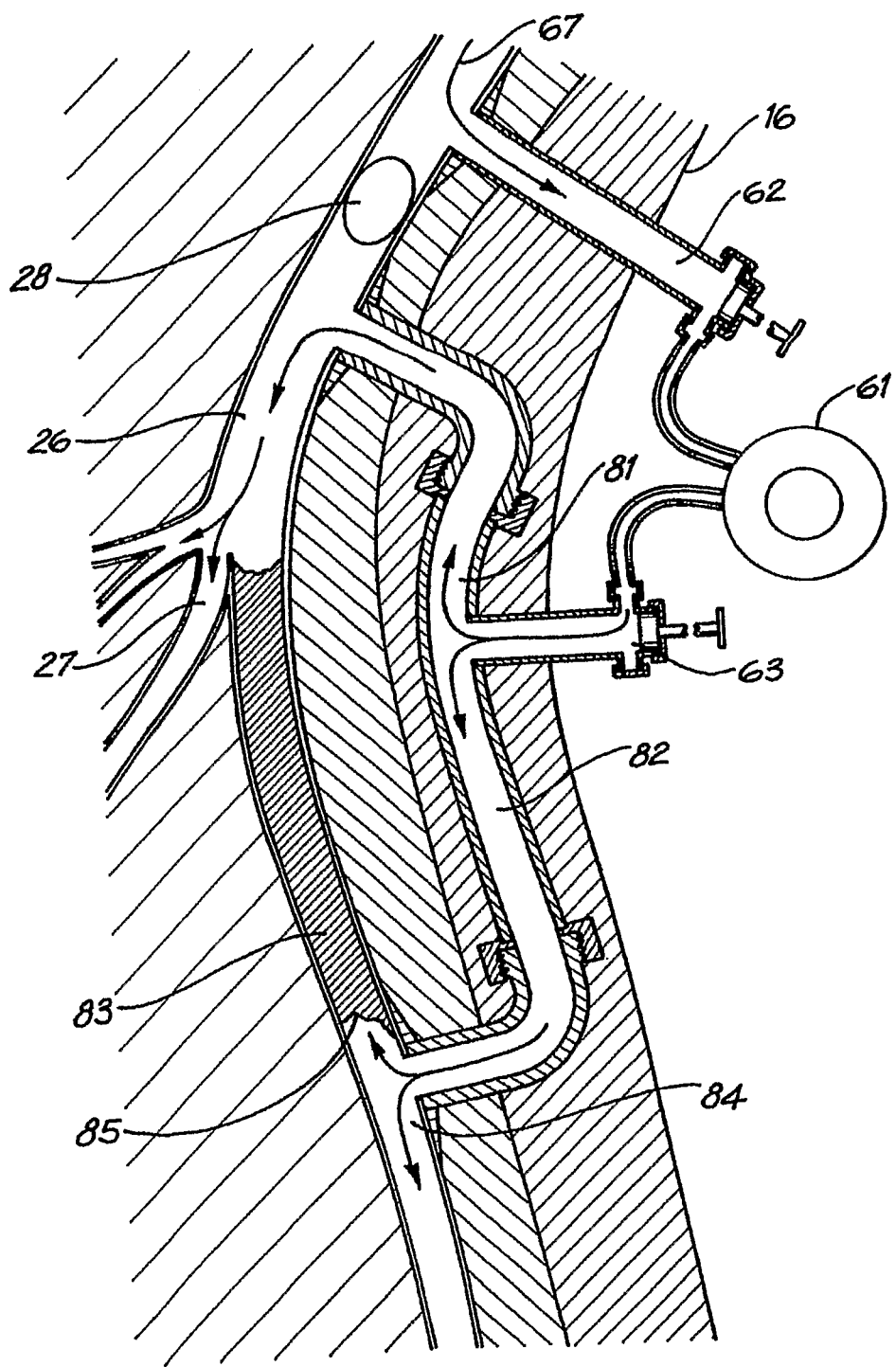
FIG. 5 is a schematic representation of a system according to certain embodiments.

The hyperperfusion system 60 shown in FIG. 4 includes a blood pump 61 in fluid communication with an inflow cannula 62 and an outflow cannula 63 both of which incorporate a high pressure access device as shown in FIGS. 2 and 3. An occlusion device 64 is positioned within the artery 65 after passing through the port 66 in the cannula 63. Blood flow is shown by arrows 67, 68, 69, 70, 71 and 72. The hyperperfusion system 80 shown in FIG. 5 is a modification of that shown in FIG. 4 in that the outflow cannula is divided downstream into a first outflow cannula portion 81 and a second outflow cannula portion 82. The first portion 81 is connected to the common femoral artery 26 and the second portion 82 is connected to the profunda femoris artery 84 which, in the section 83 is occluded by an occlusion device 85. The access device need not be of the plunger type as described above as other kinds of access devices which permit intermittent connection between the circulatory and perfusion systems may be used. For example, the access device may be a percutaneously controllable valve which, when open, permits access between the circulatory system and the perfusion system. Such a valve may be constructed from metal, tissue or polymeric material. The valve may incorporate, for example any suitable flow control means such as for example, a tilting disc, flap, ball or membrane as its flow control means.

Figure 6:
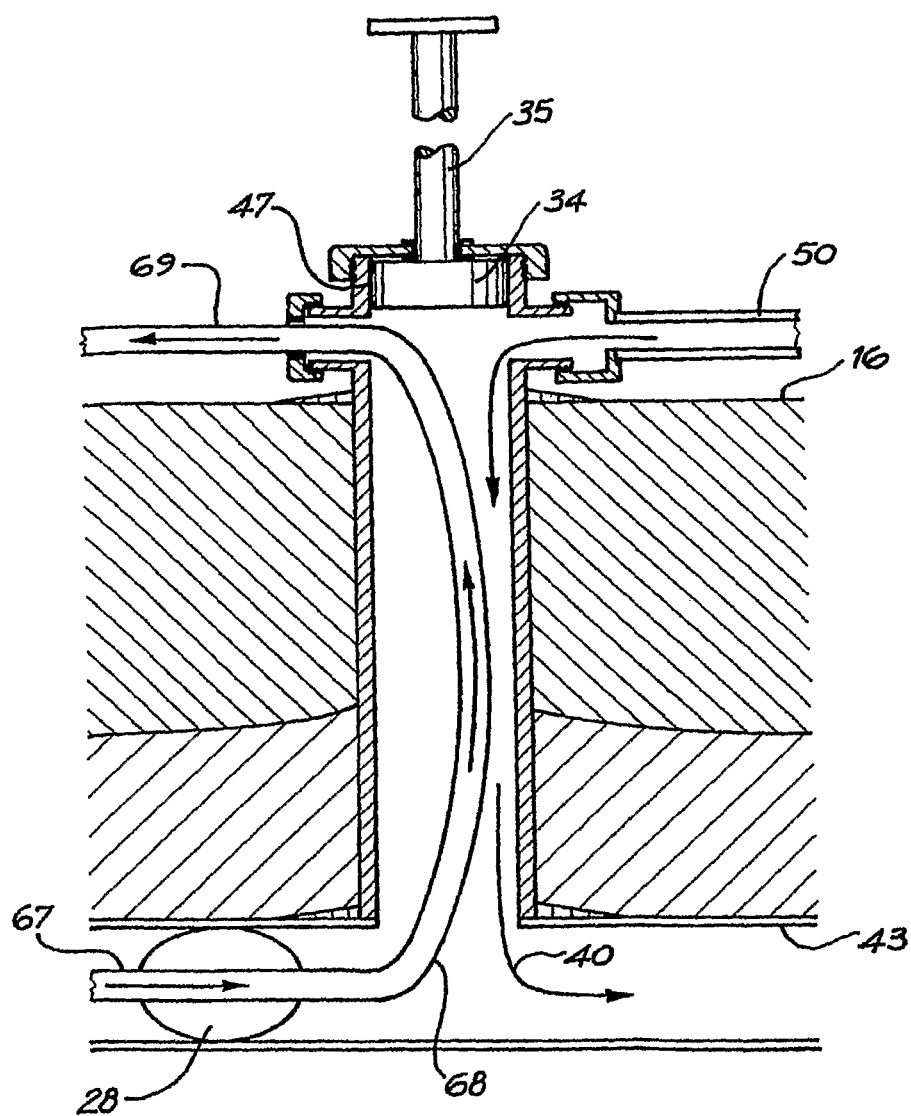
FIG. 6 is a schematic representation of a system according to certain embodiments.

The continuous access device 47 shown in FIG. 6 shows an access device that is used for both blood flows. The components of the embodiment of FIGS. 2 and 3 which are common to the embodiment of FIG. 6 carry the same reference numerals. In this instance, the balloon catheter 28 located in the native vessel 43 surrounds the lower end of blood flow tubing 68 having an inlet 67 and an outlet 69 connected to the blood pump. Inflow of blood into the vessel 43 from the pump is via tubing 50 at suprasystolic pressure. The skin is represented by numeral 16 and the direction of return flow at suprasystolic pressures is indicated by arrow 40. The right and left internal mammary arteries (RIMA, LIMA) are often used to bypass obstruction to the coronary arteries.

Figure 7:
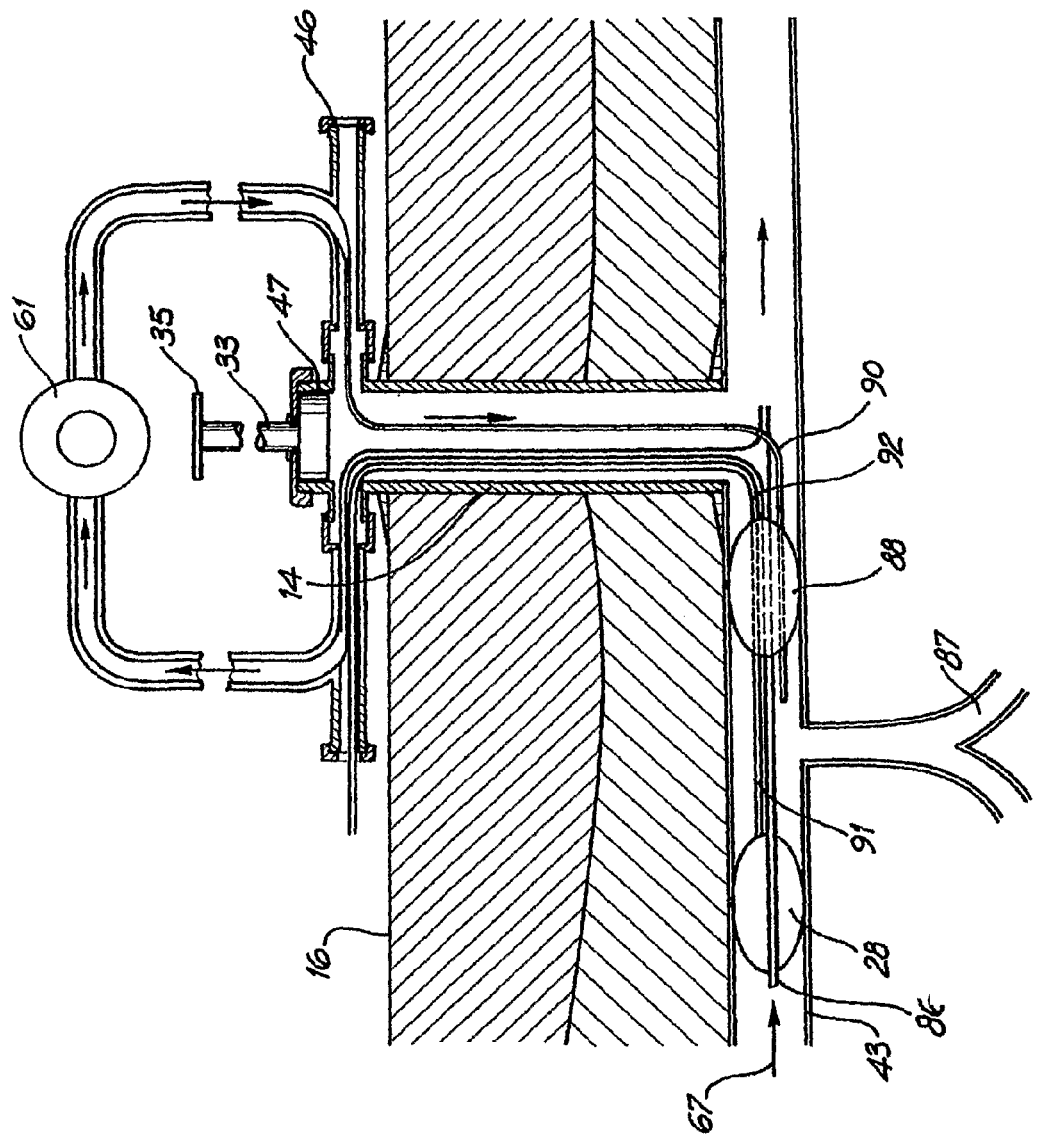
FIG. 7 is a schematic representation of a system according to certain embodiments.
Figure 8:
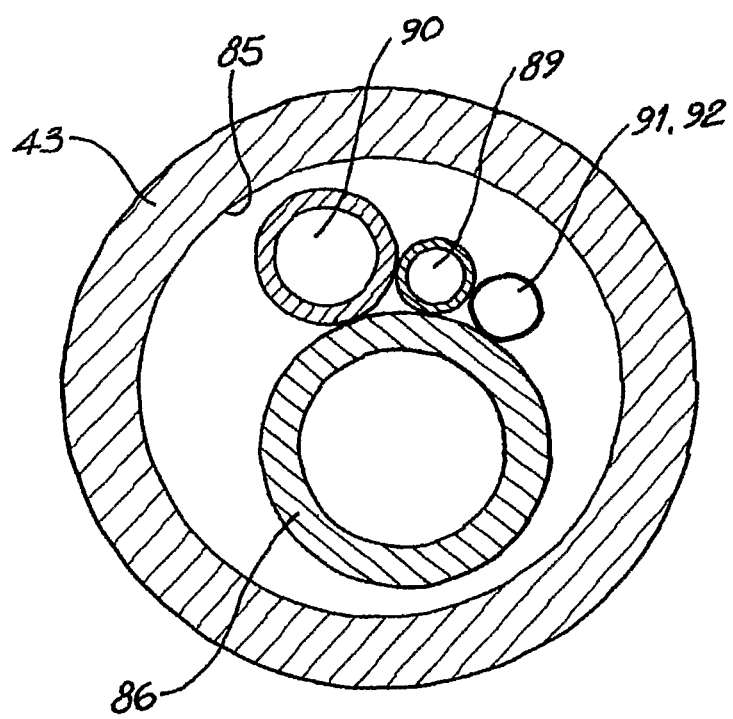
FIG. 8 is a cross sectional view of the tubing system of FIG. 7.

Isolation of these or other similar vessels is shown in FIG. 7. The main supply artery 43 which may be subclavian, aorta, iliac or femoral vessels has a proximal balloon 28 connected to the inflating catheter 91. Numeral 67 indicates the entry of the proximal balloon catheter 28. Downstream of the target artery 87 which may be RIMA, LIMA, renal or distal vessels is a distal balloon 88 connected to the deflating catheter 92. The hyperperfusion catheter is indicated by numeral 90 and the main inflow reinforced tubing by numeral 86. The tubing system of this embodiment in cross section in FIG. 8 consists of an inflow reinforced catheter 86 around which is located a pressure sensing system 89, inflating, deflating catheter 91 for the proximal balloon 28, inflating and deflating balloon catheter 92 for the distal balloon 88 and the hyperperfusing catheter 90 from the blood pump, all of which are located within the inner wall 85 of the main supply artery 43.

Figure 9:
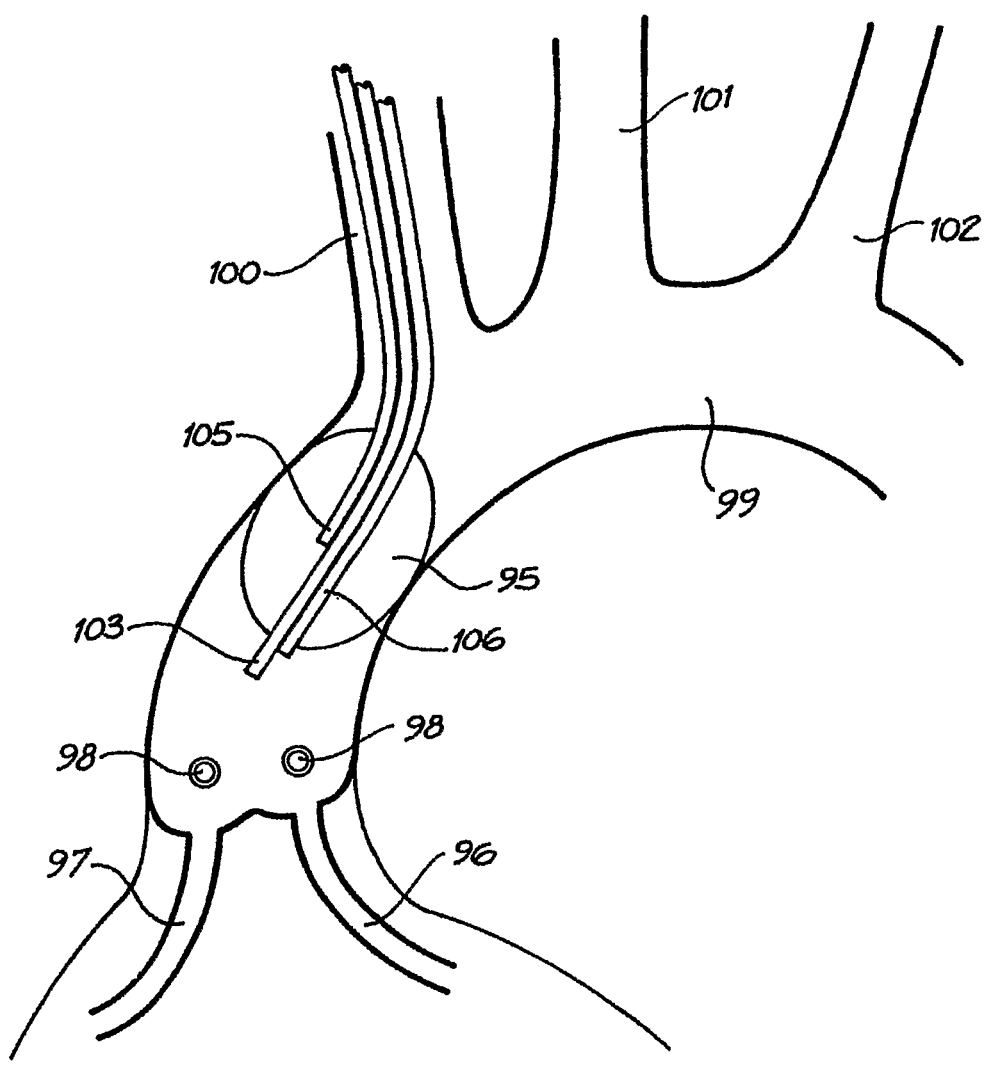
FIG. 9 is a schematic representation of a system according to certain embodiments.

The balloon system may be introduced using a continuous access device 14 or transcutaneously. FIG. 9 shows a further embodiment in which the access system is combined with intermittent inflation of a balloon in the aorta in diastole. In this situation, hyperperfusion of the coronary artery bypass grafts or the coronary arteries themselves is achieved in diastole. In this embodiment, the aim is to increase the pressure between the inflation balloon 95 and the origins of the left coronary artery 96 and the right coronary artery 97 and the coronary artery bypass graft origins 98.

As can been seen in FIG. 9, the descending aorta is identified by numeral 99. The brachiocephalic trunk is 100, the left common carotid artery is 101 and the left subclavian artery is 102. The balloon is occlusive or semi-occlusive in diastole in the ascending aorta and the pressure through the infusion catheter 103 is increased to supradiastolic or even suprasystolic pressures. The balloon is inflated not to displace volume as the standard pulsation system, but to create an isolated segment in order to hyperperfuse the vessels between the balloon and the closed aortic valve. The result is a very large increase in coronary artery flow or coronary artery bypass flow. The balloon infusion catheter is 105 which needs to be large enough to occlude or partially occlude, to inflate and deflate during diastole. The pressure sensing catheter 106 is used to measure the pressure within the hyperperfused isolated segment.

Figure 10:
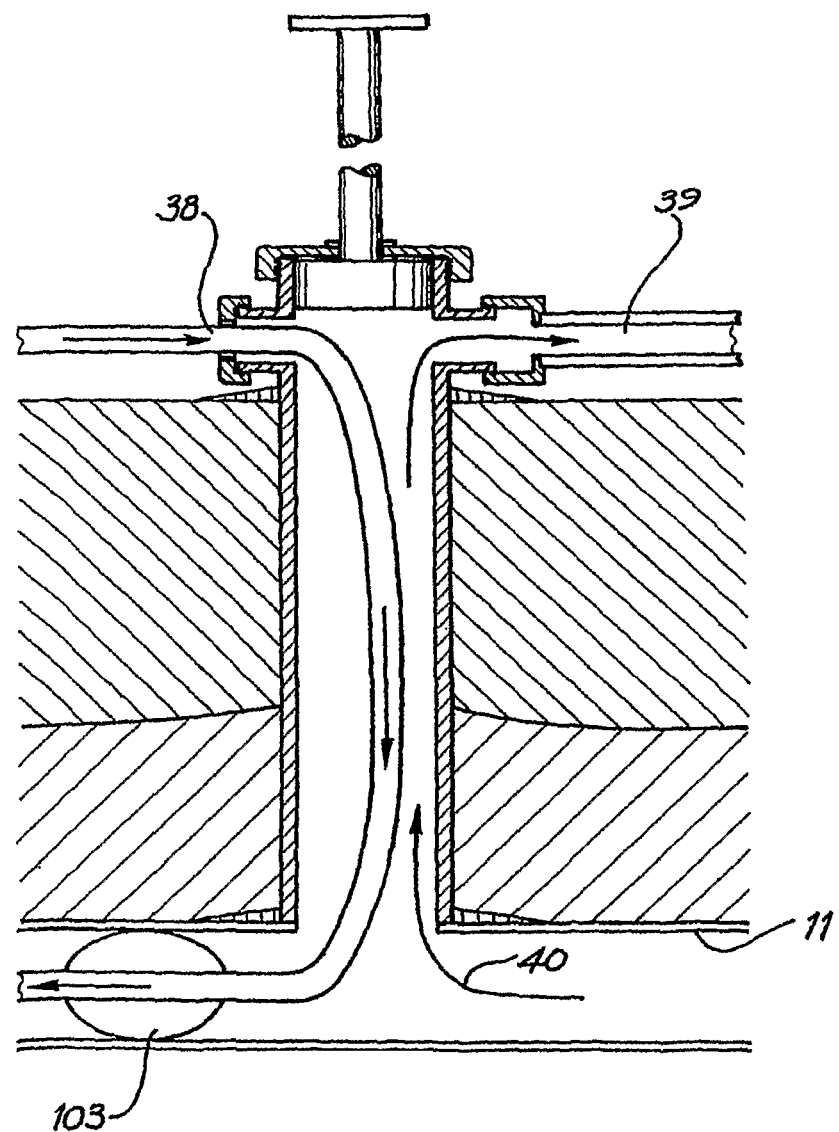
FIG. 10 is a schematic representation of a system according to certain embodiments.

FIG. 10 shows other embodiments of the systems disclosed. The inflow to the pump 39 is in direct connection with the donor vessel 11. The direction of flow indicated by arrow 40 towards the pump 38 is augmented and returned to the target vessel. For example, the right subclavian artery receives inflow during systole which is then augmented with the pump 38 and returned to the closed segment in the ascending aorta. The hyperperfusing cardiac catheter is 103, the other end is in the ascending aorta.

Figure 11:
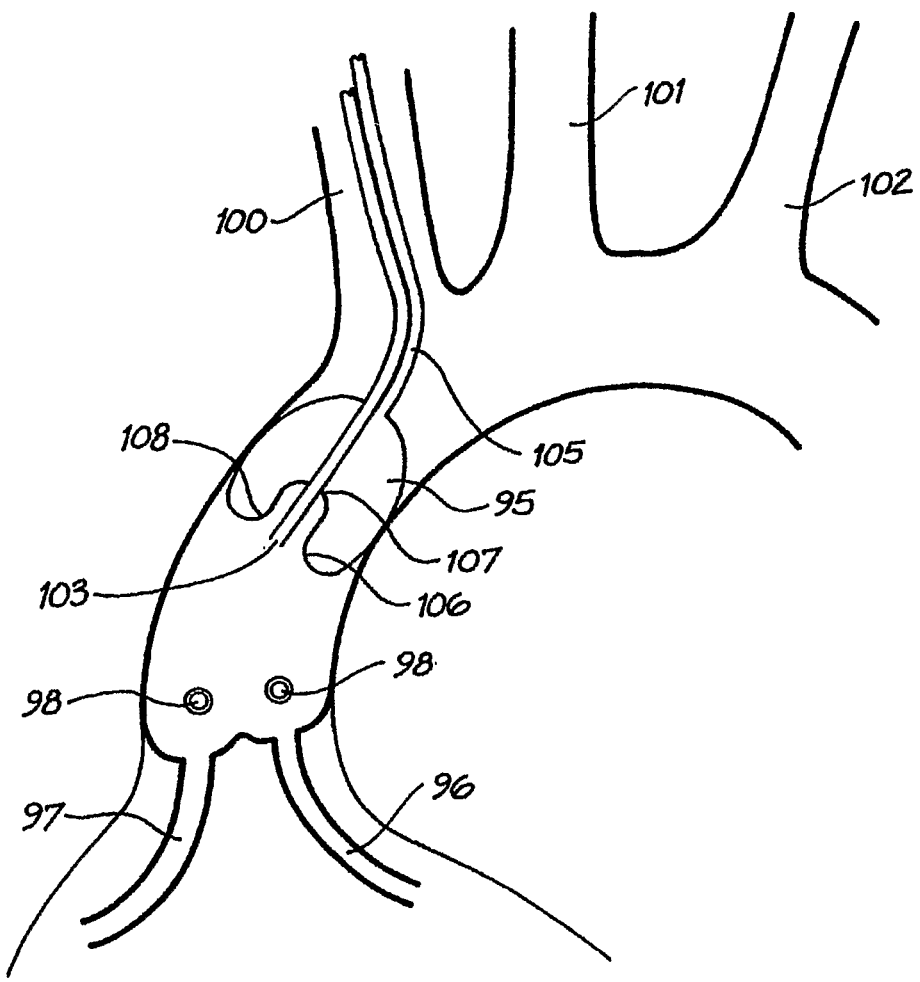
FIG. 11 is schematic representation of a system according to certain embodiments.

A further embodiment is shown in FIG. 11 where the balloon system itself acts as a generator of hyperperfusion, i.e. above normal coronary flow pressures and therefore increases coronary flow. In this situation, no separate hyperperfusion pump is required. The balloon 95 within the aorta expands in diastole only, creating a closed segment between the balloon 95 and the left and right coronary artery orifices 98. The volume within the balloon segments 106, 107 and 108 contracts increasing the volume and pressure within the closed segment between the balloon 95 and the coronary artery orifices 98. The pressure and flow in the coronary arteries therefore increases, the total increase in flow will depend upon the volume of the segments 106, 107 and 108. The pressure generated is greater than a standard counterpulsation balloon system.

Figure 12:
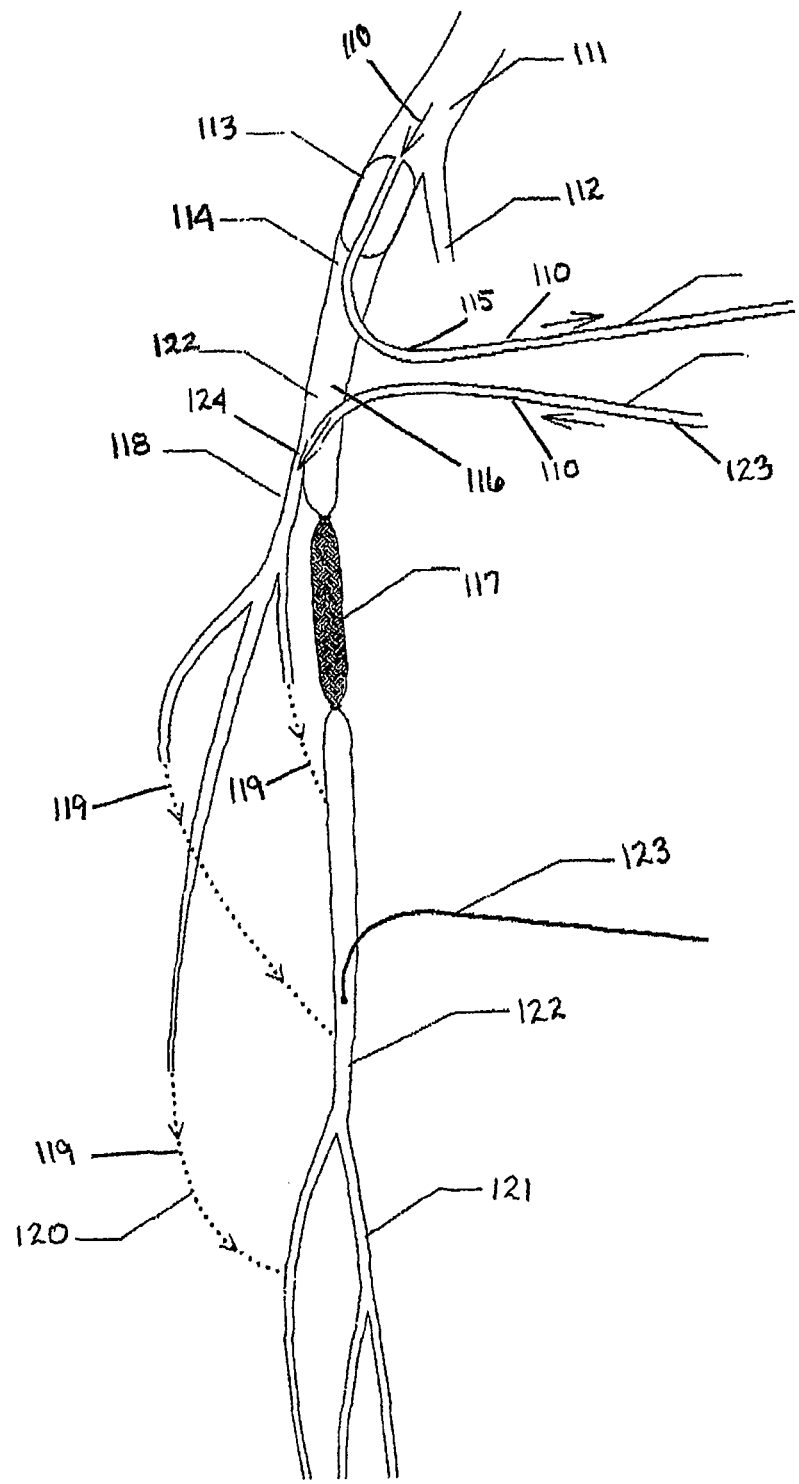
FIG. 12 is a schematic plan view of a system in accordance with certain embodiments and shows a design where the lower limb of a sheep has been rendered ischaemic by ligature. The area between the external liliac and the profunda has been hyperperfused.

FIG. 12 shows a schematic plan view of a system in accordance with certain embodiments and is an example of the configuration used in Example 1 below. FIG. 12 is a plan view of a system for treatment of an occlusion of the superficial femoral artery 117, where the occlusion prevents or substantially prevents blood flow, which may generally be applied to other arterial occlusions. In FIG. 12, the blood flowing from the common iliac artery 111 into the external iliac artery 114 as shown by arrow 110 is diverted into outflow tubing 115 using occlusive balloon 113. The blood in outflow tubing 115 flows into an external pump (not shown), which may be extracorporeal, and may be returned from the same or a different pump and into inflow tubing 116. Inflow tubing 116 introduces the blood and fluid into the common femoral artery at a controlled flow rate and pressure hyperperfusing the area between the external iliac artery 114 and the profunda femoris artery 118. The pressure of the blood returning through inflow tubing 116 is higher than the pressure of the shown in arrows 119. The blood flow circulates into collaterals 120, popliteal artery 122 and the tibioperoneal truck 121. Pressure transducer 123 is placed distally to the occlusion of the superficial femoral artery 117 and is used to measure pressure differentials in the popliteal artery 122, before, during and after hyperperfusion. The other transducer is not shown in the figure and may be located in any other major arteries, for example, the carotid artery.

Additional pressure transducers (not shown) may be placed in other portions of the body that are remote to the treatment site, such as in the carotid artery for Example 1, to measure systemic blood pressure for comparison with the pressure at pressure transducers 123.

In some embodiments, the difference between the pressure distal to the occlusion and the systemic pressure may be expressed as a ratio of distal pressure to systemic pressure. This ratio may be from about 0 to about 0.9, such as from about 0.1 to about 0.8, about 0.2 to about 0.7, about 0.3 to about 0.6 or about 0.4 to about 0.5 prior to hyperperfusion and may increase to about 0.7 to about 1.2, such as to about 0.8 to about 1.15, about 0.85 to about 1.10, about 0.9 to about 1.05 after 60 minutes of hyperperfusion and may be about 0.85 to about 1.40, such as about 0.90 to about 1.35, about 1.0 to about 1.30, about 1.05 to about 1.25, or about 1.10 to about 1.20 after 3 hours of hyperperfusion.

Figure 13:
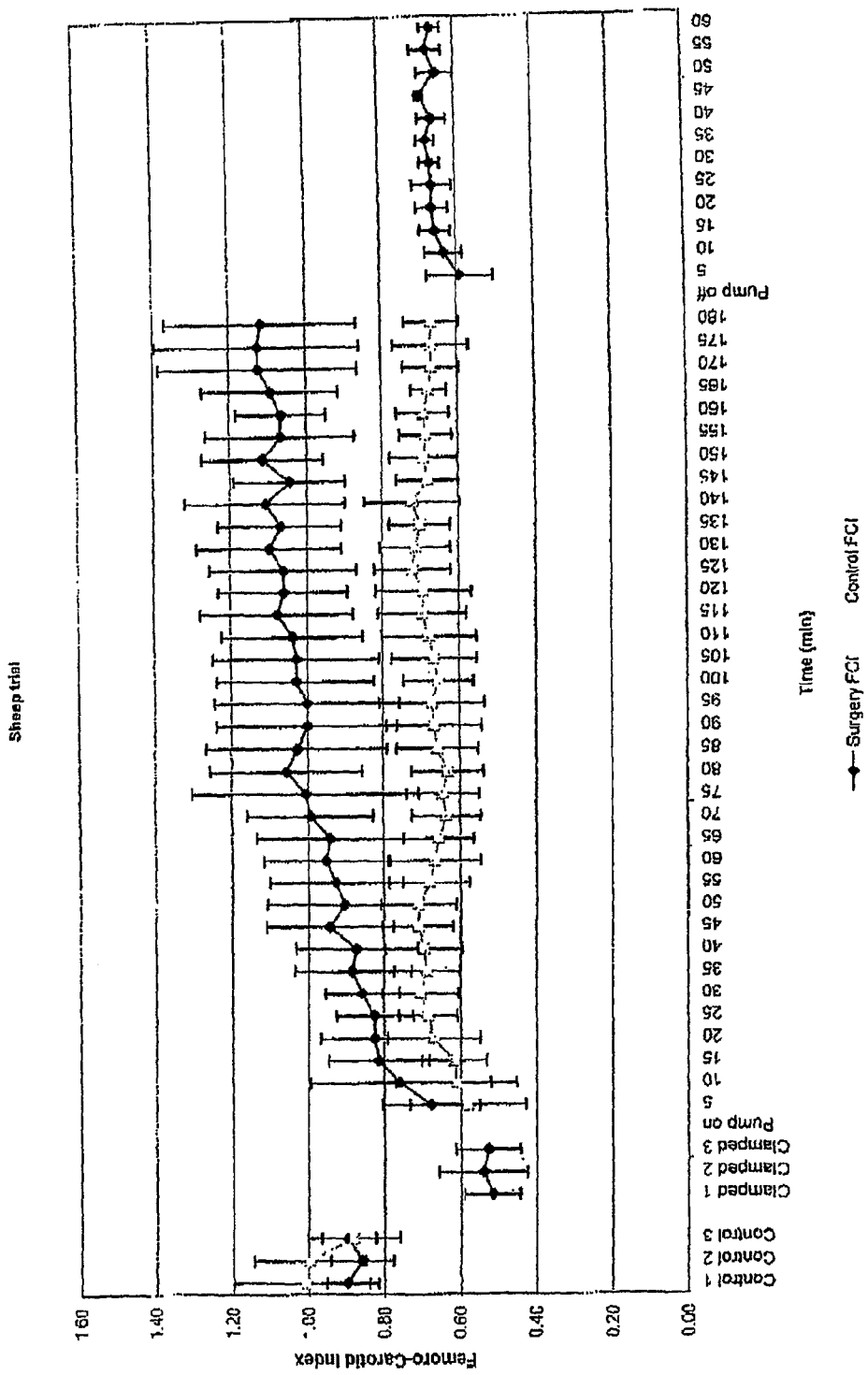
FIG. 13 is a graph showing the results of regional hyperperfusion in the hind limb as shown in FIG. 12.
Figure 14:
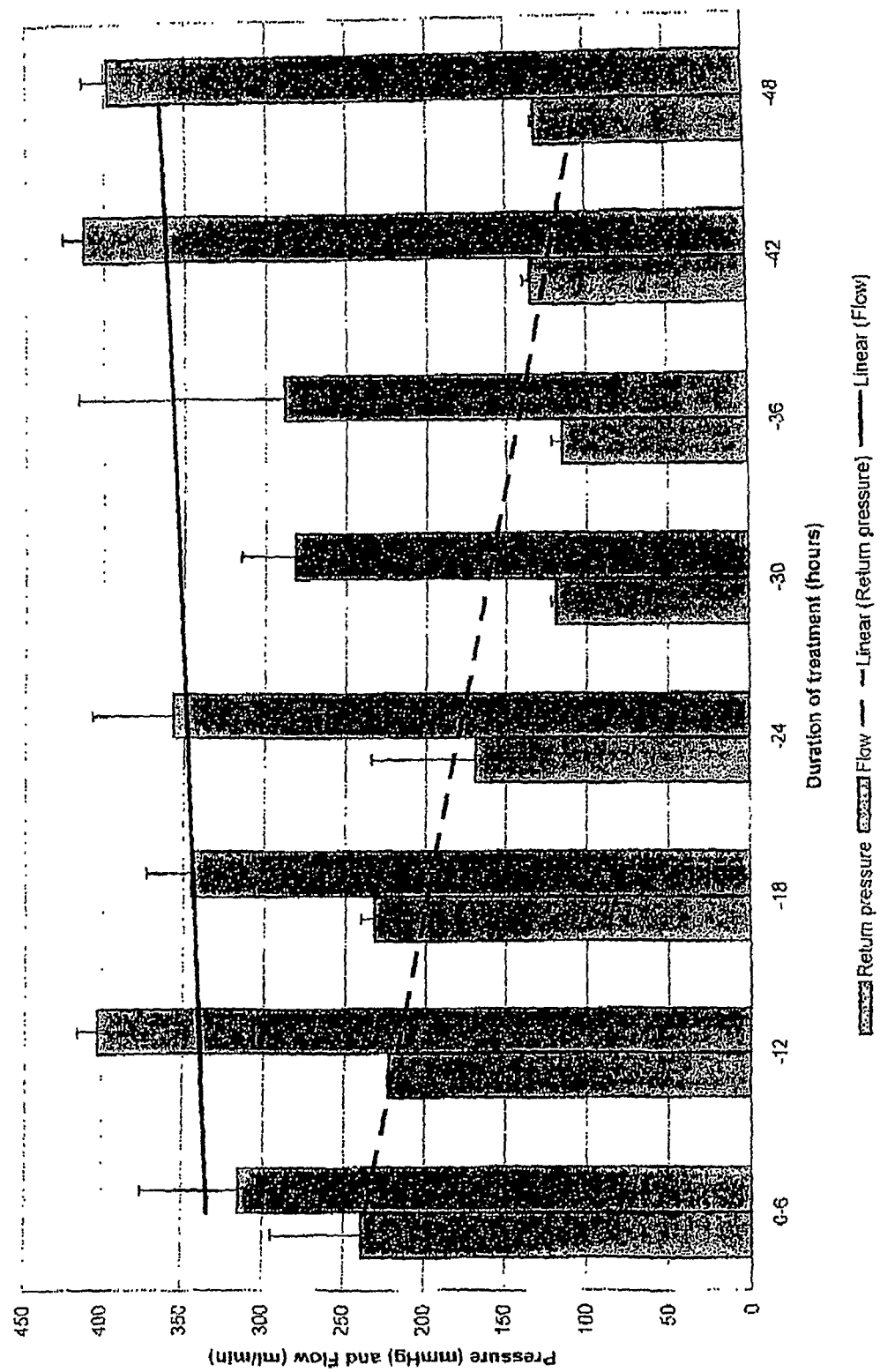
FIG. 14 is a graph showing the results of hyperperfusion in a patient over time.

FIG. 13 shows the results of the regional hyperperfusion of Example 1 in the hind limb of a sheep using a system as shown in FIG. 12. The carotid femoral index CFI is an example of the device 130 through outlet port 137 and lumen hyperperfusion index using the pressure as measured in the carotid artery using an additional pressure transducer as the systemic pressure. The hyperperfused limbs have a statistically significant increase in flow as measured by the CFI when compared with the controls. In fact, the hyperperfused limbs had increased pressure when compared to systemic blood pressure in the absence of the ligature as demonstrated by CFI's considerably greater than 1. FIG. 14 show the results of Long Term Hyperperfusion in a Human Patient as set forth in detail in Example 2 below. The results show a decrease in return pressure while maintaining similar flow rate, which indicates a reduction in peripheral resistance to blood flow and an increase in the amount of blood able to flow through the vessels into the distal portions of the leg.

Figure 15:
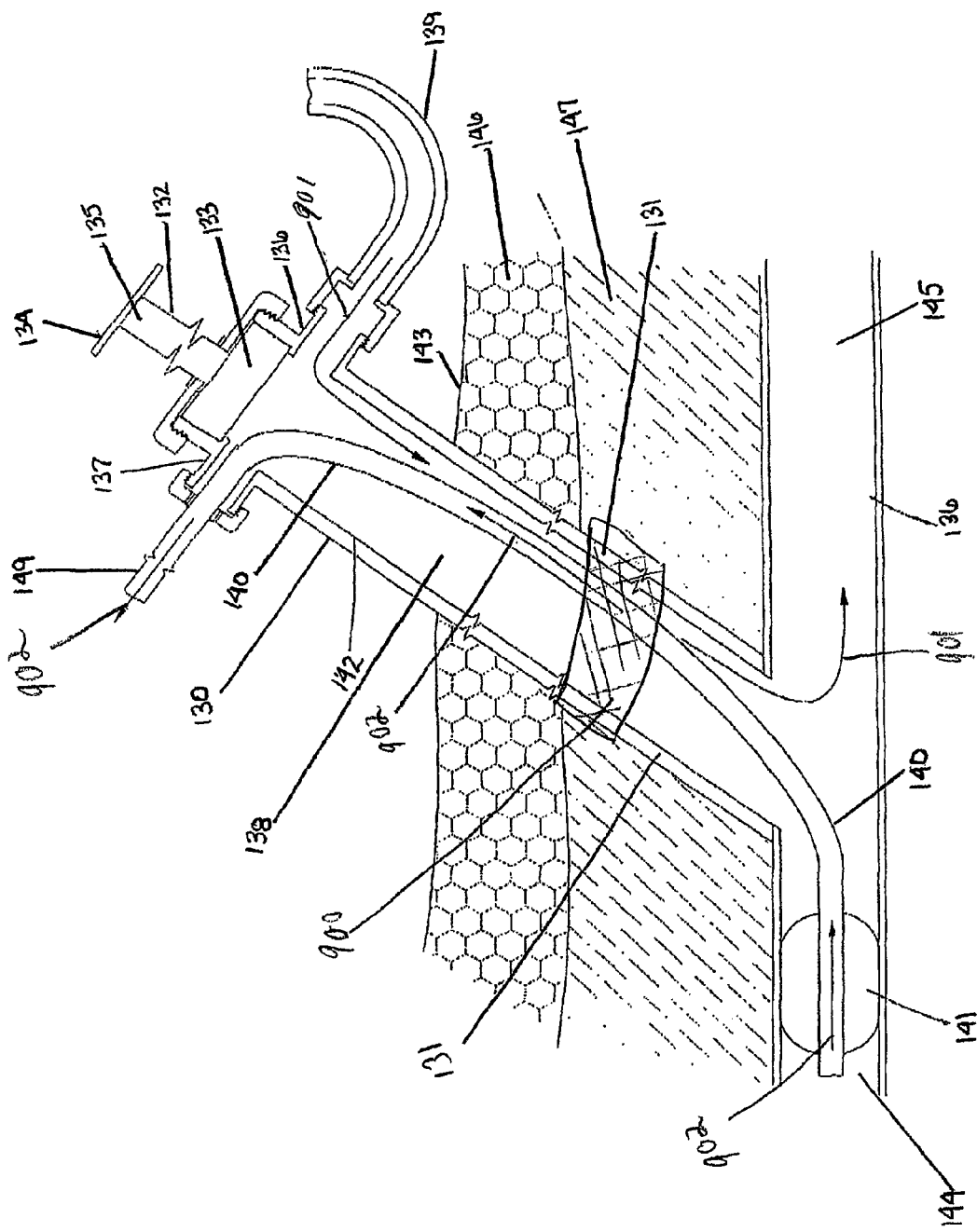
FIG. 15 is a schematic view of an access system in place for the treatment of a patient in accordance with certain embodiments.

FIG. 15 shows an embodiment of an access device 130 and system that may be used in some embodiments. Access device 130 has cannula 131 which houses lumen 138. Cannula 131 and lumen 138 access the circulatory system of the patient through skin 143, superficial fascia 146 and deep fascia 147 via arteriotomy 148. The cannula 131 has an inner surface 142. Typically, cannula 131, or the portion of cannula 131 that extends into the body, and lumen 138 is made from biocompatible materials such silicone or other suitable biocompatible elastomeric and/or thermoplastic materials or combinations thereof such as for example, polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like. In some embodiments, cannula 131 and/or lumen 138 are coated with therapeutic materials, such as antibiotics, anticoagulants, drugs or other therapeutic materials or they may be coated with materials to assist with a specific treatment, such as biocompatible lubricants, sealants or adhesives such as cyanoacrylates. In some embodiments, access device 130 may access the circulatory system at an angle other than about 90 degrees with the skin, such as at an acute angle with the skin (at the smallest angle with the skin) that is between 75 and 30 degrees, such as between 70 and 35 degrees, between 65 and 40 degrees, between 60 and 45 degrees or between 50 and 55 degrees. Access device 130 has an outflow port 137 at the external end of lumen 138 through which blood flows from vessel 136. The blood flowing through outflow port 137, as shown by arrow 902 may be at the same or different flow rate or pressure at which it was flowing through proximal portion 144 of vessel 136. Outflow port 137 may have connector means 137a for placing the lumen 138 in fluid connection with external tubing, devices or equipment, including for example, pumps, flow controllers, drug delivery devices, blood monitoring devices, such as blood pH, $S_{O2}$, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used.

Access device 130 also has inflow port 139 with inflow connection means 139a. Blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above may be supplied through inflow port 139 into lumen 138 and vessel 136 at the same or different pressure and flow rate than the fluid that is removed through outflow port 137. In some embodiments, the fluid flowing through inflow port 139 is at a higher pressure and/or flow rate than the fluid flowing through outflow port 137, the fluid flowing in proximal portion 144 of vessel 136 prior to inflation of the balloon catheter and/or the systemic blood pressure measured at a location remote to the treatment site, such as, for some embodiments, the carotid artery blood pressure. Connection means 139a may be any suitable means for providing sanitary or sterile or sterilisable communication with lumen 138, such as for example a Luer, swage, threaded or sanitary connection and may be the same as or different than connection means 137a.

Access device 130 has plunger assembly 135 having stem 132, handle 134 and head 133 which may be actuated to control access through lumen 138 through outflow port 137 and inflow port 136 via the interaction of head 133 with the internal walls 138b of lumen 138, which may form, when actuated sufficiently, a fluid tight seal. Head 133 may be constructed of any suitable biocompatible material, such as, for example, silicone or other suitable biocompatible elastomeric and/or thermoplastic materials or combinations thereof such as for example, polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like. In some embodiments, plunger assembly 135 may be actuated by application of sufficient force at handle 134 to move head 133 into or out of lumen 138. In some embodiments, the position of head 133 is controlled using an automatic control system which may be controlled based on any suitable parameter including parameters that result from analyses performed by any of the various equipment and devices mentioned above. In some embodiments, plunger assembly 135 may be locked in any position through its range of motion from fully open, whereby access to lumen 138 via outflow port 137 and inflow port 139 is unrestricted, through any number of partially open positions whereby fluid flow through outflow port 137 and inflow port 139 is partially restricted, to a completely closed position whereby fluid access to lumen 138 via outflow port 137 and inflow port 139 is completely prevented, using any suitable locking mechanism, such as a locking pin or pins. In some embodiments, the lock mechanism is sufficient to prevent back pressure of the patients normal arterial system from altering the position of head 133. In some embodiments, additional support, securing means and or reinforcing may be supplied at the arteriotomy 148 or at point at which cannula 131 penetrates skin 143 such as an artery or skin attachment cap.

Connection means may be any suitable means for providing sanitary or sterile or sterilisable communication with lumen 138, such as for example a Luer, swage, threaded or sanitary connection. In some embodiments, one or more isolation or balloon catheters 140 may be inserted into the access 138 to a proximal portion 144 of vessel 136 at which point occlusive balloon 141 may be inflated to direct blood and fluid flow from, as shown in arrow 902, proximal portion 144 of vessel 136 through outflow tubing 149 of catheter 140, thereby by substantially isolating the flow of fluid from proximal portion 144 to distal portion 145 of vessel 136. Typically, the fluid will be reintroduced to vessel 136 via inflow port 139 after the fluid or its physical, chemical or kinetic properties have been modified in some way, as shown by arrow 901. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, $CO_2$, phosphate, urea, antibodies, antibiotics or other components, such as a drug or therapeutic that is being used specifically in treatment. The isolation or balloon catheters 140 may be made from any suitable biocompatible material or materials.

FIG. 15 shows only one isolation or balloon catheter 140, but is possible to use multiple catheters and/or multiple occlusion balloons, such as 2, 3, 4, 5, 6, 7, or 8 occlusion balloons to redirect fluid flow in a vessel or system of vessels to the lumen 138 or to provide bypass of a treatment area by systemic circulation or to prevent or limit inflow to the treatment are from systemic circulation. Cannula 131 may be constructed from any suitable biocompatible material and may be rigid, semi-rigid or flexible and may have portions that are rigid or semi-rigid and portions that are flexible. In some embodiments, the external portion of cannula 131 may be sufficiently flexible to be clamped. The structure and design of the various components of the embodiment illustrated in FIG. 15 can be varied in a number of ways depending on what the device is being used to accomplish. For example, various seals and connections may be used at the inflow and outflow ports, additional inflow and/or outflow ports may be included, the shape and size of the housing and the catheter may be varied depending on the vessel size, type and location and the use for which the access device is being implemented. In some embodiments, additional support means, sealing means, securing means and/or reinforcing means, such as an artery attachment cap 157 or other suitable means, may be supplied at the arteriotomy 148 or an attachment cap 158 at the point at which cannula 131 penetrates skin 143 to further secure or adhere the cannula in place with or without a biocompatible adhesive and/or to prevent or limit opportunistic infection, irritation or inflammation at the point of penetration of the skin 143 or the vessel 136. A barrier material or cuff 900 may be included near the distal region of the access device.

This barrier or cuff may be made from a number of materials and may be attached to the housing using either mechanical or chemical means. For example, woven or felt ePTFE or Dacron may be used in certain aspects. In some aspects, as shown here, the barrier will be in the form of a band around the housing and will be made of Dacron that has been attached to the housing using a biocompatible adhesive. The cuff or barrier may provide a barrier to infection and allow tissue in growth. In some aspects, the barrier or cuff may be sufficiently wide so as to provide an adequate barrier against infection. For example, 3 to 14 mm, 4 to 12 mm, 5 to 10 mm, or 7 to 9 mm.

In certain embodiments, this device may be used to circulate blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above at higher pressures. By higher pressures in some aspects we mean anything above normal systolic pressure in the patient at the point of treatment. In certain embodiments, it may be desirable to provide access to the circulatory system where high pressure is not needed. One example is for the delivery of therapeutic modalities. In certain embodiments, it may also be desirable to switch from one pressure range to another pressure range, e.g., high pressure to low pressure, to high pressure, or low pressure to high pressure.

Figure 16:
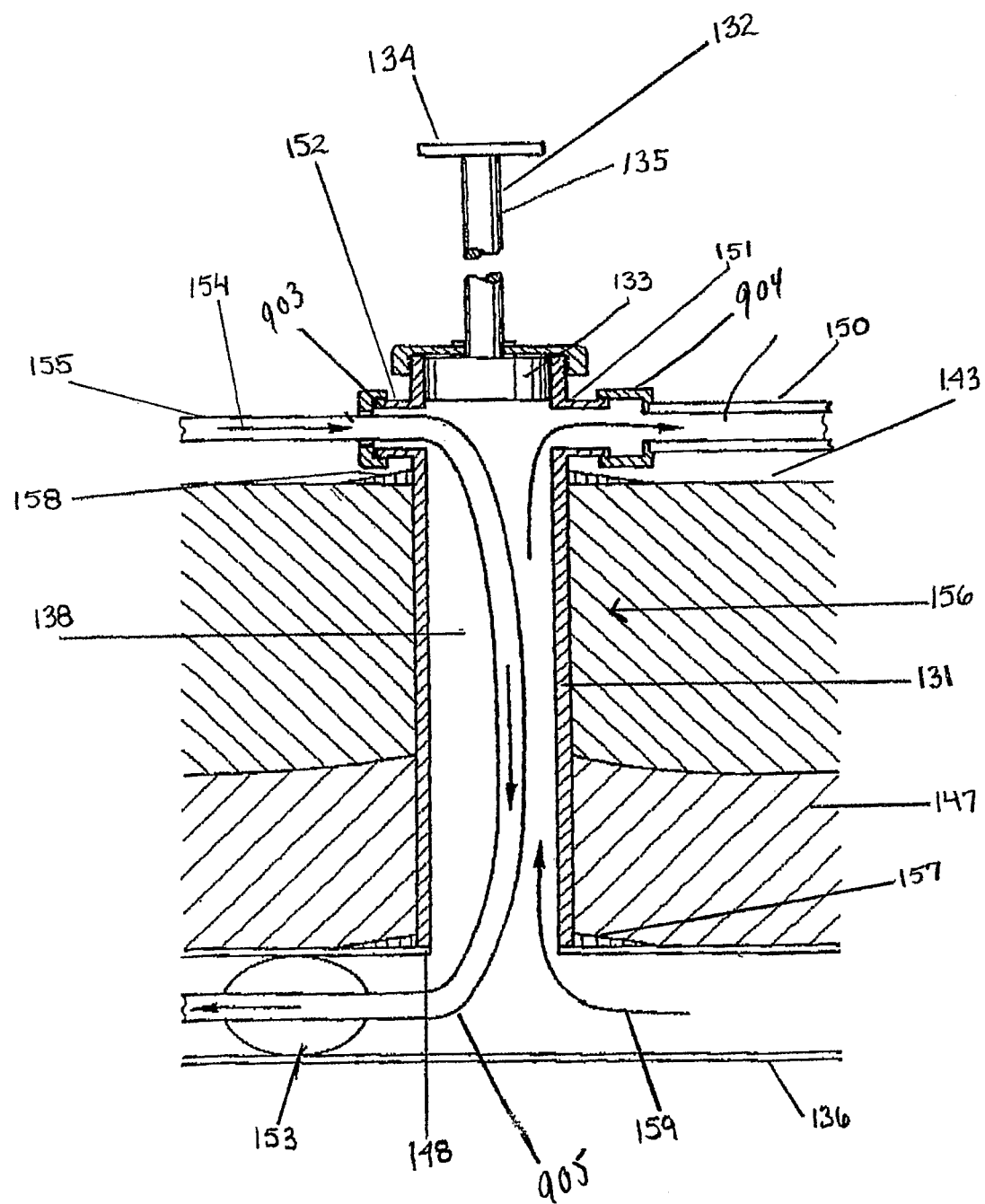
FIG. 16 is a schematic view of an access device system in place for the treatment of a patient in accordance with certain embodiments.

FIG. 16 is illustrative of certain embodiments of an access device and system according to some embodiments where the direction of flow and hyperperfusion is reversed from that shown in FIG. 15. In certain embodiments, this device may be used to circulate blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above in a portion of the circulatory system of an animal, such as a human, at increased pressures when compared to the pressure in the vessel of interest prior to use of the system. The pressure increase may be up to 50%, 200%, 300%, 10-20%, 20-49%, 51-99%, 100%, 101-199%, or 201-299% higher than the pre-treatment vessel pressure at the point of interest prior to use. In some embodiments, the pressure may be expressed as a ratio in comparison to the systemic pressure at a position remote to the treatment site as discussed above with respect to FIG. 15. In some embodiments, however, the device may be used where the pressure is not increased relative to the pre-treatment pressure, for example for delivery of various therapeutic modalities. In certain embodiments, it may also be desirable to switch from one pressure range to another pressure range, e.g., high pressure to low pressure, to high pressure, or low pressure to high pressure. In certain embodiments, it may be desirable for the perfusion pressure to be the same of pre-treatment (normotensive), or lower than pre-treatment.

Access device 156 has a cannula 131 which may extend from a position external to the skin 143 of a patient, through the skin 143, superficial fascia 146 and deep fascia 147 into vessel 136 via arteriotomy 148 and provides fluid communication through lumen 138, outflow port 151 and inflow port 152 between vessel 136 and various external equipment and devices (not shown) such as pumps, flow controllers, drug delivery devices, blood monitoring devices, such as blood pH, $S_{O2}$, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used.

Typically, cannula 131, or the portion of cannula 131 that extends into the body, and lumen 138 is made with biocompatible materials such as silicone or other suitable biocompatible elastomeric and/or thermoplastic materials or combinations thereof such as for example, polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like. In some embodiments, cannula 131 and/or lumen 138 are coated with therapeutic materials, such as antibiotics, anticoagulants or other therapeutic materials or they may be coated with materials to assist with the specific treatment, such as biocompatible lubricants, sealants or adhesives such as cyanoacrylates. In some embodiments, access device 156 may access the circulatory system at a 90 degree angle or at alternatively an angle other than about 90 degrees with the skin.

Outflow port 151 may be at the external end 138 of lumen 138 and blood and other fluid may flow from vessel 136 through lumen 138 out outflow port 151 at the same or different flow rate or pressure at which it was flowing through upstream portion of vessel 136. Outflow port 151 may have connector means 904 for connecting to outflow tubing 150, thereby placing the lumen 138 in fluid connection with external tubing, devices or equipment, including for example, pumps, flow controllers, drug delivery devices, blood monitoring devices, such as blood pH, $S_{O2}$, pulse or other blood monitoring devices, blood oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used. Connection means 151 may be any suitable means for providing sanitary or sterile or sterilisable communication with lumen 138, such as for example a Luer, threaded, swage or sanitary connection. Typically, fluid will be introduced or reintroduced to vessel 136 via inflow port 152 after the fluid or its physical, chemical or kinetic properties have been modified in some way. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess $CO$, $CO_2$, phosphate, urea, antibodies, antibiotics or other components, such as a drug or therapeutic that is being used specifically in treatment.

Inflow port 152 has inflow connection means 903 for connecting to inflow tubing 155, as shown by arrow 154, through which blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above may be supplied or reintroduced into lumen 138 and vessel 136 at the same or different pressure and flow rate than the fluid that is removed through outflow port 150. In some embodiments, the fluid flowing through inflow port 152 is at a higher pressure and/or flow rate than the fluid flowing through outflow port 151, the fluid flowing in upstream portion of vessel 136 prior to inflation of the balloon catheter and/or the systemic blood pressure measured at a location remote to the treatment site, such as, for some embodiments, the carotid artery blood pressure. Connection means 903 may be any suitable means for providing sanitary or sterile or sterilisable communication with lumen 138, such as for example a Luer, swage, threaded or sanitary connection and may be the same or different than connection means 904. In some embodiments, one or more isolation or balloon catheters 905 may be inserted into the access device 156 through inflow port 152 and lumen 138 to a downstream portion of vessel 136 at which point occlusive balloon 153 may be inflated to isolate the upstream portion from the downstream portion of vessel 136 and blood and fluid flowing through inflow port 152 may be directed through isolation catheter 905 and into downstream portion of vessel 136.

Access device 156 has plunger assembly 135 having stem 132, handle 134 and head 133 which may be actuated to control access to lumen 138 through outflow port 151 and inflow port 152 via the interaction of head 133 with internal walls of lumen 138, which may form, when actuated sufficiently, a fluid tight seal. Head 133 may be constructed of any suitable biocompatible material, such as silicone or other suitable biocompatible elastomeric and/or thermoplastic materials or combinations thereof such as for example, polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like.

In some embodiments, plunger assembly 135 may be actuated by application of sufficient force at handle 134 to move head 133 into or out of lumen 138. In some embodiments, the position of head 133 is controlled using an automatic control system which may be controlled based on any suitable parameter including parameters that result from analyses performed by any of the various equipment and devices mentioned above. In some embodiments, plunger assembly 135 may be locked in any position through its range of motion from fully open whereby access to lumen 138 via outflow port 151 and inflow port 152 is unrestricted, through any number of partially open positions whereby fluid flow through outflow port 151 and inflow port 152 is partially restricted, to a completely closed position whereby fluid access to lumen 138 via outflow port 151 and inflow port 152 is completely prevented using any suitable locking mechanism, such as for example a locking pin or pins. In some embodiments, the lock mechanism is sufficient to prevent back pressure of the patients normal arterial system from altering the position of head 133. In some embodiments, additional support means, sealing means, securing means and/or reinforcing means, such as an artery attachment cap or barrier 157 or other suitable means, may be supplied at the arteriotomy 148 or an attachment cap 158 at the point at which cannula 131 penetrates skin 143 to further secure or adhere the cannula in place with or without a biocompatible adhesive and/or to prevent or limit opportunistic infection, irritation or inflammation at the point of penetration of the skin 143 or the vessel 136.

FIG. 16 shows only one isolation or balloon catheter 153 and 905, but it is possible to use multiple catheters and/or multiple occlusion balloons, such as 2, 3, 4, 5, 6, 7, or 8 occlusion balloons to redirect fluid flow in a vessel or system of vessels the lumen 138. The structure and design of the various components of the embodiment illustrated in FIG. 16 can be varied in a number of ways depending on what the device is being used to accomplish. For example, various seals and connections may be used at the inflow and outflow ports, additional inflow and/or outflow ports may be included, the shape and size of the housing and the catheter may be varied depending on the vessel size, type and location and the use for which the access device is being implemented.

In certain embodiments, the access devices disclosed herein may be used with multiple inflow and/or outflow ports to provide additional access to a vessel for additional catheters, diagnostic devices, sampling, addition of drugs, therapeutics, nano devices, nutrients, antibiotics, anticoagulants, saline, buffers, plasma, blood or blood cells, or other suitable blood addition compounds. For example, FIGS. 17a and 17b illustrate certain embodiments of such a device.

Figure 17A:
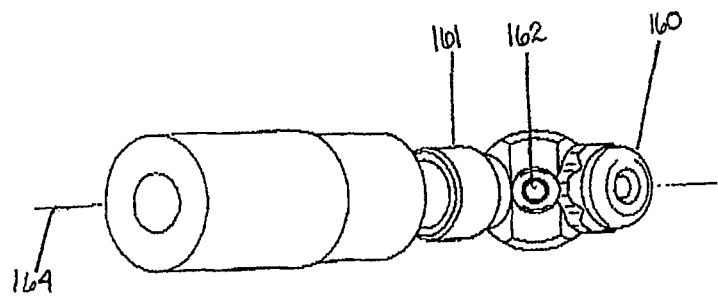
FIG. 17a is a plan view of an access system with multiple ports in accordance with certain embodiments.
Figure 17B:
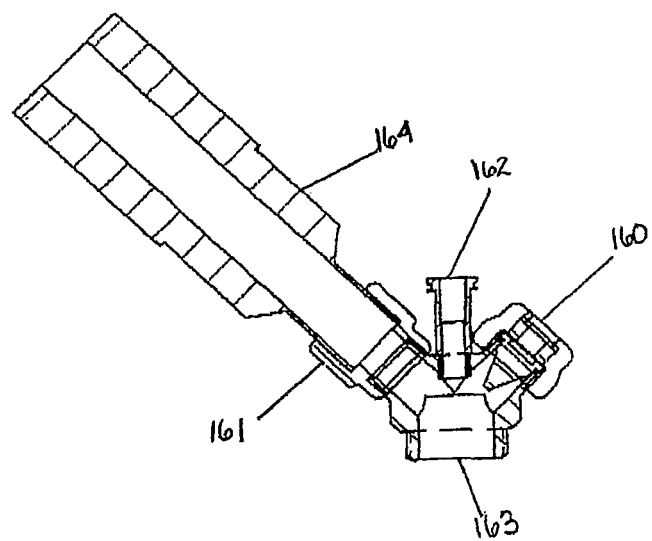
FIG. 17b is a plan view of an access system with multiple ports in accordance with certain embodiments.

FIG. 17a shows a plan top view of a device 160 and FIG. 17b shows a plan side view of the same device for use in certain embodiments having multiple access ports 160a, 161 and 162. Each access port may be used to remove blood or fluid from a vessel for further sampling, processing or diagnosing or to add any suitable blood addition compound, composition or fluid solution, such as blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above. Access port 161 is shown with a haemoreduction valve 164. Haemoreduction valve 164 may be attached using any of a variety of different connecting means such as a Luer, threaded, swage or sanitary connection and may include a silicon seal 164a. In some embodiments, access port 162 is used for supply of drip solutions such as saline, buffers or drip drug solutions or other therapeutics and in this figure it is connected using a Luer lock connection. Device 160 in FIG. 17 may be combined or attached to various other devices described herein. For example, for the devices illustrated in FIGS. 15 and 16 by removal of the plunger and other associated items in the upper portion of the device and replacing it with device 160 by connecting head 163 to the cannula. Head 163 can be attached to the access device shown in FIGS. 15 and 16 using any locking or screwing mechanisms or other know means for mechanically attaching such a device. This multiple access port device may be used for many different treatment modalities, for example, in certain embodiments it may be used as a blood pump, hyperperfusion system with catheters balloons, counterpulsation systems and/or inflation systems.

Figure 18:
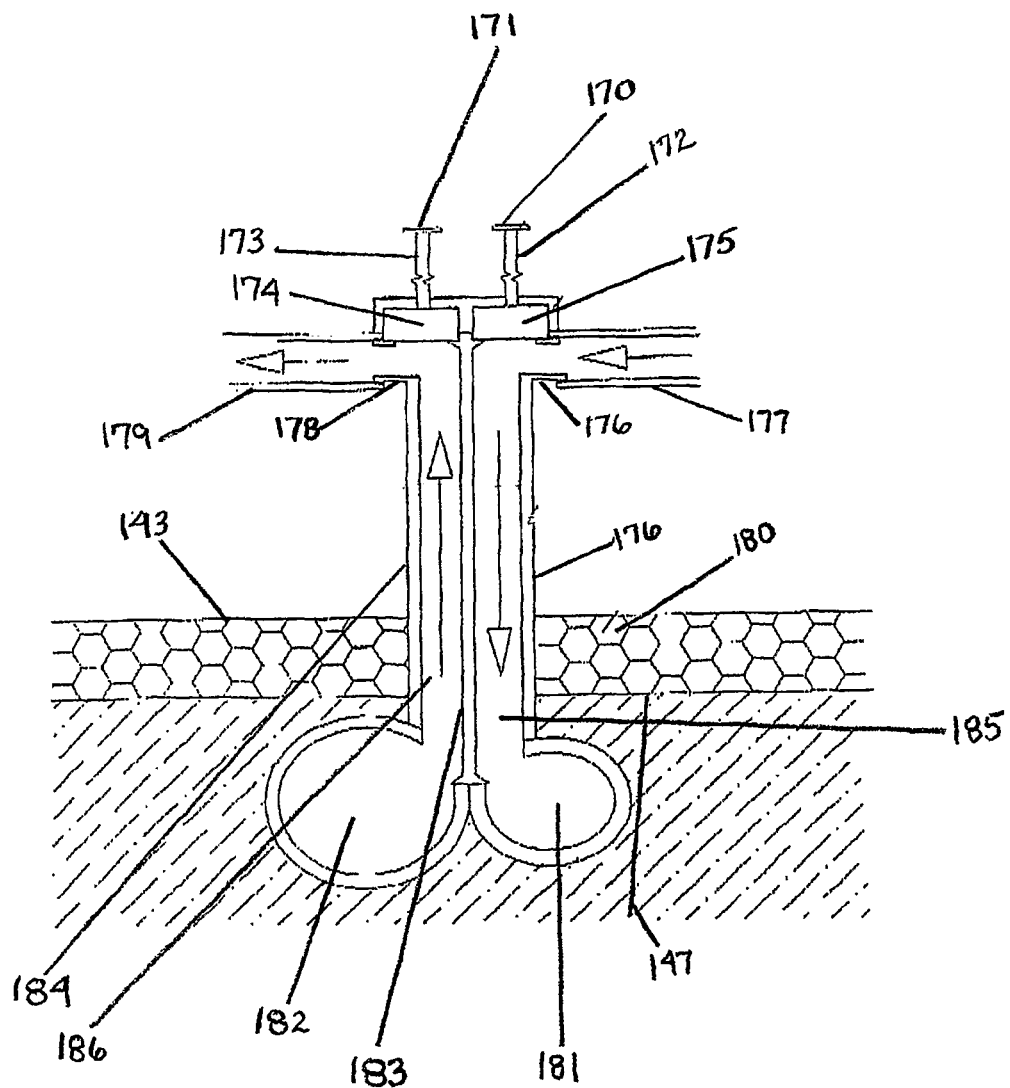
FIG. 18 is a schematic view of an access system in accordance with certain embodiments.

FIG. 18 is illustrative of an access device 184 and system that may be used in certain embodiments, especially when simultaneous arterial and venous access is desired. Access device 184 may be placed in fluid contact with one or more vessels via penetration through the skin 143, superficial fascia and deep fascia 147 and into artery 181 and vein 182 with cannula 176 having two lumens 185 and 186 which are placed in fluid contact with artery 181 and vein 182 respectively forming a fistula.

Lumens 185 and 186 are separated by lumen divide 183, which may completely or partially isolate lumens 185 and 186 from each other. In some embodiments lumen divide 183 may prevent fluid communication between lumens 185 and 186, while in other embodiments, lumen divide 183 may allow one or two way fluid communication between lumens 185 and 186. In some embodiments, lumen divide 183 may act as a filter between lumens 185 and 186 and may allow transfer of one or more components of the flowing fluid from one lumen to the other according to any suitable property of the components such as, for example, molecular weight, charge, hydrophobicity, concentration or size. In some embodiments, lumen divide 183 may be rigid or semi-rigid and may be porous, semi-porous or non-porous. In other embodiments, lumen divide 183 may be a porous, semi-porous or non-porous flexible membrane. Cannula 176 may be made of any suitable biocompatible material and may comprise a flexible, clampable portion 182.

Though shown with two lumens 185 and 186, more than two lumens, such as 3 or 4 or 5 lumens may be used in some embodiments of access device 184 and each may be separated from the others with a lumen divide 183 which may be the same or different as the other lumen divide separating the other lumens. For example, the lumen divides between lumens accessing venous blood may be porous or semi-porous among each other, while the lumen divides separating the same lumens from the lumens accessing arterial blood may be non-porous. Each lumen divide may independently be porous, semi-porous or non-porous and rigid, semi-rigid or flexible. It should be understood that combinations of the types of lumen divides are specifically contemplated.

In access device 184 blood flows from vein 182 through lumen 186 and out outflow port 178 which may be located at the external end of lumen 186 and blood and other fluid may flow from vein 182 through lumen 186 out outflow port 178 at the same or different flow rate or pressure at which it was flowing through an distal portion of vein 182. Outflow port 178 may have connection means for connecting to outflow tubing 179, thereby placing the lumen 186 in fluid connection with external tubing, devices or equipment, including for example, pumps, flow controllers, drug delivery devices, blood monitoring devices, such as blood pH, SO2, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used.

Connection means may be any suitable means for providing sanitary or sterile or sterilisable communication with lumen 186, such as for example a Luer, threaded, swage or sanitary connection. Typically, the fluid will be introduced or reintroduced into artery 181 via inflow port 176 after the fluid or its physical, chemical or kinetic properties have been modified in some way. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, CO2, phosphate, urea, antibodies, antibiotics or other components, such as a drug or therapeutic that is being used specifically in treatment.

Inflow port 176 has inflow connection means for connecting to inflow tubing 177 through which blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, blood cells and/or combinations of more than one of the above may be supplied or introduced into lumen 185 and artery 181 at the same or different pressure and flow rate than the fluid that is removed through outflow port 179. In some embodiments the fluid flowing through inflow port 176 into external end of lumen 185 is at a higher pressure and/or flow rate than the fluid flowing through outflow port 179, the fluid flowing in vein 182, the fluid flowing in a distal portion of artery 181 prior to inflation of any balloon catheters and/or the systemic blood pressure/flow rate measured at a location remote to the treatment site, such as, for some embodiments, the carotid artery blood pressure. Connection means at the out flow port may be any suitable means for providing sanitary or sterile or sterilisable communication with lumen 185, such as for example a Luer, swage, threaded or sanitary connection and may be the same or different than connection means for the in flow port. In some embodiments, one or more isolation or balloon catheters (not shown) may be inserted into the access device 184 through inflow port 176 or outflow port 179 and lumens 185 and 186 respectively to a portion of artery 181 and/or vein 182 respectively at which point the occlusive balloon may be inflated to isolate a portion of artery 181 and/or vein 182.

Access device 184 has plunger assemblies 170 and 171 having stems 172 and 173 and heads 175 and 174 each of which may be independently actuated to control access to lumens 185 and 186 through inflow port 176 and outflow port 179 via the interaction of heads 175 and 174 with the internal walls, which may form, when actuated sufficiently, a fluid tight seal. Heads 175 and 174 may be constructed of any suitable biocompatible material, such as silicone or other suitable biocompatible elastomeric or thermoplastic materials or combinations thereof such as silicone or other suitable biocompatible elastomeric and/or thermoplastic materials or combinations thereof such as for example, polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like.

In some embodiments, plungers 170 and/or 171 may be actuated by application of sufficient force at the handles to move plungers 170 and/or 171 into or out of lumens 185 and 186. In some embodiments, the position of plungers 170 and/or 171 is controlled using an automatic control system which may be controlled based on any suitable parameter including parameters that result from analyses performed by any of the various equipment and devices mentioned above. In some embodiments, plungers 170 and/or 171 may be locked in any position through their range of motion from fully open whereby access to lumens 185 and 186 via inflow port 176 and outflow port 179 is unrestricted, through any number of partially open positions whereby fluid flow through inflow port 176 and outflow port 179 is partially restricted, to a completely closed position whereby fluid access to lumens 185 and 186 via inflow port 176 and outflow port 179 is completely prevented using any suitable locking mechanism, such as a locking pin or pins.

In some embodiments, the locking mechanism is sufficient to prevent back pressure of the patient's normal circulatory system from altering the position of heads 175 and 174. In some embodiments, additional support means, sealing means, securing means and/or reinforcing means, such as an attachment cap or other suitable means, may be supplied at the point at which cannula 176 penetrates artery 181 and/or vein 182 or at the point at which cannula 176 penetrates skin 143 to further secure or adhere the housing in place with or without a biocompatible adhesive and/or to prevent or limit opportunistic infection, irritation or inflammation at the point of penetration of the skin 143, artery 181 or vein 182

The device is also capable of accessing an artery or vein individually or providing alternative access between an artery or vein. In the configuration shown, two plungers are shown, however in other aspects the access device can be configured such that only one plunger is needed and in other embodiments such that 3, 4 or 5 plungers are needed.

Figure 19:
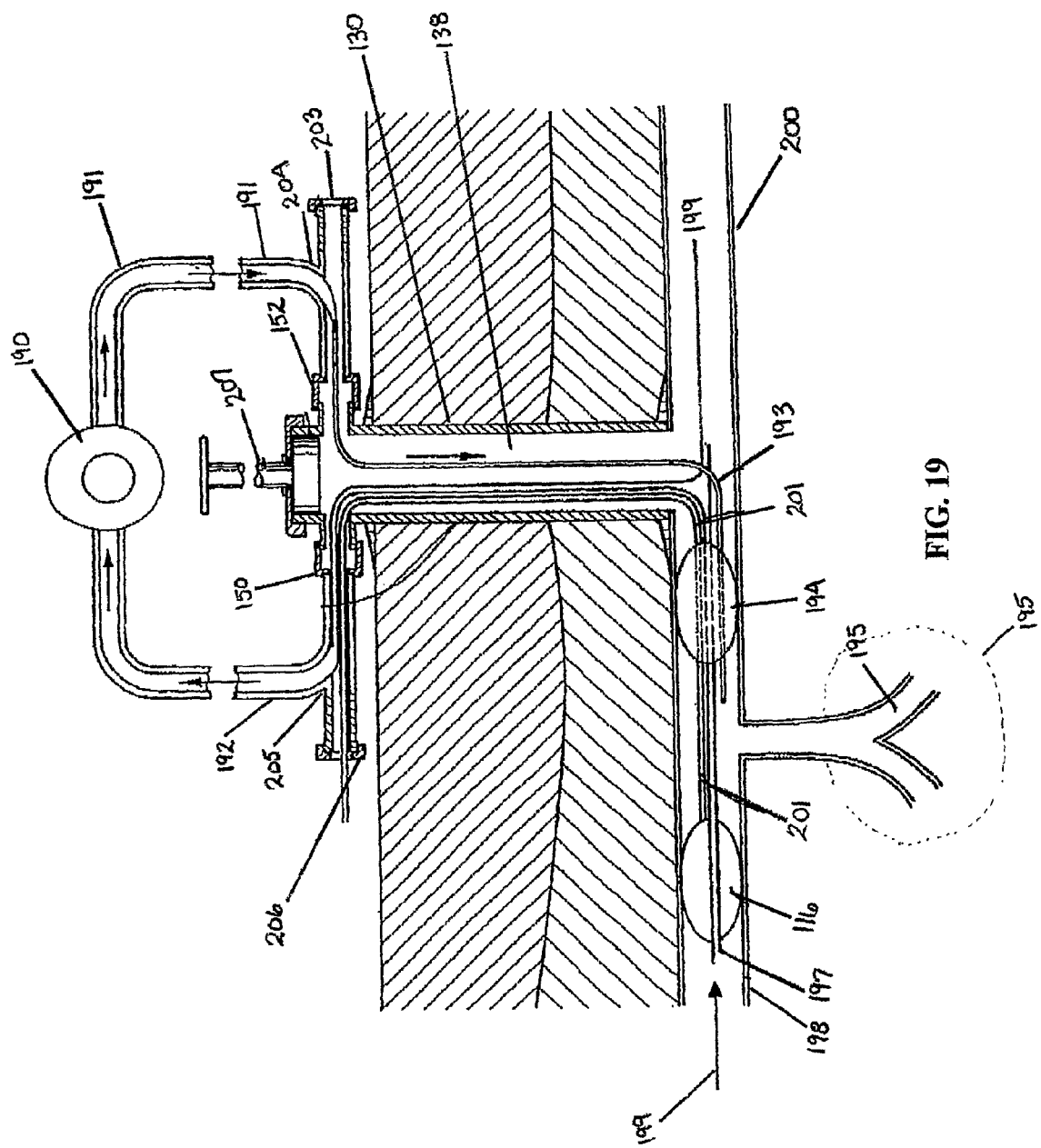
FIG. 19 is a schematic view of an access system in place for the treatment of a patient in accordance with certain embodiments.

FIG. 19 is illustrative of certain embodiments disclosed herein. FIG. 19 shows a schematic of a system that may be used to segment or isolate a portion of the circulatory system providing for treatment of the isolated area. Access device 130 may be placed in fluid communication with vessel 200 via penetration of cannula 130 through skin 143, superficial fascia 146 and deep fascia 147 into vessel 200. Access device 130 is similar to the device shown in FIG. 16, with the following changes to the tubing configurations and the catheter configurations. The device of FIG. 19 has access ports 203 and 204 attached to inflow port 152, and access ports 205 and 206 connected to outflow port 151. Isolation catheter 197 shown with inflated isolation or occlusive balloon 196 directs fluid flowing in proximal portion 198 of vessel 200 through isolation or occlusive balloons 196 and 194 to two different places: distal portion 199 of vessel 200 and through lumen 138, outflow port 151 and into outflow tubing 192, thereby bypassing isolated area 195. Isolation or occlusive balloon 194 may be inflated in a position proximal to access device 130 and distal to inflated isolation or occlusive balloon 196, thereby forming isolated area 195. Isolated area 195 may be a portion of the circulatory system or may be an organ or a portion of an organ which may then be hyperperfused. In summary, the aim of the embodiments illustrated are to isolate vessel 195 using balloons 116 and 194; to allow continuous infusion to distal part; and to use blood from proximal vessel 199 to distal part; 4—to hyperperfuse vessel 195.

The fluid flowing thorough outflow tubing 192 may be connected to additional tubing, equipment and devices such as pumps, flow controllers, drug delivery devices, blood monitoring devices, such as blood pH, $S_{O2}$, pulse or other blood monitoring devices, blood oxygenators, such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable devices and then may be pumped through pump 190 and into inflow tubing 191. In these devices or equipment the fluid may be monitored and/or sampled, may have its chemical, physical or kinetic properties modified and may have various substances added to and/or removed from it in accordance with a specific treatment regimen and according to the individual device or devices used. In some embodiments, the fluid flowing into inflow tubing 191 may be blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above.

Inflow tubing 191 may also be connected to additional tubing, equipment and devices as identified above and then sent through isolation or occlusive catheter 193 and occlusive balloon 194 into isolated area 195 at the same or different pressure and flow rate than the fluid that is removed through outflow port 151. Typically, the fluid in catheter 193 will have had its physical, chemical or kinetic properties modified in some way when compared to the fluid in proximal portion 198 of vessel 200. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, $CO_2$, phosphate, urea, antibodies, antibiotics or other components, such as a drug or therapeutic that is being used specifically in treatment. In some embodiments, the fluid flowing through catheter 193 is at a higher pressure and/or flow rate than the fluid flowing through outflow port 150, the fluid flowing in proximal portion 198 of vessel 200 prior to inflation of any balloon catheters and/or the systemic blood pressure measured at a location remote to the treatment site, such as, for some embodiments, the carotid artery blood pressure. Catheter 201 directs fluid flowing from proximal portion 198 through occlusive balloon 194 and lumen 138 and out access port 206. The fluid may then be directed to additional tubing, equipment and devices such as pumps, flow controllers, drug delivery devices, blood monitoring devices, such as blood pH, $S_{O2}$, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable devices and then it may or may not be returned via access port 204 or access port 203. In some embodiments, catheter 201 provides for diagnostic information about, and samples of, the blood flowing in proximal portion 198 of vessel 200, i.e. information about the blood prior to entering the treatment area.

Access port 203 provides access for return of fluid from catheter 201 or for addition of blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above into distal portion 199 of vessel 200. The drugs or other therapeutic agents can be introduced at 203 and would go down 199.

Figure 20:
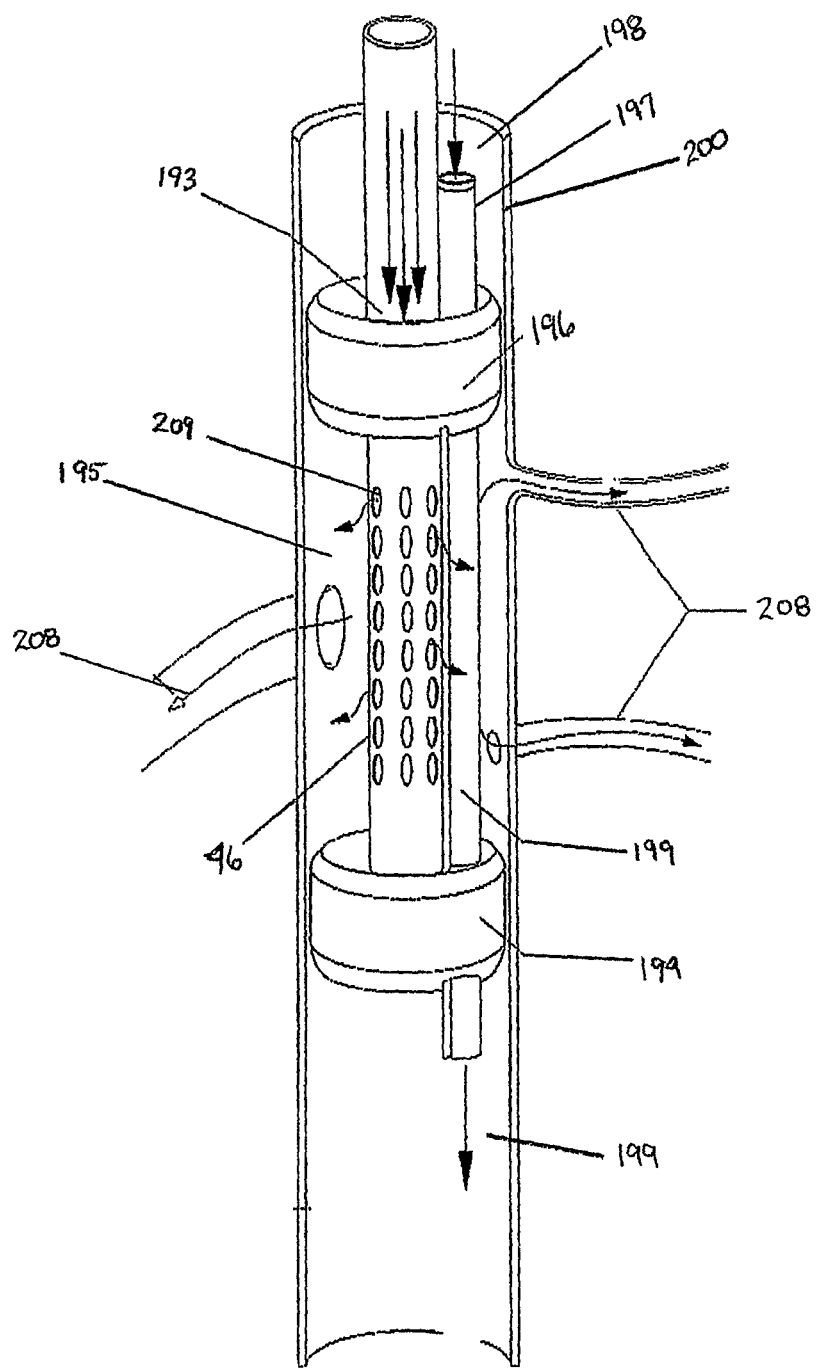
FIG. 20 is a detailed schematic view of a portion of the access system shown in FIG. 19.

FIG. 20 is a schematic enlargement of a portion of an embodiment of a balloon catheter system that may be used with the system in FIG. 19. Isolation balloons 194 and 196 have been inflated, thereby isolating the target area or target organ arterial inflows 208 from vessel 200. Catheter 193 directs fluid from the external pump, equipment and devices through the holes 209 of terminal end 193a of catheter 193 thereby infusing and/or hyperperfusing the target organ via target area or target organ arterial inflows 208. Holes 209 may be any suitable shape and size and may be varied depending on the intended use, operating pressures and flow rates required and other physical and chemical parameters.

Unlike the system in FIG. 19, in the instant system there is no catheter 201 shown and catheter 197 only directs fluid flowing in vessel 200 from proximal portion 198 to distal portion 199 and does not direct fluid out of the vessel 200 through an outflow port. In addition, fluid flowing in catheter 193 is flowing in the same direction as that in catheter 197 and thus is accessing the isolated area 195 from a different direction than in FIG. 19. It should be understood that the system in FIG. 20 may be modified to include these.

Figure 21:
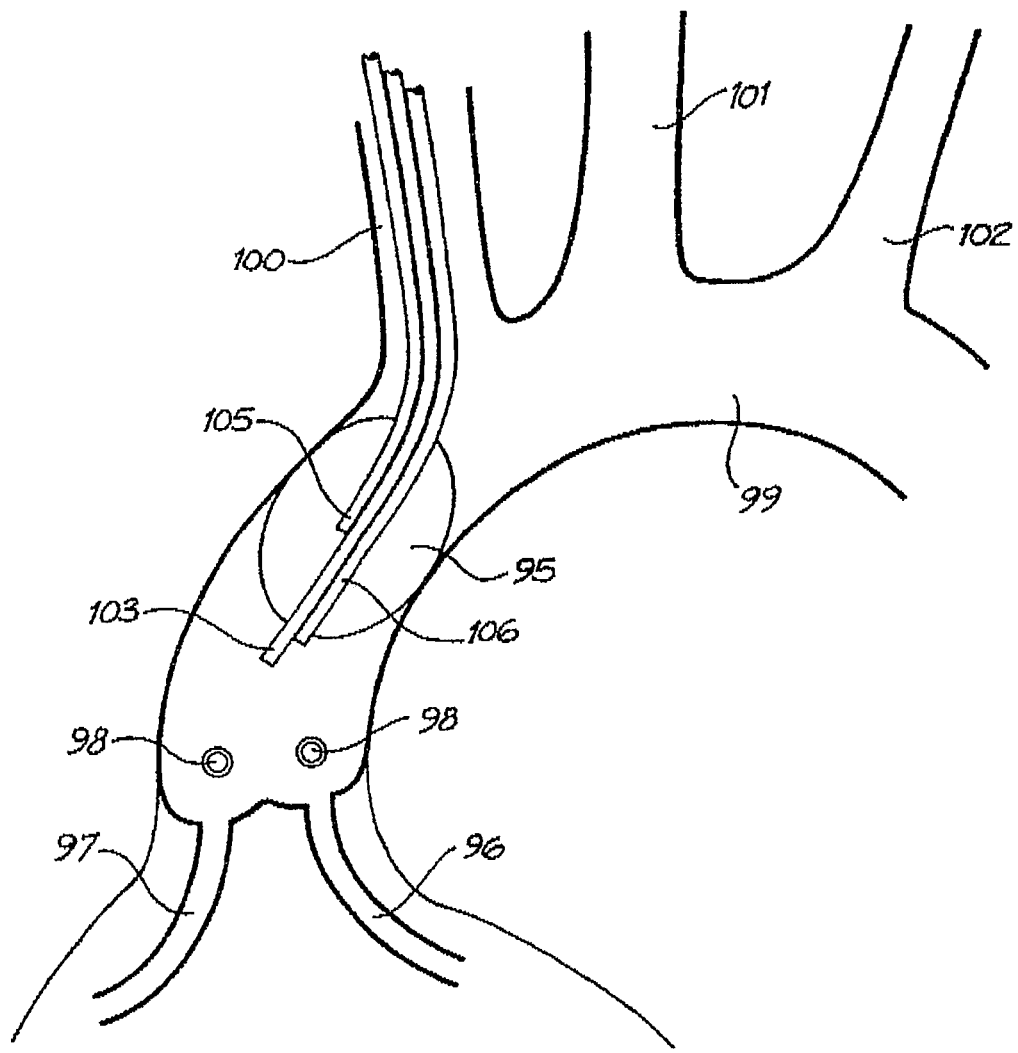
FIG. 21 is a schematic view of a catheter/balloon system in accordance with certain embodiments.

FIG. 21 shows a schematic of a system that may be used to segment or isolate a portion of the heart to permit cardiac hyperperfusion using counterpulsation systems and methods. These systems and methods also permit, if desired, delivery of blood, other fluids, drugs or drug solutions, anticoagulants, antibiotics, contrast fluids, diagnostic fluids, therapeutics, nutrients, saline, buffers, plasma, synthetic or natural blood products or factors, antibodies, blood cells and/or combinations of more than one of the above to the treated area with greater flexibility then prior art systems and methods. These substances or modalities can be introduced into the treated area at the same time that hyperperfusion is being used, before or after hyperperfusion or combinations thereof. In certain embodiments, disclosed herein use of counterpulsation systems or methods permits treatment of the isolated area and reduce the symptoms of angina pectoris, and other ischemia-related diseases, as well as other peripheral vascular diseases, by increasing coronary blood flow in ischemic areas of the heart being treated. In other words, when the balloon or balloons are inflated, as disclosed herein the systems and methods disclosed create an artificially higher pressure in the aorta, which results in greater perfusion through the coronary arteries. When the balloon or balloons deflate, just before the aortic valve opens, the pressure and volume of the aorta decrease, relieving some of the hemodynamic burden on the heart. These physiologic responses improve the patient's cardiac output and coronary circulation, improving hemodynamics.

Figure 22:
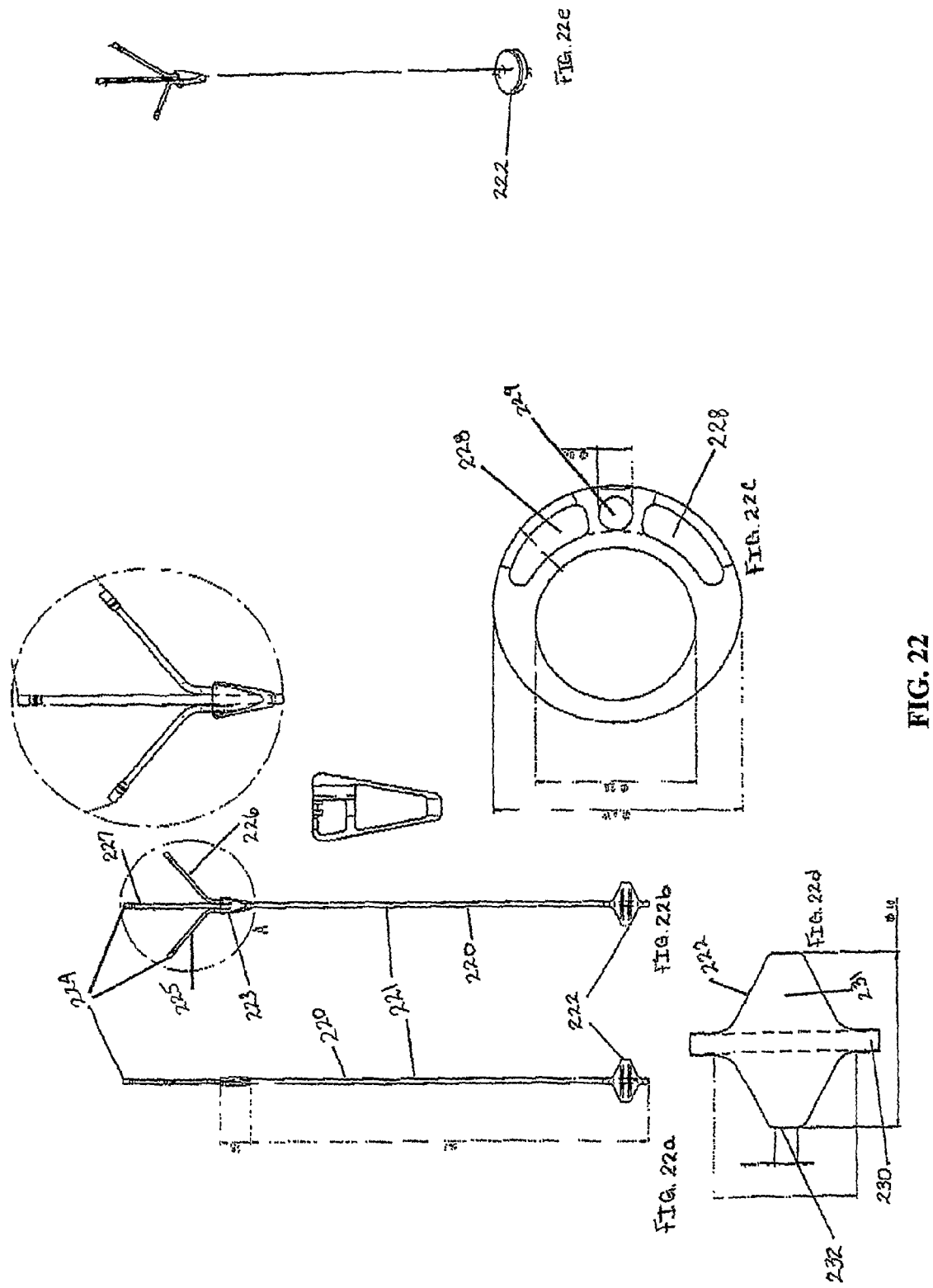
FIG. 22a-e are various schematic views of a catheter used in accordance with certain embodiments and also used in the system shown in FIG. 21.

FIGS. 22a-e are schematic enlargements of an embodiment of a balloon catheter system that may be used in embodiments including in the embodiment of FIG. 21. FIG. 22a shows a side view of catheter 220, having isolation or occlusive balloon 222, fluid flow lumen 221 having flow through end 233 and securing guide and support means 223. When placed into or through an inflow or an outflow port, catheter 220 may include a suitable sealing means for ensuring a fluid seal at the port which may or may not be placed below securing guide and support means 223 on an outer portion of flow lumen 221. Alternatively, securing guide and support means 223 may be configured to serve as a fluid seal at an inflow or outflow port of an access device according to certain embodiments through which catheter 220 has been placed. Connection means 224 provides for connection of external tubing, equipment and devices to catheter 220, may be any suitable connection depending on the use, including, for example, Luer, swage, threaded and sanitary connections. Catheter 220 and isolation or occlusive balloon 222 may be constructed of any suitable material, for example a biocompatible material such as silicone or other suitable biocompatible elastomeric and/or thermoplastic materials or combinations thereof such as polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like.

FIG. 22B is a front view of catheter 220, showing fluid flow lumen 221 with flow through end 233, isolation or occlusive balloon 222, securing guide and support means 223, pressurization port 225, pressure transducer port 226 and fluid flow port 227. Pressurization port 225 is in fluid communication with isolation or occlusive balloon 222 and may be used to inflate and deflate isolation or occlusive balloon 222 with an inert gas, such as, for example, helium, using a pressurization control system (not shown) connected to connection means 224. Isolation or occlusive balloon 222 may be alternately inflated and deflated according to any suitable isolation scheme using a pressurization control system, and, for example may be used in counterpulsation catheterization, where balloon 222 is inflated during diastole and deflated during systole. Pressure transducer port 226 is in fluid communication with isolation or occlusive balloon 222 and provides access to the pressure transducer lumen 229 to measure and/or control the pressure in isolation or occlusive balloon 222. Fluid flow port 227, provides access to fluid flow lumen 221 via connection means 224 and may be used to remove or add fluid such as for example blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, blood cells and/or combinations of more than one of the above from or to a vessel.

FIG. 22C is an end view of a slice through catheter 220 below securing guide and support means 223 and above isolation or occlusive balloon 222 showing fluid flow lumen 221, pressurization control lumens 228 and pressure transducer lumen 229. Pressurization control lumens 228 may be used in conjunction with pressurization port 225 from FIG. 22B to provide fluid communication access to isolation or occlusive balloon 222 for inflation and deflation of isolation or occlusive balloon 222 using an inert gas, such as helium. Such inflation and deflation may be controlled using any suitable manual or automatic control system. Pressure transducer lumen 229 may be used in conjunction with pressure transducer port 226 from FIG. 22B and may be used to monitor and provide information about the pressure, such as the instantaneous pressure, the average pressure, and the pressure profile during inflation, deflation and/or hold, in isolation or occlusive balloon 222 and may be used in conjunction with a manual or automatic control system to control the pressure in isolation or occlusive balloon 222 via access port 225 and pressurization control lumen 228, such as to provide feedback signals to such a system.

FIG. 22D is an exploded schematic view of isolation or occlusive balloon 222, in its deflated state. Isolation or occlusive balloon 222 may have one or more rigid or semi-rigid supports 230 to assist in positioning, placement and support of isolation or occlusive balloon 222 and balloon wall 231, when in the inflated or deflated state. Balloon wall 231 expands under pressure supplied via inflation/deflation port 232 in fluid communication with the pressurization control lumens 228, shown in FIG. 22C, and pressurization port 225 shown in FIG. 22B. Balloon wall 231 may be constructed from any suitable biocompatible material that is sufficiently elastic to sufficiently expand and contract when exposed to appropriate pressures, to accomplish the desired isolation or occlusion in accordance with some embodiments. Such biocompatible materials may include silicone or other suitable biocompatible elastomeric and/or thermoplastic materials or combinations thereof such as for example, polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like. In some embodiments, when inflated, isolation or occlusive balloon 222 may appear as shown in FIG. 22E.

Figure 23:
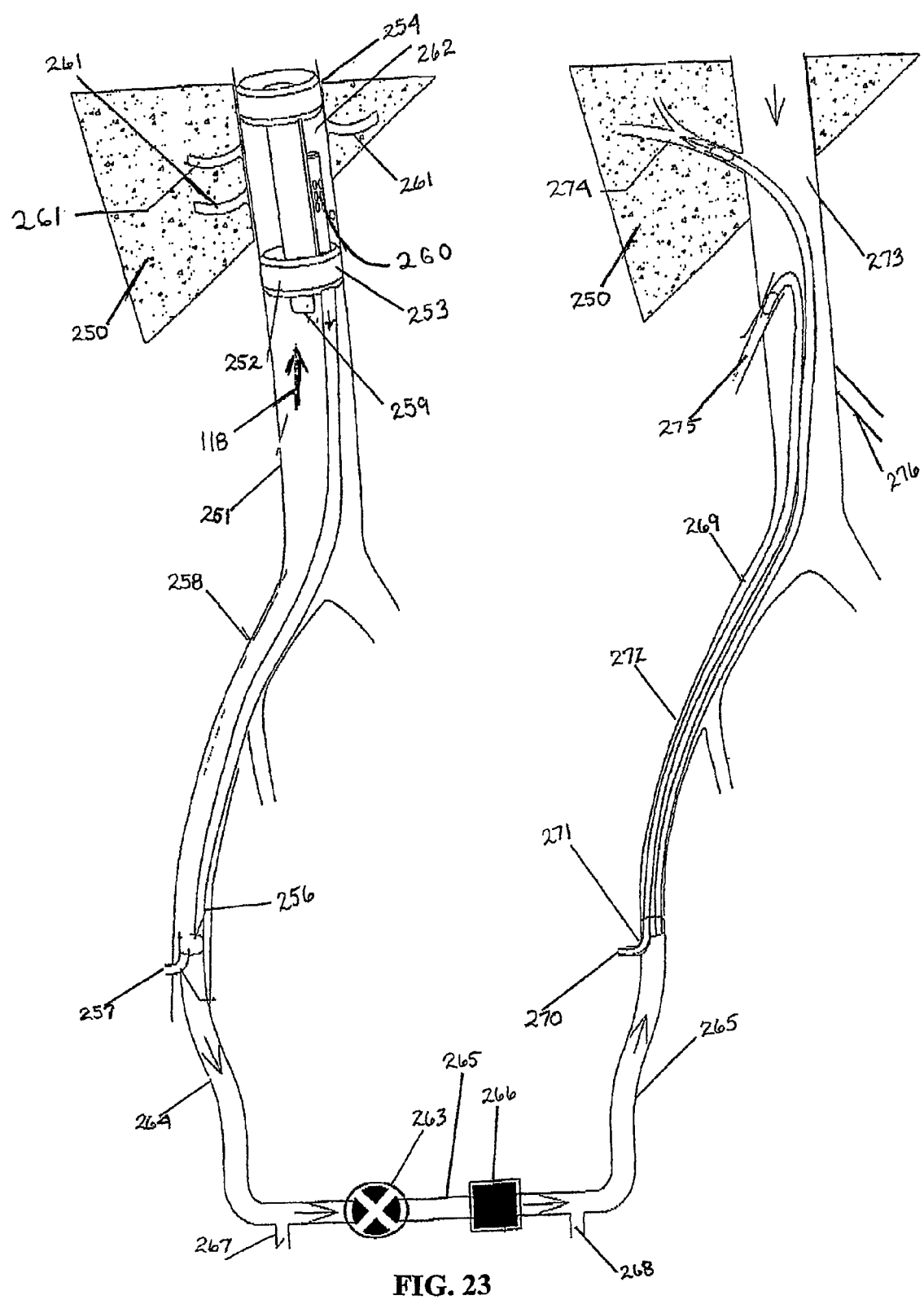
FIG. 23 is a schematic view of an arterial and venous isolation system for the liver in accordance with certain embodiments.

FIG. 23 is a schematic of a hyperperfusion system that may be used to isolate and hyperperfuse the liver 250 using an access device or devices according to some embodiments. A portion of inferior vena cava ("IVC") 251 at liver 250 may be isolated using an isolation catheter or catheters 252 having isolation or occlusive balloons 253 and 254, which may be positioned via access system 256 having access port or ports 257, by insertion at iliac vein 258. Isolation catheter or catheters 252 include flow through tube 259 and outflow catheter 260. Outflow catheter 260 may be under reduced pressure or suction relative to the pressure flowing from hepatic veins 261 into isolated portion 262 of IVC 251. Blood and fluid flowing through IVC 251 distal to isolation catheter balloons 252 and 254, via flow through tube 259 and continues towards the heart. Blood and fluid flowing into isolated portion 262 from hepatic veins 261 may be suctioned or pumped through outflow catheter 260, access system 256 and outflow port or ports 257 using pump 263 or another pump (not shown)

From outflow port or ports 257, tubing 264 transports the blood and fluid through optional equipment or devices such as pumps, flow controllers, drug delivery devices, blood monitoring devices, such as blood pH, $S_{O2}$, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device, where the blood and fluid may be monitored and/or sampled, may have its chemical, physical or kinetic properties modified and may have various substances added to and/or removed from it in accordance with a specific treatment regimen and according to the individual device or devices used.

Before or after any optional equipment or devices, outflow tubing 264 may transport the blood and fluid through a therapeutic agent concentration system 267, where therapeutics that were not consumed as part of the treatment may be captured and concentrated for reuse or disposal and where various toxic treatment by-products or degradation products may also be removed, and on to pump 263. From pump 263, tubing 265 transports the blood and fluid through optional membrane oxygenator 266, and any other optional equipment and devices such as those identified above, past infusion port 268 to the iliac artery 269 via inflow ports 270 of the same or a different access system 271 as that of access system 256. In some embodiments, such as embodiments similar to the embodiment of FIG. 18, a single access system may be used to form a fistula between the iliac vein 258 and the iliac artery 269. In other embodiments, more than one access system may be used to separately access the iliac vein 258 and the iliac artery 260. Infusion port 268 may be used to add blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above to the fluid flowing through tubing 265.

Multiple isolation or balloon catheters 272 may be fed via inflow ports 270 through the iliac artery 269, a portion of the descending aorta 273 into the coeliac trunk (not shown) and then into the hepatic artery 274 effectively isolating the gastroduodenal artery (not shown) as well. Additional isolation or hyperperfusion catheters may be used to occlude the splenic artery (not shown) and the left gastric artery (not shown) via the coeliac trunk and to occlude the superior and inferior mesenteric arteries 275 and 276 via the descending aorta 273. Each isolation or hyperperfusion catheter 272 may be used to occlude the indicated vessel and/or to supply blood and fluid from tubing 265 to the respective occluded vessel via isolation catheter 272. When blood and fluid is supplied to a vessel, the blood and fluid typically will have had its physical, chemical or kinetic properties modified in some way when compared to the fluid in the hepatic veins 261. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, $CO_2$, phosphate, urea, antibodies, antibiotics or other components, such as a drug or therapeutic that is being used specifically in treatment. In some embodiments, the fluid flowing through catheters 272 is at a higher pressure and/or flow rate than the fluid flowing through hepatic veins 261, the fluid flowing in IVC 251 prior to inflation of the isolation or occlusive balloons 253 and 254 and/or the systemic blood pressure measured at a location remote to the treatment site, such as, for some embodiments, the carotid artery blood pressure.

In some embodiments, a single isolation or balloon catheter 272 may be used in the coeliac trunk (see FIG. 25) to isolate each of the splenic artery (See FIG. 25), the left gastric artery (See FIG. 25), the gastroduodenal artery (See FIG. 25) and the hepatic artery 274. In this embodiment, the blood and fluid flowing from pump 266 through isolation or balloon catheter 272, with or without added blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above from infusion port 268, may be infused or hyperperfused into the hepatic artery and the liver via the single isolation or balloon catheter, while occluding the splenic artery, the left gastric artery and the gastroduodenal artery. By isolating the liver blood flow, the drugs and other substances may be supplied to the liver and removed from the liver prior to entering systemic circulation, thereby providing an isolated liver treatment system.

Figure 24:
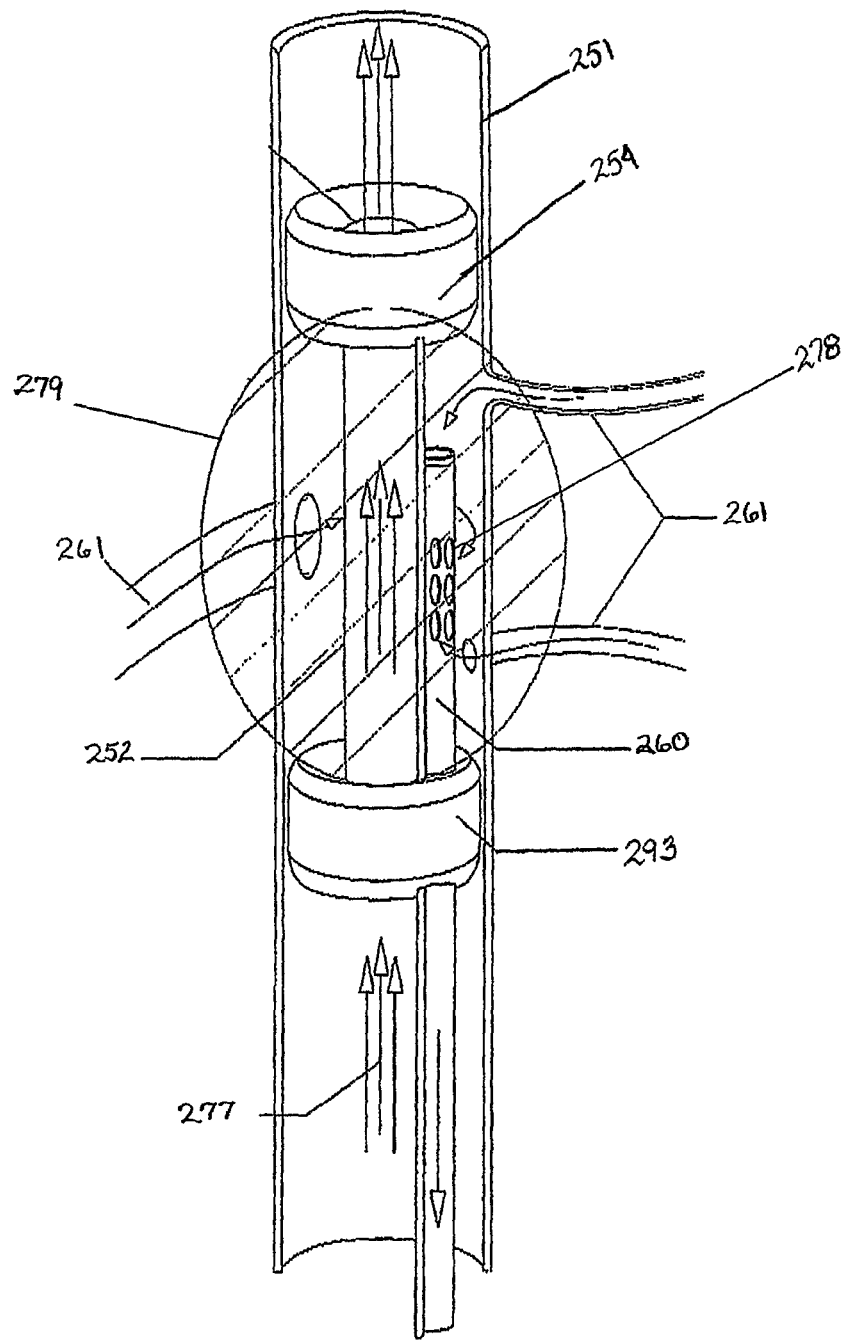
FIG. 24 is a more detailed schematic view of a portion of FIG. 23.

FIG. 24 is a detail schematic of an embodiment of isolation catheter 252 from FIG. 23 and isolation area 279. Isolation catheter 252 has isolation or occlusive balloons 253 and 254 and is positioned in IVC 251 to isolate blood entering IVC 251 from the liver 250 via hepatic veins 261 from the rest of the circulatory system. Blood flows in IVC 251 in the direction indicated by arrows 277 and through flow through tube 259 of catheter 252 and continues into the rest of the circulatory system. Blood flowing from hepatic veins 261 may be removed via holes 278 in outflow catheter 260 by placing outflow catheter 260 under suction created by an external pump 263 from FIG. 23 (not shown in this view) in conjunction with the venous pressure.

Figure 25:
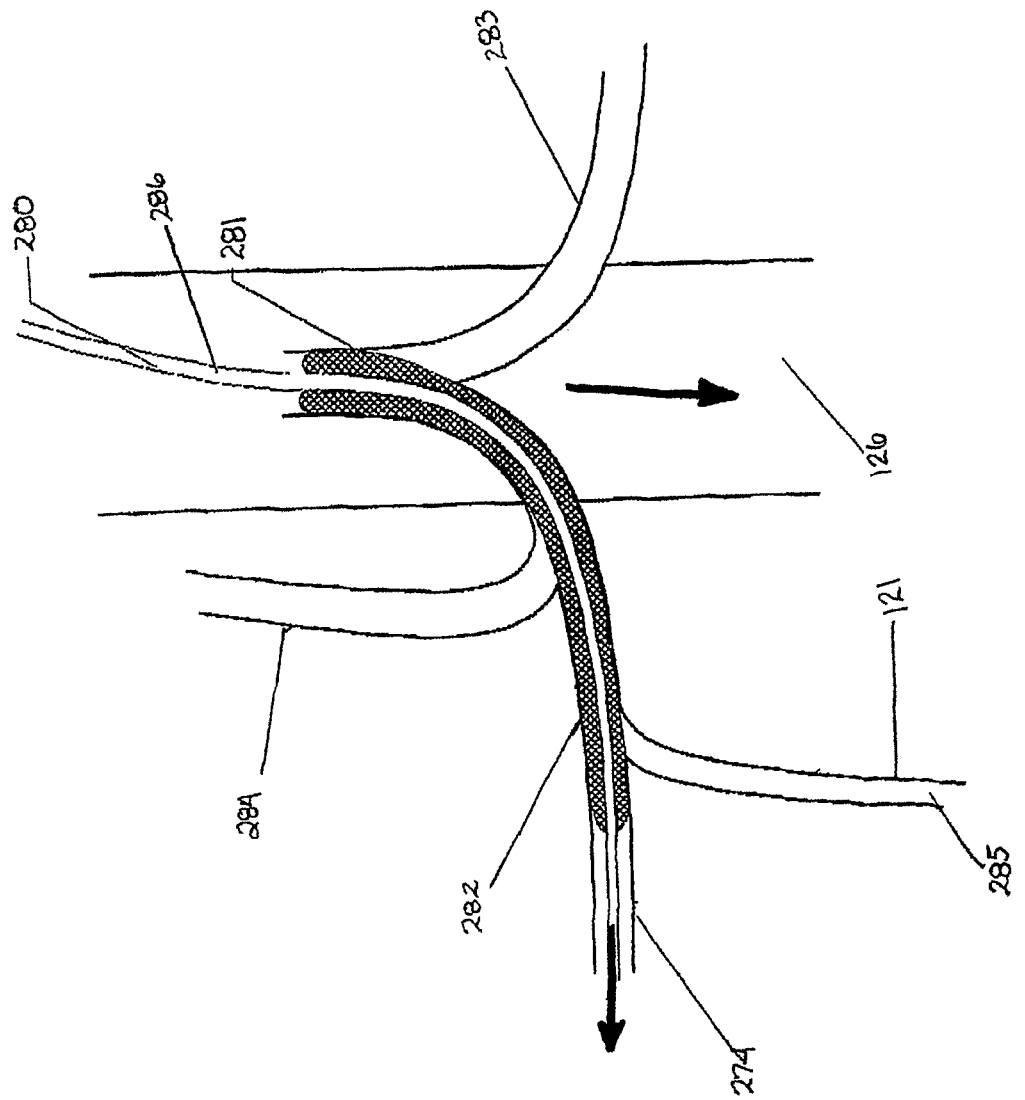
FIG. 25 is a more detailed schematic view of a portion of FIG. 23.

FIG. 25 provides a detail schematic of an embodiment 280 of an isolation catheter 272 from FIG. 23. In this embodiment, isolation catheter 280 is fed into descending aorta 273 from a point above the coeliac trunk 281 rather than from the iliac artery 269 as shown in FIG. 23. Catheter 280 has isolation or occlusive balloon 282 which extends from a point in coeliac trunk 281 that is proximal to the branches for splenic artery 283, left gastric artery 284 and gastroduodenal artery 285 into hepatic artery 274. Upon inflation of isolation or occlusive balloon 282, splenic artery 283, left gastric artery 284 and gastroduodenal artery 285 are isolated and inflow catheter 286 may infuse or hyperperfuse the blood and fluid flowing from pump 263 (See FIG. 23), with or without added blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above of the above from infusion port 268 (see FIG. 23) into the hepatic artery and the liver.

Figure 26:
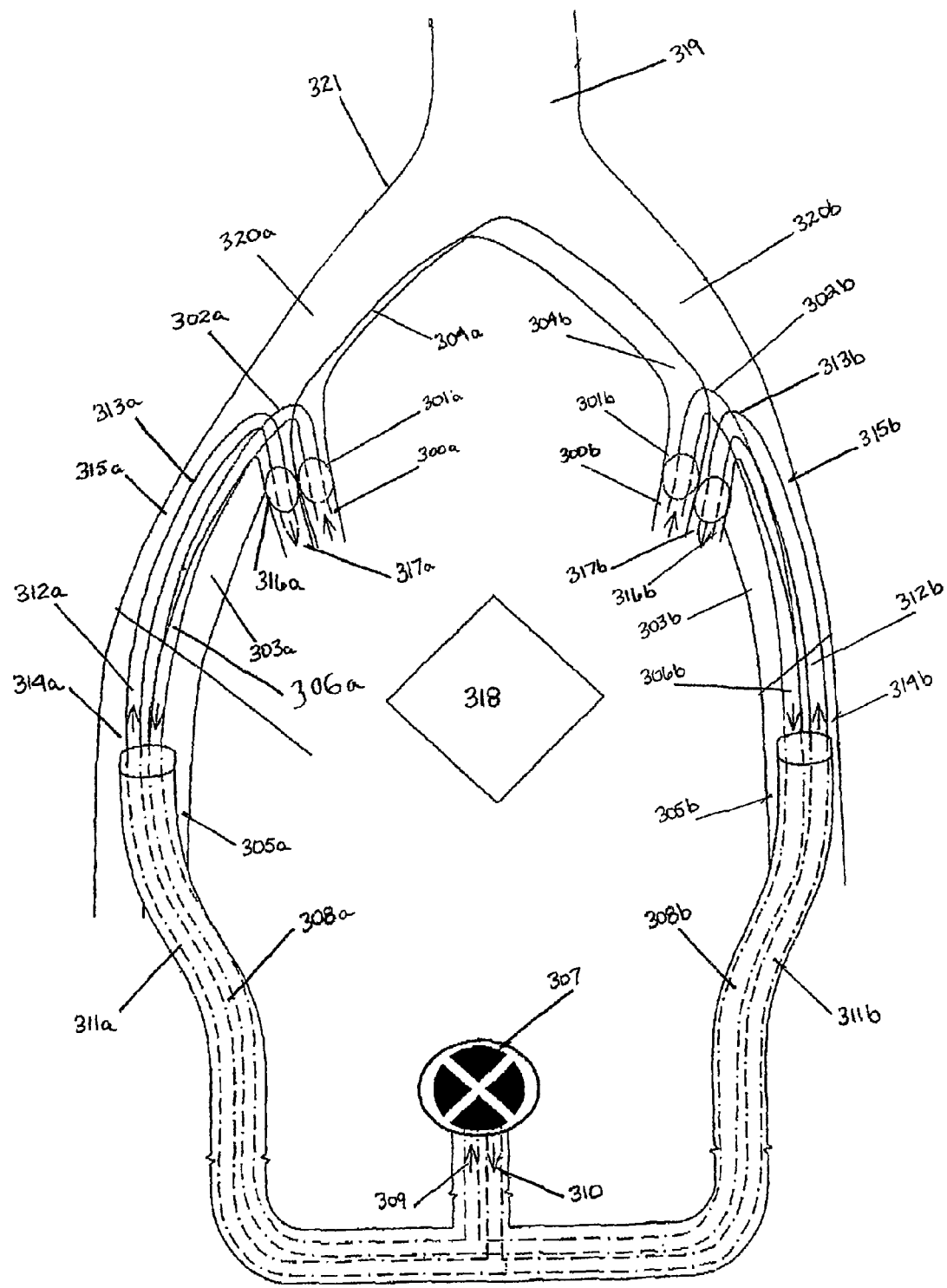
FIG. 26 is a schematic view of a system used to isolate and hyperperfuse pelvic organs, in accordance with certain embodiments.

FIG. 26 is a schematic of embodiments that may be used for vascular isolation and hyperperfusion of the pelvic organs and tissue 318. The right and left internal iliac veins 300a and 300b respectively may be isolated or occluded by inflating isolation or occlusive balloons 301a and 301b of isolation catheters 302a and 302b, thereby minimizing pelvic venous return entering the systemic circulation via right and left common iliac veins 304a and 304b and inferior vena cava (IVC) 321. Isolation catheters 302a and 302b may be inserted into position in the right and left internal iliac veins 300a and 300b at the point where they combine with the right and left external iliac veins 303a and 303b to form the right and left common iliac veins 304a and 304b using an access device (not shown) that may provide access to the right common femoral vein 305a and the left common femoral vein 305b. Blood and fluid flowing from right internal iliac vein 300a may be transported via outflow catheter 306a through right external iliac vein 302a, right common femoral vein 305a and the access device (not shown) out of the circulatory system into outflow tubing 308a towards pump 307. Blood and fluid flowing from the left internal iliac vein 300b may be transported via outflow catheter 306b through left external iliac vein 302b, right common femoral vein 305b and the access device (not shown) out of the circulatory system into outflow tubing 308b towards pump 307.

Prior to reaching pump 307, the blood flowing in outflow tubing 308a and 308b may be combined. Before and/or after this combination, before and/or after entering pump 307 via pump entry 309, before and/or after leaving pump 307 via pump exit 310 and/or before and/or after splitting into inflow tubing 311a and 311b, the blood and fluid may be processed or analysed in one or more devices or instruments such as for example pumps, flow controllers, drug delivery devices, blood monitoring devices, such as blood pH, $SO_2$, pulse or other blood monitoring devices, blood oxygenators such as membrane or bubble oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used. Typically, the fluid in inflow tubing 311a and 311bb will have had its physical, chemical or kinetic properties modified in some way when compared to the fluid from outflow tubing 308a and 308b. For example, the fluid may be returned at a different flow rate or pressure, or at a different temperature, pH or $SO_2$, or with nutrients or other components such as therapeutics, drugs, or other factors added, or with different components removed, such as toxins, harmful chemicals or drugs, excess cellular degradation products, excess CO, $CO_2$, phosphate, urea, antibodies, antibiotics or other components, such as a drug or therapeutic that is being used specifically in treatment.

After entering pump 307 via pump entry 309, the blood and fluid will be pumped through pump exit 310 at which point it may be split into inflow tubing 311a and 311b. Inflow tubing 311a may transport the blood and fluid through an access device, which may be the same device (such as when a fistula embodiment is used) or a different device than the access device used for the outflow tubing 308a, to inflow catheter 312a of isolation or balloon catheter 313a. Inflow catheter 312a may access the circulatory system at the right common femoral artery 314a and may transport blood and fluid through the right external iliac artery 315a, through isolation or occlusive balloon 316a and into the right internal iliac artery 317a where the blood and fluid infuses or hyperperfuses the pelvic organs and tissue 318. Isolation or occlusive balloon 316a may be positioned at the point of origin of right internal iliac artery 317a, and when inflated may isolate right internal iliac artery 317a from blood flowing from abdominal aorta 319 through right common iliac artery 320a, thereby minimizing infusion of systemic circulation.

Similarly, inflow tubing 311b may transport the blood and fluid through an access device, which may be the same device (such as when a fistula embodiment is used) or a different device than the access device used for the outflow tubing 308b, to inflow catheter 312b of isolation catheter 313b. Inflow catheter 312b may access the circulatory system at the left common femoral artery 314b and may transport blood and fluid through the left external iliac artery 315b, through isolation or occlusive balloon 316b and into the left internal iliac artery 317b where the blood and fluid perfuses or hyperperfuses the pelvic organs and tissue 318. Isolation or occlusive balloon 316b may be positioned at the point of origin of left internal iliac artery 317b, and when inflated may isolate left internal iliac artery 317b from blood flowing from abdominal aorta 319 through left common iliac artery 320b, thereby minimizing infusion of systemic circulation.

Figure 27:
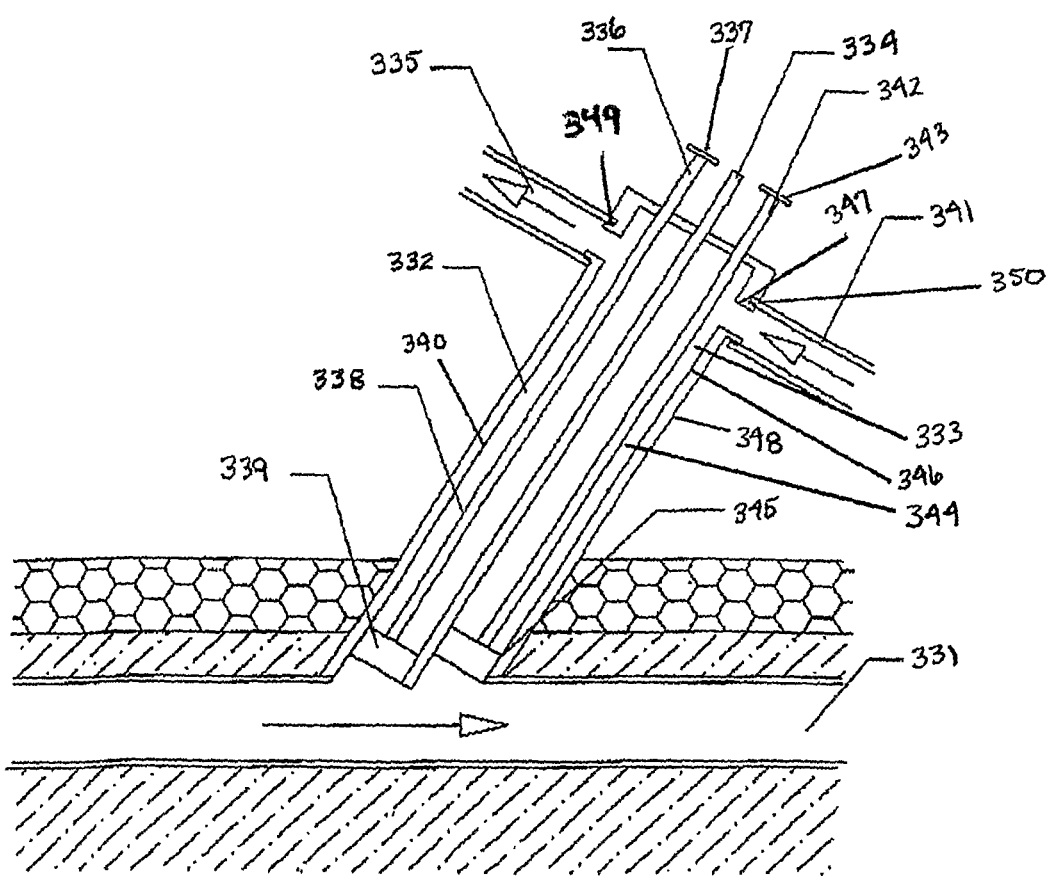
FIG. 27 is a schematic view of a system used to hyperperfuse without the use of balloons.

FIG. 27 is a schematic of an access system according to some embodiments that does not use isolation or occlusive balloons to control flow in a vessel. Access device 330 provides fluid access to vessel 331 by penetration of vessel 331, such as with an interposition graft or an arteriotomy, with cannula 348 via outflow lumen 332 and inflow lumen 333 which are separated by movable spatula 334. Access to outflow lumen 332, outflow port 346 and outflow tubing 335 may be controlled using plunger assembly 336. Plunger assembly 336 has handle 337, stem 338 and head 339. When in position, head 339 prevents fluid communication between vessel 331 and outflow lumen 332 by forming a fluid tight seal when interacting with the wall 340 of outflow lumen 332. As shown in FIG. 27, handle 337 has been fully actuated into lumen 332, by exerting a force on handle 337 thereby moving plunger head 339 toward vessel 331 via stem 338 and preventing fluid access into outflow lumen 332 from vessel 331.

Similarly, access to inflow lumen 333, inflow port 347 and inflow tubing 341 may be controlled using plunger assembly 342. Plunger assembly 342 has handle 343, stem 344 and head 345. Head 345 may limit fluid communication between inflow lumen 333 and vessel 331 by forming a fluid tight seal when interacting with the wall 346 of inflow lumen 333. As shown in FIG. 27, handle 343 has been fully actuated into lumen 333, by exerting a force on handle 343 thereby moving head 345 toward vessel 331 via stem 344 and preventing fluid access into outflow lumen 332 from vessel 331.

Heads 339 and 345 may be constructed of any suitable biocompatible material, such as silicone or other suitable biocompatible elastomeric and/or thermoplastic materials or combinations thereof such as polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like. In some embodiments, plunger assemblies 336 and 342 may be actuated by application of sufficient force at handles 337 and 343 to move plunger assemblies 336 and 342 into or out of lumens 332 and 333. In some embodiments, the position of plunger assemblies 336 and 342 is controlled using an automatic control system. In some embodiments, plunger assemblies 336 and 342 may be locked in any position through their range of motion from fully open whereby access to lumens 332 and 333 via outflow port 346 and inflow port 347 is unrestricted, through any number of partially open positions whereby fluid flow through outflow port 346 and inflow port 347 is partially restricted, to a completely closed position whereby fluid access to lumens 332 and 333 via outflow ports 346 and inflow port 347 is completely prevented using any suitable locking mechanism such as a locking pin or pins. In some embodiments, the locking mechanism is sufficient to prevent back pressure of the patients normal circulatory system from altering the position of heads 339 and 345.

Movable spatula 334 may be actuated into vessel 331, thereby partially or completely occluding vessel 331 and directing blood and fluid in vessel 331 into outflow lumen 332. Movable spatula 334 may be actuated though any number of positions relative to vessel 331 from fully occluding vessel 331 through partially occluding vessel 331 to no occlusion of vessel 331 and may be locked into any of these positions using any suitable locking mechanism or system such as a locking pin or pins.

When plunger assembly 336 is sufficiently withdrawn from outflow lumen 332, blood may flow through outflow lumen 332 through outflow port 346 and into outflow tubing 335. Outflow port 346 may have an outflow connector or connection means 349 for connecting to outflow tubing 335, thereby placing outflow lumen 332 in fluid communication with external tubing, devices or equipment, including for example, pumps, flow controllers, drug delivery devices, blood monitoring devices, such as blood pH, SO2, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used. Connection means 349 may be any suitable means for providing sanitary or sterile or sterilisable communication with outflow lumen 332, such as for example a Luer, threaded, swage or sanitary connection. Typically, the fluid will be introduced or reintroduced to vessel 331 via inflow port 347 after the fluid or its physical, chemical or kinetic properties have been modified in some way. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, CO2, phosphate, urea, antibodies, antibiotics or other components, such as a drug or therapeutic that is being used specifically in treatment.

Inflow port 347 has an inflow connector or connection means 350 for connecting to inflow tubing 341 through blood, other fluids, drugs or drug solutions, anticoagulants, antibiotics, contrast fluids, diagnostic fluids, therapeutics, nutrients, saline, buffers, plasma, synthetic or natural blood products or factors, antibodies, proteins or fragments thereof, peptides or fragments thereof, genes or fragments thereof, DNA, RNA, nucleic acids, nano devices, blood cells and/or combinations of more than one of the above may be supplied or reintroduced into lumen 333 and vessel 331 at the same or different pressure and flow rate than the fluid that is removed through outflow port 346 when plunger assembly 342 is sufficiently withdrawn from inflow lumen 333. In some embodiments, the fluid flowing through inflow port 347 is at a higher pressure and/or flow rate than the fluid flowing through outflow port 346, the fluid flowing in upstream (proximal) portion 351 of vessel 331 prior to occlusion of the vessel 331 with movable spatula 334 and/or the systemic blood pressure measured at a location remote to the treatment site, such as, for some embodiments, the carotid artery blood pressure Connection means 350 may be any suitable means for providing sanitary or sterile or sterilisable communication with lumen 333, such as for example a Luer, swage, threaded or sanitary connection and may be the same or different than connection means 349.

Figure 28:
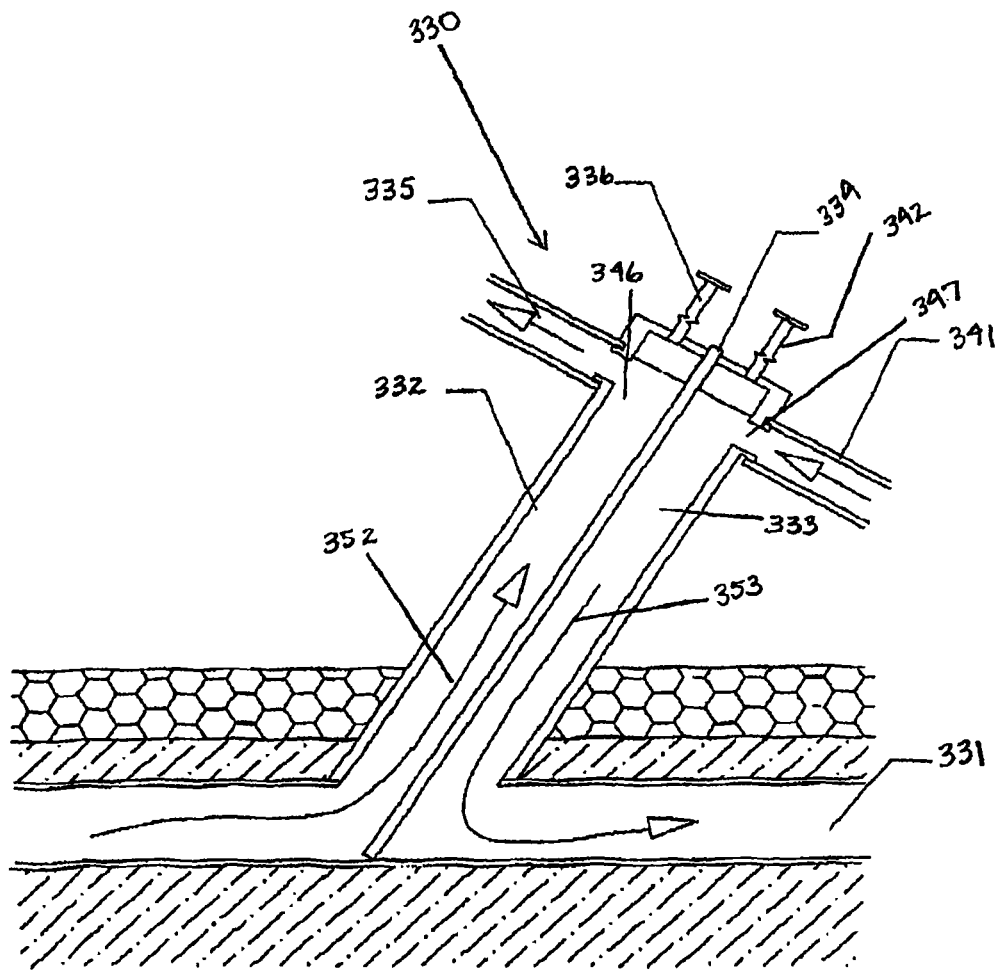
FIG. 28 is a schematic view of the embodiment as shown in FIG. 27 in the open position.

FIG. 28 is a schematic of some embodiments of the access device 330 according to FIG. 27. In FIG. 28, plunger assemblies 336 and 342 have been actuated to fully open outflow lumen 332 and inflow lumen 342 to place them in fluid communication with vessel 331. In addition, movable spatula 334 has been fully actuated into vessel 331, thereby occluding it and directing blood flow into outflow lumen 332 as shown by arrow 352 where it may flow through outlet port 346 into tubing 335 and to various external equipment and devices. In addition, fluid may be introduced into vessel 331 from inflow tubing 341, through inflow port 347 and inflow lumen 333 as indicated by arrow 353.

Figure 29:
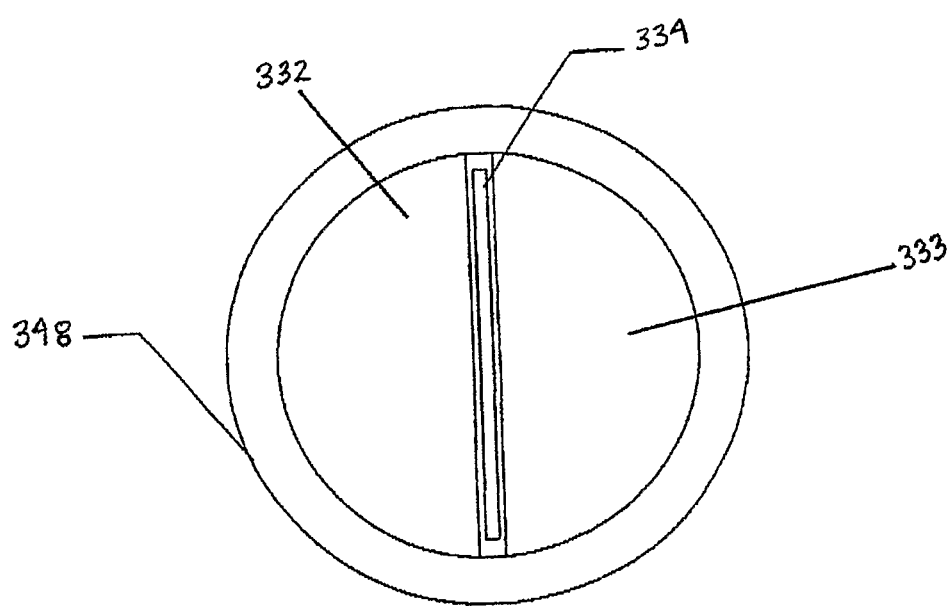
FIG. 29 is a cross section view of the dividing system shown in FIGS. 27 and 28.

FIG. 29 shows a cross section view of access device 330 looking down cannula 348 and outflow and inflow lumens 332 and 333 with movable spatula 334 when not inserted into a vessel and when the plunger assemblies (not shown) are in the fully opened position.

Figure 30:
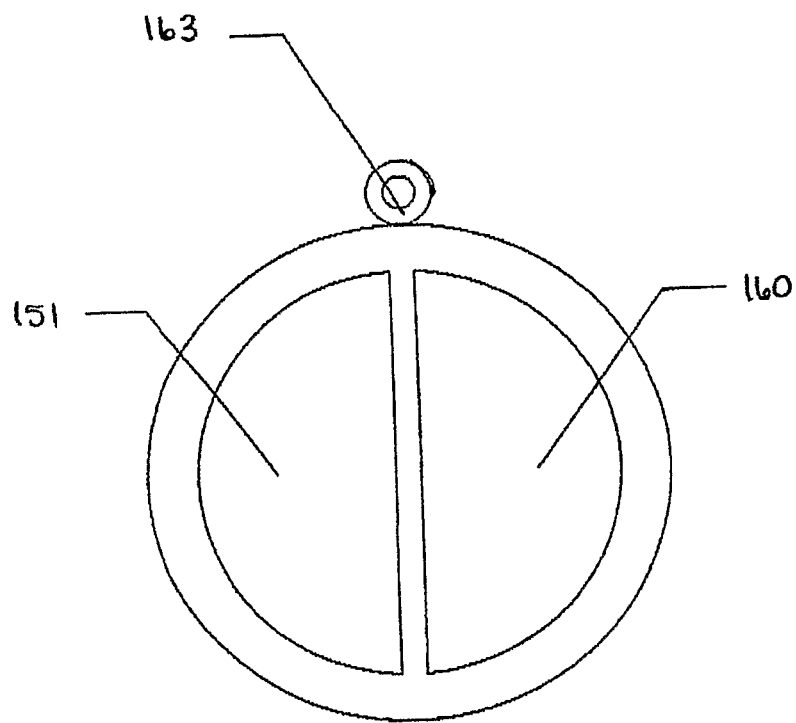
FIG. 30 is a cross section view of the separate tuber external to the dividing system according to FIGS. 27 and 28.

FIG. 30 shows another view in cross section view looking down the cannula 348. The separate tube external to the dividing system is 163. See also FIGS. 27 and 28.

Figure 31:
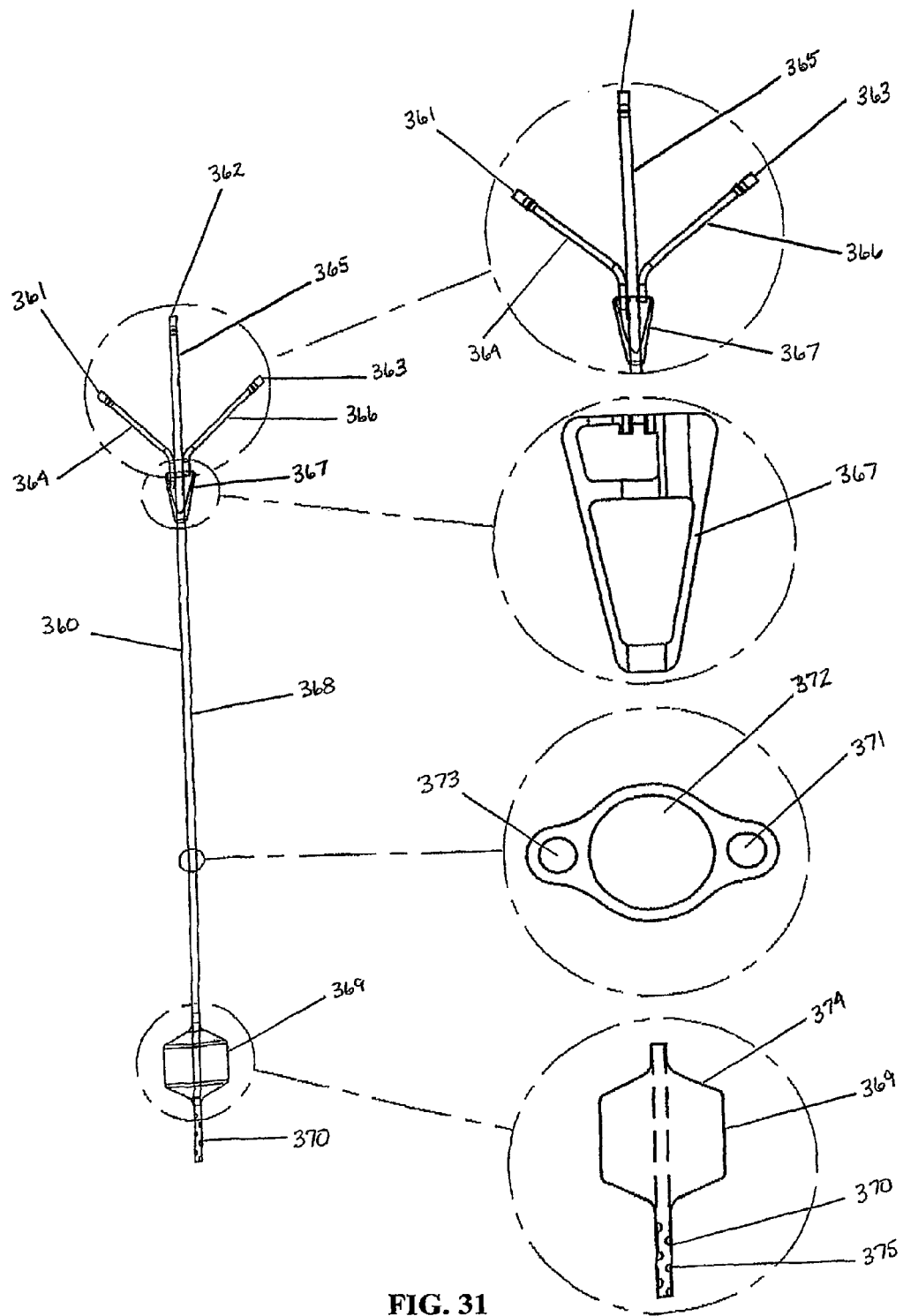
FIG. 31 is a schematic of an isolation or balloon catheter used in accordance with certain embodiments.

FIG. 31 is a schematic of an isolation or balloon catheter 360 that may be used with some embodiments, including embodiments that involve hyperperfusion or infusion. Balloon catheter 360 has multiple access ports: pressurization port 364, fluid flow port 365 and pressure transducer port 366. Pressurization port 364 has connector or connection means 361, which may be any suitable connector or connection such as, for example, a Luer, swage, threaded or sanitary connector or connection. Pressurization port 364 may be placed in fluid connection with pressurization lumen 373 using securing guide 367. Inert gas, such as helium, may be injected and/or withdrawn into and/or from isolation or occlusive balloon 369 to expand or contract balloon 369 by connecting a pressurization control system to connector 361 and adding or removing gas via pressurization port 364 and pressurization lumen 373.

Fluid flow port 365 has connector or connection means 362, which may be any suitable connector or connection such as, for example, a Luer, swage, threaded or sanitary connector or connection. Fluid flow port 365 may be placed in fluid connection with fluid flow lumen 372 using securing guide and support means 367 and may be used to add or withdraw blood and fluid from or to a vessel through inflow/outflow port 370 having openings 375, through which the fluid may be added or withdrawn. When placed into or through an inflow or an outflow port, catheter 360 may include a suitable sealing means for ensuring a fluid tight seal at the port which may or may not be placed below securing guide and support means 367 on an outer portion of fluid flow lumen 372. Alternatively, securing guide and support means 367 may be configured to serve as a fluid tight seal at an inflow or outflow port of an access device through which catheter 367 has been placed.

Pressure transducer port 366 has connector or connection means 363, which may be any suitable connector or connection such as, for example, a Luer, swage, threaded or sanitary connector or connection. Pressure transducer port 366 may be placed in fluid connection with pressure transducer lumen 371 using securing guide 367 and may be used in conjunction with a pressure transducer to measure pressure in balloon 369 and provide feedback signals to a pressurization control system connected to pressurization port 364 to assist in controlling inflation and deflation of balloon 369. Alternatively, the pressure transducer may measure and report the pressure in balloon 369 without providing feedback signals.

Balloon 369 may include one or more rigid or semi-rigid supports 374 to assist in positioning, placement and support of balloon 369 and balloon wall 376, when in the inflated or deflated state. Balloon wall 376 expands under pressure supplied via pressurization port 364 in fluid communication with the pressurization control lumen 373 and pressurization port 364. Balloon wall 376 may be constructed from any suitable biocompatible material that is sufficiently elastic to sufficiently expand and contract when exposed to the desired pressures, to accomplish the desired isolation or occlusion in accordance with some embodiments. Such biocompatible materials may include silicone or other suitable biocompatible elastomeric and/or thermoplastic materials or combinations thereof such as polyvinylchlorides, nitriles, polytetrafluoroethylenes, polyethersulfones, polysulfones, polyurethanes, polyolefins, polyamines, polyamides, PET's, polyesters, polyethers and random or block copolymers of such materials, cross linked embodiments of such materials, layered combinations of such materials and the like.

Figure 32:
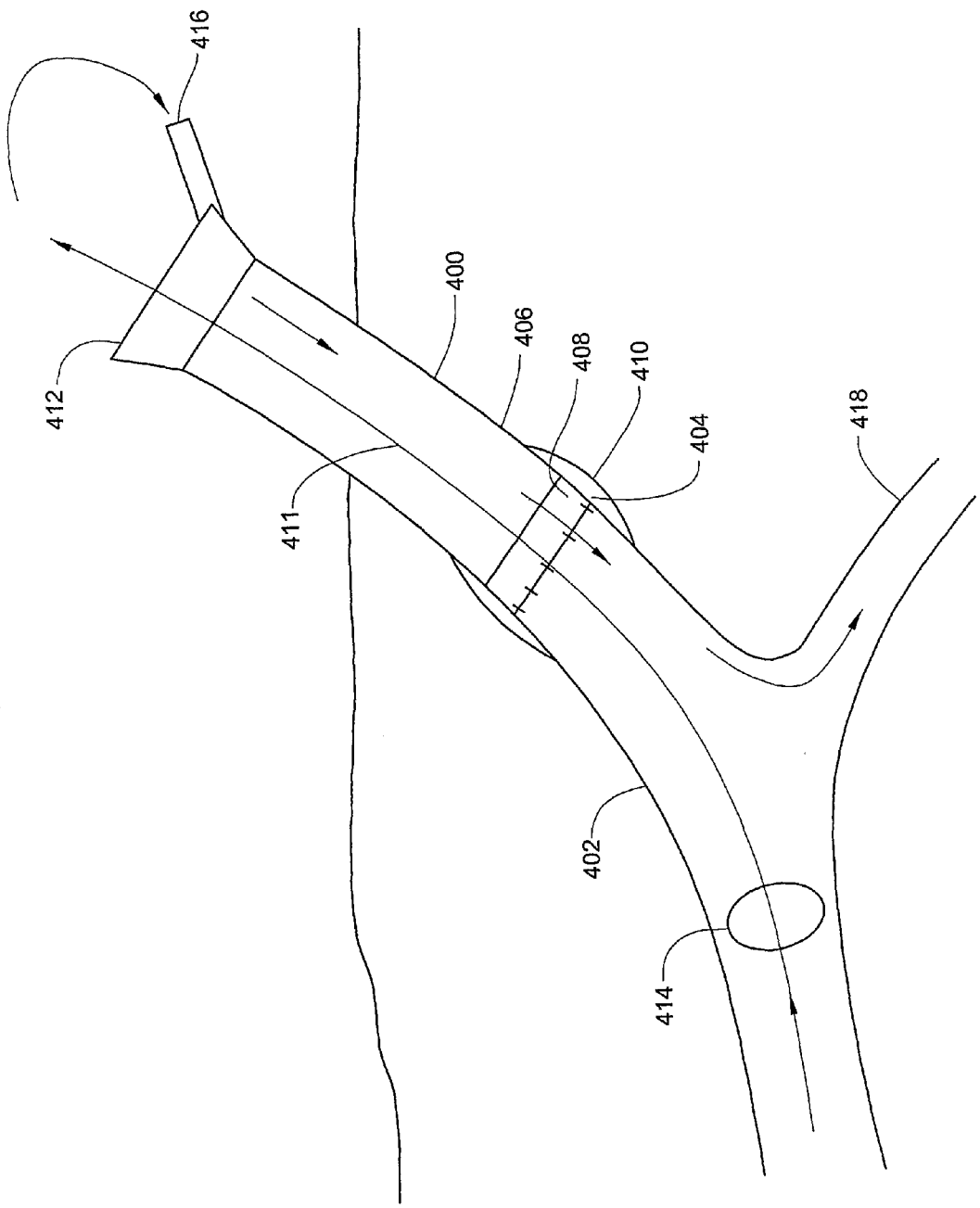
FIG. 32 is a schematic of an access system where the lumen of the access device is anastomosed end-to-end to the lumen of the host vessel in accordance with certain embodiments.

FIG. 32 is a schematic of an access system where the lumen of the access device is connected to the lumen end of the vessel in accordance with certain embodiments. FIG. 32 shows access device 400 placed in line with the direction of fluid flow in vessel 402 by transecting vessel 402 at transection point 404 and inserting lumen 406 of access device 400 in direct fluid communication along the normal flow direction with vessel 402 using suturing sleeve 408 and secondary sealing sleeve 410 thereby creating an anastomosis between vessel 402 and access device 400. Suturing sleeve 408 provides for suturing of access device 400 to vessel 402, while secondary sealing sleeve 410 limits leakage of fluid from the vessel at the connection between the access device 400 and the vessel 402 and provides for reinforcement of the positioning of access device 400 and of the anastomosis. When using this configuration it often desirable that the vessel be transected as close as possible to the occlusion. The distal end of the transected vessel adjacent to the occlusion may be clamped, tied or otherwise sealed to prevent leakage of fluid from the vessel and to avoid infection. Balloon catheter 411 is shown inserted through outflow port 412 into vessel 400 and is positioned proximate to a branch in vessel 400.

When inflated balloon 414 occludes vessel 402 and redirects fluid flowing in vessel 402 through balloon catheter 411 and outflow port 412 and into external tubing, devices or equipment, including for example, pumps, flow controllers, drug delivery devices, blood monitoring devices, such as blood pH, CO2, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used. The fluid may then be returned through inflow port 416 and lumen 406 of access device 400 and into branch 418 of vessel 402.

Typically, the fluid will be introduced or reintroduced to vessel 402 via inflow port 416 after the fluid or its physical, chemical or kinetic properties have been modified in some way. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, CO2, phosphate, urea, antibodies, antibiotics or other components, such as a drug or therapeutic that is being used specifically in treatment. In some embodiments, the fluid is returned at a flow rate or pressure that is at a higher pressure and/or flow rate than the fluid flowing through outflow port 412, the fluid flowing in proximal portion 401 of vessel 402 prior to occlusion of the vessel 402 with balloon 414 and/or the systemic blood pressure measured at a location remote to the treatment site, such as, for some embodiments, the carotid artery blood pressure. Lumen 406, balloon catheter 411, suturing sleeve 408 and secondary sealing sleeve 410 may be constructed from suitable materials, such as biocompatible materials, non-biocompatible materials, or non-biocompatible materials that are coated with biocompatible materials, that have appropriate properties to serve their intended function. Examples of such biocompatible and/or non-biocompatible materials are disclosed herein. Where non-biocompatible materials may come in contact with the anatomic structure, the components made from non-biocompatible materials may often be covered or coated with biocompatible material.

Figure 33:
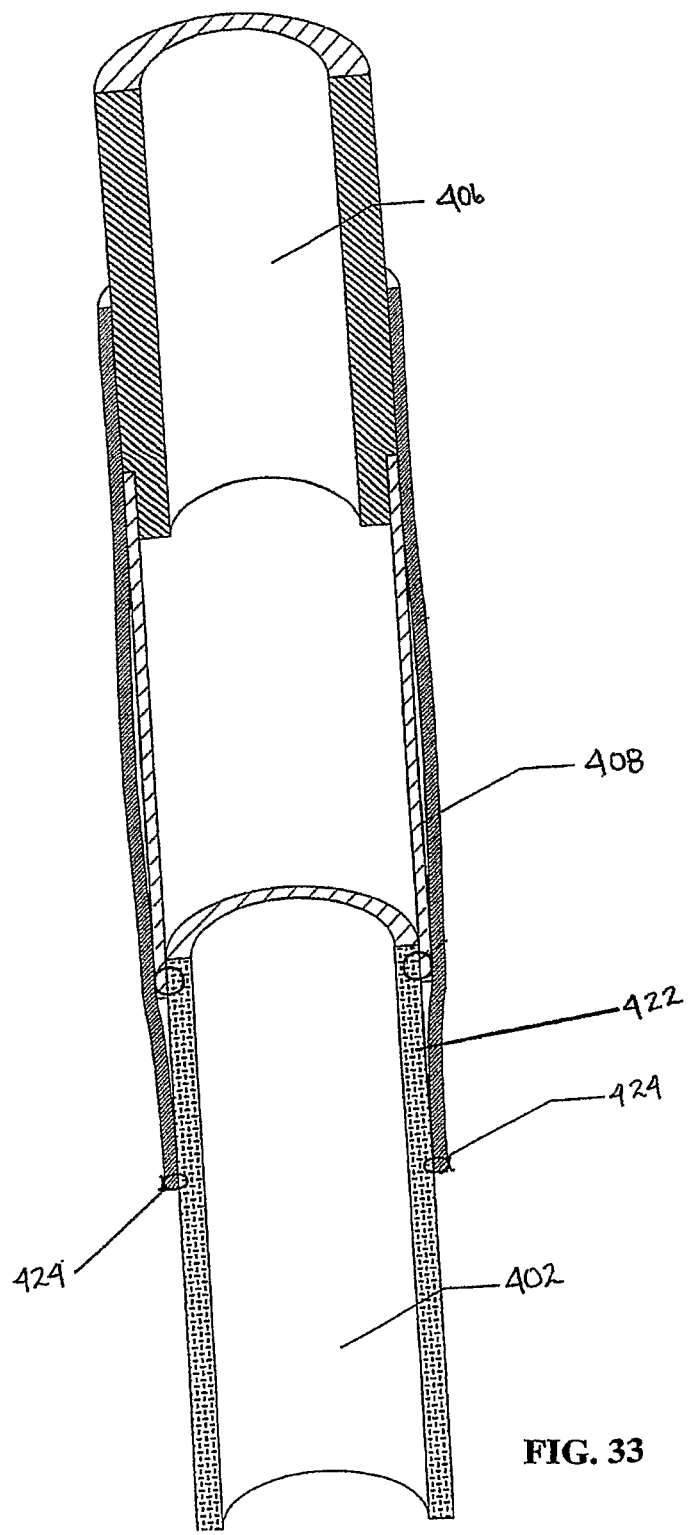
FIG. 33 is a detailed schematic of the system shown in FIG. 32 of the lumen of the access device anastomosed end-to-end to the lumen of the host vessel.

FIG. 33 is a more detailed schematic of the system shown in FIG. 32 showing lumen 406 of the access device 400 as connected to the transected end of the vessel 402. Lumen 406 of access device 400 is in fluid communication with vessel 402 via suturing sleeve 408 which may be sutured to wall 422 of vessel 402. Sealing sleeve (or secondary sealing sleeve or re-enforcing skirt) 410 may be sutured directly to vessel 402 using adventitial sutures 424 or other sutures. The sealing sleeve 410 is also attached to the lumen 406 with sutures or other attachments means such as glue, adhesive or other bonding.

Figure 34:
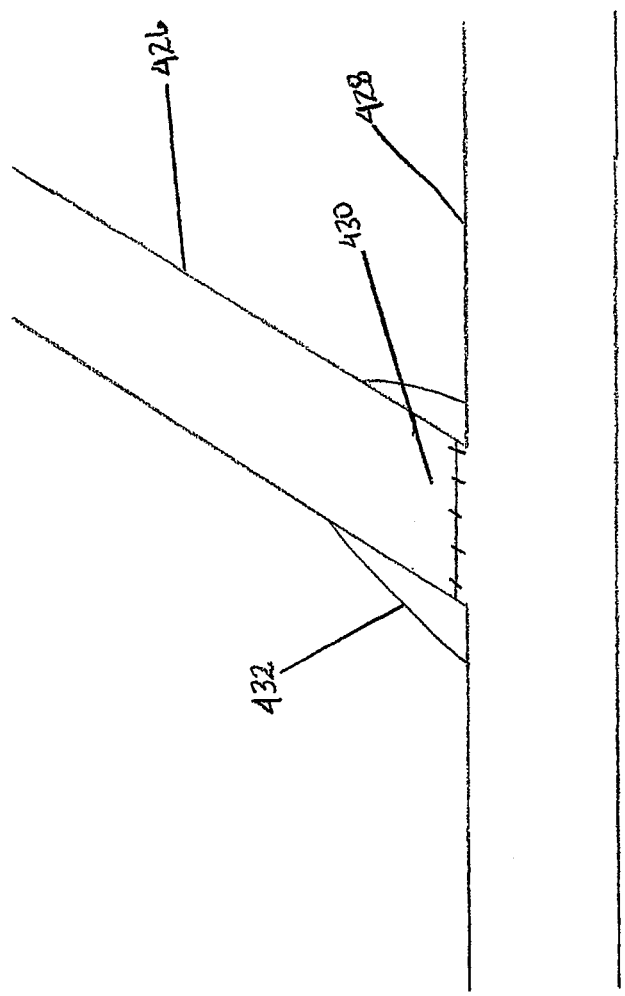
FIG. 34 is a schematic of an access system with a reinforcing skirt anastomosed end-to-side with the lumen of the host vessel in accordance with certain embodiments.

FIG. 34 shows a schematic view of an access device 426 accessing a vessel 428 via a side wall of the vessel typically at the desired angle as disclosed herein. Similar to FIGS. 32 and 33, access device 426 may be connected to vessel 428 via suturing sleeve 430 and sealing sleeve 432. The sealing sleeve or re-enforcing skirt illustrated in FIGS. 32, 33, and 34 may be used with many of the other embodiments disclosed herein if desired. This sleeve or skirt may provide additional support or reinforcement structure to assist in securing the skin, vessel or tissue against the housing or lumen. This may help minimize movement of the device at the attachment point and/or to reduce the possibility of infection. These reinforcement structures or skirts may be manufactured from biocompatible and/or non-biocompatible materials or combinations thereof as disclosed herein. For example, see FIGS. 32, 33, and 34. These figures show the reinforcing skirt illustrated may prevent or reduce fluid or blood leaking from the suturing sleeve. In certain embodiments it may be desirable to use a second skirt (see, for example, 408 in FIG. 33) or outer protective layer. One advantage to an additional skirt is to further reduce the chance of infections at the site on the patient where the device has been attached. The at least one reinforcement structure or skirt may be used with many of the embodiments disclosed in this application and may have different configurations to that illustrated in this disclosure. In addition, the at least one second skirt or outer protective layer may have different configuration as well.

Figure 36:
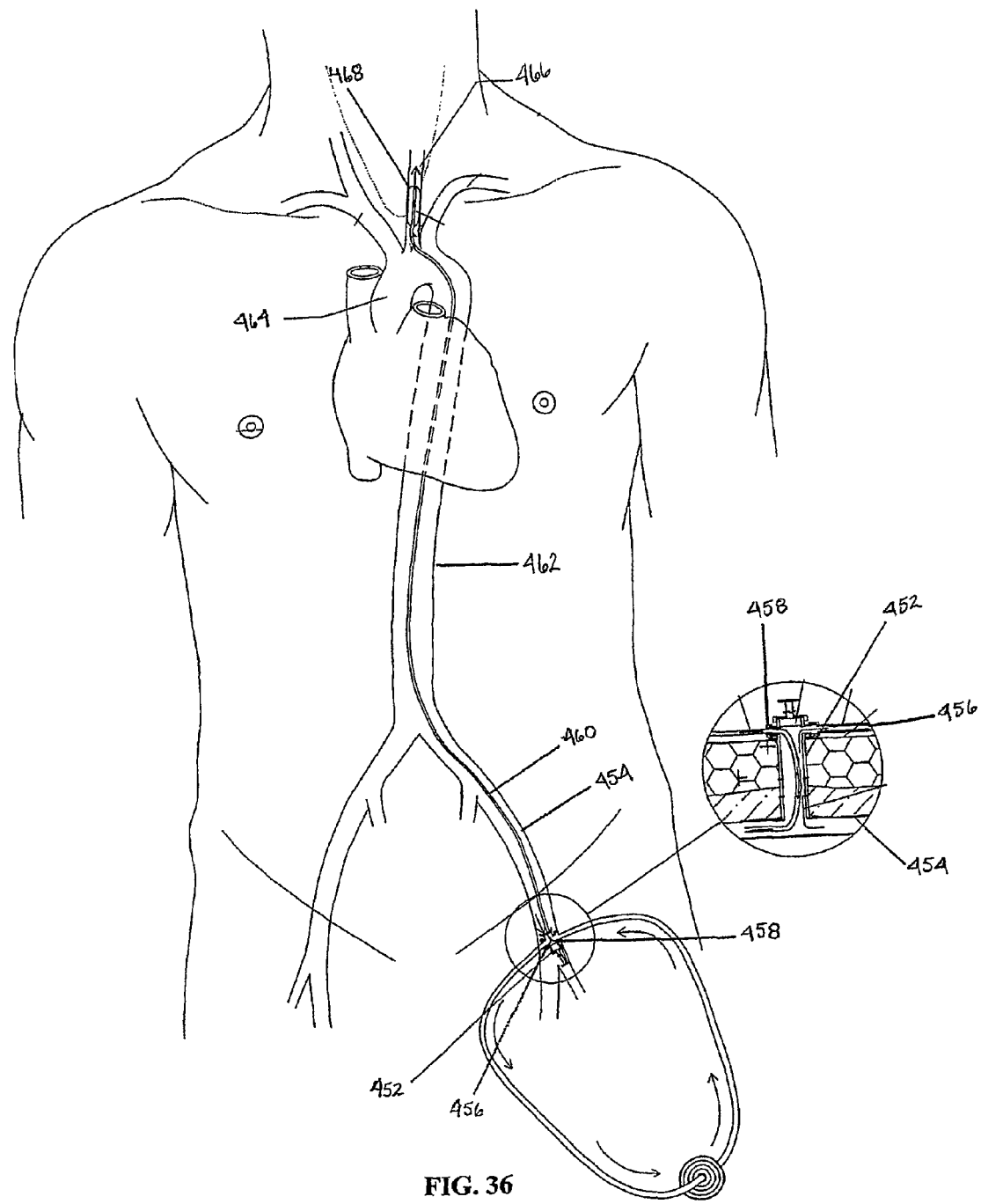
FIG. 36 is a schematic of view of a system used to treat the brain, in accordance with certain embodiments.

FIG. 36 is a schematic of certain embodiments of a system for treatment of the brain. Access device 452 is inserted into the common femoral artery 454. By way of example, access device 452 as shown in the figure is an access device according to the embodiment in FIG. 16. Access device 454 has outflow port 456 and inflow port 458. Balloon catheter 460 is directed through inflow port 458 into common femoral artery 454, through the various portions of the abdominal and thoracic aorta 462, through aortic arch 464 and into left common carotid artery 466. In use, balloon 468 of balloon catheter 460 may be inflated to occlude and isolate the left common carotid artery 454 from the flow from the heart and to provide for treatment. Access device 452 is used to withdraw fluid from common femoral artery 454 into external tubing, devices or equipment, including for example, pumps, flow controllers, drug delivery devices, blood monitoring devices, such as blood pH, SO2, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used. The fluid may then be returned through balloon catheter 460 and into the left common carotid artery 454.

Typically, the fluid will be introduced or reintroduced to left common carotid artery 454 via balloon catheter 460 after the fluid or its physical, chemical or kinetic properties have been modified in some way. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, CO2, phosphate, urea, antibodies, antibiotics or other components, such as a drug or therapeutic that is being used specifically in treatment. In some embodiments, the fluid is returned at a flow rate or pressure that is at a higher pressure and/or flow rate than the fluid flowing in left common carotid artery 454 prior to occlusion with balloon 468 and/or the systemic blood pressure measured at a location remote to the treatment site. In a similar way the right common carotid vessel can be perfused to provide increased blood flow to the right hemisphere or the left hemisphere via the Circle of Willis when there is occlusion or near occlusion of the left internal carotid artery. Similarly, the right side of the brain can be perfused via the left common carotid artery in cases of occlusion or near occlusion of the right internal carotid artery.

Figure 37:
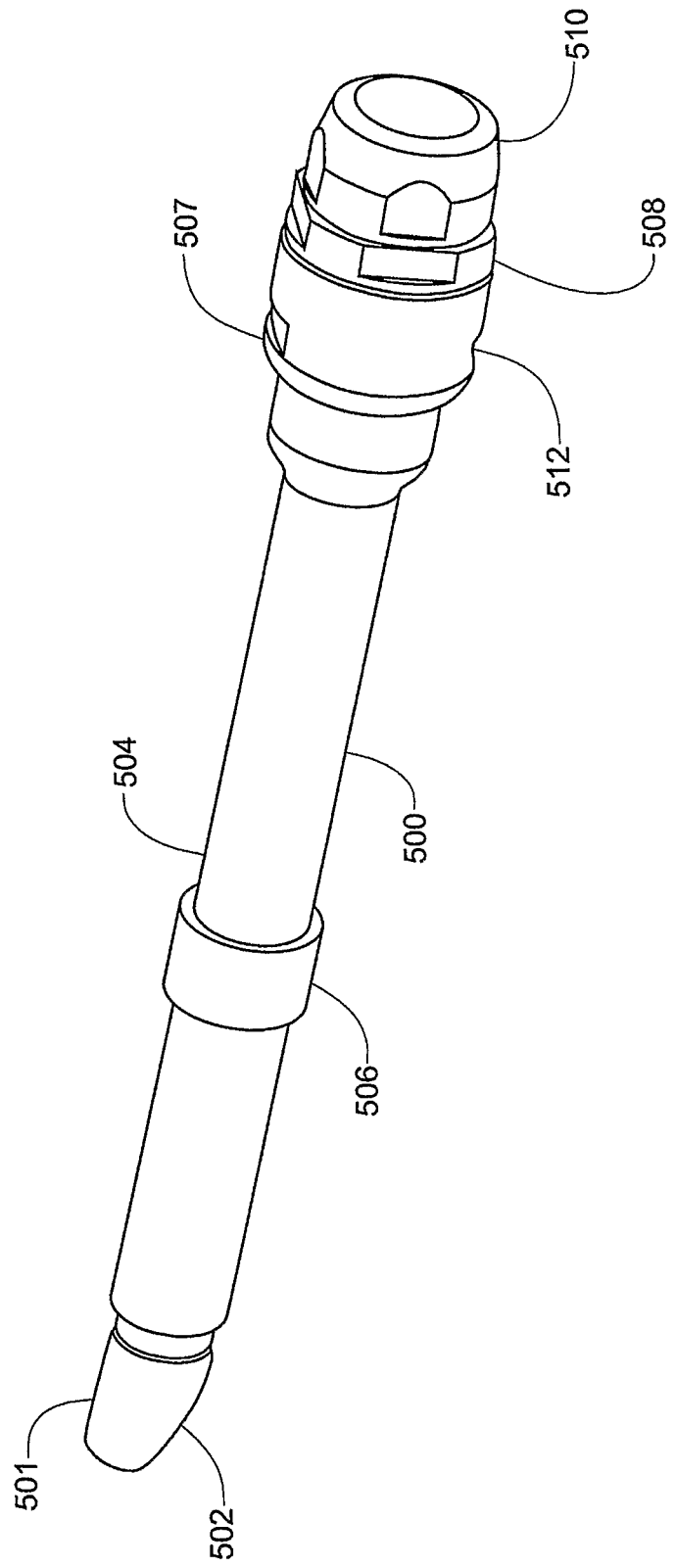
FIG. 37 is a schematic of an embodiment of an access device in a hold or non-treatment configuration.

FIG. 37 is a schematic of certain embodiments of an access device 500. Access device 500 has suture foot 502 at access end 501, which, when in use, provides fluid communication between a vessel (not shown) and lumen 504 by providing for suture of access device 500 to a vessel. Access device 500 has sleeve 506 which provides for support of the device 500 and lumen 504 and sealing and/or leak minimization/elimination at the point of penetration to the skin or penetration of the vessel. Access device 500 has flow port 507 that has been capped with connector 508 and end cap 510. Flow port 507 may be inserted into lumen 504 and bonded, sealed or otherwise connected to lumen 504 to provide for connection to various devices using various flow and/or end caps. Connector 508 facilitates connection of end cap 510 to access device 500 at external end 512 in order to place the access device 500 into the hold configuration shown in the figure such that no flow is occurring through lumen 504 and the device 500 is not in use. When access device 500 is inserted into a vessel, this configuration is used between or before treatments. In such instances, end cap 510 is connected to device 500 to limit or prevent infection and to isolate the vessel access when the access device 500.

Access device 500, suture foot 502, lumen 504, sleeve 506, flow port 507, connector 508 and end cap 510 may be constructed from any suitable materials, such as biocompatible materials or non-biocompatible materials that are coated with biocompatible materials as described elsewhere herein, that have appropriate properties to serve their intended function as disclosed herein. In some aspects, sleeve 506 and/or suture foot 502 may be constructed from polyester, PTFE or ePTFE. In some embodiments, lumen 504 may comprise wholly or in part silicone and flow port 507, connector 508 and end cap 510 may comprise metal, such as stainless steel, or a plastic or a combination of thereof.

Figure 38:
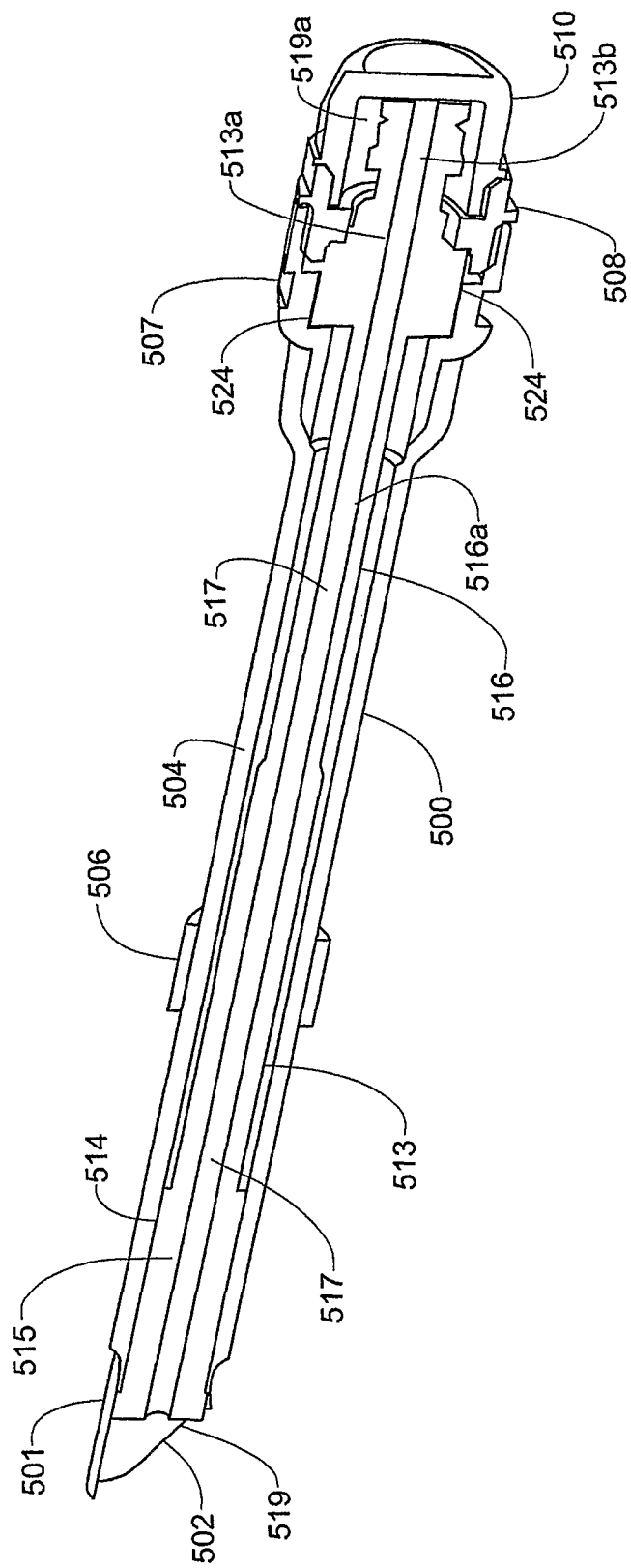
FIG. 38 is a cross sectional view of the device according to FIG. 37.

FIG. 38 is a cross sectional view of the device according to FIG. 37. Access device 500 has suture foot 502 at access end 501, which, when in use, provides fluid communication between a vessel (not shown) and lumen 504 by providing for suture of access device 500 to a vessel. Access device 500 has sleeve 506 which provides for support of the device 500 and lumen 504 and sealing and/or leak minimization/elimination at the point of penetration to the skin or penetration of the vessel. Access device 500 has flow port 507 that has been capped with connector 508 and end cap 510. Flow port 507 may be inserted into lumen 504 and bonded, sealed or otherwise connected or sealed to lumen 504 to provide for connection to various devices using various flow and/or end caps. Connector 508 facilitates connection of end cap 510 to access device 500 at external end 512 in order to place the access device 500 into the hold configuration shown in the figure such that no flow is occurring through lumen 504 and the device 500 is not in use. When access device 500 is inserted into a vessel, this configuration may be used between or before treatments. In such instances, end cap 510 is connected to device 500 to limit or prevent infection and to isolate the vessel access when the access device 500.

Access device 500, suture foot 502, lumen 504, sleeve 506, flow port 507, connector 508 and end cap 510 may be constructed from any suitable materials, such as biocompatible materials or non-biocompatible materials that are coated with biocompatible materials or combinations of these materials as described elsewhere herein, that have appropriate properties to serve their intended function as disclosed herein. In some aspects, the lumen 504 may be made, wholly or in part of silicone. In some embodiments, lumen 504 may be constructed of more than one biocompatible or coated non-biocompatible material. For example, in some embodiments, lumen 504 may comprise a flexible portion that is silicone and a second portion that is metal or PTFE or other suitable material that may be bonded to the silicone portion using a fast cure adhesive or other suitable adhesive or bonding material. In some aspects, sleeve 506 and/or suture foot 502 may be constructed from polyester, PTFE or ePTFE. In some embodiments, flow port 507, connector 508 and end cap 510 may comprise metal, such as stainless steel, or a plastic or a combination of thereof.

As shown, access device 500 has plunger 513 inserted in lumen 504. Plunger 513 may comprise a cannulated plunger shaft 516. As shown, or may comprise a solid plunger shaft and may have plunger head 514, which may have ribs 515 or may be un-ribbed. In some embodiments, ribs 515 may serve to seal lumen 504 to prevent access to lumen 504 by fluid flowing in a vessel, while providing for a more easily movable plunger 513 within lumen 504 by providing a more limited contact surface area between plunger head 514 and lumen 504 when compared to an un-ribbed plunger head. In certain aspects, the plunger 513 and plunger shaft 516 may be made of metal, wholly or in part, and plunger head 514 may be made of HDPE. Alternatively, they may be constructed from any suitable materials, such as biocompatible materials or non-biocompatible materials that are coated with biocompatible materials or combinations of these materials as described elsewhere herein, that have appropriate properties to serve their intended function as disclosed herein.

The plunger shaft 516 may be cannulated to provide for access to lumen 504 and/or to a vessel for angiographic purposes and for addition of therapeutics, such as any therapeutics as described herein, such as, for example drip solutions such as saline, dextrose or heparin solutions. In this figure, access device 500 is shown with a stylet 517 in place within the cannula of plunger shaft 516. In the figure, the plunger shaft cannula 516a is shown centered within the plunger and extending from end 512 of access device 500, and through the plunger shaft 516 and plunger head 514. In other embodiments, the plunger shaft cannula 516a may be position of center within the plunger shaft 516, while in other embodiments, the plunger shaft 516 may include none, 1, 2, 3, or 4 cannulae each having an individual cooperating stylet, or stylet 517 may be configured with multiple shafts to fit into each individual cannula. The stylet 517 made be made of metal or from any suitable materials, such as biocompatible materials or non-biocompatible materials that are coated with biocompatible materials or combinations of these materials as described elsewhere herein, that have appropriate properties to serve their intended function as disclosed herein.

The stylet 517 may be provided to prevent fluids or blood from leaking through the cannula in the plunger head 514. The end portion 519 of stylet 517 may cooperate with the plunger head 514 to provide an interference fit with the plunger head 514 sufficient, to prevent, substantially prevent or reduce fluid or blood pressure from loosening the stylet and to prevent, substantially prevent or reduce leaking of fluids or blood through the plunger shaft cannula 516a. In some aspects, the stylet length is such that it sits slightly protruded when fully inserted into plunger shaft cannula 516a and through plunger head 514. The amount of such protrusion may be for example, but not limited to, between 0.25 to 0.75 mm, 0.1 to 1 mm, 0.2 to 0.8 mm, or 0.3 to 0.6 mm. In some embodiments, the stylet distal end 519a may be constructed to connect to the distal end of plunger shaft 516 using an suitable connection, such as a lure connection or a threaded connection to hold the stylet 517 in place when end cap 510 is removed, while in other embodiments it may just be placed within plunger shaft cannula 516a. End portion 519a of stylet 517 is in certain aspects shaped to reduce the likelihood of thrombus formation, for example, it may have a round shape.

Figure 39:
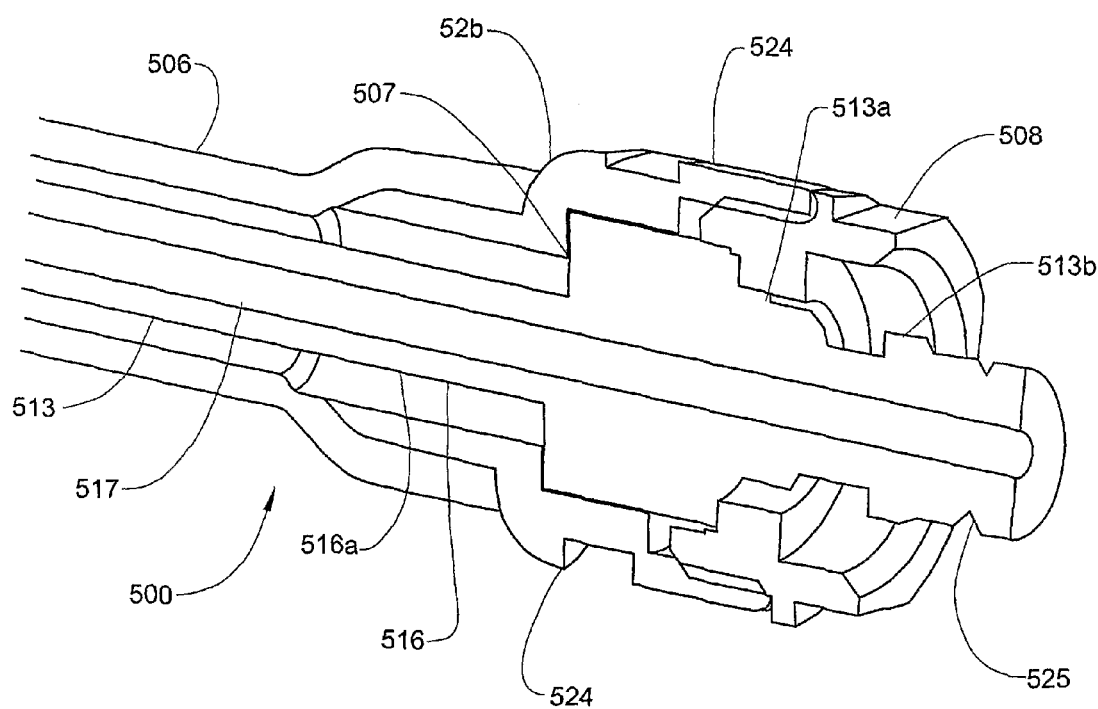
FIG. 39 is a detail cross sectional view of a portion of the device according to FIG. 38.

FIG. 39 is a detail cross sectional view of a portion of the device according to FIG. 38 with the end cap removed. This figure shows some of the details related to the distal end of an embodiment of the device shown in FIG. 38. As shown, lumen 504 has flow port 507, placed within it. Connector 508 holds sealing members 524 against sealing shoulder 526 of flow port 507. Sealing members 524 seal lumen 504 to prevent infiltration of lumen 504 by foreign material, to provide structural support for distal end of plunger shaft 516 and to prevent over-insertion of plunger 513 into lumen 504 by interacting with shoulder 513a of plunger 513. Shoulder 513a may be configured to assist alone or in conjunction with connection means 513b with connection of a removal device or tool to remove the plunger from lumen 504 or with connection of a therapeutic or other fluid or device supply. In the embodiment shown, stylet 517 is inserted into plunger shaft cannula 516a and is sealed in place, in part via sealing member 525.

Figure 40:
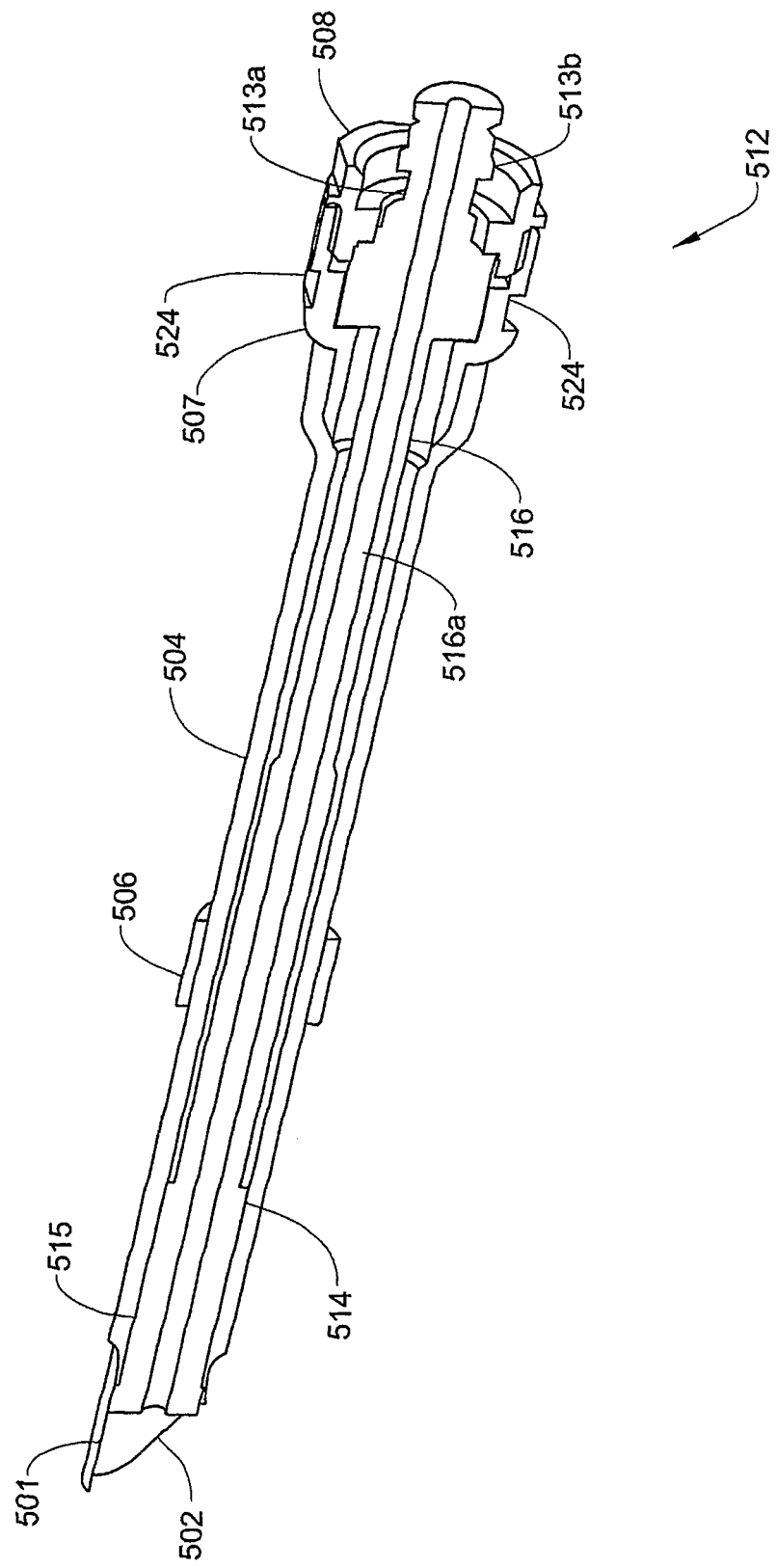
FIG. 40 is a cross sectional view of the device according to FIG. 38 with the stylet removed.
Figure 41:
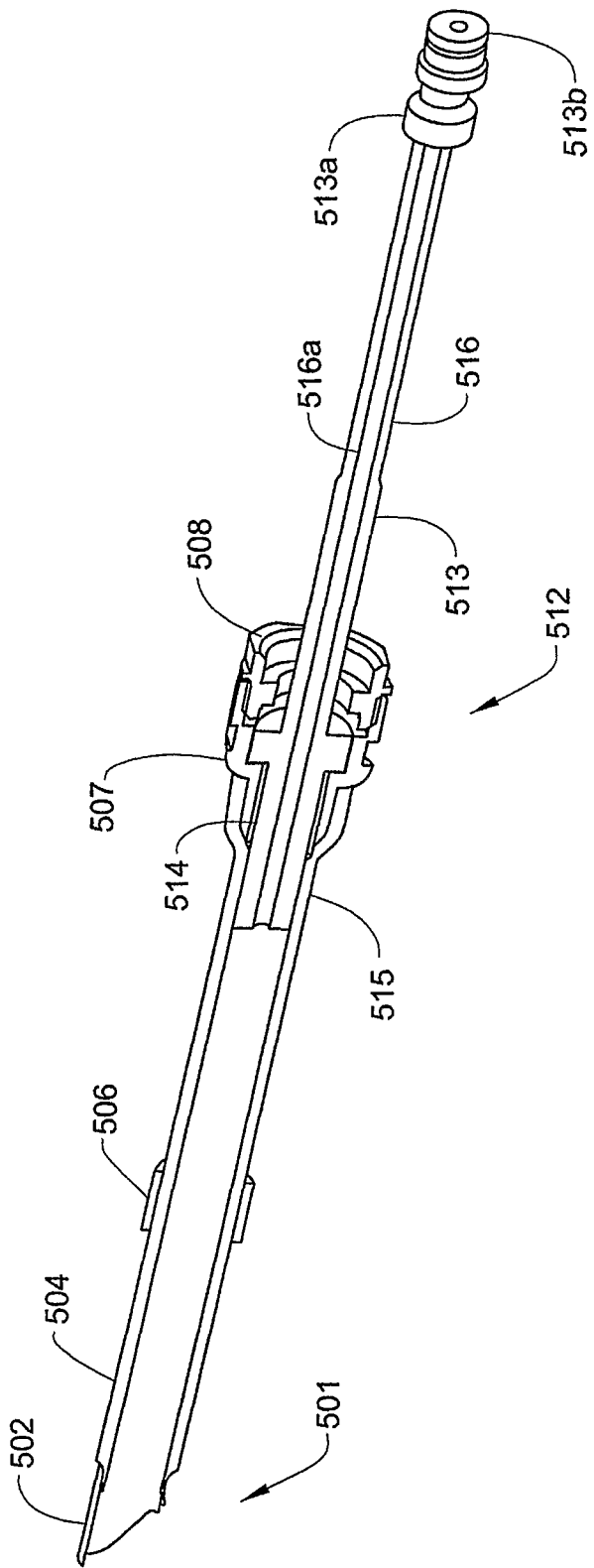
FIG. 41 is a cross sectional view of the device according to FIG. 40 with the plunger partially removed.
Figure 42:
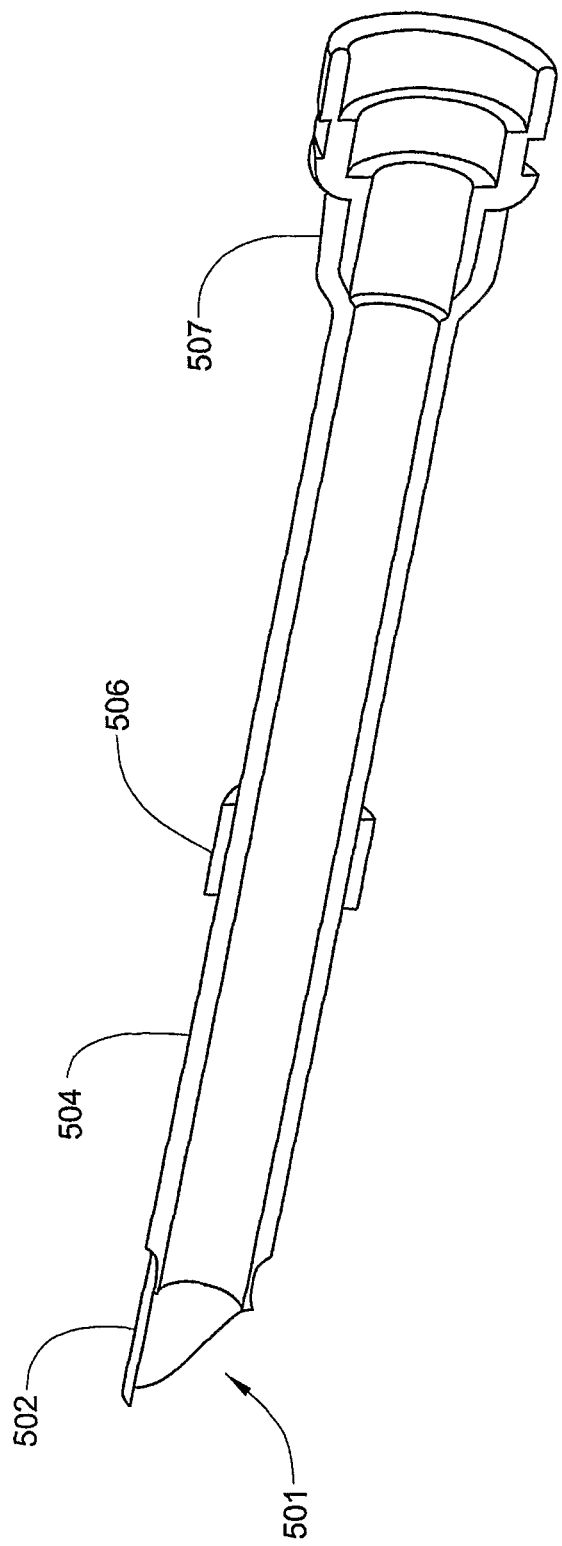
FIG. 42 is a cross sectional view of the device according to FIG. 41 with the plunger and connector completely removed.

FIG. 40 is a cross sectional view of the device according to FIG. 38 with the end cap and the stylet removed. In this configuration, access device 500 may be used for supply of or addition of therapeutics through plunger shaft cannula 516a, such as any therapeutics as described herein, such as, for example drip solutions such as saline, dextrose or heparin solutions of for access for angiography or other test procedures into a vessel by connecting appropriate equipment and solutions to the distal end of plunger shaft 516. The cannulation diameter in this embodiment is compatible with diagnostic catheters such as for example a 5 French catheter. In some aspects, the outer diameter of plunger shaft 516 may be less than the diameter of the plunger head 514 to allow addition of an appropriate flow of any solution (e.g. saline and/or heparin) to be backfilled behind the plunger head 514. The plunger shaft 516 may be sufficiently stiff to withstand longitudinal force during insertion and extraction. In some embodiments, the plunger shaft 516 may have cut outs at the distal end to permit back flushing of the device with sterile solutions and venting of solution so as not over pressurize the device assembly. In certain aspects, the plunger shaft may have a smooth or substantially smooth surface to create a desired interface with shaft seals. In some aspects, the plunger shaft 516 may have a threaded end which allows simple connection of replaceable plunger heads 514. FIG. 41 is a cross sectional view of the access device 500 according to FIGS. 37 to 40 with the plunger partially removed and FIG. 42 is a cross sectional view of the access device 500 according to FIG. 42 with the plunger and connector completely removed. In the configuration in FIG. 42, access device 500 is configured to receive additional connections, access or treatment caps in preparation for treating a patient. Lumen 504 is shown fully open for flow of fluid there through or for insertion of balloon catheters or other devices.

Figure 43:
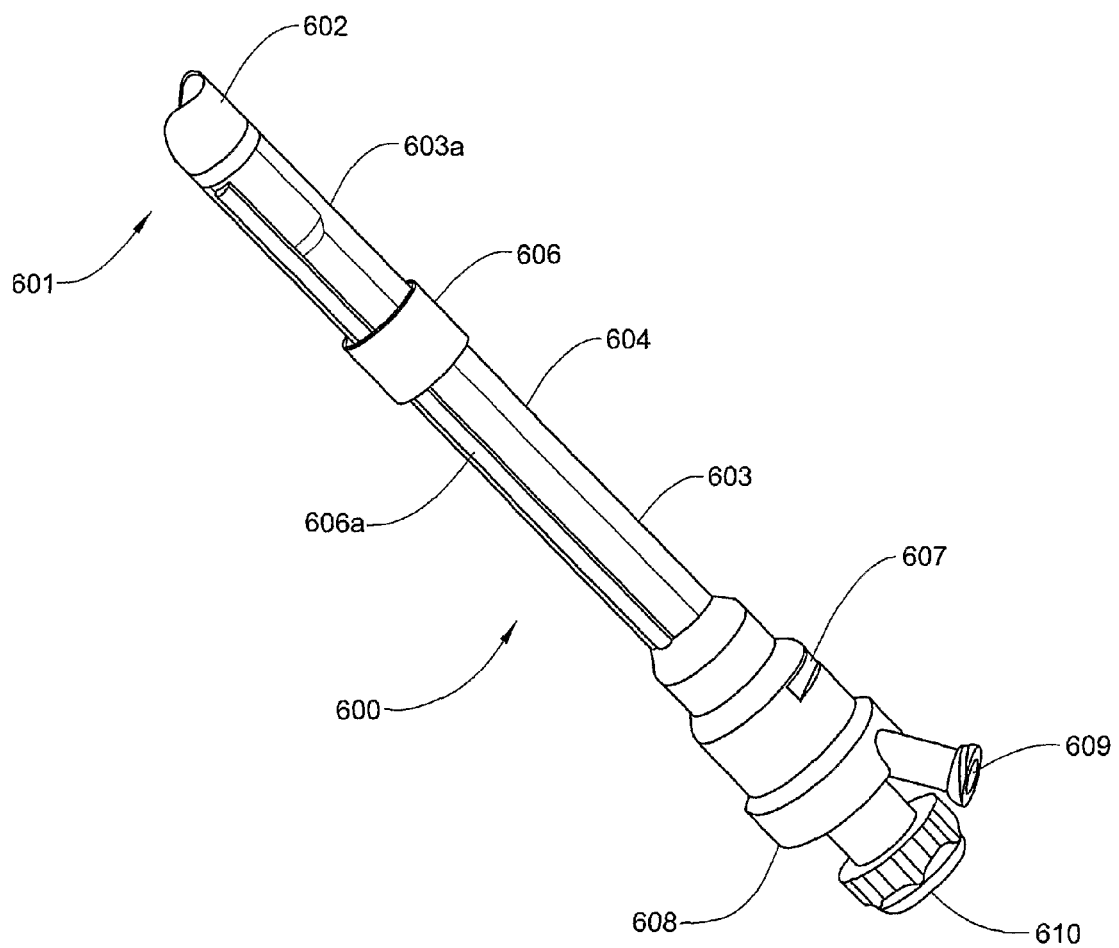
FIG. 43 is a schematic of an embodiment of an access device with a multi-access treatment cap or head.

FIG. 43 is a schematic of an embodiment of an access device 600 with a multi-access treatment cap 608. Access device 600 has suture foot 602 at access end 601, which, when in use, provides fluid communication between a vessel (not shown) and lumen 604 by providing for suture of access device 600 to a vessel. In the embodiment shown, lumen 604 may be comprised of two different portions, 603 and 603*a* which may be constructed of different materials, such as any combination of the biocompatible materials or coated non-biocompatible materials as described herein and may be bonded or otherwise connected or adhered to each other. For example, in some embodiments, portion 603*a* may comprise PTFE and portion 603 may comprise silicone and the portions may be bonded to each other or adhered to each other using an adhesive, such as a fast curing adhesive. Access device 600 has sleeve 606 which provides for support of the device 600 and lumen 604 and sealing and/or leak minimization/elimination at the point of penetration to the skin or penetration of the vessel. In addition, sleeve 606 provides support to and/or connection of re-enforcing member 606*a* against lumen 604.

Access device 600 has flow port 607 that has been capped with multi-access treatment cap 608. Flow port 607 may be inserted into lumen 604 and bonded, sealed or otherwise connected to portion 603 of lumen 604 to provide for connection to various devices using various flow and/or end caps. Multi-access treatment cap 608 may be connected to flow port 607 using any suitable connection, such as threaded, lure, swage or any other connection described herein. Multi-access treatment cap 608 may have access ports 609 and 610 which may be connected to the various external tubing, equipment and devices described herein for treatment of a patient. When access device 600 is inserted into a vessel, the configuration shown may be used in conjunction with such tubing, equipment and devices to treat a patient.

Access device 600, suture foot 602, lumen 604, sleeve 606, reinforcing member 606*a*, flow port 607 and multi-access treatment cap 608 may be constructed from any suitable materials, such as biocompatible materials or non-biocompatible materials that are coated with biocompatible materials as described elsewhere herein, that have appropriate properties to serve their intended function as disclosed herein. In some aspects, sleeve 606 and/or suture foot 602 may be constructed from polyester, PTFE or ePTFE. In some embodiments, lumen 604 may comprise wholly or in part silicone and flow port 607 and multi-access treatment cap 608 may comprise metal, such as stainless steel, or a plastic or a combination of thereof.

Figure 44:
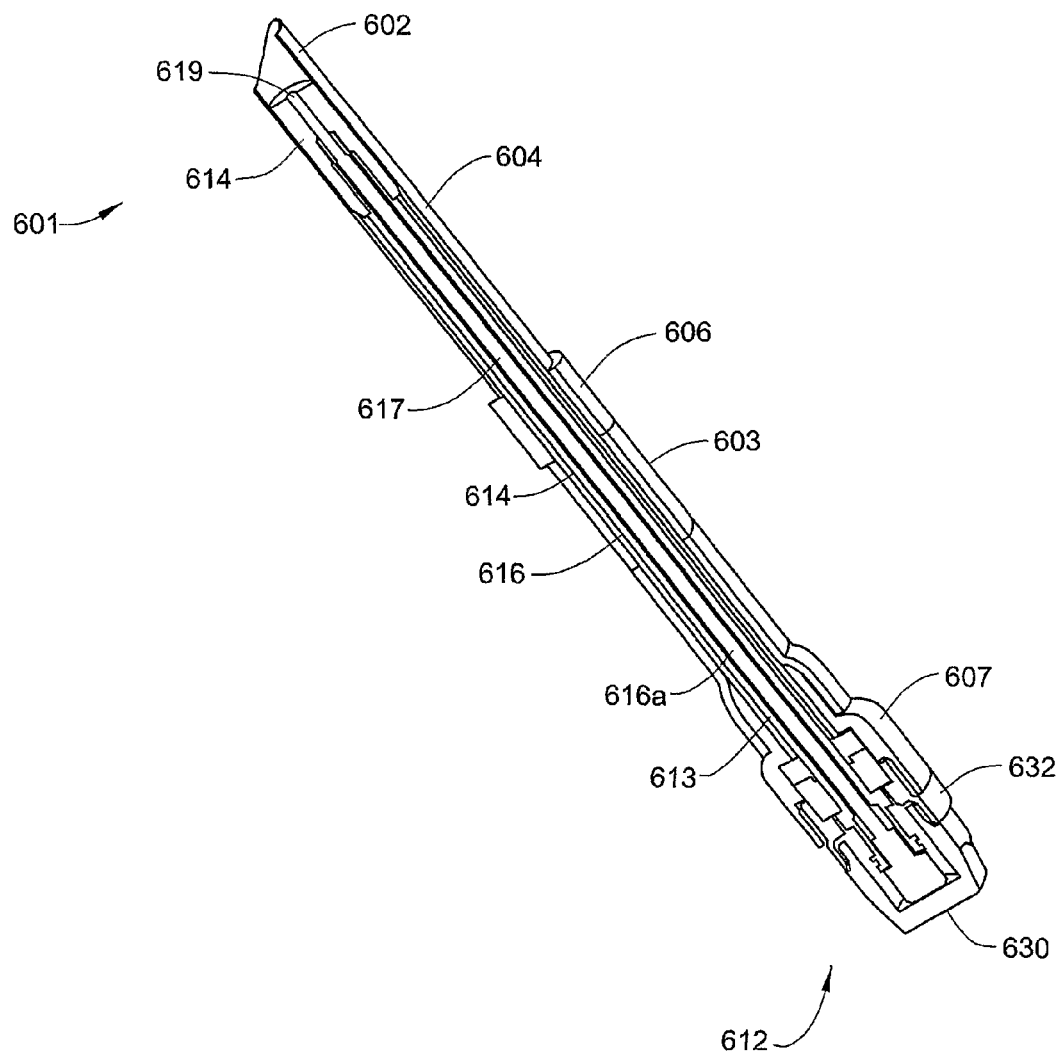
FIG. 44 is a cross sectional view of the embodiment of FIG. 43 with an end cap rather.

FIG. 44 is a cross sectional view of the embodiment of FIG. 43 with an end cap 630 and connector 632 rather than a multi-access treatment cap 608. Access device 600 has suture foot 602 at access end 601, which, when in use, provides fluid communication between a vessel (not shown) and lumen 604 by providing for suture of access device 600 to a vessel. Access device 600 has sleeve 606 which provides for support of the device 600 and lumen 504, sealing and/or leak minimization/elimination at the point of penetration to the skin or penetration of the vessel and for prevention or reduction of infection. Access device 600 has flow port 607 that has been capped with connector 632 and end cap 630. Flow port 607 may be inserted into lumen 604 and bonded, sealed or connected to portion 603 of lumen 604 to provide for connection to various devices using various flow and/or end caps. Connector 632 facilitates connection of end cap 630 to access device 600 at external end 612 in order to place the access device 600 into the hold configuration shown in the figure such that no flow is occurring through lumen 604 and the device 600 is not in use. When access device 600 is inserted into a vessel, this configuration may be used between or before treatments. In such instances, end cap 630 is connected to device 600 to limit or prevent infection and to isolate the vessel access when the access device 600.

Access device 600, suture foot 602, lumen 604, sleeve 606, flow port 607, connector 632 and end cap 630 may be constructed from any suitable materials, such as biocompatible materials or non-biocompatible materials that are coated with biocompatible materials or combinations of these materials as described elsewhere herein, that have appropriate properties to serve their intended function as disclosed herein. In some aspects, the lumen 604 may be made, wholly or in part of silicone. In some embodiments, lumen 604 may be constructed of more than one biocompatible or coated non-biocompatible material described herein. For example, in some embodiments, lumen 604 may comprise a flexible portion that is silicone and a second portion that is metal or PTFE or other suitable material that may be bonded to the silicone portion using a fast cure adhesive or other suitable adhesive or bonding material. In some embodiments, lumen 604 comprises portion 603*a*, which may be PTFE and portion 603, which may be silicone. In other embodiments, portions 603 and 603*a* may be any suitable combination of the biocompatible and coated biocompatible materials described herein and each of such combinations is specifically contemplated. In some aspects, sleeve 606 and/or suture foot 602 may be constructed from polyester, PTFE or ePTFE. In some embodiments, flow port 607, connector 632 and end cap 630 may comprise metal, such as stainless steel, or a plastic or a combination of thereof.

As shown, access device 600 has a plunger 613 inserted in lumen 604. Plunger 613 may comprise a cannulated plunger shaft 616 as shown, or may comprise a solid plunger shaft and may have plunger head 614, which may be un-ribbed as shown or may have ribs. In some embodiments, plunger head 614 may serve to seal lumen 604 to prevent access to lumen 604 by fluid flowing in a vessel. In certain aspects, the plunger 613 and plunger shaft 616 may be made of metal, wholly or in part and plunger head 614 may be made of HDPE. Alternatively, they may be constructed from any suitable materials, such as biocompatible materials or non-biocompatible materials that are coated with biocompatible materials or combinations of these materials as described elsewhere herein, that have appropriate properties to serve their intended function as disclosed herein.

The plunger shaft 616 may be cannulated to provide for access to lumen 604 or to a vessel for angiographic purposes and for addition of therapeutics, such as any therapeutics as described herein, such as, for example drip solutions such as saline, dextrose or heparin solutions. In this figure, access device 600 is shown with a stylet 617 in place within the cannula of plunger shaft 616. In the figure, the plunger shaft cannula 616a is shown centered. In other embodiments, the plunger shaft cannula 616a may be position of center within the plunger shaft 616, while in other embodiments, the plunger shaft 616 may include none, 1, 2, 3, or 4 cannulae each having an individual cooperating stylet, or stylet 617 may be configured with multiple shafts to fit into each individual cannula. The stylet 617 may be made of metal or from any suitable materials, such as biocompatible materials or non-biocompatible materials that are coated with biocompatible materials or combinations of these materials as described elsewhere herein, which have appropriate properties to serve their intended function as disclosed herein.

The stylet 617 may be provided to prevent fluids or blood from leaking through the cannula in the plunger head 614. The end portion 619 of stylet 617 may cooperate with the plunger head 614 to provide an interference fit with the plunger head 614 sufficient, to prevent, substantially prevent or reduce fluid or blood pressure from loosening the stylet and to prevent, substantially prevent or reduce leaking of fluids or blood through the plunger shaft cannula 616a. In some aspects, the stylet length is such that it sits slightly protruded when fully inserted into plunger shaft cannula 616a and through plunger head 614. The amount of such protrusion may be for example, but not limited to, between 0.25 to 0.75 mm, 0.1 to 1 mm, 0.2 to 0.8 mm, or 0.3 to 0.6 mm. In some embodiments, the stylet distal end 619a may be constructed to connect to the distal end of plunger shaft 616 using an suitable connection, such as a lure connection or a threaded connection to hold the stylet 617 in place when end cap 510 is removed, while in other embodiments it may just be placed within plunger shaft cannula 616a. End portion 619a of stylet 617 is in certain aspects shaped to reduce the likelihood of thrombus formation, for example, it may have a round shape.

Figure 45:
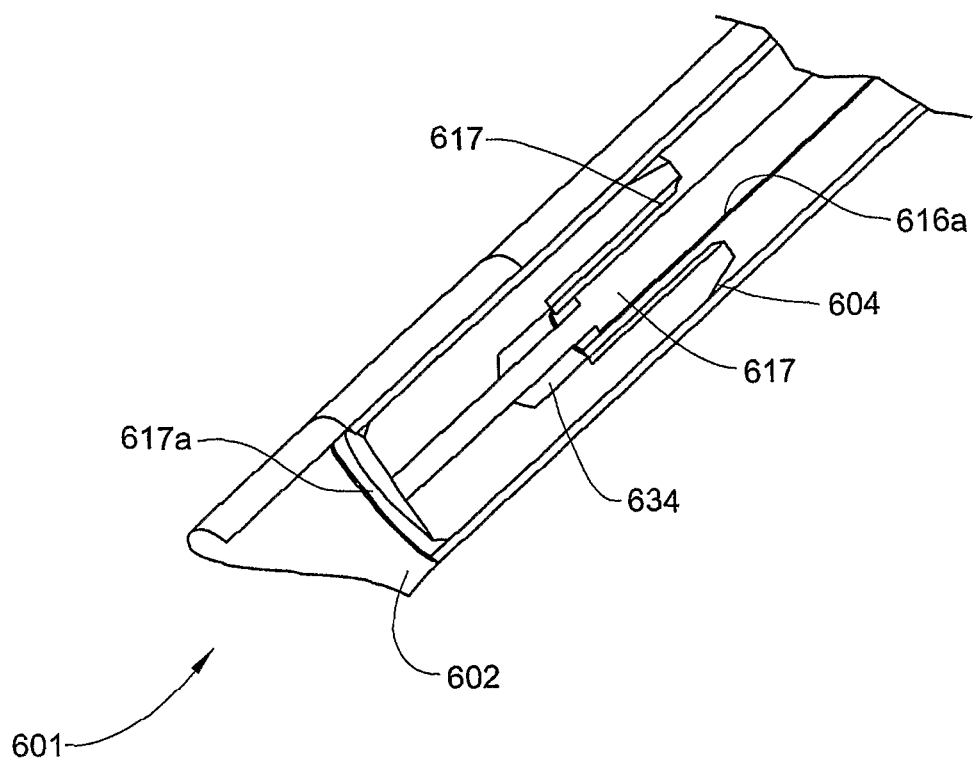
FIG. 45 is a detail cross sectional view of a portion of the embodiment of FIG. 44.

FIG. 45 is a detail cross sectional view of a portion of the embodiment of FIG. 44 showing the access end 601 of access device 600. As shown, suture foot 602 is bonded to lumen 604. Plunger head 614 is placed in access end 601 to prevent flow of fluid into lumen 604. Similarly, stylet 617 seals plunger shaft cannula 616a. Sealing member 634 interacts with stylet 617 to provide support for the access end 617a of stylet 617 and to assist stylet 617 with sealing plunger shaft cannula 616a.

Figure 46:
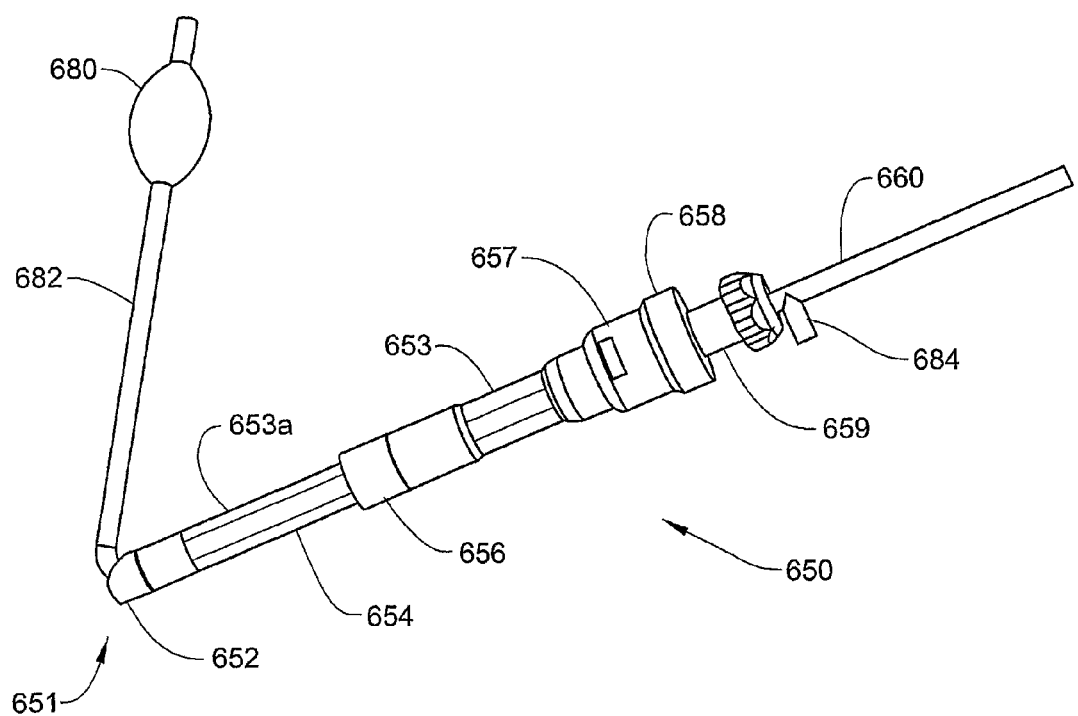
FIG. 46 is a schematic of an embodiment of an access device in a treatment configuration.

FIG. 46 is a schematic of an embodiment of an access device 650 in a treatment configuration. Access device 650 has suture foot 652 at access end 651, which, when in use, provides fluid communication between a vessel (not shown) and lumen 654 by providing for suture of access device 650 to a vessel. In the embodiment shown, lumen 654 may be comprised of two different portions, 653 and 653a which may be constructed of different materials, such as any combination of the biocompatible materials or coated non-biocompatible materials as described herein and may be bonded or otherwise connected or adhered to each other. For example, in some embodiments, portion 653a may comprise PTFE and portion 653 may comprise silicone and the portions may be bonded to each other or adhered to each other using an adhesive, such as a fast curing adhesive. Access device 650 has sleeve 656 which provides for support of the device 650 and lumen 654 and sealing and/or leak minimization/elimination at the point of penetration to the skin or penetration of the vessel.

Access device 650 has flow port 657 that has been capped with treatment cap 658. Flow port 657 may be inserted into lumen 654 and bonded, sealed or otherwise connected to portion 653 of lumen 654 to provide for connection to various devices using various flow and/or end caps. Treatment cap 658 may be connected to flow port 657 using any suitable connection, such as threaded, lure, swage or any other connection described herein. Treatment cap 658 may have access port 659 which may be connected to the various external tubing, equipment and devices described herein for treatment of a patient. When access device 650 is inserted into a vessel, the configuration shown may be used in conjunction with such tubing, equipment and devices to treat a patient. In the embodiment shown, balloon catheter 660 has been placed through access port 659 and lumen 654. Balloon catheter 660 has balloon 680, flow lumen 682 and inflation lumen 684. Balloon 680 may be inflated using inflation lumen 684 to occlude or isolate a vessel, a portion of the circulatory system, an organ and/or other tissue and fluid may be pumped or otherwise sent through flow lumen 682 either into or out of a vessel, a portion of the circulatory system, an organ and/or other tissue as part of a treatment.

Access device 650, suture foot 652, lumen 654, sleeve 606, flow port 657, treatment cap 608, balloon catheter 660, balloon 680, flow lumen 682 and inflation lumen 684 may be constructed from any suitable materials, such as biocompatible materials or non-biocompatible materials that are coated with biocompatible materials as described elsewhere herein, that have appropriate properties to serve their intended function as disclosed herein. In some aspects, sleeve 656 and/or suture foot 652 may be constructed from polyester, PTFE or ePTFE. In some embodiments, lumen 654 may comprise wholly or in part silicone and flow port 657 and treatment cap 658 may comprise metal, such as stainless steel, or a plastic or a combination of thereof.

FIG. 47 is a cross sectional view of the embodiment of FIG. 46. As shown, balloon catheter 660 is inserted through sealing member 686, 688, 690 and into lumen 604. Sealing members 686, 688 and 690 may be any suitable sealing members, such as o-rings or gaskets and may be constructed from any suitable biocompatible or coated non-biocompatible material described herein, such as for example silicone. Other sealing members may be used in certain embodiments such as check valves and/or flow control valves. In some aspects, it is desirable that the selected valve allow fluid, or substantially allow, fluid to flow in one direction only. It is desirable that the sealing member used prevent fluid from moving backwards by using the fluid itself (for example with a duckbill valve) or other valve configurations such as a spring valve and/or a check valve. In some embodiments, sealing member 688 may be a duckbill valve which may be may be constructed from any suitable biocompatible or coated non-biocompatible material described herein, such as for example silicone. Any suitable duckbill valve configurations may be used In some embodiments, the duckbill valve may prevent or limit backflow through the port in which it is inserted, while providing access to lumen 604 for balloon catheters that may be threaded through the lobes of the duckbill valve. The leaflets of the duckbill valve may be of suitable materials that may form around completely or in part, such a balloon catheter in order to limit leakage or backflow through the relevant access port.

Figure 48:
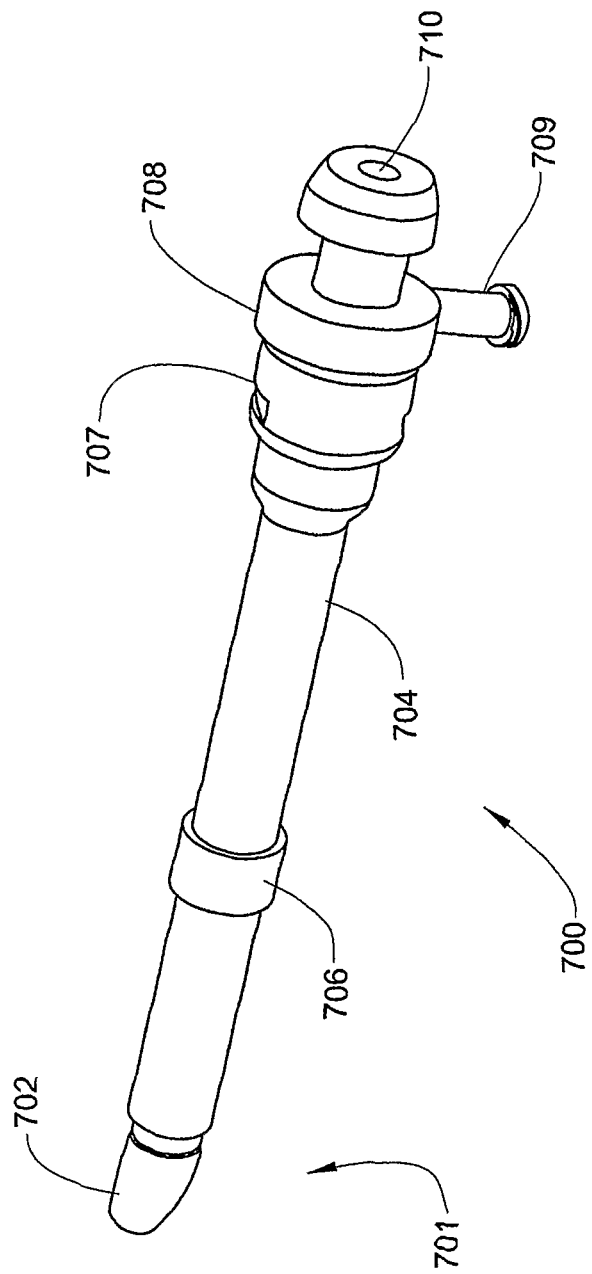
FIG. 48 is a schematic of an embodiment of an access device with a vortex cap or head.

FIG. 48 is a schematic of an embodiment of an access device 700 with a vortexing cap 708. Access device 700 has suture foot 702 at access end 701, which, when in use, provides fluid communication between a vessel (not shown) and lumen 704 by providing for suture of access device 700 to a vessel. Access device 700 has sleeve 706 which provides for support of the device 700 and lumen 704 and sealing and/or leak minimization/elimination at the point of penetration to the skin or penetration of the vessel. Access device 700 has flow port 707 that has been capped with vortexing cap 708. Flow port 707 may be inserted into lumen 704 and bonded, sealed or otherwise connected to lumen 704 to provide for connection to various devices using various flow and/or end caps. Vortexing cap 708 may be connected to flow port 707 using any suitable connection, such as threaded, lure, swage or any other connection described herein. Vortexing cap 708 may have vortexing port 709 and access port 710 which may be connected to the various external tubing, equipment and devices described herein for treatment of a patient using any suitable connection means described herein. When access device 700 is inserted into a vessel, the configuration shown may be used in conjunction with such tubing, equipment and devices to treat a patient.

Access device 700, suture foot 702, lumen 704, sleeve 706, flow port 707 and vortexing cap 708 may be constructed from any suitable materials, such as biocompatible materials or non-biocompatible materials that are coated with biocompatible materials as described elsewhere herein, that have appropriate properties to serve their intended function as disclosed herein. In some aspects, sleeve 706 and/or suture foot 702 may be constructed from polyester, PTFE or ePTFE. In some embodiments, lumen 704 may comprise wholly or in part silicone and flow port 707 and vortexing cap 708 may comprise metal, such as stainless steel, or a plastic or a combination of thereof.

Figure 49:
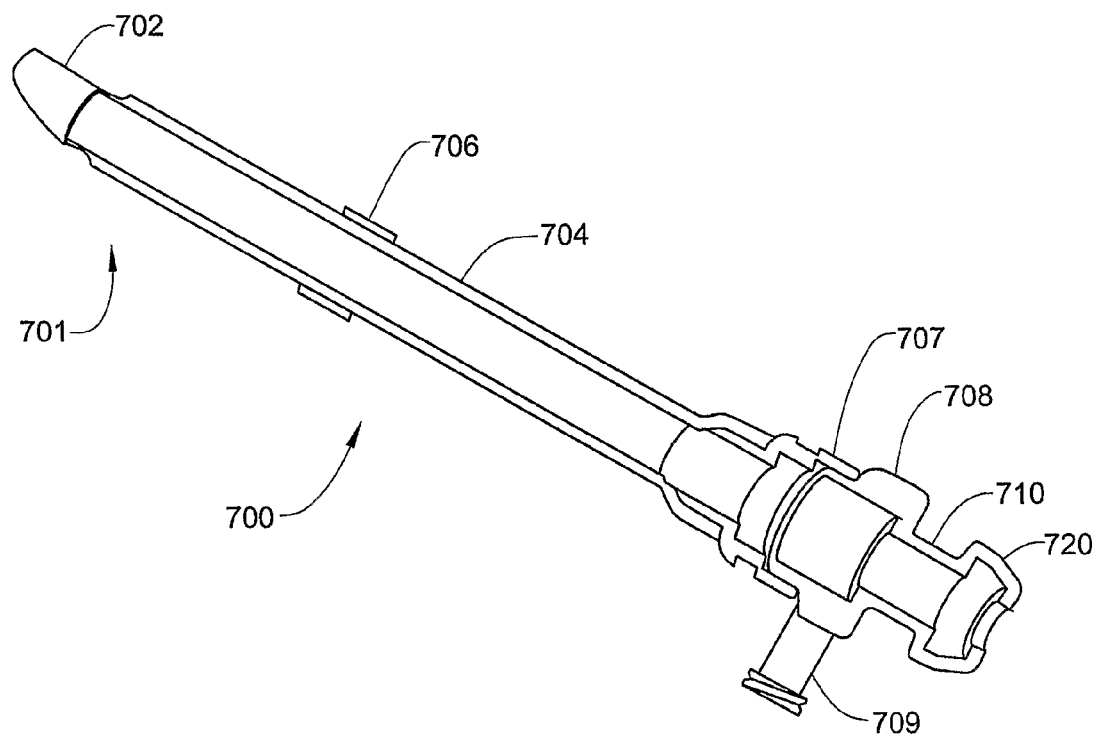
FIG. 49 is a cross sectional view of the embodiment of FIG. 48.

FIG. 49 is a cross sectional view of the embodiment of FIG. 48 showing the internal portion of lumen 704, flow port 707 and vortexing cap 708. Vortexing cap is shown with connection cap 720 which may facilitate connection of tubing, devices and equipment, which may be any tubing, devices or equipment as described herein to access device 700.

Figure 50:
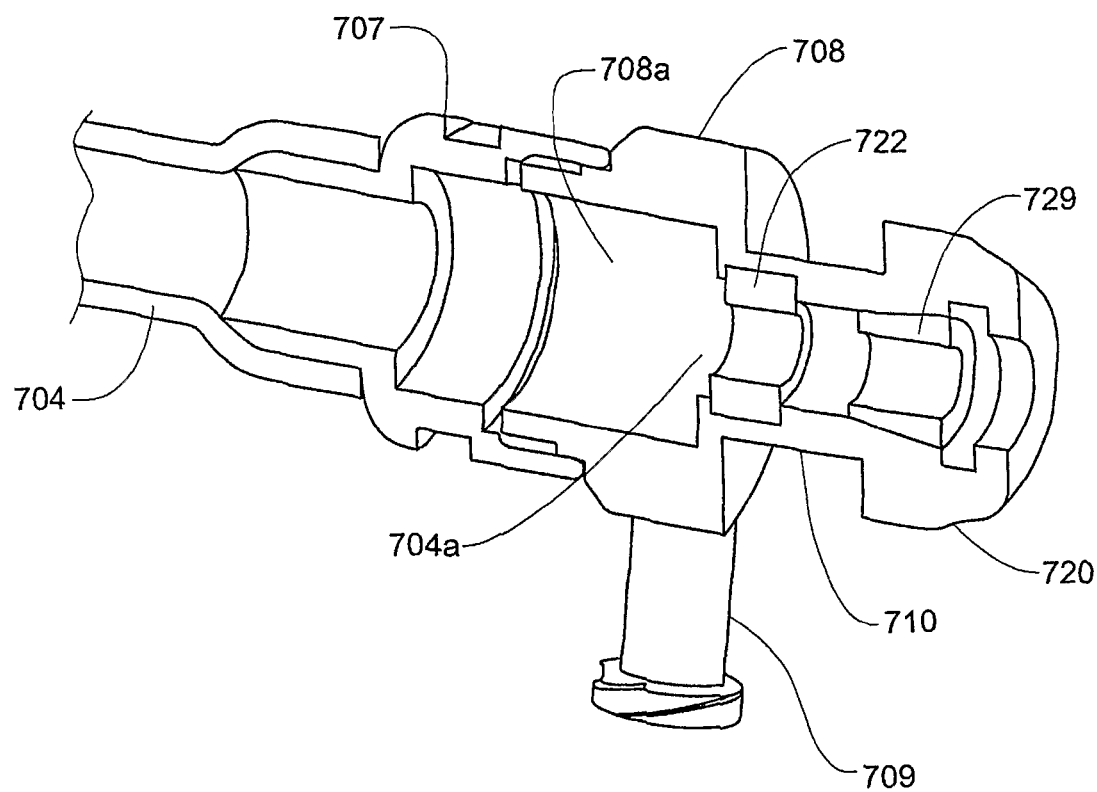
FIG. 50 is a detail cross sectional view of a portion of the embodiment of FIG. 49.

FIG. 50 is a detail cross sectional view of a portion of the embodiment of FIG. 49, showing a cross section of vortexing cap 708. As shown, vortexing cap 708 includes sealing members 722 and 724 for sealing to tubing, devices and equipment that may be placed through access port 710. In use fluid is removed through access port 710 using a balloon catheter (not shown) and sent to various external tubing, devices and equipment, including for example, pumps, flow controllers, drug delivery devices, blood monitoring devices, such as blood pH, SO2, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used. The fluid may then be returned through vortexing port 709 and into lumen 704 and the vessel (not shown).

Typically, the fluid will be introduced through vortexing port 709 after the fluid or its physical, chemical or kinetic properties have been modified in some way. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, CO2, phosphate, urea, antibodies, antibiotics or other components, such as a drug or therapeutic that is being used specifically in treatment. In some embodiments, the fluid is returned at a flow rate or pressure that is at a higher pressure and/or flow rate than the fluid flowing in the vessel prior to occlusion with an occlusion balloon and/or the systemic blood pressure measured at a location remote to the treatment site. Vortexing port 709 is specifically configured to return the fluid along the internal walls 708a of vortexing cap 708 and lumen 704 in order to reduce the potential for shear damage to various components in the returning fluid. In certain aspects, the Vortex head is designed to minimize areas, or substantially minimize areas, of stasis when pumping the blood or fluid into the access device body. In some embodiments this is accomplished by configuring vortexing port such that it penetrates vortexing cap 708 substantially tangentially and with a curved triangular shaped concavity 709a. By configuring the penetration of port 709 in such a fashion the fluid may flow along the walls of the vortexing cap in a descending spiral into lumen 704 with reduced shear and velocity affects on the returning fluid and may flow around a balloon catheter that has been inserted through access port 710.

Figure 51:
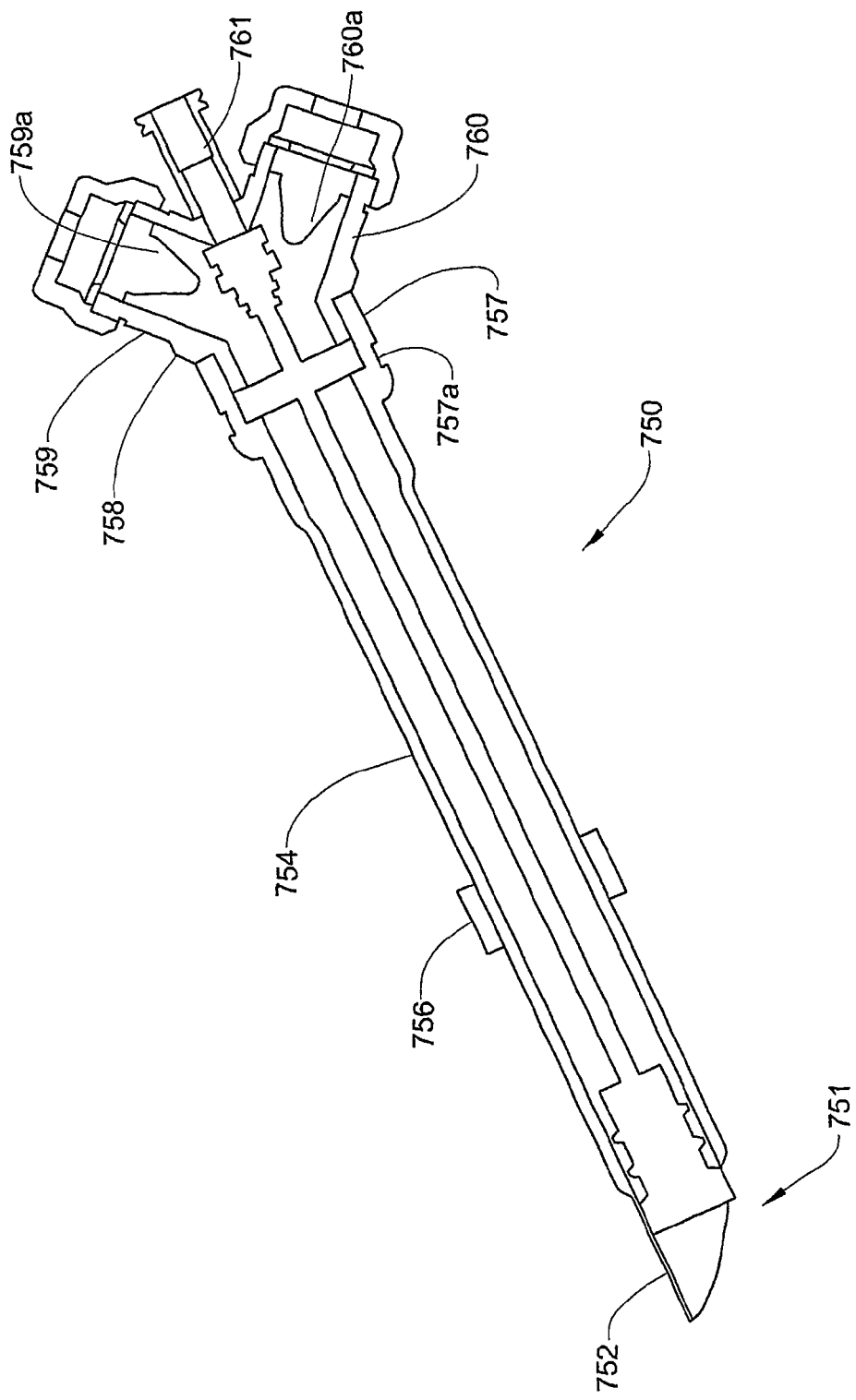
FIG. 51 is a cross sectional view of an embodiment of an access device with a multi-access treatment cap.

FIG. 51 is a cross sectional view of an embodiment of an access device 750 with a multi-access treatment cap 758. Access device 750 has suture foot 752 at access end 751, which, when in use, provides fluid communication between a vessel (not shown) and lumen 754 by providing for suture of access device 750 to a vessel. Access device 750 has sleeve 756 which provides for support of the device 750 and lumen 754 and sealing and/or leak minimization/elimination at the point of penetration to the skin or penetration of the vessel. Access device 750 has flow port 757 that has been capped with multi-access treatment cap 758. Flow port 757 may be inserted into lumen 754 and bonded, sealed or otherwise connected to lumen 754 to provide for connection to various devices using various flow and/or end caps. Multi-access treatment cap 758 may be connected to flow port 757 using any suitable connection, such as for example, a threaded, lure, swage or any other connection as described herein. Multi-access treatment cap 758 may have access ports 759, 760 and 761 which may be connected to the various external tubing, equipment and devices described herein for treatment of a patient. When access device 750 is inserted into a vessel, the configuration shown may be used in conjunction with such tubing, equipment and devices to treat a patient. Duckbill valves 759a and 760a have been inserted into access ports 759 and 760 respectively and are held in place by connecting caps 762 and 763 and may be any sealing membrane or suitable duckbill valve, such as those described herein. Multi access treatment cap 758 may seal to flow port 757 by interaction with sealing member 757a, which may be any suitable sealing member, such as an o-ring or a gasket.

Access device 750, suture foot 752, lumen 754, sleeve 756, flow port 757, duckbill valves 759 and 760, sealing member 757a and multi-access treatment cap 758 may be constructed from any suitable materials, such as biocompatible materials or non-biocompatible materials that are coated with biocompatible materials as described elsewhere herein, that have appropriate properties to serve their intended function as disclosed herein. In some aspects, sleeve 756 and/or suture foot 752 may be constructed from polyester, PTFE or ePTFE. In some embodiments, lumen 754 may comprise wholly or in part silicone and flow port 757 and multi-access treatment cap 758 may comprise metal, such as stainless steel, or a plastic or a combination of thereof.

Figure 52:
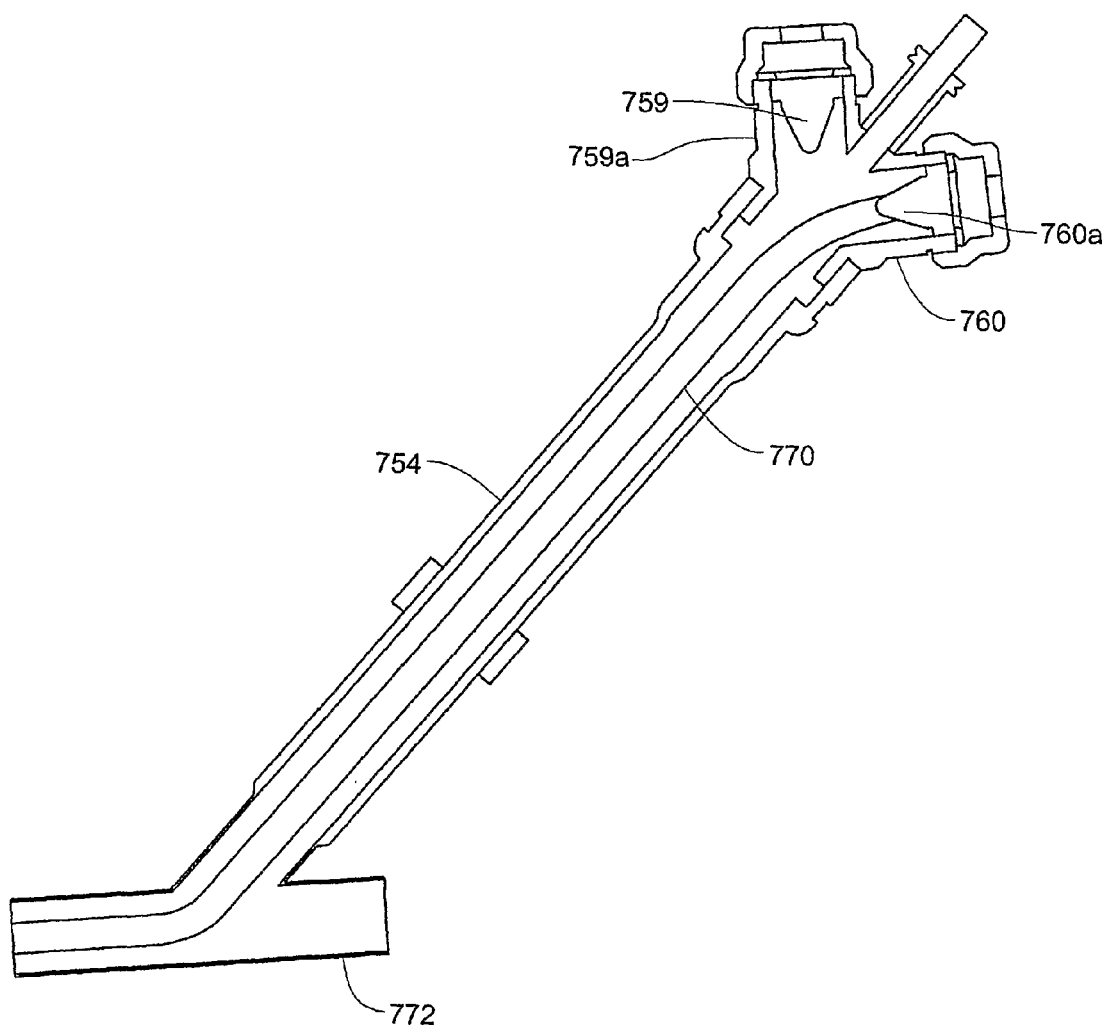
FIG. 52 is a cross sectional view of an embodiment of an access device in a treatment configuration.

FIG. 52 is a cross sectional view of an embodiment of an access device according to FIG. 51 in a treatment configuration. As shown, a catheter 770 has been inserted through access port 760 and duckbill valve 760a, through lumen 754 and into vessel 772. Using this configuration, fluid may be removed or returned through catheter 770 and/or through access port 759 and duckbill valve 759a. In use fluid may be removed from or introduced into vessel 772 through access port 760 using catheter 770 and/or through access port 759 and sent to/returned from various external tubing, devices and equipment, including for example, pumps, flow controllers, drug delivery devices, blood monitoring devices, such as blood pH, SO2, pulse or other blood monitoring devices, blood oxygenators such as bubble or membrane oxygenators, sampling devices, nutrient suppliers, such as saline or dextrose drips, dialysis or other blood cleaning or scrubbing devices, including chemical and physical filters, balloon catheter monitoring and control devices such as counterpulsation devices for cardiac applications or balloon pressurization controllers, blood temperature control devices or any other suitable device. In these devices or equipment the fluid may be monitored and/or sampled, may have its chemical, physical or kinetic properties modified and may have various substances added to and/or removed from it in accordance with a specific treatment regimen and according to the individual device or devices used. The fluid may then be returned through catheter 770 and access port 760 or through access port 759 and duckbill valve 759a and into lumen 704 and the vessel 772.

Typically, the fluid will be returned after the fluid or its physical, chemical or kinetic properties have been modified in some way. For example, the fluid may be returned at a different flow rate or pressure, or at a different temperature, pH or $S_{O2}$, or with nutrients or other components such as therapeutics, drugs, or other factors added, or with different components removed, such as toxins, harmful chemicals or drugs, excess cellular degradation products, excess CO, CO2, phosphate, urea, antibodies, antibiotics or other components, such as a drug or therapeutic that is being used specifically in treatment. In some embodiments, the fluid is returned at a flow rate or pressure that is at a higher pressure and/or flow rate than the fluid flowing in the vessel prior to occlusion with an occlusion balloon and/or the systemic blood pressure measured at a location remote to the treatment site.

Figure 53:
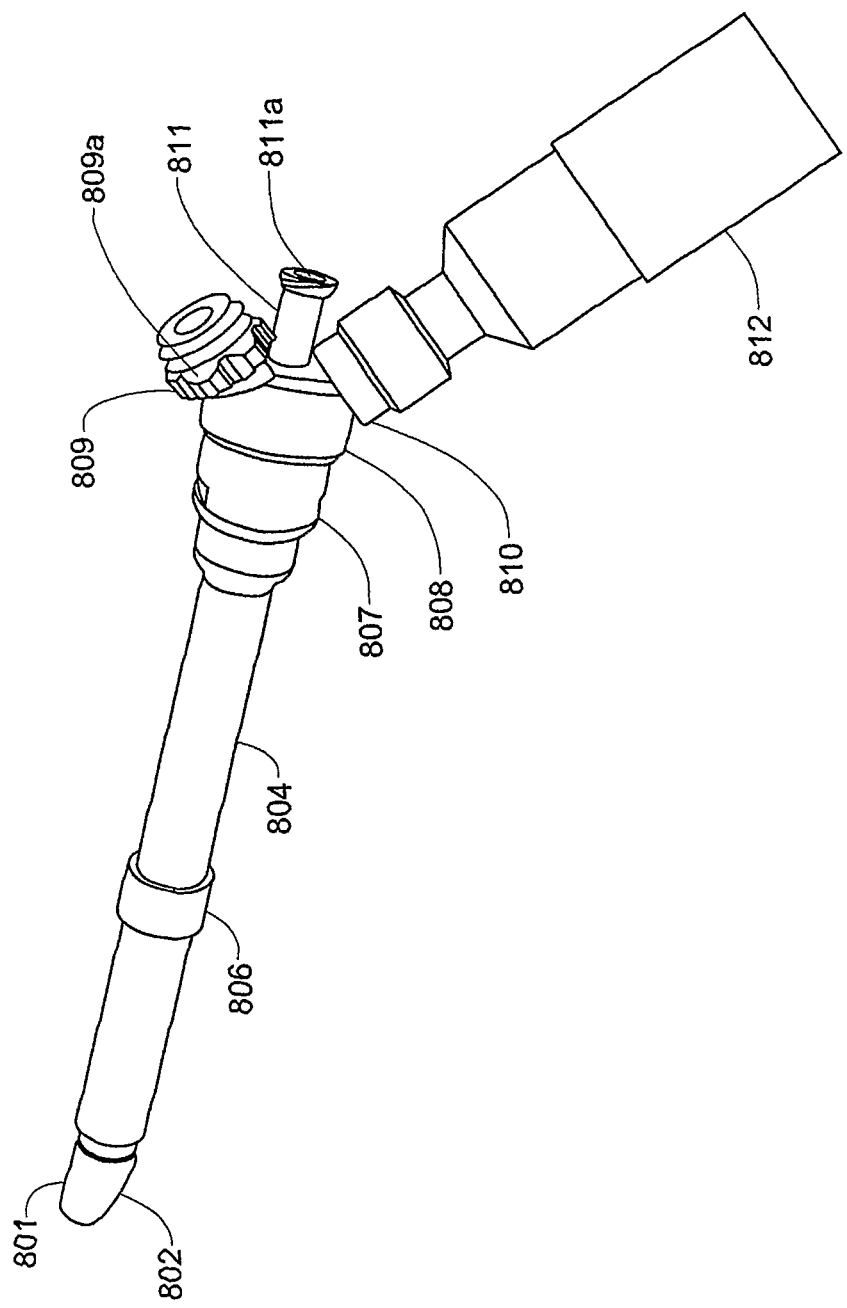
FIG. 53 is a schematic of an embodiment of an access device with a multi-access treatment cap.

FIG. 53 is a schematic of an embodiment of an access device 800 with a multi-access treatment cap 810. Access device 800 has suture foot 802 at access end 801, which, when in use, provides fluid communication between a vessel (not shown) and lumen 804 by providing for suture of access device 800 to a vessel. Access device 800 has sleeve 806 which provides for support of the device 800 and lumen 804 and sealing and/or leak minimization/elimination at the point of penetration to the skin or penetration of the vessel.

Access device 800 has flow port 807 that has been capped with multi-access treatment cap 808. Flow port 807 may be inserted into lumen 804 and bonded, sealed or otherwise connected to lumen 804 to provide for connection to various devices using various flow and/or end caps. Multi-access treatment cap 808 may be connected to flow port 807 using any suitable connection, such as threaded, lure, swage or any other connection described herein. Multi-access treatment cap 808 may have access ports 809, 810 and 811 which may be connected to the various external tubing, equipment and devices described herein for treatment of a patient. When access device 800 is inserted into a vessel, the configuration shown may be used in conjunction with such tubing, equipment and devices to treat a patient. Access port 809 is shown with a connection cap 809a attached. Access port 810 is shown with hemoreduction valve 812 attached. Access port 811 is shown with a luer connection end 811a.

Access device 800, suture foot 802, lumen 804, sleeve 806, flow port 807, multi-access treatment cap 808 and hemoreduction valve 812 may be constructed from any suitable materials, such as biocompatible materials or non-biocompatible materials that are coated with biocompatible materials as described elsewhere herein, that have appropriate properties to serve their intended function as disclosed herein. In some aspects, sleeve 806 and/or suture foot 802 may be constructed from polyester, PTFE or ePTFE. In some embodiments, lumen 804 may comprise wholly or in part silicone and flow port 807 and multi-access treatment cap 808 may comprise metal, such as stainless steel, or a plastic or a combination of thereof.

Figure 54:
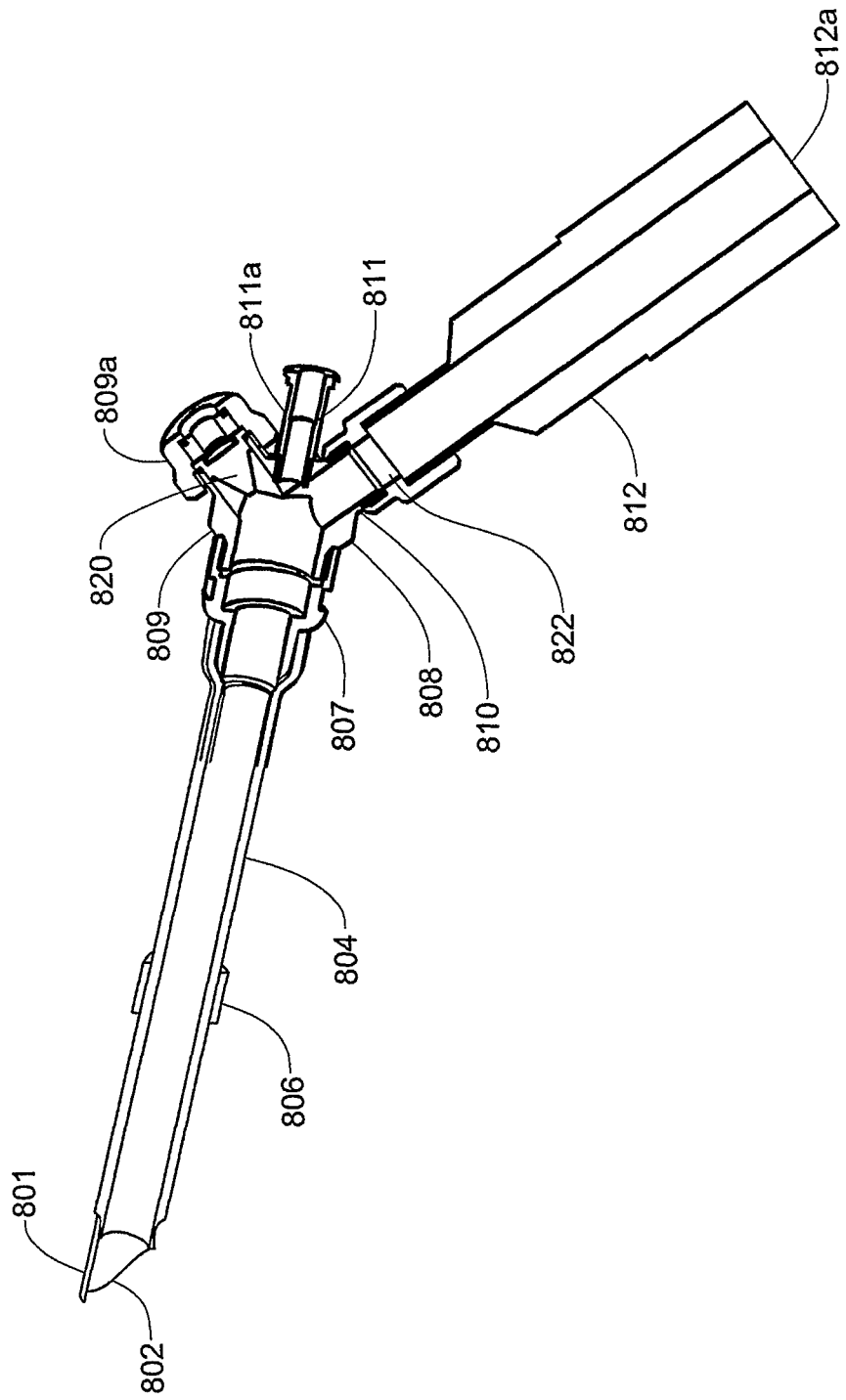
FIG. 54 is a cross sectional view of the embodiment of FIG. 53.

FIG. 54 is a cross sectional view of an embodiment of the access device according to FIG. 53 showing the internal portion of lumen 804, flow port 807 and multi-access treatment cap 808. Connection cap 809a is shown holding duckbill valve 820 in access port 809. Connection cap 809a may connected to access port 809 using any suitable connection means described herein. In some embodiments, duckbill valve 820 may be inserted into access port 809 and connection cap 809a may be connected to, such as threaded onto, access port 809 thereby holding duckbill valve 820 in place. Duckbill valve 820 may be any suitable duckbill valve for limiting or preventing backflow, while providing access to lumen 804 for balloon catheters. In certain embodiments, other sealing members may be used for example, but not limited to, check valves and/or flow control valves. In some aspects, it is desirable that the selected valve allow fluid, or substantially allow, fluid to flow in one direction only and that the sealing member used prevent fluid from moving backwards by using the fluid itself, other mechanical valve configurations such as a spring valve and/or a check valve, or combinations thereof. These sealing members may be may be constructed from any suitable material that performs the desired function.

Duckbill valve 820 may be constructed from any suitable materials, such as biocompatible materials or non-biocompatible materials that are coated with biocompatible materials as described elsewhere herein, that have appropriate properties to serve their intended function as disclosed herein. Hemoreduction valve 812 may be connected to access port 810 using any suitable connection, such as any suitable connection described herein. Hemoreduction valve 812 may be any suitable valve and may be controlled using any suitable means. As shown in the figure, hemoreduction valve has iris diaphragm 822, which may be opened, partially opened and closed by twisting hemoreduction valve 812 about an access 812a running centrally through the hemoreduction valve 812 and access port 810. In some embodiments, iris diaphragm 822 may comprise a tube of flexible material that is fixed rigidly at each end of the tube, such that when hemoreduction valve 812 is twisted and moved toward the access port 810, the flexible material twists into the center of the flow path similar to the iris of a camera lens. As the material is twisted further, the size of the available flow path is reduced, until the flow path is completely blocked. Such a diaphragm provides for a concentric circular opening throughout its open positions, provides generally for no leakage and is gentle on fragile materials, such as blood cells or other blood components. Iris diaphragm 822 may be made from any suitable materials, such as biocompatible materials or non-biocompatible materials that are coated with biocompatible materials as described elsewhere herein, that have appropriate properties to serve their intended function as disclosed herein.

Figure 55:
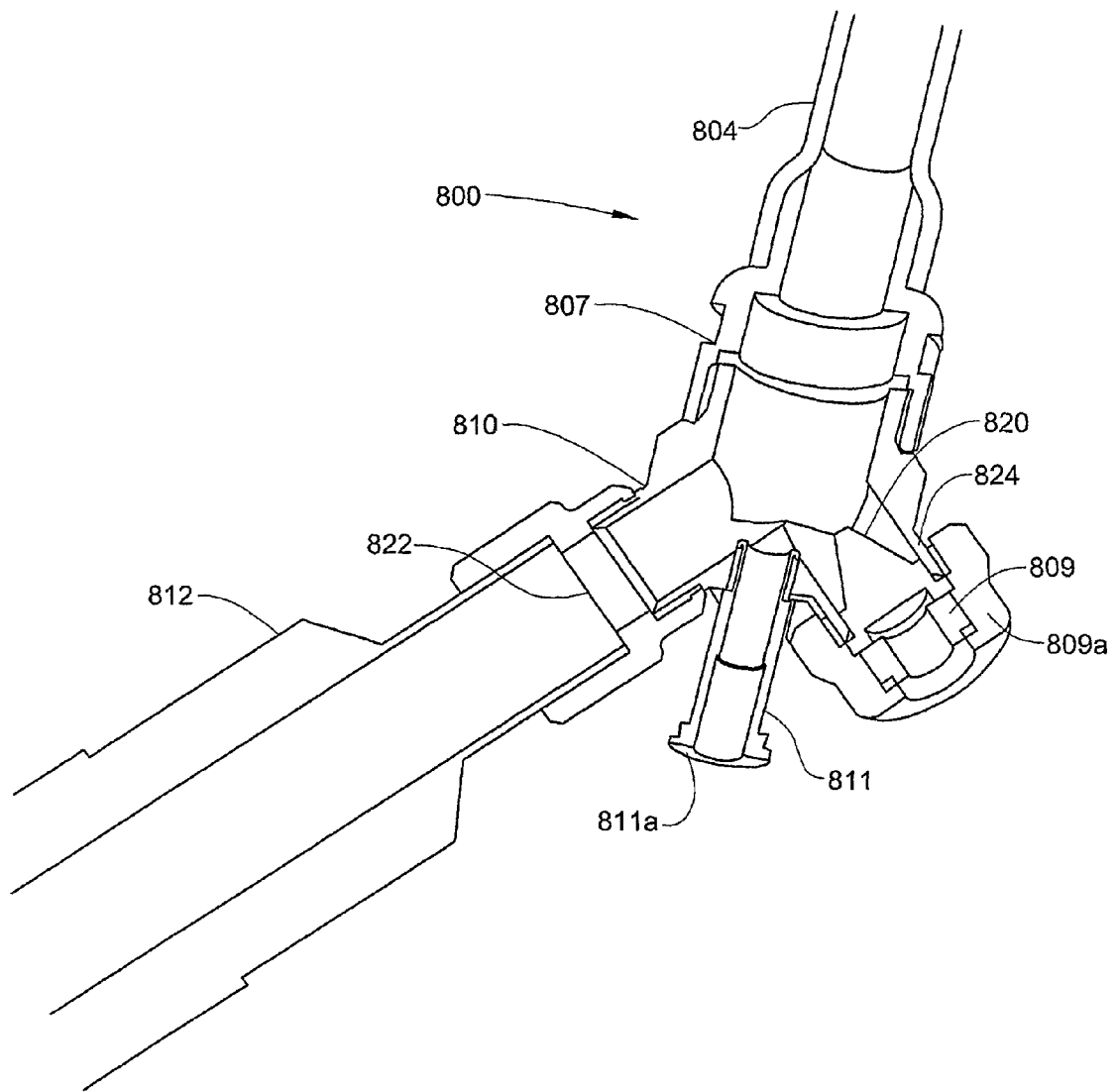
FIG. 55 is a detail cross sectional view of a portion of the embodiment of FIG. 53.

FIG. 55 is a detail cross sectional view of a portion of an embodiment of the access device according to FIG. 53. As shown, access port 809 has duckbill valve 820 inserted therein. Connection cap 809a may hold duckbill valve 820 in place by compression of gasket or o-ring 824 against duckbill valve shoulder 826 which interacts with the face of access port 809 and holds duckbill valve 820 and prevents duckbill valve 820 from entering further into access port 809. By threading or connecting connection cap 809a onto access port 809 and compressing gasket or o-ring 824, duckbill valve 820 is held in place and a seal may be formed preventing or limiting leakage of fluid out of access port 809.

Figure 56:
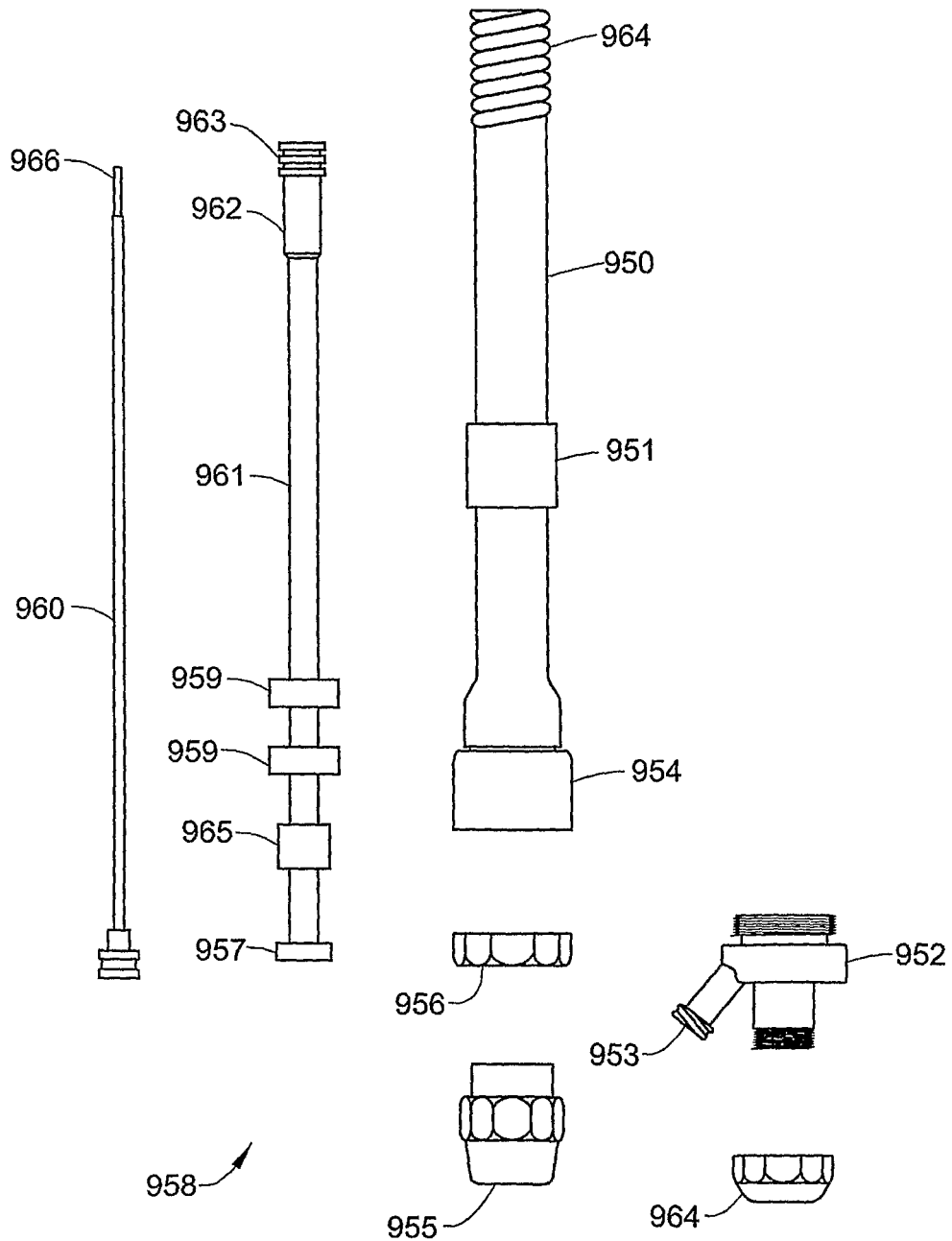
FIG. 56 is partially disassembled view of an access device embodiment.

FIG. 56 is partially disassembled view of components of an access device 958 in accordance with certain embodiments. Shown in this view are the access housing or tube 950, a sleeve 951 surrounding the access housing, an access device head 954 connected to, or in communication with the housing 950, and a sewing cuff 964. A multi-access head 952 (with an access port 953) that can be attached to or screwed onto the access device head 954 is also shown. Other components are a catheter cap 964, a safety cap 955, and a lock ring 956. The plunger 957 with a central access port and lure lock connection has an O-ring seal compressor 956 located in the upper portion of the plunger and two O-ring seals 959 located below the O-ring seal compressor on the plunger shaft. The plunger 957 has a plunger shaft 961, a plunger tip region 962 which have multiply ribs 963. Also shown in FIG. 56 is the stylet 960 with a shaft and the stylet tip 966.

Figure 57:
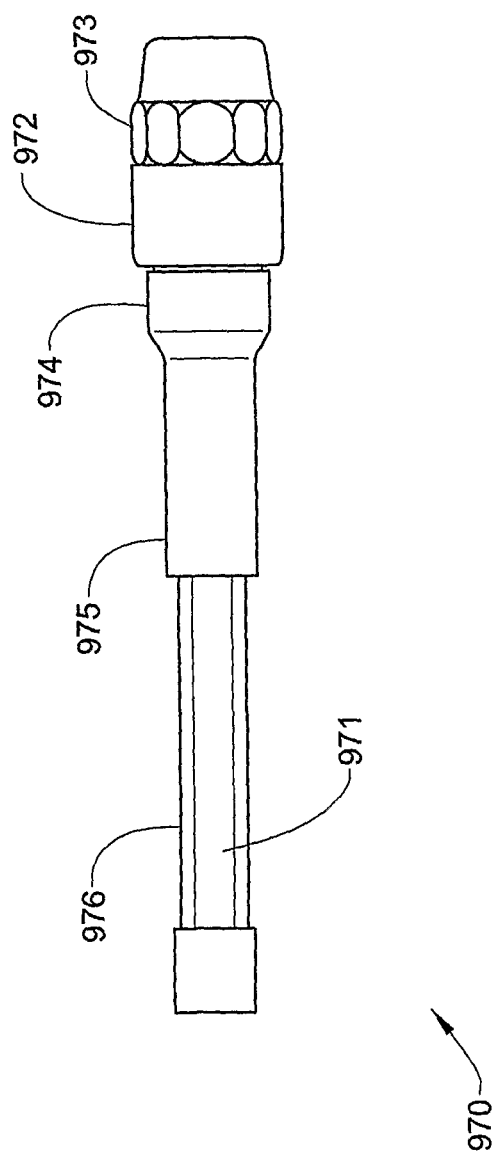
FIG. 57 is an assembled view of an access device embodiment.

FIG. 57 is an assembled view of an access device 970 in accordance with certain embodiments. The Figure shows, among other things, and access device with a plunger 971, access housing or tube 976 and the clampable portion of the tubing 975, an access device head 972 connected to, the access housing with a safety cap 973. The access device housing in this embodiment is made up of two portions of tubing 976 and 975. The housing will be biocompatible, or a portion of it will be biocompatible and will extend through the skin line and the subcutaneous tissue and be capable of being in fluid communication with vessel(s) of the circulatory system. The housing may be made of many materials, for example, silicone, inert elastic plastics, thermoplastics and/or elastomer materials, and may be coated with various materials if desired. As in the embodiment shown in this figure that portion of the housing that will be subject to clamping off may be made of materials that are sufficiently flexible, resistant to cracking, resistant to tearing, or combinations thereof of these properties such that the housing can be clamped off multiply times. In certain aspects, the housing may be made of a single material or combinations of materials, or combinations of portions of material with different diameters that are interfitting. In certain aspects, the housing made be made of outer tubing and an inner sleeve or different portions of the housing may be constructed of different combinations of materials.

Figure 58:
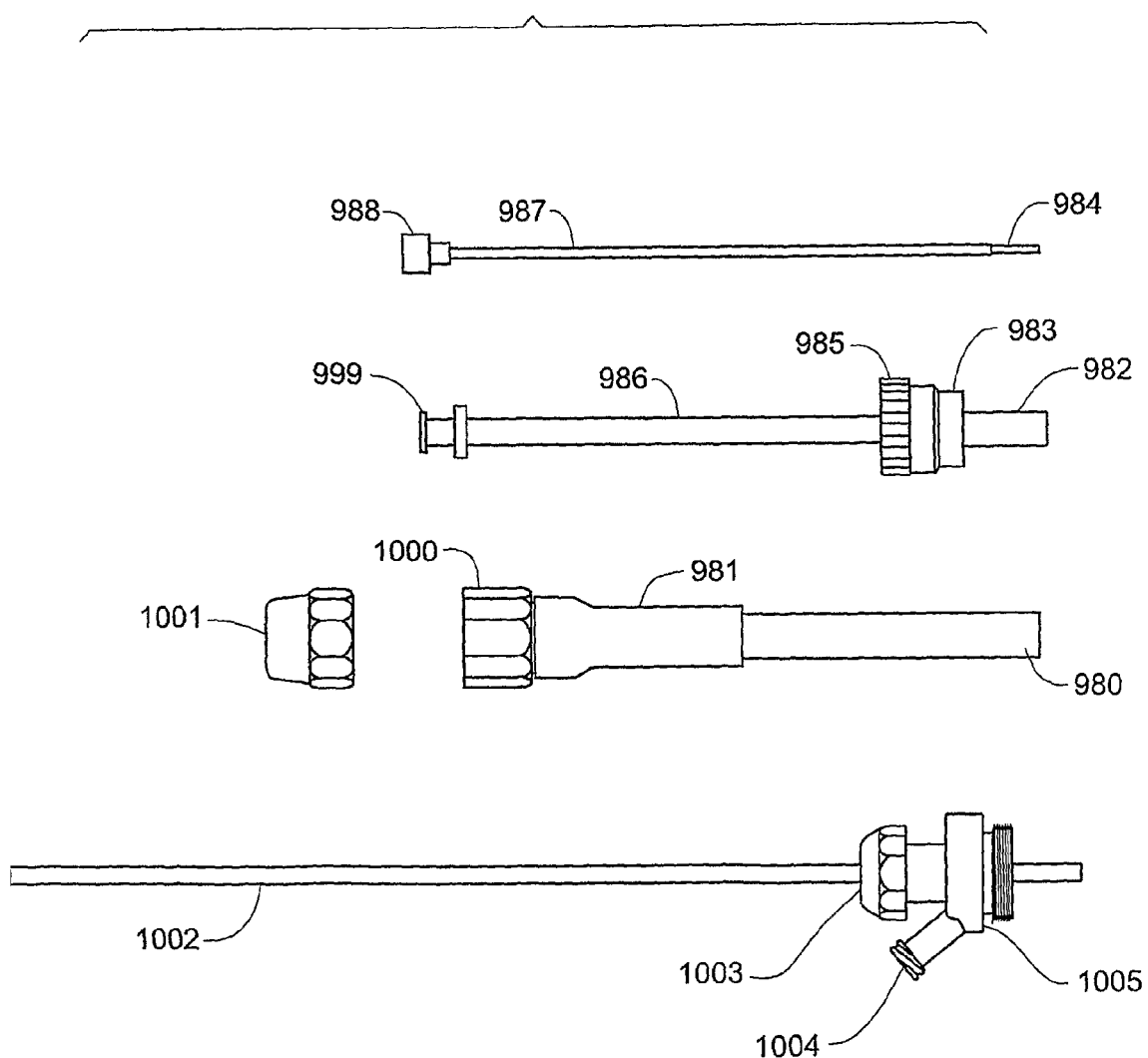
FIG. 58 is a partially dissembled view of the access device embodiment.
Figure 59:
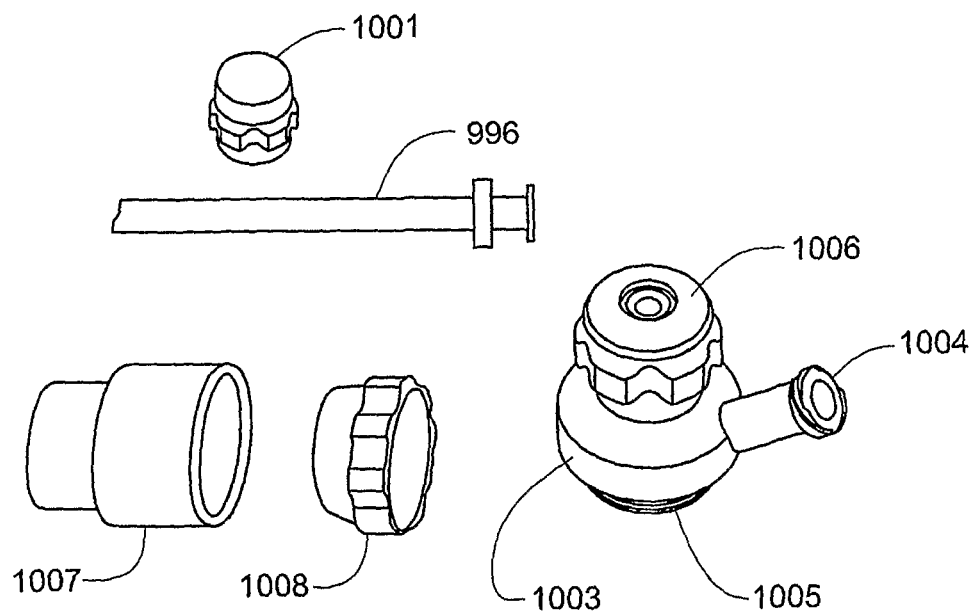
FIG. 59 is a close up view of some of the components shown in FIGS. 58 and 57.

FIG. 58 is a partially dissembled view of the access device in accordance with certain embodiments. Show in this view, among other things, are the access housing or tubing 980, clampable tubing 981 and a metal access device head 1000. The access device head 1000 is connected to, or in communication with, the housing or tubing 981. Also shown are a metal multi-access head 1005 (with an access port 1004, metal catheter cap 1003 and part of the catheter tubing 1002). The multi-access head 1005 can be attached to, or screwed, onto the metal access device head 1000. Also shown is a metal safety cap 1001. Also shown are the plunger assembly 999 with central access port, a metal lure lock connector, the metal plunger shaft 986, metal lock ring 985, non-metal o-ring seal 983, non metal plunger tip 982. Also shown are in FIG. 58 is the stylet 987 with a metal shaft, the upper portion of the stylet 988 and the stylet tip 984 located in the lower region of the stylet. The plunger assembly 999 should be compatible with and allow insertion of the stylet 987 and the fit or cooperation between the plunger and the stylet should be sufficient to create an appropriate seal. The plunger assembly shaft 986 shown here is cannulated to provide for access to the lumen or the stylet. FIG. 59 is a close up view of some of the components shown in FIG. 58. Shown in this view are, among other things, safety cap 1001, a portion of the plunger assembly including a portion of the plunger shaft 986, multi-access head 1005 (with an access port 1004, metal catheter cap 1003 and catheter access port 1006). Also shown is a portion of the plunger head 1007 located in the upper portion of plunger assembly and a lock ring 1008 that may be connected to the plunger head and the multi-access head 1005.

Figure 60:
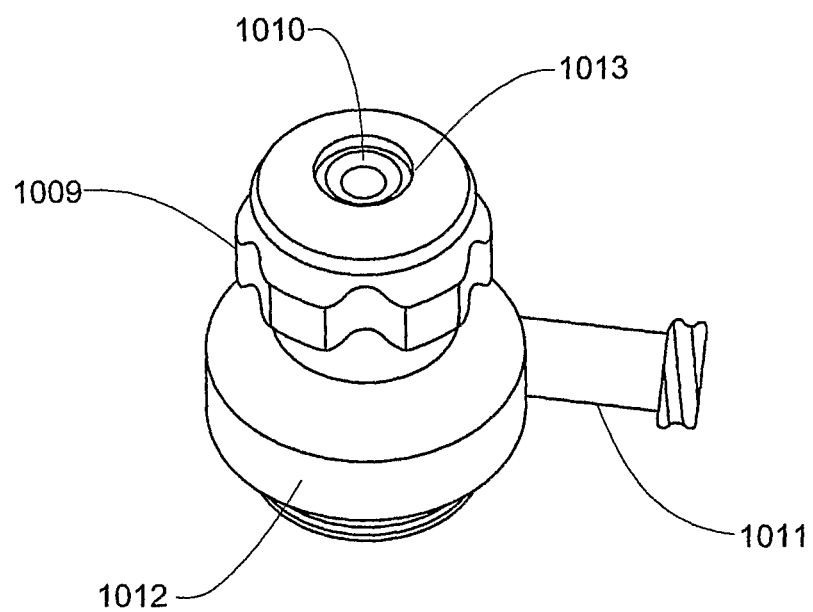
FIG. 60 is a view of the vortex cap connector head.

FIG. 60 is a view of a multi-access head 1012 that may be used with certain disclosed embodiments. The multi-access head 1012 has an access port 1011, a catheter cap 1009 with a catheter access port 1013 with a duckbill seal 1010 in place. The duckbill sealing member may be constructed from any suitable biocompatible or non-biocompatible material as described herein, such as for example silicone. Many suitable duckbill valve configurations may be used. In some embodiments, the duckbill valve may prevent or limit backflow through the port in which it is inserted, while providing access to lumen for balloon catheters that may be threaded through the lobes of the duckbill valve. The leaflets of the duckbill valve may be of suitable materials that may form around completely or in part, such a balloon catheter in order to limit leakage or backflow through the relevant access port.

Figure 61:
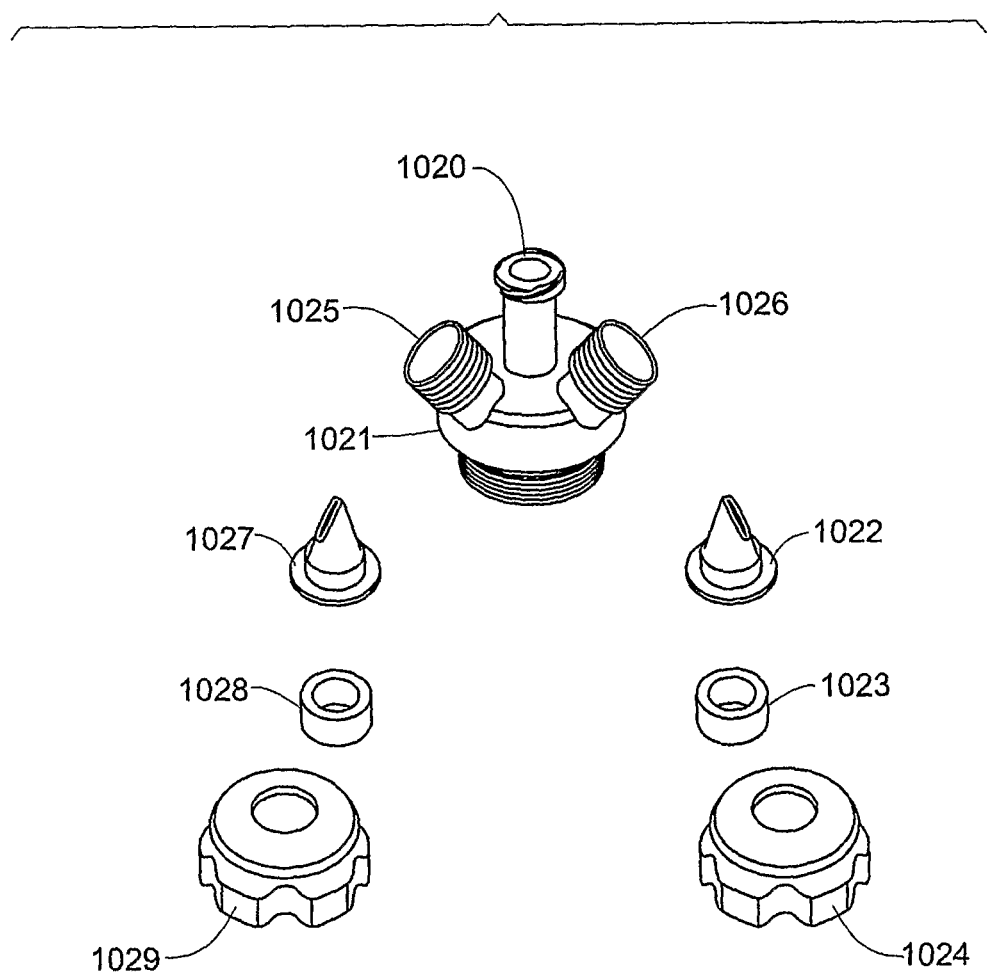
FIG. 61 is a view of another connector head embodiment.

FIG. 61 is a view of a multi-access head 1021 that may be used with certain disclosed embodiments. The multi-access head 1021 shown has 3 access ports: a central access port 1020, and two side access ports 1025 and 1026. Associated with the access port 1026 is a duck bill seal 1022, o-ring seal 1023 and access port cap 1024. Associated port 1025 is a duck bill seal 1027, o-ring seal 1028 and access port cap 1029. The materials used to assembly a duck bill and the use and function of such seals has been disclosed elsewhere in the specification.

Figure 35A:
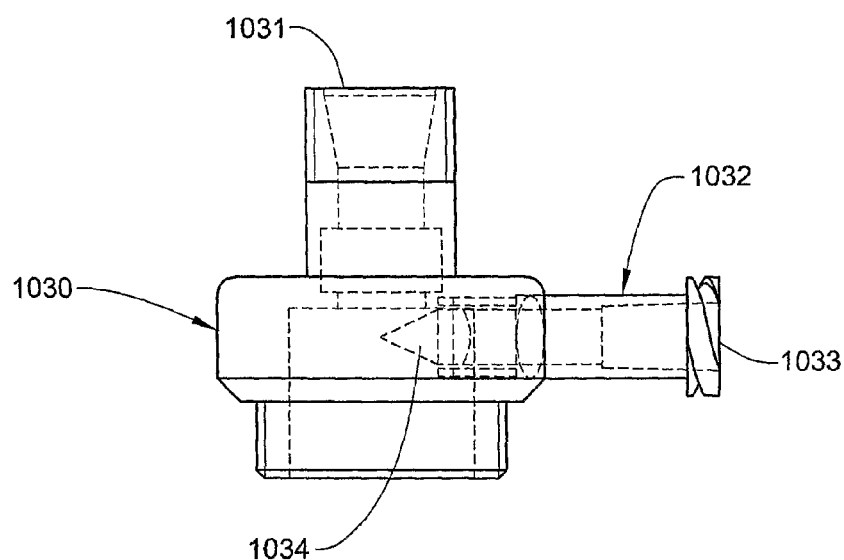
FIG. 35a is a cross section view of the vortex head shown in FIG. 35.
Figure 35B:
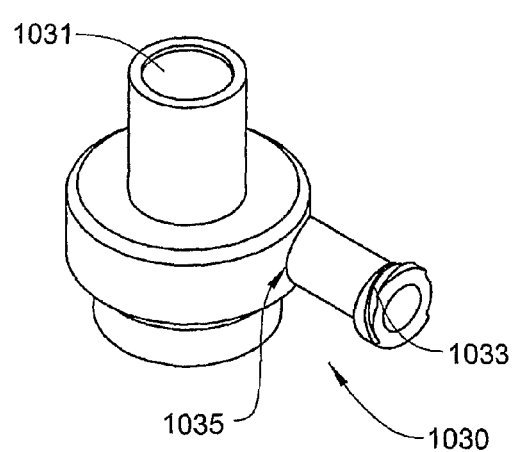
FIG. 35b is schematic view of a vortex head embodiment.
Figure 35C:
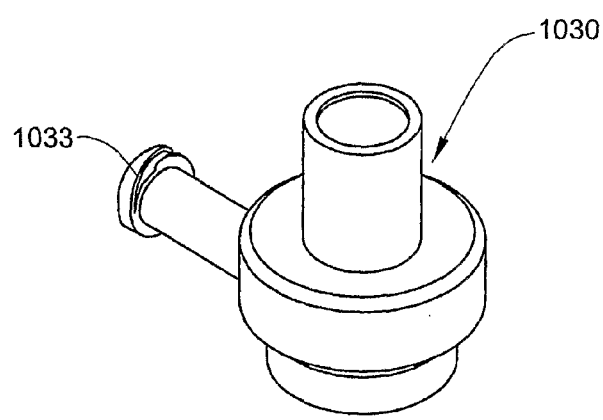
FIG. 35c is schematic view of a the vortex head embodiment from a different perspective.

FIGS. 35a and b is view of a vortex head connector that may in accordance with certain embodiments. FIG. 35a shows the vortex head connector 1030 in cross section. Also shown in this figure are the balloon catheter access port 1031 that is configured to receive an appropriate seal not shown, the connector port or pipe which in this embodiment is shown fitted with a luer type connection fitting 1033. In FIG. 35a the tapped female tread 1034 for attachment of the connector luer pipe is shown. In FIG. 62b the location of the master bond adhesive 1035 is shown. FIGS. 35b and 35c shown the vortex head in schematic view from different perspectives. The Vortex head is designed to minimize areas, or substantially minimize areas, of stasis when pumping the blood or fluid into the access device body. The vortex assembly configured to return the fluid and/or blood through 1032 along the internal walls of the vortexing cap and lumen in order to reduce the potential for shear damage to various components in the returning fluid. By configuring the return of fluid and/or blood in such a fashion the fluid may flow along the walls of the vortexing cap in a descending spiral into lumen with reduced shear and velocity affects on the returning fluid and may flow around a balloon catheter that has been inserted through access port 1031.

In certain aspects, the Vortex head is designed to minimize areas, or substantially minimize areas, of stasis when pumping the blood or fluid into the access device body.

In certain embodiments, another approach to controlling the direction and amount of blood flow via an endoluminal balloon system (see, for example, 28 in FIGS. 1,5,6,7; 64 in FIG. 4; 88 in FIG. 7; 103 in FIG. 10; 116 and 194 in FIG. 18) is to replace one or more of the endoluminal balloons with at least one externally applied vascular occlusive balloon (exoluminal balloon system). FIG. 62 illustrates such a system. FIG. 62 is similar to FIG. 1. In FIG. 62 the external balloon is 1050 with the one way valve 1051. The flow is directed into the pump via inflating the balloon and isolating the limb or organ from the remainder of the body. Thereafter, deflation restores normal flow.

In certain embodiments the plungers may be replaced by externally occlusive balloons. FIG. 63 illustrates such a system. In FIG. 63, the plungers 33,34,35 in FIGS. 2 and 3 have been replaced by externally occlusive balloons; 1050 with the control valves 1051. The system illustrated in FIG. 63 controls the flow through the inflow system and also the outflow from the pump. These balloons 1050 minimize the dead space between the native vessel and the access devices.

Figure 64:
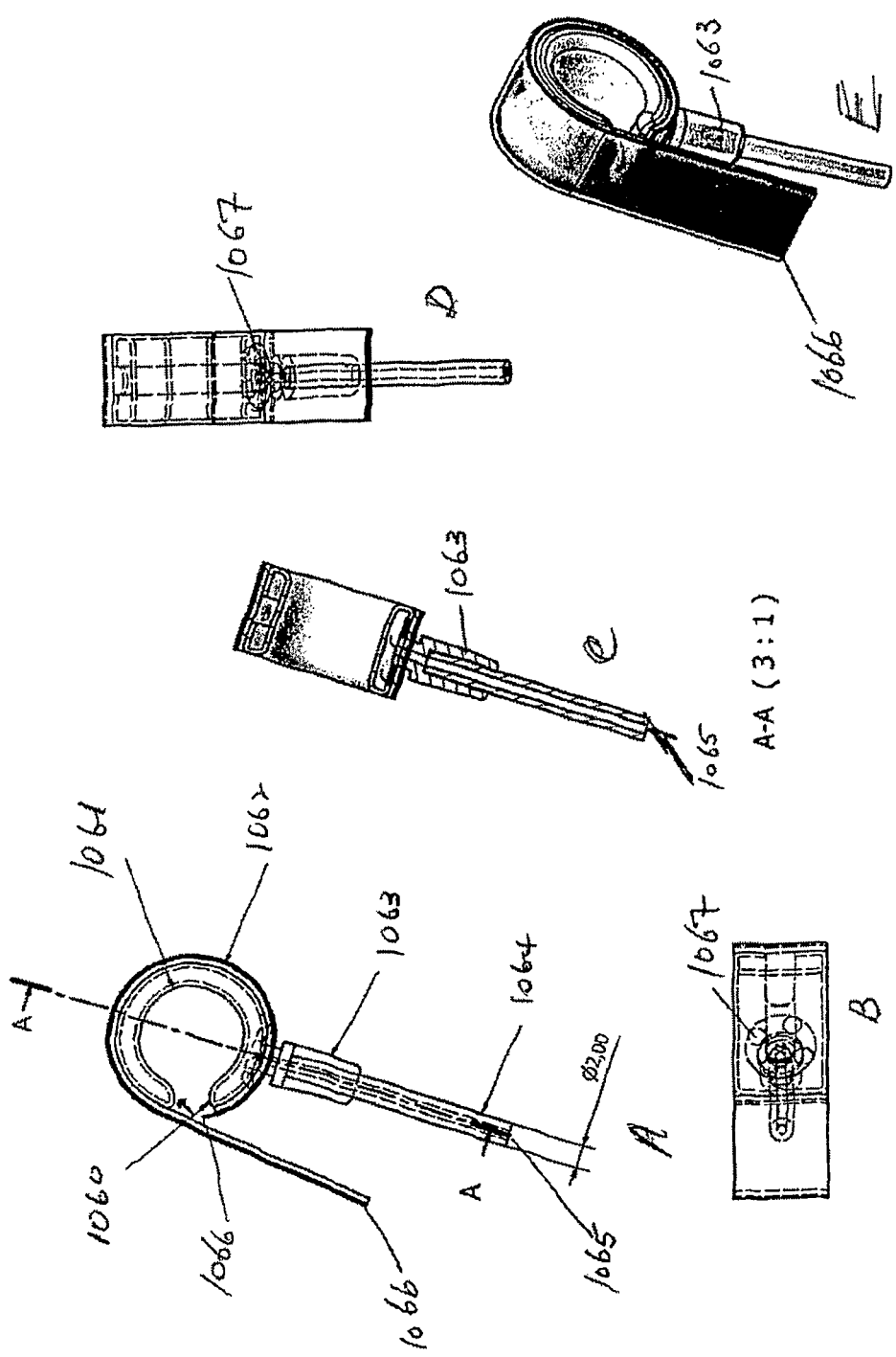
FIGS. 64A-64E is a schematic of an occlusive balloon vascular occluder in accordance with certain embodiments.
Figure 65:
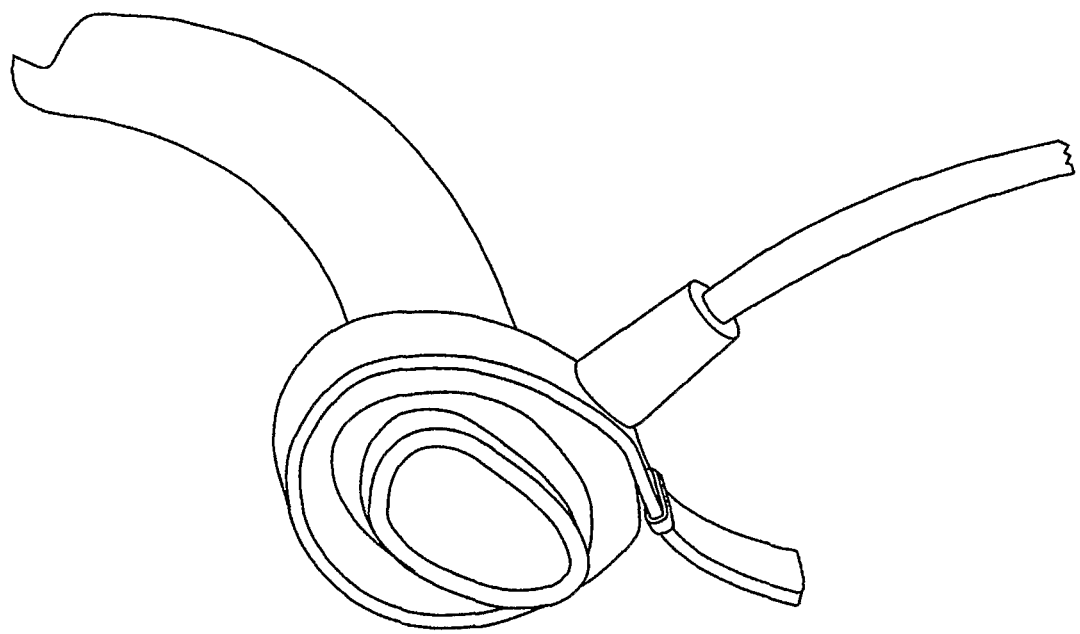
FIG. 65 is the assembled extravascular occlusive balloon shown in FIGS. 64A-64E.

FIG. 64A to E are the schematics of an occlusive balloon vascular occluder. In FIG. 64A, the vessel to be occluded is surrounded by the inner radius of the balloon 1061. The two ends of the balloon 1060 can be occluded by the two ends of the belt 1066. The belt 1066 is continuous with the outer part of the balloon 1062. The connection to the inflating tube 1065 is 1063. The studs connecting the inflow tube 1064 to the balloon are 1067 shown in 69B and D. FIG. 64C is the plan view whilst the oblique view is shown in 64E. FIG. 65 is the completed extravascular occlusive balloon.

External balloon systems may be useful for use in selective cerebral hyperperfusion. An example of the use of an external balloon and regional hyperperfusion is in the treatment of embolic stroke. The hyperperfusion cannulae can be placed into the external carotid vessel with the extrinsic balloon obstructing the proximal common carotid artery. Control of the ipsilateral cerebral hemisphere flow may be achieved as hyperperfusion is pan-cycle—the cerebral flow can be increased without increasing the peak inflow pressure, thereby minimizing intracerebral haemorrhage. For example, in studies using pharmacological infusions to increase the blood flow to the penumbra (viable but non-functional neural tissue) the mean pressure where patients have returned to normal function (i.e., regain speech, power or sensation) is 156/98/mmHg. This pressure equates to 117 mm Hg pan-cycle. It is also well known that capillary fragility is related to the pulse pressure, i.e., the difference between systolic and diastolic pressure, which is therefore minimal with pan-cycle hyperperfusion. Therefore, it is possible to increase the flow to the ischaemic brain minimizing the risk of intracerebral haemorrhage. This is a problem with trying to increase the blood flow to ischaemic brain.

Figure 66:
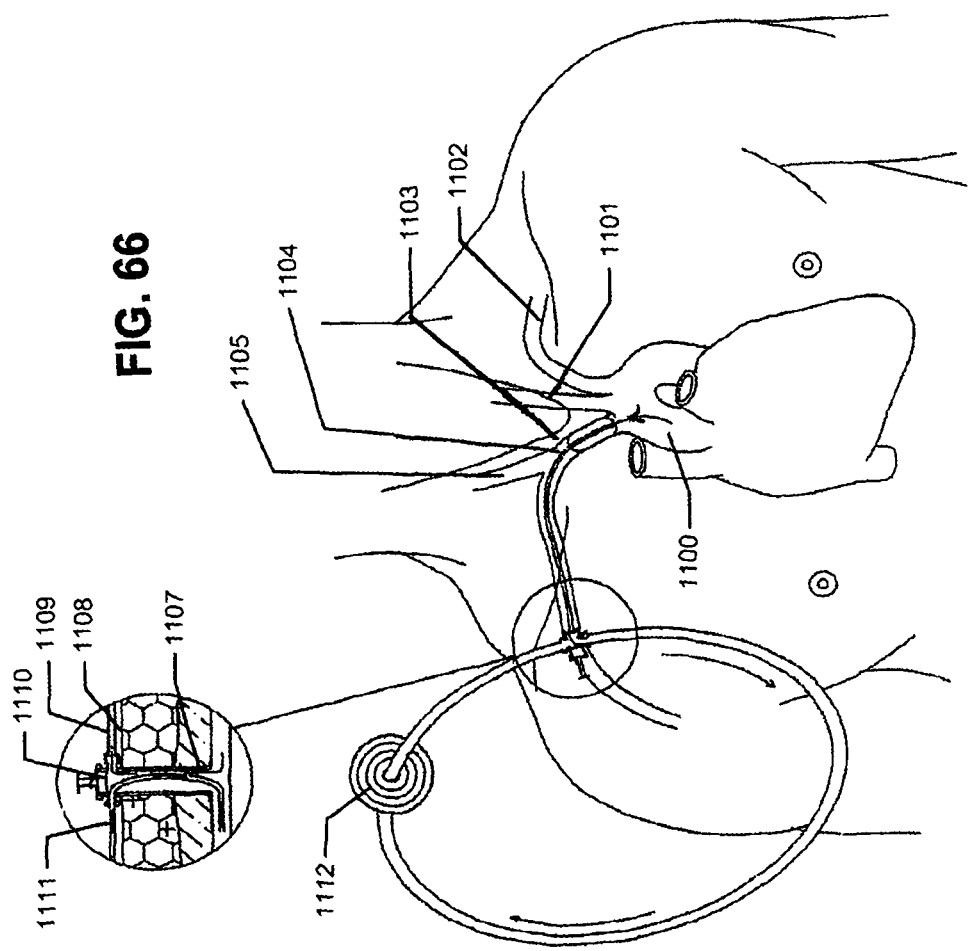
FIG. 66 illustrates a schematic of certain embodiments for use in regional cerebral hyperperfusion.

FIG. 66 illustrates a schaematic of certain embodiments for regional cerebral hyperperfusion where the right subclavian vessels provide the source of blood supply to the cerebrum. Similarly, the common femoral iliac or any other non-cerebral supply may be used to supplement cerebral flow. In FIG. 66, the aortic arch is 1100, the left common carotid 1101, the left subclavian 1102, the innominate artery 1103, the balloon and catheter 1104 and the right common carotid vessel 1105. The left subclavian vessel supplies increased flow from the pump 1112. The direction of flow is shown by the arrows. The proximal innominate vessel supplies the increased flow to the cerebrum via the pump. The anastomosis is 1107, skin line 1108, access tubing 1109, plunger 1110 and inflow tubing 1111. In this way, the blood flow to the cerebrum can be controlled and regulated. By attaching cooling systems to the pump, the cerebral metabolism can also be controlled. For every 1° C. decrease in cerebral temperature there is a 67% decrease in metabolic rate. This is known to minimize ischemic damage. Also other cerebral preservation agents can be selectively delivered to specific areas of the cerebrum.

In certain embodiments it may be desirable to prevent or minimize bleeding with hyperperfusion. Hyperperfusion patients may be extremely anticoagulated and inflow pressures may be very high, and as a result bleeding may be common with certain patients. As collaterals dilate the skin flow increases dramatically. As a result, the drain sites and access system exits of certain disclosed embodiments may contribute to the problem of continuing blood loss. To minimize, or attempt to minimize the problem a number of steps may be taken, including but not limited to one or more of the following: double anastomoses being performed at the junction of the vessels and the access system, fluid sealing devices placed around the access systems to increase the lateral pressure on the skin subcutaneous tissue, and sealing circumferential devices, which increase the pressure on transcutaneous exits of the balloon control device.

Figure 67:
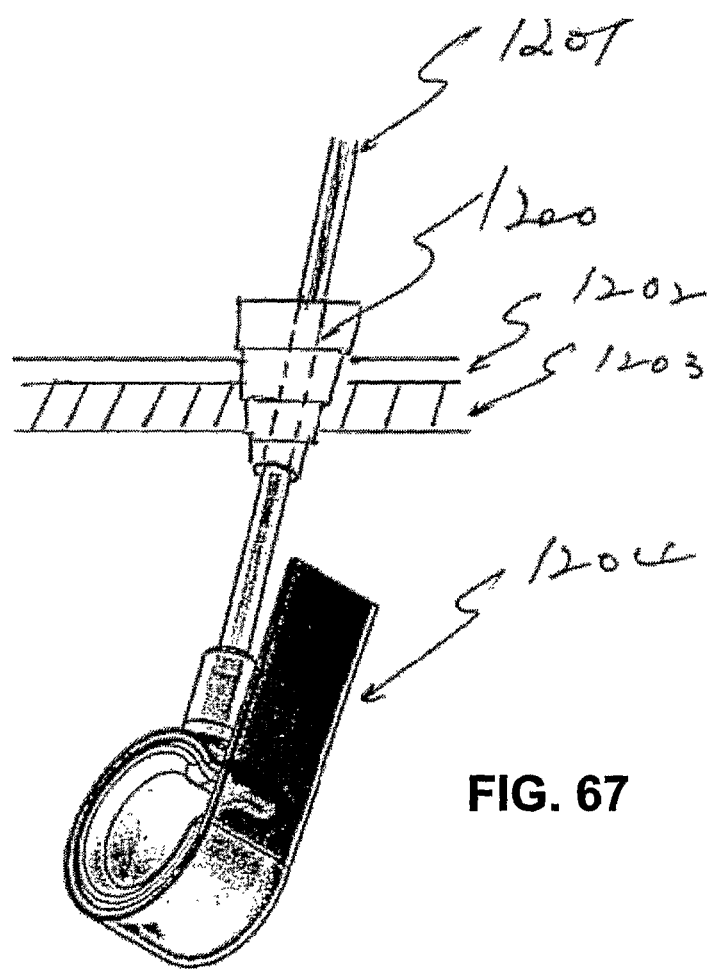
FIG. 67 illustrates a blood and/or fluid sealing device according to certain embodiments.

FIG. 67 illustrates certain embodiments of such a blood sealing device. In FIG. 67 the blood sealing device is 1200. The connection to the inflation system is 1201. The skin is 1202 and the subcutaneous tissue is 1203. The balloon vessel compressive device is 1204. A similar device is used circumferentially around the bodies of the access system for the same reason. The mechanism of action is believed to be related to the pressure applied to the skin and subcutaneous tissue by the circumferential sealing device. The device can be fixed in place by suture without damaging the tubing 1201

Example 1

To assess the safety and efficacy of the Access Device and the hyperperfusion treatment animal trials were conducted on healthy 40-50 kg sheep (Merino cross-bred wethers). The purpose of this example was to demonstrate treatment of arterial ischemia and the revascularising of an ischemic limb in large animals using certain embodiments of the devices disclosed. Another purpose was to test and demonstrate the safety of the treatment and efficacy of the treatment in the animal model available. Twelve (12) animals were used in this study—six in the 'treatment' group, and six in the 'control' group. All animals had a groin incision made and the femoral artery and profunda femoris artery identified and dissected. In all animals an 18 G cannula was placed in the distal femoral artery to record baseline pressures for 15 minutes. Another 18 G cannula was inserted into the carotid artery in the neck to record the systemic blood pressure during the experiment in a region remote from the treatment site. In all animals the femoral artery was then occluded with a ligation and an occlusive vascular clamp. This occlusion was placed proximal (above) the pressure transducer so that the transducer was now recording the blood pressure in the ischemic region of the femoral artery. This was continued for 15 minutes to achieve a steady pressure with the occlusion in place.

In the treatment animals: The femoral and profunda femoris arteries were controlled with Vessiloops, and an arteriotomy (incision in the artery) was performed and the cannulae were inserted in the femoral artery. The pump cannulae were attached to the extracorporeal pump (Rotaflow, Maquet). The pump was then turned on and set to an initial flow rate of 200 mL/min. Pressure and flow measurements were taken every 15 mins for the next 3 hours. After 3 hours, the pump was turned off but left connected to the artery. Pressure measurements were measured for the next 30 mins to obtain baseline pressures following the treatment.

In the control animals: The pump cannulae were not connected to the femoral artery. The distal and systemic blood pressures were measured and recorded for the 3 hours of the 'treatment' phase, and then the subsequent 30 mins (to match the treatment animal group. In all animals, the pump cannulae were then removed, the femoral artery repaired, and the incision closed in layers. The sheep were all revived and returned to the pen.

Results: The baseline measurements, both before and after the placement of the occlusion, were not different between the two groups. When the pump was attached to the femoral artery in the treatment group an initial increase was observed as shown in FIG. 13 in the distal pressure. This distal pressure was observed to increase with time in the treatment group during the duration of the 3 hour experiment. The control group also shows an increase that is less. See FIG. 14. When the ratio of distal pressure to systemic pressure was observed, it was found that the ratio increased from 0.4 (prior to hyperperfusion treatment) to 1.0 after approximately 60 minutes, to approximately 1.25 following three hours of treatment. In other words, the pressure below the occlusion in the artery was 25% higher than the pressure that the heart was producing.

At the end of the pumping treatment in the treatment group, the distal blood pressure initially dropped to below the pressure when the occlusion was first made at the start of the experiment. Over the next 15 minutes the distal pressure slowly increased. This is indicative that the distal arteries were dilated when the pump was turned off (hence larger diameter and lower pressure) and then gradually returned to their normal vascular tone (muscle in the artery wall slowly returning to normal and reducing the diameter—thereby causing a slight increase in the pressure).

Example 2

Human ethics committee approval was sought and received to commence a pilot trial of the treatment in humans. This trial was limited to patients that have no other treatment option for their lower limb ischemia other than amputation.

Patient 1: This is a 52 year old male with severe peripheral ischemia due to a very large blood clot in his left leg. This thrombus involved his popliteal, tibial and peroneal arteries (all major arteries from the level of his knee down). In the opinion of three vascular surgeons, there were no other treatment options other than below knee amputation in this patient.

A peripheral access device, as shown in FIGS. 57, 58, and 59, was implanted in the patient's femoral artery approximately at the mid-thigh level. Following implantation of the device, catheters were inserted through the peripheral access device and connected to the extracorporeal pump (Rotaflow, Maquet). The pump was initially set to run at approximately 200-300 mL/min, and generated an initial return pressure of 150-200 mmHg. Pressure and flow measurements were recorded about every 15 mins. In total this patient received 52 hours of intermittent 'on-pump' treatment over 5 days. The patient was first treated and hyperperfused for 31 hours and then taken off treatment for two days and then hyperperfused for 21 hours. Between treatments the catheters and balloons where removed, the plunger moved into a closed position to prevent back flow of blood from the vessel and to assure that fluids did not reminded in the housing. Furthermore, the housing was clamped off to seal it from outside contamination. Thereafter a new set of catheters was inserted into the patient and the hyperperfusion continued for 21 hours.

Over the 52 hours of treatment the flow rate of blood through the pump was maintained at approximately 300-400 mL/min. Over the duration of the treatment the return pressure from the pump continued to fall. During the first 6 hours of treatment the mean return pressure was approximately 240 mmHg (at 320 mL/min flow), by 18-24 hours this has reduced to approximately 170 mmHg (at 355 mL/min flow), and by the end of the treatment the return pressure was 130 mmHg (at 400 mL/min flow). This reduction in return pressure with a similar flow indicates that peripheral resistance was decreasing and more blood was able to move through the vessels and into the distal areas of the leg. Angiograms of the limb showed that the blockage of the major arteries had not changed and therefore the additional flow down the leg must have travelled through the small collateral arteries. The patient's leg was observed to become warm and pink within the first 60 minutes of the hyperperfusion treatment and stayed that way for the duration of the treatment. The patient described feeling warmth in his leg, decreased pain, and increased sensation.

During the follow-up period (about 12 months), the patient has not had any adverse events from this treatment and has had no further interventions to the arteries of his leg. His leg remains warm, pink, and well perfused. All ischemic ulcers have healed and remained healed. The patient describes a significant reduction in pain and increase in warmth.

Patient 2: This patient is a 57 year old male (RB) with diabetes and severe bilateral peripheral artery disease. He has previously undergone a left below knee amputation.

The access device is similar to that shown in FIG. 4 and was implanted in the patient's right femoral artery, and during the same procedure medical and lateral fasciotomies were performed due to muscle death and compartment syndrome in the calf. Hyperperfusion was commenced immediately. During the duration of the hyperperfusion treatment (approximately 30 hours over a four day period) the return pressure increased (from 130 mmHg to 200 mmHg) while the flow decreased (330 mL/min to 200 mL/min). Despite our best efforts we were unable to increase the flow. The patient's leg began bleeding uncontrollably from the fasciotomies on the second day of treatment and this continued for the remainder of the treatment. However, this is still a good indication that increased blood flow to the periphery was occurring. The patient became systemically unwell and developed disseminated intravascular coagulopathy (DIC). The treatment was halted and the patient progressed to amputation.

Prophetic Example 3

Limb hyperperfusion following amputation for the improvement of a stump will be achieved using the embodiments disclosed herein. Using the embodiments disclosed herein it will be possible to reduce infection rate, wound healing rate, and ischemic conditions in the stump following amputation. Amputations are associated with a very high rate of infection, commonly stated as approximately 15% (BMJ 2005; 330: 1104). Additionally, poor wound healing due to poor blood flow (ischemia) affects 5-30% of patients that have undergone an amputation. Repeatable perfusion treatment of these patient will be beneficial as it will allow the perfusion (either with or without isolation of the limb circulation from the systemic circulation) medication to prevent or treat wound infection at the surgical site, and also will allow the hyperperfusion of blood using the same treatment modality as is used for whole limb treatment, or for sub-total occlusion of the major arteries in the limb to stimulate the development of larger, and new, arteries to increase blood flow to the remainder of the limb.

A patient will have had his leg amputated at the appropriate level. After amputation a peripheral access device, as shown for example in FIGS. 57, 58, and 59, may be implanted in the patient's femoral artery approximately at the mid-thigh level. Following implantation of the device catheters may be inserted through the peripheral access device and connected to the extracorporeal pump (Rotaflow, Maquet). The antibiotic may be provided through a catheter at an appropriate rate to prevent or reduce infection and to improve wound healing rate at the stump. At the same time the stump area left after amputation would be hyperperfused. The pump may be initially set to run at approximately 200-300 mL/min, and generated an initial return pressure of 150-200 mmHg. Pressure and flow measurements may be recorded about every 15 min. The antibiotic would then be delivered to the area of the amputated leg to prevent or reduce infection. At the same time the stump area left after amputation would be hyperperfused. In total this patient would receive approximately 52 hours of intermittent 'on-pump' treatment and medication over 5 consecutive days. The amount of treatment time and the antibiotic delivered could be modified depending on how the amputated leg responds to the treatment and what, if any infections are detected. Thereafter, the catheters and balloons may be removed and the plunger may be moved into a closed position to prevent back flow of blood from the vessel and to assure that no fluids remain in the housing. Furthermore, the housing may be clamped off to seal it from outside contamination. At the beginning of the next treatment period a new set of catheters may be inserted into the patient and the hyperperfusion and antibiotic treatment continued. This process would be repeated over the five days. Over the 52 hours of treatment the flow rate of blood through the pump would be maintained at approximately 300-400 mL/min. Over the duration of the treatment the return pressure from the pump will continued to fall. During the first 6 hours of treatment the mean return pressure will be approximately 240 mmHg (at 320 mL/min flow), by 18-24 hours this will be reduced to approximately 170 mmHg (at 355 mL/min flow), and by the end of the treatment the return pressure will be approximately 130 mmHg (at 400 mL/min flow). This reduction in return pressure with a similar flow indicates that peripheral resistance will be decreasing and more blood will be able to move through the vessels and into the amputated distal areas of the stump. Angiograms may be taken of the stump and will show that the blockage of the major arteries had not changed and therefore the additional flow down the leg must have travelled through the small collateral arteries. The patient's stump leg would be observed to become warm and pink within the first 60 minutes of the hyperperfusion treatment and would stay that way for the duration of the treatment. The patient would described feeling warmth in his leg, decreased pain, and increased sensation. The patient would also be found to have no infection or greatly reduced infection due to the antibiotic treatment.

Prophetic Example 4

As in example three, limb treatment following amputation to deliver targets antibiotics or other medications to the stump region will achieve reduced infection rate and wound healing rate without hyperperfusion or with minimal hyperperfusion.

A patient will have had his leg amputated at the appropriate level. After amputation a peripheral access device, as shown for example in FIGS. 34-42, and 52, will be implanted in the patient's femoral artery approximately at the mid-thigh level. Following implantation of the device catheters will be inserted through the peripheral access device and connected to the extracorporeal pump (Rotaflow, Maquet). The appropriate antibiotic will be provided through a catheter at a delivery rate and dose level sufficient to prevent or reduce infection and to improve wound healing rate at the stump. The pump would initially be set to run at approximately 50-300 mL/min (depending on the level of the amputation and the tissue mass being perfused), and may generate an initial return pressure of 200-300 mmHg. Pressure and flow measurements would be recorded about every 15 min. Thereafter, the catheters and balloons would be removed and the plunger would be moved into a closed position to prevent back flow of blood from the vessel and to assure that no fluids remain in the housing. Furthermore, the housing would be clamped off to seal it from outside contamination. At the beginning of the next treatment period a new set of catheters would be inserted into the patient and the hyperperfusion and antibiotic treatment continued. This process would be repeated over the five days. Over 5 days the patient would receive about 50 hours of treatment time. At the end of the 5 days, the patient would be found to have no infection, or greatly reduced infection, better wound healing and this would be due to the application of the antibiotic to the specified treatment area. The access device used will permit intermittent access to the wound and infected area as needed through the access device system. The amount of treatment time and the antibiotic delivered could be modified depending on how the amputated leg responds to the treatment and what, if any infections are detected.

Prophetic Example 5

As in example three, limb treatment following amputation to deliver targets antibiotics or other medications to the stump region will achieve reduced infection rate and wound healing rate with hyperperfusion.

A patient will have had his leg amputated at the appropriate level. After amputation a peripheral access device, as shown in FIGS. 37-42, and 52 will be implanted in the patient's femoral artery approximately at the mid-thigh level. Following implantation of the device catheters will be inserted through the peripheral access device and connected to the extracorporeal pump (Rotaflow, Maquet). The appropriate antibiotic will be provided through a catheter at a delivery rate and dose level sufficient to prevent or reduce infection and to improve wound healing rate at the stump. The pump would initially be set to run at approximately 50-300 mL/min (depending on the level of the amputation and tissue mass being perfused), and may generate an initial return pressure from normotensive to 300 mmHg. Pressure and flow measurements may be recorded about every 15 mins. Over 5 days the patient would receive about 50 hours of treatment time. At the end of the 5 days, the patient would be found to have no infection, or greatly reduced infection, better wound healing and this would be due to the application of the antibiotic to the specified treatment area and hyperperfusion of the treatment area. The access device used will permit intermittent access to the wound and infected area as needed through the access device system.

Prophetic Example 6

Limb hyperperfusion will also be used for the treatment of sub-total occlusion. Many patients with peripheral arterial disease in their limb do not have a total occlusion of the major artery (for example the femoral arteries in the legs, or brachial arteries in the arms). These patients without a total occlusion to the artery, referred to as a sub-total occlusion, may also be suitable for isolated limb hyperperfusion using the embodiments disclosed herein. In sub-total occlusion treatment there will often be the need for a distal occlusion to be temporarily created in order to develop a length of major artery that will be isolated from the rest of the systemic circulation and will be hyperperfused in order to stimulate the development of collateral vessels. This distal occlusion will be desirable in order to generate the increased blood pressure in the isolated section of artery that will often be required to drive the increased blood flow into the collateral arteries.

Patient: A patient, such as a 50 year old male, with peripheral ischemia due to a sub-total occlusion in his right leg will be treated using an embodiment disclosed herein. This thrombus involved will be his popliteal, tibial and peroneal arteries (all major arteries from the level of his knee down).

A distal occlusion will be temporarily created in order to develop a length of major artery that will be isolated from the rest of the systemic circulation. This distal occlusion will be hyperperfused in order to stimulate the development of collateral vessels. A peripheral access device, as shown in FIG. 37-42 will be implanted in the patient's femoral artery approximately at the mid-thigh level. Following implantation of the device catheters will be inserted through the peripheral access device and connected to the extracorporeal pump (Rotaflow, Maquet) in the arrangement as illustrated in FIG. 19. The pump will be initially set to run at approximately 200-300 mL/min, and generated an initial return pressure of 150-200 mmHg. Pressure and flow measurements will be recorded about every 15 mins. In total this patient will receive 50 hours of intermittent 'on-pump' treatment over 5 days. The patient will be hyperperfused for approximately 10 hours each day. Thereafter, the catheters and balloons will be removed, the plunger will be moved into a closed position to prevent back flow of blood from the vessel and to assure that no fluids reminded in the housing. Furthermore, the housing will be clamped off to seal it from outside contamination. The next day a new set of catheters will be inserted into the patient and the hyperperfusion continued. This process will be repeated over the four to six days. Over the 50 hours of treatment the flow rate of blood through the pump will be maintained at approximately 300-400 mL/min. Over the duration of the treatment the return pressure from the pump continued to fall. During the first 6 hours of treatment the mean return pressure will be approximately 200 to 270 mmHg (at 300-400 mL/min flow), by 18-24 hours this will be reduced to approximately 150-200 mmHg (at 300-400 mL/min flow), and by the end of the treatment the return pressure will be 110-150 mmHg (at 375-425 ml/min flow). This reduction in return pressure with a similar flow will indicate that peripheral resistance was decreasing and more blood was able to move through the vessels and into the distal areas of the leg. Angiograms taken of the limb will show that the blockage of the major arteries will not have not changed and therefore the additional flow down the leg must have travelled through the small collateral arteries. The patient's leg will be observed to become warm and pink within the first 40-120 minutes of the hyperperfusion treatment and stayed that way for the duration of the treatment. The patient will describe feeling warmth in his leg, decreased pain, and increased sensation.

During the follow-up period (about 12 months), the patient will have not had any adverse events from this treatment and will have had no further interventions to the arteries of his leg. His leg will remain warm, pink, and well perfused. All ischemic ulcers have healed and remained healed. The patient will describe a significant reduction in pain and increase in warmth.

Example 7

Patient: This is a 85 year old male with severe gangrenous fingers and the last three digits appear purple to visual observation with an ischemic ulcer on the tips of two of the fingers. Patient complained about severe pain in these digits.

A peripheral access device, as shown for example in FIGS. 37-42, and 52 may be used and implanted in the patient's shoulder at the axillary artery. Following implantation of the device, catheters (DLP 13Fr RCSP catheters) were inserted through the peripheral access device and connected to the extracorporeal pump (Rotaflow, Maquet). The pump was initially set to run at approximately 300 mL/min, and generated an initial return pressure of between 124-135 mmHg. Pressure and flow measurements were recorded about every 30 mins. In total this patient received 56 hours of intermittent 'on-pump' treatment over 2 weeks. The patient was first treated and hyperperfused for 27 hours and then taken off treatment for 6 days and then hyperperfused for 29 hours. Between treatments the catheters and balloons where removed, the plunger moved into a closed position to prevent back flow of blood from the vessel and to assure that fluids did not reminded in the housing. Furthermore, the housing was clamped off to seal it from outside contamination. Thereafter a new set of catheters was inserted into the patient and the hyperperfusion continued for 29 hours.

Over the first 27 hours of treatment the flow rate of blood through the pump was maintained at approximately 493 mL/min. Over the duration of the treatment the return pressure from the pump continued to fall. The patient's hand was observed to become warm and pink within the first 30 minutes of the hyperperfusion treatment and stayed that way for the duration of the treatment. The patient described feeling warmth in his hand and fingers, decreased pain, and increased sensation.

The patient's device was removed after 2 weeks of implantation. At 1-week follow-up, the patient's fingers appeared pink. The gangrenous tip on the fourth digit was well demarcated. Pain has been significantly reduced compared with pre-treatment, the patient has not had any adverse events from this treatment and has had no further interventions to the fingers in his hand. At 2 week follow up, the patient's fingers have further improved. The patient felt no pain associated with the fingers. The clinical observations had improved slightly since the previous follow-up (one week before). The observations indicated continued healing.

Thermograms were taken of the patient during screening, 1-week post-treatment and 2 weeks post-treatment. It is worth noting that although this type of thermography is only accurate to within ±2° C., it was very precise in terms of showing temperature differences. The colour scale was kept constant so as not to be misleading. An observation from thermography was the skin temperature distribution, which was indicative of the level of perfusion in the area. In a pre-treatment visible image of patient taken during the screening visit, the last three digits appear purple. Patient complained about severe pain in these digits. During a screening visit, it was apparent from the thermogram that the last three digits of the left hand were colder when compared with the patient's other fingers. The last three digits of the right (normal) hand show similar temperatures to that of the index finger. In another thermogram taken during pre-treatment the significantly colder fingers of the diseased hand were shown. This is indicative of poor circulation in these fingers. In a visual image of the patient taken after one week post treatment, the third and fifth digits appeared pink, and the gangrenous tip of the fourth digit was well demarcated, which was indicative of healing. Despite good clinical observations, the thermographic image showed little to no change in the temperature distribution when compared to the pre-treatment thermograms. In a visual image of the patient's hand taken two weeks post treatment, although the finger tips still appeared purple, the problem areas were well demarcated, indicating restored perfusion up to the demarcation. In a thermogram taken 2 weeks post-treatment, the distribution of heat in the diseased fingers appeared very similar to that of the normal hand. The heat distribution in the three diseased fingers resembled that of the normal index finger.

Prophetic Example 8

Oncology: Currently there are approximately 5,000 new cases of cancer per million of the population per annum. This equates to approximately 1.5 million new cases of cancer in the US every year. Chemotherapy is one of the most common forms of treatment for cancer, often in combination with surgery and/or radiation therapy. Chemotherapy may also be used in neoadjuvant chemotherapy (preoperative treatment) for shrinking the primary tumour, thereby rendering local therapy (surgery or radiotherapy) less destructive or more effective. Adjuvant chemotherapy (postoperative treatment) can be used when there is little evidence of cancer present, but there is risk of recurrence. This can help reduce chances of resistance developing if the tumour does develop. It is also useful in killing any cancerous cells that have spread to other parts of the body. This is often effective as the newly growing tumours are fast-dividing, and therefore very susceptible.

Chemotherapy treatment can be physically exhausting for the patient. Current chemotherapeutic techniques have a range of side effects mainly affecting the fast-dividing cells of the body—for example, those cells in the immune system, gastrointestinal tract and hair follicles. Important common side-effects include: nausea and vomiting, diarrhoea or constipation, anaemia, malnutrition, memory loss, depression of the immune system and hence (potentially lethal) infections and sepsis, haemorrhage, secondary neoplasms, cardiotoxicity, hepatotoxicity, nephrotoxicity, ototoxicity, death, and/or combinations thereof. Using embodiments disclosed herein it will be possible to target chemotherapy to a specific region or organ or body part thereby isolating the effects of the chemotherapy to the selected organ, region, or body part.

When patients present with identified or suspected tumours in organs, regions, or body parts that are suitable for isolation (suitable organs include, but are not limited to, brain, thyroid gland, parathyroid glands, breast, liver, gallbladder, kidneys, spleen, pancreas, small intestine, large intestine, bladder, uterus, vagina, prostate, testes) an access device as disclosed herein will be implanted in a suitable peripheral artery (such as the femoral artery, axillary artery) and arterial isolation catheters placed through the device. These arterial isolation catheters may have occlusive balloons and will be suitable for perfusion of fluids. One or more catheters may be placed through the access device to completely or substantially completely control blood flow to the organ, body part, or region. In the case of organs that receive a blood supply from multiple sources (such as the liver which receives blood from the hepatic artery and the portal vein) multiple arterial occlusion catheters may be used.

It may be desirable to anastomose (join) the access device to an arterio-venous fistula (as shown in FIG. 18) in order to allow simultaneous arterial and venous access. Alternatively, a second access device may be anastomosed to a suitable peripheral vein to allow venous access. Using either of these configurations, occlusive venous drainage catheters may be placed in the specific veins in order to control, or largely control, the venous drainage from the selected organ, region, or body part. An example of this is the catheter described in FIGS. 23 and 24 to control the venous drainage from the liver into the inferior vena cava (IVC). When the arterial and venous occlusive catheters are used through one or more access devices simultaneously, the blood supply and drainage from a specific organ, region, or body part may be totally, substantially, or partial controlled. Once the blood supply and drainage will be controlled at the desired level, it will be possible to deliver therapeutic agents to the isolated organ, region or body part while preventing or limiting wholly, substantially or partially, the circulation of these agents in the systemic circulation. For example, patients with hepatocellular carcinoma (HCC; liver cancer) will be able to have one or more access devices implanted in their peripheral arteries and veins, and through these devices have catheters placed to control the hepatic artery, hepatic veins, and the superior and inferior mesenteric arteries (the major supply to the portal vein which also supplies the liver). Specific therapeutic agents directed at the HCC may then be delivered to the liver and drained from the hepatic veins so that it does not affect the rest of the body. These therapeutic agents may be currently available agents such as cis-platin, currently available agents in higher than normal doses (since the organ is isolated from the systemic circulation), or novel agents which may be known but have no safe method of delivery due to their systemic toxic effects (such as nephrotoxicity, or pleural oedema). In addition to delivery of pharmaceuticals, other treatment modalities are also possible into the isolated organ, region, or body part such as hyperthermia, hypothermia, or hyper- or hypo-oxygenation of the blood, without affecting, substantially affecting, or partially affecting the rest of the systemic circulation.

Another application of the disclosed embodiments will be in the Stem cell delivery and genetic engineering area. Using certain embodiments disclosed herein it may also be possible to target stem cell therapy or genetic engineering therapy to isolated organs, regions, or body parts with the use of the Access Device. For example, in a patient with a renal pathology a stem cell or genetic engineering therapy may be able to provide a significant clinical benefit to the kidney, however it may pose a greater risk to other organs such as the liver, heart, or brain. In this situation, it will be possible, using the systems, methods, and/or devices disclosed herein to position isolation catheters in the renal artery (or arteries) and renal vein (or veins) so that the kidney will be isolated, substantially isolated, or partially isolated from the rest of the systemic circulation. This will allow the kidney to be treated separately, substantially separately, or partially separately from the rest of the body on an intermittent, repeatable basis as required. This approach will allow the clinician to treat the pathology in isolation, substantial isolation, or partial isolation with a reduced risk of causing adverse events in other organs or regions of the body, and in doing this, may allow drugs or therapies that are currently available, but without a safe mechanism of delivery, to be safely and effectively managed.

One advantage of the embodiments disclosed herein is that the therapeutic agents or therapeutic treatments can be delivered more effectively to the targeted treatment region while at the same time minimizing, partially minimizing, reducing, or substantially reducing the delivery of the therapeutic agents or treatments to areas of the body that will not be treated and thus reduce, substantially reduce, or partially reduce unwanted side effects. Another advantage of the embodiments disclosed herein is that that therapeutic agents or therapeutic treatments will be delivered more effectively to the targeted treatment region while at the same time minimizing, partially minimizing, reducing, or substantially reducing the time that the therapeutic agents or treatments are in contact with the treatment region and/or body, and thus reducing, substantially reducing, or partially reducing unwanted side effects. Using the embodiments disclosed herein the time that therapeutic agents or therapeutic treatments will be in contact, substantial contact, or partial contact with the treatment area may be reduced by about 90% to about 5%, about 90% to about 10%, about 80% to about 20%, about 70% to about 30%, about 70% to about 20%, about 60% to about 40%, about 60% to about 10%, about 60% to about 20%, or about 50% to about 30%. Using the embodiments disclosed herein the time that therapeutic agents or therapeutic treatments will be in contact, substantial contact, or partial contact with the body may be reduced by about 90% to about 5%, about 90% to about 10%, about 80% to about 20%, about 70% to about 30%, about 70% to about 20%, about 60% to about 40%, about 60% to about 10%, about 60% to about 20%, or about 50% to about 30%. Using the embodiments disclosed herein the time that therapeutic agents or therapeutic treatments will be in contact, substantial contact, or partial contact with the non treatment areas of the body may be reduced by about 90% to about 5%, about 90% to about 10%, about 80% to about 20%, about 70% to about 30%, about 70% to about 20%, about 60% to about 40%, about 60% to about 10%, about 60% to about 20%, or about 50% to about 30%.

Another advantage to the embodiments disclosed herein is that therapeutic agents or therapeutic treatments that cause too many unwanted side effects will now be available for potentially use. Using the embodiments disclosed herein it will be possible to use the above variations in different combinations to delivered more effectively to therapeutic treatments or agents while at the same time minimizing, partially minimizing, reducing, or substantially reducing substantially reducing, or partially reducing unwanted side effects After human ethics committee approval was sought and received to commence the trial treatment in humans. A number of patients where treated with certain embodiments of the devices, systems and methods disclosed. The outcome and certain details of these treatments is shown in Table 1 below:

TABLE 1

| Patient | MB551 | RB567 | FW853 | GH237* | EC968 | MB840 |
|---|---|---|---|---|---|---|
| Age/Sex | 52/M | 57/M | 85/M | 61/M | 86/M | 86/F |
| Site of Blockage * | CFA, FA, POPA, PTA, ATA | Unknown | PTA, ATA, PNA | Distal FA, & graft | Palmar Arch | POPA, PTA, PNA |
| Site of Anastomosis | CFA | CFA | CFA | #1: L. CFA #2: L FA | Axillary A. | FA |
| No. of Implanted Devices | 1 | 1 | 1 | 2 | 1 | 1 |
| PAD Tubing Assembly | 20-000277 | 20-000324 | 20-000324 | 20-000324 | 20-000324 | 20-000559 |
| PAD Connector Numbers | 20-000200 | 20-000321 | 20-000321 | 20-000321 20-000492 20-000312 | 20-000321 | 20-000492 |
| Leakage at Anastomosis | Yes | Yes | Yes | Negligible | Yes | Negligible |
| Infection | No | No | No | No | No | Yes |
| Device Leaks | Negligible | Negligible | Negligible | Negligible | Negligible | Negligible |
| Implantation Date | 19 Jul. 2006 | 23 Jan. 2007 | 07 Feb 2007 | 31 Aug. 2007 | 08 Sep. 2007 | 09 Nov. 2007 |
| Implantation (days) | 5 | 4 | 6 | 17 | 21 | 21 |
| Pumping Sessions | 2 | 1 | 2 | 2 | 2 | 2 |
| Pumping Hours | 19 28 | 59.5 | 6.5 18 | 33.5 24 | 27 29 | 28.5 24.25 |
| Mean flow (ml/min) | 349 355 | 294 | 276 193 | 308 788 | 498 372 | 437 444 |
| Mean Pressure (mmHg) | 234 121 | 196 | 179 303 | 285 184 | 154 169 | 211 217 |
| Latest follow-up | 24 months | ~1 week | 3 days | 6 months | 6 months | 3 weeks |
| Outcome at Latest Follow | Leg viable. Decrease in pain. Healed Ulcer | BKA[1]. Compartment syndrom leg was beyond rescue due to advanced tissue necrosis prior to treatment. | BKA at Royal Melbourne Hospital - 3 months after treatment | Leg viable. Ulcers healed | Gangrene formed scab and has fallen off. Fingers appear pink and well-perfused-hand saved. | Post-treatment Infection AKA[2] |

| Patient | MM565 | IM879 | JV313 | MI731 | GC319 |
|---|---|---|---|---|---|
| Age/Sex | 86/F | 79/M | 65/M | 76/M | 72/M |
| Site of Blockage * | FA, POPA, PTA, ATA | FA | POPA, PTA, ATA, PNA | PTA, ATA, PNA | FA, POPA, PTA, ATA, PNA |

TABLE 1-continued

| Site of Anastomosis | R: CFA L: CFA | Ext Iliac A | Prox: CFA Dist: FA | Pros: CFA Dist: FA | CFA. |
|---|---|---|---|---|---|
| No. of Implanted Devices | 2 | 1 | 2 | 2 | 1 |
| PAD Tubing Assembly | 20-000559 | 20-000559 | 20-000559 | 20-000559 | 20-000559 |
| PAD Connector Numbers | 20-000492/ 20-000312 | 20-000321 | 20-000321 | 20-000321 | 20-000321 |
| Leakage at Anastomosis | Negligible | Negligible | Negligible | Negligible | Negligible |
| Infection | No | No | No | No | No |
| Device Leaks | Negligible | Negligible | Negligible | Negligible | Negligible |
| Implantation Date | 21 Nov. 2007 | 30 Jan. 2008 | 20 Feb. 2008 | 12 Mar. 2008 | 14 May 2008 |
| Implantation (days) | 13 | 5 | 5 | 4 | 5 |
| Pumping Sessions | 2 | 1 | 2 | 2 | 2 |
| Pumping Hours | 24 11.5 | 17.5 | 26 36 | 26.5 30 | 19.75 22.75 |
| Mean flow (ml/min) | 894 474 | 112 | 567 686 | 615 601 | 385 393 |
| Mean Pressure (mmHg) | 181 200 | 130 | 175 171 | 187 206 | 244 290 |
| Latest follow-up | 1 month | 3 months | 3 months | 3 months | 3 weeks |
| Outcome at Latest Follow | Died of exacerbation of pre-treatment respiratory failure. | BKA Severe respiratory disease (not-device-related). Amputation site viable. | Decrease in pain. Leg and foot viable. | Forefoot amputated. Amputation site viable. Leg viable. | Ulcer still present but healing. Severe ulcer pain persists. Foot warmer than before treatment. |

While certain embodiments have been shown and described herein, it will be obvious that such embodiments are provided by way of example only. Numerous variations, changes, and substitutions will now occur to those skilled in the art based on the disclosure herein without departing from the inventions disclosed and taught. It should be understood that various alternatives to the embodiments of the inventions described herein may be employed in practicing the inventions. It is intended that the following claims define the scope of the inventions and that methods, devices and systems within the scope of these claims and their equivalents be covered thereby.

What is claimed is:

1. A system for providing localized treatment of a patient comprising:
a) an access device which provides fluid access intermittently and recurrently to a blood vessel of the patient, the access device comprising a cannula having an inflow port, an inflow lumen, an outflow lumen and an outflow port, a first plunger assembly movable through the inflow lumen and which controls access of fluid entering the cannula from the inflow port, the first plunger assembly being movable between an opened position where it allows fluid access into the vessel from the inflow lumen and a closed position where it prevents fluid access into the vessel from the inflow lumen, a second plunger assembly movable through the outflow lumen and which controls access of fluid exiting the cannula from the outflow port, the second plunger assembly being movable between an opened position where it allows fluid access into the outflow lumen from the vessel and a closed position where it prevents fluid access into the outflow lumen from the vessel;
b) a movable spatula which separates the inflow lumen and the outflow lumen, wherein a vascular end of the movable spatula is shaped to provide substantially leak proof interaction with a wall of a blood vessel,
wherein the spatula is moveable through a first position where the blood vessel is fully occluded, a second position where the blood vessel is partially occluded, and a third position where the blood vessel is not occluded, and wherein the spatula may be locked into the first, second, or third positions using a locking mechanism, whereby the spatula continues to separate the inflow lumen and the outflow lumen when in the first, second and third positions, and directs blood and fluid from the vessel into the outflow lumen when in the first and second positions;
c) one or more external blood modification systems comprising at least one pump;
d) one or more outflow systems providing fluid communication between the blood vessel and the one or more external blood modification systems through the outflow port;
e) one or more inflow systems providing fluid communication between the one or more external blood modification systems and the blood vessel through the inflow port.

2. The system according to claim 1, wherein the or each external blood modification system further comprises at least one or more additional devices selected from a group consisting of: pumps, flow controllers, drug delivery devices, blood monitoring devices, blood oxygenators, sampling devices, nutrient suppliers, dialysis or other blood cleaning or scrubbing devices and/or blood temperature control devices.

3. The system according to claim 1, wherein the access device forms a fistula between a vein and an artery.

4. The system according to claim 1, wherein the spatula is biocompatible.

5. The system according to claim 1, wherein the locking mechanism comprises a locking pin or pins.

* * * * *